United States Patent
Marrinucci et al.

(12) 
(10) Patent No.: US 12,287,321 B2
(45) Date of Patent: Apr. 29, 2025

(54) OPTICAL MULTIANALYTE DETECTION

(71) Applicant: Truvian Sciences, Inc., San Diego, CA (US)

(72) Inventors: Dena Marrinucci, San Diego, CA (US); Nicholas Haase, San Diego, CA (US); Ryan Morgan, San Diego, CA (US); Michael Adams, San Diego, CA (US); Derek Arndt, San Diego, CA (US); Graeme Cross, San Diego, CA (US); Jeffrey A. Hawkins, San Diego, CA (US); David Hecht, San Diego, CA (US); Johnny Steve Rachele, San Diego, CA (US); Roger Taylor, San Diego, CA (US); Scott Thompson, San Diego, CA (US); Kyoung-Ho Kim, San Diego, CA (US); David Luke McDonald, San Diego, CA (US); Michael White, San Diego, CA (US); Kevin Yang, San Diego, CA (US)

(73) Assignee: Truvian Sciences, Inc., San Diego, CA (US)

( * ) Notice: Subject to any disclaimer, the term of this patent is extended or adjusted under 35 U.S.C. 154(b) by 0 days.

(21) Appl. No.: 18/464,185

(22) Filed: Sep. 8, 2023

(65) Prior Publication Data
US 2025/0085271 A1 Mar. 13, 2025

(51) Int. Cl.
*G01N 33/49* (2006.01)
*B01L 3/00* (2006.01)
(Continued)

(52) U.S. Cl.
CPC ............ *G01N 33/492* (2013.01); *B01L 3/502* (2013.01); *C12Q 1/6816* (2013.01);
(Continued)

(58) Field of Classification Search
CPC ............ G01N 33/492; G01N 21/6428; G01N 2021/1765; G01N 2021/3155;
(Continued)

(56) References Cited

U.S. PATENT DOCUMENTS

| | | |
|---|---|---|
| D838,380 S | 1/2019 | Self et al. |
| D936,856 S | 11/2021 | Hawkins et al. |

(Continued)

FOREIGN PATENT DOCUMENTS

| | | |
|---|---|---|
| CN | 1206832 A | 2/1999 |
| CN | 110531065 A | 12/2019 |

(Continued)

OTHER PUBLICATIONS

Hawkins, "Rethinking the Clinical Laboratory Test Value Chain: Using New Technologies and New Approaches to Lower Costs, Speed Time-to-Answer, and Contribute to Improved Patient Outcomes," Truvian Slide Deck pp. 1-19 (Apr. 27, 2021).

(Continued)

*Primary Examiner* — Jill A Warden
*Assistant Examiner* — Jacqueline Brazin
(74) *Attorney, Agent, or Firm* — Snell & Wilmer, L.L.P.; April Wurster

(57) ABSTRACT

Provided herein are systems, devices, and methods for performing optical multianalyte detection in a sample, such as a human blood sample. The system processes sample in a single-use support pack that holds the blood sample and contains pipette tips, buffers, reagent preparation wells and a monolayer. Sample is transferred from the sample pack to a single-use disc consumable that contains microwells prefilled with dried chemistries, plasma separation features, and a hematocrit channel. The instrument comprises a cell imager, an absorbance module comprising a spectrophotometer, a fluorescent laser scanning module, and a camera. The (Continued)

system uses only a small amount of blood from a single heparinized sample, to simultaneously provide results for a full panel of routine blood tests spanning elecochemistry, clinical chemistry, hematology, immunoassays and combinations thereof.

19 Claims, 76 Drawing Sheets

(51) Int. Cl.
    *C12Q 1/6816* (2018.01)
    *G01N 21/17* (2006.01)
    *G01N 21/31* (2006.01)
    *G01N 21/64* (2006.01)

(52) U.S. Cl.
    CPC ...... *G01N 21/6428* (2013.01); *B01L 2200/04* (2013.01); *B01L 2200/0642* (2013.01); *B01L 2200/143* (2013.01); *B01L 2200/16* (2013.01); *B01L 2300/021* (2013.01); *B01L 2300/0645* (2013.01); *B01L 2300/0663* (2013.01); *G01N 2021/1765* (2013.01); *G01N 2021/3155* (2013.01); *G01N 2021/6417* (2013.01); *G01N 2021/6439* (2013.01)

(58) Field of Classification Search
    CPC .... G01N 2021/6417; G01N 2021/6439; B01L 3/502; B01L 2200/04; B01L 2200/0642; B01L 2200/143; B01L 2200/16; B01L 2300/021; B01L 2300/0645; B01L 2300/0663; C12Q 1/6816
    USPC ......................................................... 422/400
    See application file for complete search history.

(56) References Cited

U.S. PATENT DOCUMENTS

| | | |
|---|---|---|
| D954,295 S | 6/2022 | Hawkins et al. |
| D959,019 S | 7/2022 | Hawkins et al. |
| D960,386 S | 8/2022 | Hawkins et al. |
| D968,643 S | 11/2022 | Hawkins et al. |
| 11,638,918 B2 | 5/2023 | Kleinemolen et al. |
| 2006/0257992 A1 | 11/2006 | McDevitt et al. |
| 2007/0190525 A1 | 8/2007 | Gu et al. |
| 2012/0041315 A1* | 2/2012 | Mycek ............... G01N 21/6486 600/476 |
| 2016/0069919 A1* | 3/2016 | Holmes ................. G01N 21/51 435/14 |
| 2017/0067871 A1* | 3/2017 | DeLouise ............ B01L 3/5085 |
| 2017/0120259 A1* | 5/2017 | Takeuchi ................ B04B 5/02 |
| 2017/0176481 A1 | 6/2017 | Accurso |
| 2019/0300948 A1* | 10/2019 | Cuppens ................ B01L 3/545 |
| 2019/0388596 A1 | 12/2019 | Camisani |
| 2020/0064254 A1 | 2/2020 | Vanderklein et al. |
| 2022/0111385 A1* | 4/2022 | Yang ........................ B01L 3/52 |
| 2022/0266242 A1* | 8/2022 | Samsoondar ...... G01N 33/4925 |
| 2023/0132344 A1 | 4/2023 | Dong |

FOREIGN PATENT DOCUMENTS

| | | |
|---|---|---|
| JP | 6016168 B2 | 10/2016 |
| WO | 2005083423 A2 | 9/2005 |
| WO | 2020176607 A1 | 9/2020 |
| WO | 2020227643 A1 | 11/2020 |
| WO | 2021236675 A1 | 11/2021 |
| WO | 2021236683 A1 | 11/2021 |
| WO | 2022066741 A2 | 3/2022 |
| WO | 2022271948 A1 | 12/2022 |

OTHER PUBLICATIONS

Theranos' Elizabeth Holmes Speaks at AACC Meeting. "Theranos Science & Technology: The Miniaturization of Laboratory Testing," American Association for Clinical Chemistry [Video] [Screen captures from video retrieved on the Internet at URL: https://www.mpo-mag.com/contents/view_videos/2016-08-02/theranos-elizabeth-holmes-speaks-at-aacc-meeting/] pp. 1-6 (Aug. 2, 2016).

WO: International Search Report for PCT/US2024/044242 mailed Dec. 20, 2024 (15 pages).

EP: Extended Search Report in European Application No. 24199072.0, dated Feb. 5, 2025 (12 pages).

\* cited by examiner

2100

```
┌─────────────────────────────────────────────────────────────┐
│ SCANNING, BY A DETECTION INSTRUMENT OF A MULTI-MODALITY     │
│ BLOOD ANALYSIS SYSTEM, USER-RELATED INFORMATION OF A SAMPLE │
│ INTO A COMPUTER SYSTEM                                      │
│                         2105                                │
└─────────────────────────────────────────────────────────────┘
                              ↓
┌─────────────────────────────────────────────────────────────┐
│ RECEIVING, BY THE DETECTION INSTRUMENT, A DISC COMPRISING   │
│ ONE OR MORE SAMPLES IN ONE OF A PLURALITY OF ORIENTATIONS   │
│ INTO A DISC TRAY                                            │
│                         2110                                │
└─────────────────────────────────────────────────────────────┘
                              ↓
┌─────────────────────────────────────────────────────────────┐
│ MEASURING, BY THE DETECTION INSTRUMENT IN A CLINICAL        │
│ CHEMISTRY MODE, BY THE COMPUTING SYSTEM CONTROLLING A       │
│ CLINICAL CHEMISTRY MODULE OF THE MULTI-MODALITY BLOOD       │
│ ANALYSIS SYSTEM, AT LEAST ONE OF AN OPTICAL ABSORBANCE AND A│
│ SCATTERING VALUE                                            │
│                         2115                                │
└─────────────────────────────────────────────────────────────┘
                              ↓
┌─────────────────────────────────────────────────────────────┐
│ MEASURING IN AN IMMUNOASSAY MODE, BY THE COMPUTING SYSTEM   │
│ CONTROLLING AN IMMUNOASSAY (IA) MODULE OF THE MULTI-        │
│ MODALITY BLOOD ANALYSIS SYSTEM, ONE OR MORE VESSELS OF THE  │
│ DISC                                                        │
│                         2120                                │
└─────────────────────────────────────────────────────────────┘
                              ↓
┌─────────────────────────────────────────────────────────────┐
│ MEASURING IN A HEMATOLOGY MODE, BY THE COMPUTING SYSTEM     │
│ CONTROLLING A HEMATOLOGY MODULE OF THE MULTI-MODALITY       │
│ BLOOD ANALYSIS SYSTEM, ONE OR MORE HEMATOLOGY ASSAYS OF A   │
│ GENERAL DISC WELL IN A SUPPORT PACK                         │
│                         2125                                │
└─────────────────────────────────────────────────────────────┘
```

FIG. 21

Precision Performance Meets Acceptance Criteria

Reproducibility Study Design:
- 180 total runs with low, normal, and high controls
- Each assay level = 60 Runs
  - 4 Replicates/Level/Day
  - 5 days
  - 3 Instruments (single site)
- CV represents the sum of repeatability (within-run), between-day and between-instrument variances

Reproducibility Summary:
- ✓ TruWellness Panel™ is performing well across all levels on multiple machines over multiple days
- ✓ Met CV acceptance criteria for 74/75 (99%) of all levels
- ✓ 100% of all levels meet the CV acceptance criteria if single RBC normal level outlier is excluded from analysis
  - ✓ An updated QC metric in development suppresses reporting this type of outlier

Comprehensive Metabolic Panel (CMP)

| Measurand | Level | Mean | CV (%) |
|---|---|---|---|
| Glucose (mg/dL) | Low | 56 | 3.0 |
| | Normal | 115 | 2.2 |
| | High | 350 | 1.9 |
| BUN (mg/dL) | Low | 14 | 5.1 |
| | Normal | 41 | 2.9 |
| | High | 79 | 3.2 |
| CRE (mg/dL) | Low | 0.89 | 3.0 |
| | Normal | 1.87 | 2.3 |
| | High | 6.49 | 1.5 |
| Calcium (mg/dL) | Low | 5.3 | 4.4 |
| | Normal | 9.5 | 3.1 |
| | High | 11.6 | 2.4 |
| Total Protein (g/dL) | Low | 3.9 | 3.4 |
| | Normal | 5.6 | 2.7 |
| | High | 6.8 | 1.9 |
| ALB (mg/dL) | Low | 2.7 | 4.5 |
| | Normal | 3.7 | 3.4 |
| | High | 4.5 | 3.1 |
| TBIL (mg/dL) | Low | 0.6 | 7.3 |
| | Normal | 3.3 | 2.8 |
| | High | 7.7 | 1.9 |
| ALP (U/L) | Low | 25 | 10.7 |
| | Normal | 129 | 4.7 |
| | High | 277 | 2.6 |
| AST (U/L) | Low | 43 | 2.4 |
| | Normal | 107 | 1.9 |
| | High | 246 | 1.3 |
| ALT (U/L) | Low | 28 | 4.3 |
| | Normal | 81 | 2.4 |
| | High | 173 | 2.0 |

Complete Blood Count (CBC)

| Measurand | Level | Mean | CV (%) |
|---|---|---|---|
| RBC ($10^6$ cells/µL) | Low | 2.01 | 2.7 |
| | Normal* | 4.11 | 3.6 |
| | High | 5.24 | 2.5 |
| WBC ($10^3$ cells/µL) | Low | 4.6 | 5.0 |
| | Normal | 8.8 | 2.0 |
| | High | 26.6 | 2.2 |
| PLT ($10^3$ cells/µL) | Low | 53 | 7.5 |
| | Normal | 215 | 2.8 |
| | High | 413 | 3.4 |
| HCT (%) | Low | 15.3 | 3.3 |
| | Normal | 35.0 | 1.9 |
| | High | 47.0 | 1.0 |
| HGB (g/dL) | Low | 5.8 | 2.9 |
| | Normal | 11.4 | 2.6 |
| | High | 17.9 | 1.4 |
| MCV (fL) | Low | 77 | 3.6 |
| | Normal | 85 | 4.6 |
| | High | 98 | 2.5 |

Lipid Panel

| Measurand | Level | Mean | CV (%) |
|---|---|---|---|
| Chol (mg/dL) | Low | 101 | 3.4 |
| | Normal | 176 | 2.5 |
| | High | 259 | 2.3 |
| Trig (mg/dL) | Low | 92 | 2.3 |
| | Normal | 129 | 2.3 |
| | High | 191 | 2.0 |
| HDL (mg/dL) | Low | 17 | 9.9 |
| | Normal | 44 | 4.5 |
| | High | 75 | 4.3 |
| non-HDL (mg/dL) | Low | 84 | 3.5 |
| | Normal | 132 | 2.8 |
| | High | 184 | 2.7 |
| VLDL (mg/dL) | Low | 19 | 3.0 |
| | Normal | 26 | 2.7 |
| | High | 38 | 2.3 |
| LDL (mg/dL) | Low | 66 | 4.2 |
| | Normal | 106 | 3.3 |
| | High | 146 | 3.2 |
| Chol/HDL (ratio) | Low | 6 | 7.8 |
| | Normal | 4 | 3.6 |
| | High | 3 | 3.8 |

Thyroid & HbA1c

| Measurand | Level | Mean | CV (%) |
|---|---|---|---|
| TSH (mIU/L) | Low | 1.2 | 7.0 |
| | Normal | 4.1 | 5.9 |
| | High | 10.5 | 4.9 |
| HbA1c (%) | Low | 7.0 | 1.9 |
| | Normal | 7.0 | 1.5 |
| | High | 6.8 | 1.2 |

FIG. 23

Suitable Thresholds for HIL Interferences Established

| H Index Hemolysis (mg/dl) | | | | | |
|---|---|---|---|---|---|
| CMP | | CBC | | Lipid Panel | |
| Glucose | >500 | RBC | 250 | Chol | 175 |
| BUN | >800 | WBC | 1000 | Trig | 100 |
| CRE | >500 | PLT | 1000 | HDL | 400 |
| Calcium | >500 | HCT | 900 | Thyroid & HbA1c | |
| Total Protein | 800 | HGB | NA | TSH | >800 |
| ALB | >800 | Lymphocytes | 1000 | HbA1c | N/A |
| TBIL | 50 | Neutrophils | 1000 | | |
| ALP | 50 | Other | 1000 | | |
| AST | 50 | | | | |
| ALT | 400 | | | | |

HIL Interference Summary:
✓ *TruWellness Panel*™ features integrated sample quality assessment (SQA) to determine levels of HIL in samples
✓ Tolerance to HIL interferences is established for all assays and is comparable to FDA-cleared predicate methods

FIG. 27A

Suitable Thresholds for HIL Interferences Established

Index Ranges Corrected/Uncorrected (mg/dL)

| CMP | | CBC | | Lipid Panel | | Thyroid & HbA1c | |
|---|---|---|---|---|---|---|---|
| Glucose | 10 / >20 | RBC | 40 / 36 | Chol | 5 / 10 | TSH | >45 / >45 |
| BUN | >45 / >45 | WBC | 40 / 40 | Trig | 5 / 7.5 | HbA1c | >45 / >45 |
| CRE | >10 / >10 | PLT | 40 / 18 | HDL | >20 / 20 | | |
| Calcium | >30 / >30 | HCT | 40 / 20 | | | | |
| Total Protein | 15 / 10 | HGB | >45 / >45 | | | | |
| ALB | >45 / >45 | Lymphocytes | 40 / 40 | | | | |
| TBIL | N/A | Neutrophils | N/A | | | | |
| ALP | >45 / >45 | Other | 40 / 40 | | | | |
| AST | 45 / 20 | | | | | | |
| ALT | 45 / 20 | | | | | | |

Limits (mg/dL)

| CMP | | CBC | | Lipid Panel | | Thyroid & HbA1c | |
|---|---|---|---|---|---|---|---|
| Glucose | 500 | RBC | 720 | Chol | >1000 | TSH | >1000 |
| BUN | >1000 | WBC | 800 | Trig | N/A | HbA1c | >1000 |
| CRE | >1000 | PLT | 800 | HDL | 1000 | | |
| Calcium | 750 | HCT | 800 | | | | |
| Total Protein | >1000 | HGB | >1000 | | | | |
| ALB | >1000 | Lymphocytes | 800 | | | | |
| TBIL | 750 | Neutrophils | 800 | | | | |
| ALP | >1000 | Other | 800 | | | | |
| AST | 300 | | | | | | |
| ALT | 300 | | | | | | |

HIL Interference Summary:
✓ *TruWellness Panel* features integrated sample quality assessment (SQA) to determine levels of HIL in samples
✓ Tolerance to HIL interferences is established for all assays and is comparable to FDA-cleared predicate methods

FIG. 27B

Comprehensive Metabolic Panel

| Measurand | Results Range | Correlation Coefficient (r) |
|---|---|---|
| Glucose | 100 - 396 mg/dL | 0.99 |
| BUN | 5.03 - 128 mg/dL | 1.00 |
| CRE | 0.29 - 12.2 mg/dL | 1.00 |
| eGFR | 12.9 - 145 mL/min/1.73 m² | 0.95 |
| Calcium | 2.20 - 11.8 mg/dL | 0.94 |
| Total Protein | 1.90 - 8.60 g/dL | 0.97 |
| ALB | 1.26 - 5.20 g/dL | 0.97 |
| TBIL | 0.01 - 6.49 mg/dL | 0.98 |
| ALP | 21.0 - 210 U/L | 0.88 |
| AST | 10.0 - 494 U/L | 1.00 |
| ALT | 6.00 - 681 U/L | 0.92 |

FIG. 31A

Comprehensive Metabolic Panel

| Measurand | Slope (95% CI) | Intercept (95% CI) | Median Relative Bias | Median Bias |
|---|---|---|---|---|
| Glucose | 1.00 (0.97, 1.03) | 0.00 (-1.00, 3.50) | 0.0 % | 0.00 mg/dL |
| BUN | 1.01 (0.99, 1.03) | -0.37 (-0.62, -0.07) | 0.0 % | 0.00 mg/dL |
| CRE | 0.93 (0.89, 0.98) | -0.05 (-0.09, -0.02) | -13.0 % | 0.00 mg/dL |
| eGFR | 1.01 (0.96, 1.06) | 8.64 (4.27, 14.10) | 11.0 % | 9.90 mL/min/1.73 m² |
| Calcium | 1.00 (0.99, 1.03) | -0.95 (-1.39, -0.52) | -7.0 % | -0.60 mg/dL |
| Total Protein | 1.00 (0.97, 1.03) | 0.10 (0.10, 0.38) | 2.5 % | 0.10 g/dL |
| ALB | 1.00 (0.91, 1.08) | 0.10 (0.10, 0.47) | 2.3 % | 0.10 g/dL |
| TBL | 1.00 (1.01, 1.10) | -0.02 (-0.05, 0.00) | 0.4 % | 0.00 mg/dL |
| ALP | 1.00 (0.91, 1.05) | -8.00 (-11.8, -2.15) | -12.0 % | -8.00 U/L |
| AST | 0.93 (0.88, 0.98) | -0.89 (-2.07, 0.17) | -11.0 % | -3.00 U/L |
| ALT | 0.82 (0.77, 0.87) | -0.24 (-1.56, 1.33) | -19.0 % | -5.00 U/L |

FIG. 31B

Complete Blood Count

| Measurand | Results Range | Correlation Coefficient (r) |
|---|---|---|
| RBC | 2.83 - 5.79 × 10⁶ cells/µL | 0.95 |
| WBC | 2.70 - 12.9 × 10³ cells/µL | 0.98 |
| PLT | 113 - 492 × 10³ cells/µL | 0.96 |
| HCT | 27.4 - 51.8 % | 0.92 |
| HGB | 6.90 - 18.3 g/dL | 0.97 |
| MCV | 67.1 - 102 fL | 0.85 |
| Lymphocytes (Absolute) | 0.40 - 4.20 × 10³ cells/µL | 0.97 |
| Neutrophils (Absolute) | 1.20 - 9.90 × 10³ cells/µL | 0.98 |
| Other (Absolute) | 0.10 - 1.20 × 10³ cells/µL | 0.88 |
| Lymphocytes (%) | 4.80 - 54.4 % | 0.97 |
| Neutrophils (%) | 38.0 - 90.7 % | 0.95 |
| Other (%) | 1.00 - 15.7 % | 0.57 |

FIG. 31C

Complete Blood Count

| Measurand | Slope (95% CI) | Intercept (95% CI) | Median Relative Bias | Median Bias |
|---|---|---|---|---|
| RBC | 1.03 (0.99, 1.07) | -0.14 (-0.33, 0.04) | 0.3% | 0.00 x 10⁶ cells/μL |
| WBC | 0.99 (0.93, 1.06) | 0.31 (0.00, 0.40) | 0.0% | 0.00 x 10³ cells/μL |
| PLT | 1.03 (0.99, 1.07) | -3.14 (-12.40, 5.02) | 1.1% | 2.80 x 10³ cells/μL |
| HCT | 1.02 (0.97, 1.07) | -1.32 (-3.58, 0.65) | -1.0% | 0.00 % |
| HGB | 1.07 (1.04, 1.10) | -1.16 (-1.68, -0.78) | -1.5% | -0.20 g/dL |
| MCV | 1.11 (1.02, 1.20) | -1.14 (-2.11, -3.28) | -1.9% | -1.70 fL |
| Lymphocytes (Absolute) | 1.00 (1.00, 1.00) | 0.00 (-0.10, 0.00) | 0.0% | 0.00 x 10³ cells/μL |
| Neutrophils (Absolute) | 1.00 (1.00, 1.04) | 0.00 (-0.10, 0.10) | 0.0% | 0.00 x 10³ cells/μL |
| Other (Absolute) | 0.67 (0.60, 1.00) | 0.13 (0.00, 0.14) | 0.0% | 0.00 x 10³ cells/μL |
| Lymphocytes (%) | 1.02 (0.99, 1.05) | -1.12 (-2.02, -0.10) | -1.0% | 0.00 % |
| Neutrophils (%) | 0.98 (0.94, 1.00) | 2.11 (-0.78, 4.55) | 1.6% | 1.00 % |
| Other (%) | 0.59 (0.52, 0.67) | 2.69 (1.97, 3.42) | -9.1% | -0.70 % |

FIG. 31D

Lipid Panel

| Measurand | Results Range | Correlation Coefficient (r) |
|---|---|---|
| Chol | 23.0 - 354 mg/dL | 0.98 |
| Trig | 29.0 - 729 mg/dL | 1.00 |
| HDL | 14.4 - 106 mg/dL | 0.95 |
| non-HDL | 34.0 - 339 mg/dL | 0.98 |
| VLDL | 6.00 - 178 mg/dL | 1.00 |
| LDL | 17.3 - 220 mg/dL | 0.98 |
| Chol/HDL | 1.52 - 10.5 (ratio) | 0.89 |

Thyroid & HbA1c

| Measurand | Results Range | Correlation Coefficient (r) |
|---|---|---|
| TSH | 0.34 - 21.0 mIU/L | 0.97 |
| HbA1c | 4.20 - 12.4 % | 0.98 |

FIG. 31E

Lipid Panel

| Measurand | Slope (95% CI) | Intercept (95% CI) | Median Relative Bias | Median Bias |
|---|---|---|---|---|
| Chol | 1.04 (1.02, 1.07) | -1.60 (-2.02, -1.13) | -1.8% | -9.00 mg/dL |
| Trig | 0.99 (0.97, 1.00) | -5.41 (-7.00, -3.85) | -5.0% | -7.00 mg/dL |
| HDL | 1.08 (1.02, 1.11) | -1.15 (-1.94, -1.95) | -2.1% | -1.10 mg/dL |
| non-HDL | 0.96 (0.94, 0.99) | -2.09 (-4.99, 1.27) | -5.0% | -0.80 mg/dL |
| VLDL | 0.99 (0.98, 1.00) | -1.18 (-1.40, -0.84) | -5.0% | -1.40 mg/dL |
| LDL | 1.00 (0.97, 1.03) | -5.18 (-8.20, -2.60) | -5.0% | -5.20 mg/dL |
| Chol/HDL | 0.95 (0.91, 0.98) | 0.11 (0.00, 0.23) | -1.6% | 0.00 (ratio) |

Thyroid & HbA1c

| Measurand | Slope (95% CI) | Intercept (95% CI) | Median Relative Bias | Median Bias |
|---|---|---|---|---|
| TSH | 0.99 (0.94, 1.09) | 0.08 (0.02, 0.15) | 4.1% | 0.06 mIU/L |
| HbA1c | 1.05 (1.01, 1.10) | -0.33 (-0.56, -0.10) | -0.6% | 0.00 % |

FIG. 31F

OPTICAL MULTIANALYTE DETECTION

FIELD

This disclosure relates to optical systems, devices and methods for performing multianalyte detection in a biological sample, such as a human blood sample.

BACKGROUND

Timely access to actionable data from routine blood tests can support wellness, inform medical care, and save lives. In fact, 70% of medical decisions are based on blood tests. These tests provide insight into a person's immunological, metabolic, and dietary health. Routine blood testing is important to identify early-stage conditions, and with 60% of adults living with at least one chronic disease, testing is important to preserve the quality of life for those already afflicted. Blood testing in today's world is often inconvenient, time consuming, and relies on a centralized laboratory model leveraging traditional send-outs to laboratories that process blood samples on numerous analyzers spanning multiple assay types. To support these analyzers, a large blood draw into multiple tube types is required from patients, which typically requires an appointment to complete the blood draw, sometimes at a different facility. The samples are then transported to a centralized laboratory for testing, while patients can sometimes wait several days for their results to be reported back to them. Above all, patients must follow up with a separate appointment with their health care provider to discuss the results in person in many cases, especially if the test results are abnormal. This cumbersome process, which is both disjointed and time-consuming, is a key factor for why 40% of patients do not follow up on testing orders. Poor compliance in test result follow-up can have major consequences in patient care, including missed diagnoses and suboptimal patient outcomes.

One avenue to improve patient follow-up with blood test orders is the adoption of point-of-care (POC) testing systems or direct-to-consumer (DTC) devices. These make testing accessible when and where a test is needed, removing many of the pre-analytical challenges involved in centralized testing and offering shorter turnaround time, which in turn enables real-time physician review of the results during the patient's visit. Regrettably, despite these advantages, the currently available POC instruments have significant limitations including restricted test menus, limited support for multiple assay types, and a lack of the accuracy and/or precision afforded by large central laboratory analyzers.

This disclosure resolves these and other issues of the art.

SUMMARY

The subject of this disclosure is an automated and integrated compact blood testing device. The platform can simultaneously perform clinical chemistry, immunoassay, and hematology assays with only 300 µL of blood. In addition to the small sample volume required, the system can perform all assays with blood from a single collection tube type.

In some examples, a method is disclosed to determine from a single collection tube clinical chemistry, immunoassay, and hematology detection results. To perform a test, an operator inserts a blood sample into the support pack, places it into the instrument with the disc, and initiates the run through the touch screen interface. From there, the device processes the blood and runs the panel of tests, which are measured with optical modules such as a cell imager 243, an absorbance module 383, a laser scanning module 373, and a camera. Proprietary onboard algorithms, using an onboard computer, compute the results in real-time and a report is shown on the device through the touchscreen interface at the end of each run. Upon completion of the run, the report can be saved and/or printed and the consumables are then automatically ejected for disposal. If configured with internet access, the report can be transmitted to the cloud for integration into a laboratory information system (LIS) or an electronic medical record (EMR).

Certain illustrative aspects are described herein in connection with the following description and the appended drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE DRAWINGS

The above and further aspects of the disclosure are further discussed with reference to the following description in conjunction with the accompanying drawings, in which like numerals indicate like structural elements and features in various figures. The drawings are not necessarily to scale, emphasis instead being placed upon illustrating principles of the systems, devices and methods for performing multianalyte detection on a biological sample. The figures depict one or more implementations of the inventive devices, by way of example only, not by way of limitation.

FIG. 21 illustrates a flowchart for a method, according to an embodiment.

FIG. 23 shows performance acceptance criteria.

FIGS. 24, 25, 26, 27A, 27B, 28, 29, 30 and 31A-31F all show performance data.

DETAILED DESCRIPTION

Figure 1A:
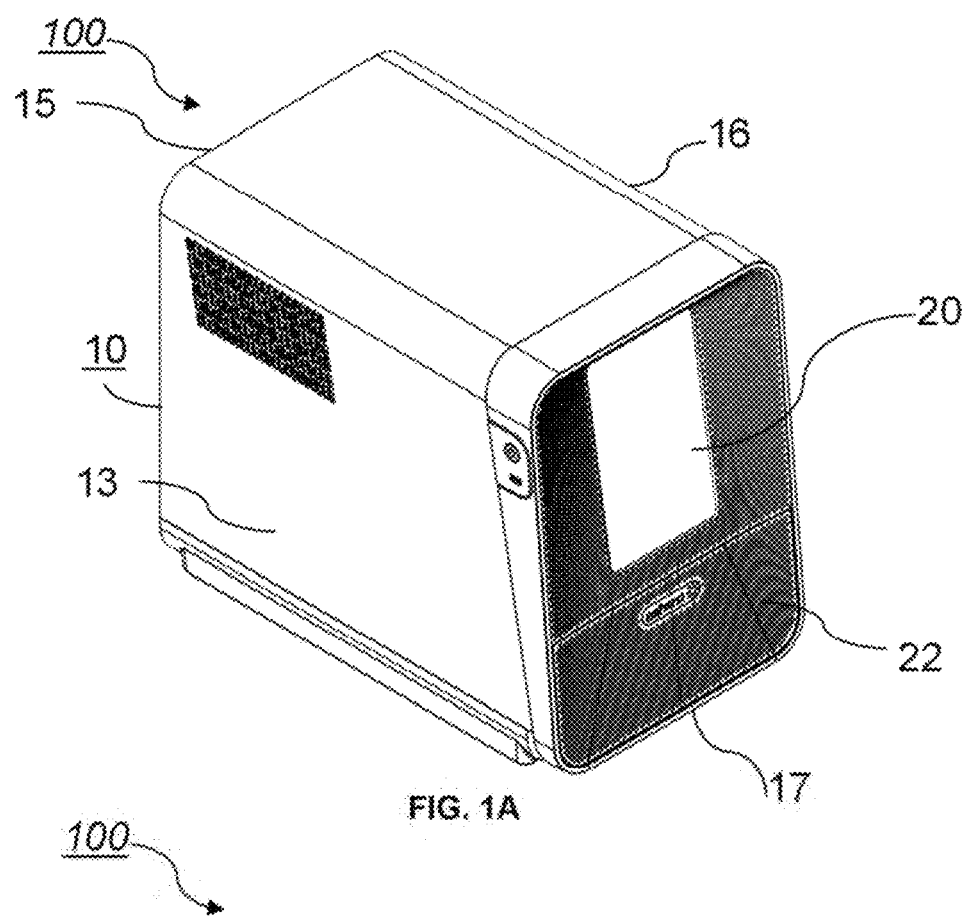
FIG. 1A shows a forward perspective view of an exemplary multi-modality processing platform system, in accordance with an exemplary embodiment.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

Definitions

It must also be noted that, as used in the specification and the appended claims, the singular forms "a," "an" and "the" include plural referents such as "at least one" or "one or more" unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In this disclosure, relative terms, such as "about," "substantially," or "approximately" are used to indicate a possible variation of 10% in the stated value.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the systems, devices and methods for performing multianalyte detection on a biological sample.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

An "analyte" is anything that can be detected in a sample. Analytes may be natural, biological or synthetic. Suitable analytes include organic and inorganic molecules, including biomolecules. In an embodiment, the analyte may be an environmental pollutant (including pesticides, insecticides, toxins, etc.); a chemical (including solvents, organic materials, etc.); therapeutic molecules (including therapeutic and abused drugs, antibiotics, etc.); biomolecules (including hormones, cytokines, proteins, lipids, carbohydrates, cellular membrane antigens and receptors (neural, hormonal, nutrient, and cell surface receptors) or their ligands, etc); whole cells (including procaryotic (such as pathogenic bacteria) and eucaryotic cells, including mammalian tumor cells); viruses (including retroviruses, herpesviruses, adenoviruses, lentviruses, etc.); and spores; etc.

As discussed herein, "cartridge" or "consumable" means a device that includes reagents and sample to perform or partially perform an assay.

As discussed herein, "clinical chemistry module" includes one or more assays used to calculate the presence and concentration of certain substances within samples through the use of biochemical analysis (e.g., chemical reactions). Substances analyzed through the clinical chemistry module can include certain metabolites, electrolytes, proteins, and/or drugs.

As discussed herein, "detection result" or "result" means the result from processing a sample. A detection result for an assay can be "detected", "not detected", "positive", or "negative" or a value, or a value range. In some embodiments, the detection result is reviewed by the physician while the patient waits, i.e., the patient need not follow up with a separate appointment with their health care provider to discuss the results. In some embodiments, the result from the described diagnostic instrument is obtained in 1-60 minutes, in 1-45 minutes, in 1-30 minutes, in 1-25 minutes, in 1-10 minutes, in 1-5 minutes or in 1 minute.

As used herein, "diagnostic instrument" or "analysis device" or "processing instrument" is a manual, semi-automated or automated instrument that gathers information leading to the identification of a disease or disorder. The diagnostic instrument described herein is a point-of-care (POC) testing instrument. The diagnostic instrument described herein does not rely on a centralized laboratory model leveraging traditional send-outs to laboratories that process blood samples on numerous analyzers spanning multiple assay types. This fast turn-around-time enables real-time physician review of the results during the patient's visit. In some embodiments, the diagnostic instrument sits on a standard laboratory bench, is powered by a standard power outlet, lacks internet connectivity, has internet connectivity and combinations thereof. In some embodiments, the diagnostic instrument does not require floor space, custom plumbing, custom electrical power set up, expensive waste management practices or combinations thereof. In some embodiments, the sample does not require upfront pre-analytical processing. In some embodiments, the only upfront pre-analytical processing required for the sample is inverting the sample to mix it. In some embodiments, the diagnostic instrument uses a high precision pipettor to handle sample and liquid reagents, on-board centrifugation to separate whole blood into plasma, and closed-loop thermal control, which is required for various assays.

Figure 10A:
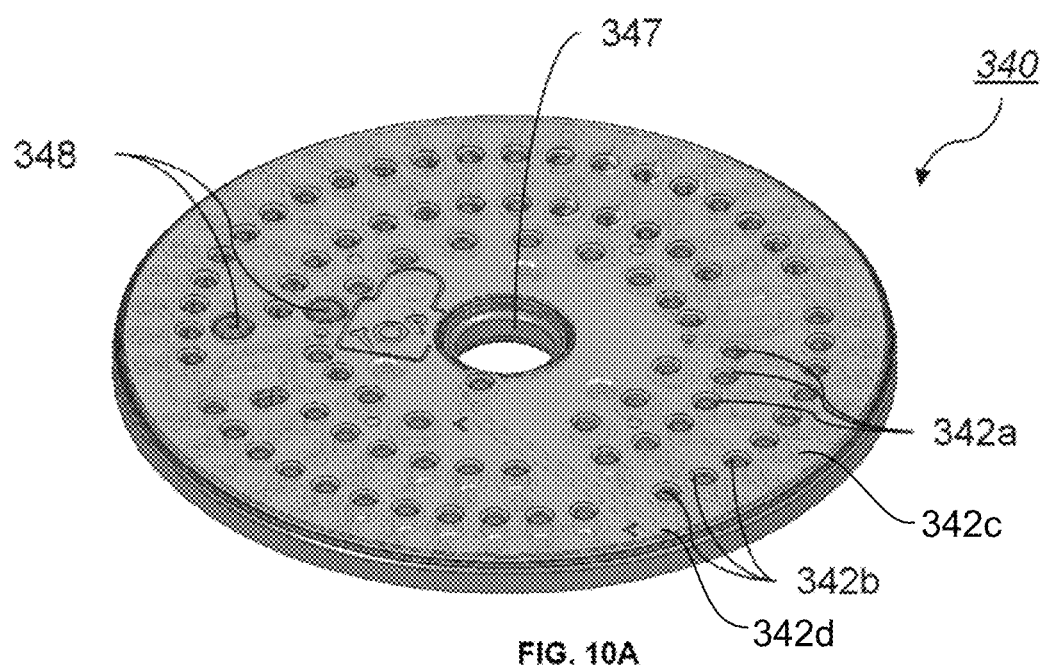
FIG. 10A shows a perspective view of an exemplary multi-well plate used in the system of FIGS. 1A and 1i, in accordance with an exemplary embodiment.
Figure 10B:
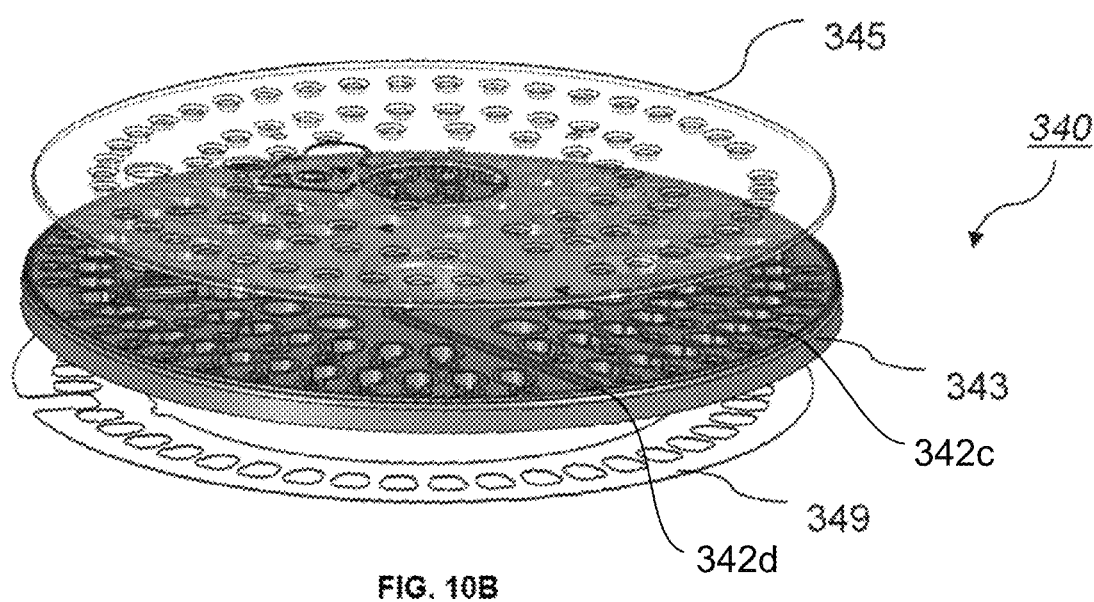
FIG. 10B shows an exploded view of the exemplary multi-well plate of FIG. 10A, in accordance with an exemplary embodiment.

As discussed herein, "disc" or "plate" or "multi-welled plate" means a device that includes reagents (without sample to perform or partially perform an assay). An exemplary disc is shown in U.S. patent no. USD954295S, by Truvian Sciences, Inc. which is incorporated herein by reference in its entirety. In some embodiments, the disc is a single-use disc consumable that comprises microwells pre-filled with dried chemistries, plasma separation features (FIG. 10A, 342c and FIG. 10B, 342c), and a hematocrit channel (FIG. 10A, 342d, and FIG. 10B, 342d). As such, the disc has features for more than one modality. In some embodiments, the disc has features to process assays for 1-3, 1-5, 1-10, or 1-20 modalities. In some embodiments, the disc has features to obtain detection results for 1-3, 1-5, 1-10, or 1-20 modalities. In some embodiments, the support pack has features for four modules: electrochemistry, clinical chemistry, immunoassay, and hematology and can run assays and generate results for all four modules. The disclosed support pack is a shared resource across the electrochemistry module, clinical chemistry module, immunoassay module and hematology module. In some embodiments, the support pack has features for all four modules: electrochemistry, clinical chemistry, immunoassay, and hematology and can run assay(s) and detect assay(s) from the electrochemistry module, clinical chemistry module, immunoassay module, and hematology module. In some embodiments, the support pack has features for all four modules: electrochemistry, clinical chemistry, immunoassay, and hematology and can process assay(s) from the electrochemistry module, clinical chemistry module, immunoassay module, and hematology module but can only and detect assay(s) from the electrochemistry module and/or hematology module.

The disclosed disc is a shared resource across the electrochemistry module, clinical chemistry module, immunoassay module and hematology module. In some embodiments, the disc has features for four modules: electrochemistry, clinical chemistry, immunoassay, and hematology and can run assays and generate results for all four modules. In some embodiments, the disc has features for all four modules: electrochemistry, clinical chemistry, immunoassay, and hematology and can process assays for one, two, three, or four modules but can only detect assay(s) from the electrochemistry, clinical chemistry, and/or IA modules. In some embodiments, the disc has features for all four modules: electrochemistry, clinical chemistry, immunoassay, and hematology and can process assays for one, two, three or all four modules and can detect assay(s) from only one module such as the clinical chemistry module or IA module.

As used herein, "distal" or "proximal" are used in the following description with respect to a position or direction relative to a reference point (e.g., such as an operator). "distal" or "distally" are a position distant from or in a direction away from the reference point. "proximal" or "proximally" or "proximate" are a position near or in a direction toward the reference point.

As used herein "dried chemistries" means dry reagents to which a sample is added.

As used herein "electrochemistry module" includes one or more assays that utilizes electrochemical measurement to detect an analyte.

As used herein, "immunoassay module" includes one or more assays used to calculate the presence and concentration of certain substances within samples through the use of an antibody and an antigen.

As used herein, "hematology module" includes one or more assays that yield information on the qualitative and quantitative composition of cellular components of the blood.

As used herein, "homing" can mean locating features on the monolayer assay device of the hematology module by the cell imager 243 and/or locating features embedded in the disc by the camera.

As used herein, "immunoassays" are understood as functioning by the binding of an antibody to the analyte of interest (the antigen). In some embodiments, one antibody is connected to a bead, while the other is connected to a small fluorescent molecule. One antibody-coated bead will bind many antigens, and each antigen will have a fluorescent antibody bound to it. In some embodiments, the immunoassay relies on binding of an antibody to an antigen and creates a turbid suspension that is measured via the absorbance module 383. In some embodiments, the immunoassay relies on binding of an antibody to an antigen and creates a turbid suspension that is measured via the clinical chemistry detection module (which can be camera 442, high speed camera, 5MP CCD camera, digital camera, digital single lens reflex (D-SLR) camera, high-definition camera and the like).

As used herein, "multimodal" or "different modalities" refers to a system incorporating two or more assays employing a different type of modality/technique. For example, one could combine clinical chemistry assays, immunoassays, hematology assays, nucleic acid assays, receptor-based assays, cytometric assays, colorimetric assays, enzymatic assays, electrophoretic assays, electrochemical assays, electrolyte assays, spectroscopic assays, chromatographic assays, microscopic assays, topographic assays, calorimetric assays, turbidmetric assays, agglutination assays, radioisotope assays, viscometric assays, coagulation assays, clotting time assays, protein synthesis assays, histological assays, culture assays, or osmolarity assays in a multimodal assay.

As used herein, "operator" may include, but is not limited to a doctor, surgeon, technician, a phlebotomist, or other healthcare professional, or any other suitable individual, or any aspects associated with the multi-modal system of this disclosure.

As used herein, "optical module" may include a module to collect assay data, and to provide results. The optical module's role is to perform photoelectric and electro-optic conversion. The transmitter converts the electrical signal into an optical signal.

As discussed herein, "support pack" or "reaction carrier" or "service pack" includes a single use device that holds the blood sample and comprises pipette tips, buffers, reagent preparation wells, a monolayer and combinations thereof. An exemplary support pack is shown in U.S. patent no. USD838380S1 by Truvian Sciences, Inc. which is hereby incorporated by reference in its entirety. The support pack is a shared resource across the electrochemistry module, clinical chemistry module, immunoassay module and hematology module. As such the support pack has features for all four modules: electrochemistry, clinical chemistry, immunoassay, and hematology but can only run assay(s) and detect assay(s) from the hematology module and/or electrochemistry module. In some embodiments, the support pack has features for all four modules: electrochemistry, clinical chemistry, immunoassay, and hematology and can process assays for one, two, three, or all four modules but can only detect assay(s) from the hematology module and/or electrochemistry module. In some embodiments, the support pack has features for all four modules: electrochemistry, clinical chemistry, immunoassay, and hematology and can process assays for one, two, three, or all four modules and can detect assay(s) from all four modules. In some embodiments, at least a part of the TSH assay is processed on the support pack. In some embodiments, at least a part of the electrochemistry assays are processed on the support pack, disc or both.

As discussed herein, "sample" is used in its broadest sense. In one sense, it is meant to include a specimen or culture obtained from any source, as well as biological and environmental samples, including one or more blood samples in a tube comprising Lithium Heparin capillary sample or Lithium Heparin Venipuncture. In some embodiments, the sample is in a "green topped blood tube." In some embodiments, the sample is a non-venipuncture collected sample (e.g., alternative capillary samples). In some embodiments, the sample is collected without relying on trained phlebotomists. In some embodiments, the sample used in the described detection instrument does not require a large blood draw (e.g., not greater than 400 μL). In some embodiments, the sample used in the described detection instrument does not require more than one blood tube for collection.

As used herein "scanner system," "item 700," and "scanner system 700" mean the system used to scan a cartridge(s) upon loading. In some embodiments the scanner system includes one camera, 2 cameras, 3 cameras, 4 cameras, 5 cameras, 6 cameras, 7 cameras, or 1-10 cameras. In some embodiments, disclosed herein the scanner system comprises camera 442 and barcode scanner 800.

As used herein, "system" means a set of things working together, for example, herein a system includes the diagnostic instrument (comprising a plurality of modules), a cartridge(s) (which can include a multi-well plate and service pack), one or more detection modules, and sample to render one more detection results. In some embodiments, the system disclosed herein is a point-of-care (POC) testing system.

As used herein, "resource" means one or more materials (e.g., reagent, patient sample, etc.) and/or capabilities (e.g., centrifuging operations, panel preparation operations, resource sharing operations [e.g., pipetting from one location to another location, moving a system component from one location to another location, sharing a captured image and/or detected result of optical characteristics of a test such as an assay with one module to another module, etc.]) available to the diagnostic instrument which are technologically accessible.

Biological samples may be relatively small sample volume (e.g., a 5-500 μl blood sample, preferably 300 μl) and can be obtained from animals (including humans) and encompass fluids, solids, tissues, and gases. Biological samples include whole blood and blood products, such as plasma, serum and the like. In many embodiments, e.g., for the detection of human proteins, the sample is a blood sample that is treated as outlined herein. Environmental samples include environmental material such as surface matter, soil, water, crystals and industrial samples. Such examples are not, however, to be construed as limiting the sample types applicable to the present technology.

As used herein, "well" or "wells" or "vessel" or "reaction vessel" is used in connection with wells of a multi-well plate and/or a support pack provided herein and includes wells for performing sample preparation, analytical analysis to determine the concentration of an analyte of interest.

Unless defined otherwise, all technical and scientific terms used herein have the same meaning as commonly understood by one of ordinary skill in the art to which the systems, devices and methods for performing multianalyte detection in a biological sample belongs.

SUMMARY

Traditional diagnostic testing in a clinical setting typically involves the drawing of large sample volumes from a patient by invasive means and long waiting periods between sample collection and testing. Also, diagnostic test results are commonly communicated to patients through a healthcare professional, and are not directly accessible to the patient, e.g., through an internet or mobile interface in the absence of a physician. In biological samples, different analytes are often present at vastly different concentrations that can range from very high concentrations (e.g., in the range of 250-500 mg/dL in a diabetic patient; e.g., fasting blood glucose in a healthy subject) to very low concentrations (e.g., below 1 ng/ml; e.g., certain inflammatory cytokines in a healthy subject). To account for the differences in analyte chemistries and concentrations, in traditional clinical settings, different analytes are typically tested separately on an analyte-by-analyte basis, using specially designated instruments for individual analytes, and using relatively large reaction volumes (e.g., 1 ml). Independent analyte testing commonly requires the drawing of relatively large samples from patients (e.g., 1-15 ml of blood), typically by invasive means (e.g., a needle). Samples from multiple patients are traditionally collected long before any of the samples are tested for a given analyte to allow for the subsequent parallel testing of multiple samples for the same analyte. Such a traditional process commonly involves substantial waiting periods for the patient between sample collection, sample testing, and the communication of results. Moreover, such a traditional process also typically involves substantial sample handling, e.g., for purposes of sample storage between sample collection and sample testing, and to stabilize samples during storage (e.g., aliquoting and freezing of samples). Additionally, independent testing of different analytes is generally not coordinated in time. Thus, if sample stability is a problem with respect to any given analyte, variability and inaccuracies can be introduced into test results if the testing of different analytes in a panel or of different samples is not coordinated in time.

The systems, devices and methods described herein include integrated and miniaturized technologies into a benchtop device that can simultaneously execute electrochemistry, immunoassay, clinical chemistry, and/or hematology assays from a single, small sample of blood, about 50-500 µL of blood. Assays on the system include complete blood count with 3-part differential, comprehensive metabolic, lipid, thyroid, and diabetes subpanels. The system processes the sample without freezing it. The system processes the sample without coordinating the process with other samples from different patients.

The systems, devices and methods described herein allow for the highly coordinated performance of different assays across multiple (2 or more) modalities on a single patient sample. Assays contemplated for use with the herein disclose system and method can include Complete Blood Count (e.g., WBC, RBC, Hemoglobin, Hematocrit, MCV, RDW, MCH*, MCHC*, Platelets, MPV, PDW, Neutrophils (%), Lymphocytes (%), Other (%). Neutrophils (Absolute), Lymphocytes (Absolute), Other (Absolute), etc.), Metabolic Panel (e.g., Glucose, BUN, Creatinine, eGFR*, Calcium, Protein, Total, Albumin, Bilirubin, Total, Alkaline Phosphatase, AST (SGOT), ALT (SGPT), etc.), Sodium, Potassium, Chloride, Bicarbonate, Lipid Panel (e.g., Cholesterol, Total, Triglycerides, HDL Cholesterol, Non-HDL Cholesterol*, VLDL Cholesterol*, LDL Cholesterol*, Cholesterol/HDL Ratio*, Hemoglobin A1c Panel, Hemoglobin A1c, Thyroid Panel, TSH (Thyroid Stimulating Hormone), etc.). The assays are directly measured tests except for assays denoted with an asterisk which have calculated parameters. The systems, devices and methods described herein further allow for the highly coordinated performance of multiple (more than 1) different assay modalities using a blood sample stored in a single blood tube type from a single blood draw from a patient.

Different assay modalities can be conducted in parallel in different pluralities of wells of a cartridge or plurality of cartridges. In some embodiments of the methods provided herein, the sample of a single patient is analyzed for a plurality of analytes in a multi-well plate and support pack across a plurality of modalities in parallel. The systems, devices and methods described herein enable "spatial multiplexing," i.e., the parallel performance of different analytical assays, of a plurality of modalities, on the same blood sample in different wells of the same cartridge or in different cartridges (e.g., use of a multi-well plate and a support pack).

Disclosed is a diagnostic instrument comprising at least two modalities wherein the two modalities are selected from the group comprising or consisting of electrochemistry, clinical chemistry, immunology, and hematology and each modality comprises at least one assay and wherein each assay is run simultaneously. In some embodiments, the immune assay module cannot detect an analyte at the same time the clinical chemistry module detects an analyte. In some embodiments, the hematology module can detect an analyte at the same time the immune assay module detects an analyte or at the same time the clinical chemistry module detects an analyte. In some embodiments, the hematology module cannot detect an analyte at the same time the electrochemistry assay module detects an analyte. Running different assays from different modalities requires precise control of thermal requirements for each assay/module, controlling optical interference, result processing and combinations thereof.

The systems, devices and methods described herein disclose a multi-modality (inclusive of a comprehensive metabolic panel (CMP), complete blood count with differential (CBC), lipid panel, hemoglobin A1C (HbA1c), and thyroid stimulating hormone (TSH) tests) diagnostic system. The systems, devices and methods described herein disclose a multi-modality diagnostic instrument. The systems, devices and methods described herein disclose a multi-modality diagnostic cartridge, i.e., a cartridge with reagents capable of carrying out diagnostic assays of different modalities. The systems, devices and methods described herein disclose a multi-modality diagnostic disc and/or support pack.

In some aspects, the multi-modality diagnostic system includes clinical chemistry module and an immunoassay module. In some aspects, the multi-modality diagnostic system includes a hematology module and an immunoassay module. In some aspects, the multi-modality diagnostic system includes a clinical chemistry module and a hematology module. In some aspects, the multi-modality diagnostic system includes a clinical chemistry module, an immunoassay module and a hematology module. In some aspects, the multi-modality diagnostic system includes an electrochemistry module, clinical chemistry module, an immunoassay module and a hematology module. In some aspects, the multi-modality diagnostic system includes clinical chemistry module and an electrochemistry module. In some aspects, the multi-modality diagnostic system includes an electrochemistry module and an immunoassay module. In some aspects, the multi-modality diagnostic system includes an electrochemistry module and a hematology module. Further, in some embodiments, the diagnostic cartridge holds a single sample. In some embodiments, the single sample is blood in a single blood tube type. In some embodiments, if the instrument will perform electrochemical sensing, the sample must be in a lithium heparin blood tube. In some embodiments, if the instrument will detect an analyte via cell imaging, absorbance, laser scanning or a camera (i.e., not electrochemical sensing), the sample may be in a blood tube containing lithium heparin or sodium heparin. In some embodiments, if the instrument will detect an analyte via cell imaging, absorbance, laser scanning, electrical sensor (provided sodium is not detected), or a camera, the sample may be in a blood tube containing lithium heparin or sodium heparin.

In some embodiments, the diagnostic cartridge holds more than 1 sample, e.g., 1-10 samples, in such situations the samples may be from the same patient or from different patients, in the same blood tube type or in different blood tube types, and combinations thereof.

Multi-Modality Assay Processing Platform System

Turning to FIG. 1A, a multi-modality assay processing platform system 100 is shown with a plurality of modules configured to perform multi-modality analyses including electrochemistry, hematology, clinical chemistry, and immunoassay modalities. Specifically, the processing platform system 100 can process a comprehensive metabolic panel (CMP), complete blood count with differential (CBC), lipid panel, hemoglobin A1C (HbA1c), thyroid stimulating hormone (TSH) tests and combinations thereof. In some embodiments, the System 100 obtains results for a comprehensive metabolic panel (CMP), complete blood count with differential (CBC), lipid panel, hemoglobin A1C (HbA1c), and thyroid stimulating hormone (TSH) tests and reports results from all assays/panels. In some embodiments, the System 100 obtains results for a comprehensive metabolic panel (CMP), complete blood count with differential (CBC), lipid panel, hemoglobin A1C (HbA1c), and thyroid stimulating hormone (TSH) tests but does not report results for each assay/panel. In some embodiments, while the system processes a comprehensive metabolic panel (CMP), complete blood count with differential (CBC), lipid panel, hemoglobin A1C (HbA1c), and thyroid stimulating hormone (TSH) tests it reports results from only one of the comprehensive metabolic panel (CMP), complete blood count with differential (CBC), lipid panel, hemoglobin A1C (HbA1c), or thyroid stimulating hormone (TSH) tests. In some embodiments, the system reports results from only two, three, or four of the comprehensive metabolic panel (CMP), complete blood count with differential (CBC), lipid panel, hemoglobin A1C (HbA1c), or thyroid stimulating hormone (TSH) tests, detection of sodium, potassium, chloride, and/or bicarbonate.

System 100 can perform parallel and robust analysis of multiple analytes across a plurality of modalities. A multi-analyte set can, for example, be related to the consumer's health or general wellness. A multianalyte set can include, e.g., one or more analytes of different analyte classes, such as a small molecule analyte (e.g., <500 Da; cholesterol, glucose), large molecule analytes (e.g., >10 kDa; cytokines, hemoglobin, DNA), or a cell (e.g., a bacterial or eukaryotic cell; mammalian cell; red blood cell or leukocyte). The system 100 can include an outer housing 10 that includes an enclosure in which components of system 100 can reside. Such components can include a hematology module 240, clinical chemistry module 380, and immunoassay (IA) module 370, electrochemistry module 390, pipette system 400, plate capture module 500, and other components and subsystems thereof described more particularly below. In some aspects, module 240 and modules 370, 380 can each operate independently and/or operate sharing one or more resources. As stated, system 100 can include several main components, namely, a sample, sample transfer tool (e.g., system 400), first prepare instrument (e.g., multi-well plate 340), second prepare instrument 230, and one or more measurement tools (e.g., camera 442, cell imager 243, spectrophotometer (single or dual beam, a photomultiplier tube (PMT) or a CCD spectrometer), electrical sensor, and/or fluorescent laser scanning module 373).

The multi-modality assay processing platform system 100 has a small footprint compared to central laboratory diagnostic systems. In some embodiments, the disclosed diagnostic system measures H=17.25 inches, L=20 inches, W=12.5 inches. In some embodiments, the disclosed diagnostic system measures H=13-25 inches, L=10-30 inches, W=8-20 inches, In some aspects, the hematology module 240 is described herein in relatively succinct mode and can include or otherwise use several main components, namely, a sample, sample transfer tool (e.g., system 400), first prepare instrument (e.g., multi-well plate 340), second prepare instrument (e.g., service pack 230), third prepare instrument (e.g., assay device 170), and hematology measurement tools (e.g., a cell imaging camera 203 comprising a lens 260 and/or a camera 442). The cell imager 243 can be a phase-contrast microscopy, brightfield microscope, and or confocal microscope. The cell imager 243 comprises a lens 264, condenser lens 207, and illumination source 205.

In some aspects, the immunoassay module 370 is described herein in relatively succinct mode. Module 370 can include or otherwise use several main components, namely, a sample, sample transfer tool (e.g., system 400), first prepare instrument (e.g., multi-well plate 340), second prepare instrument (e.g., service pack 230), and immunoassay detection tool(s) (e.g., camera 442, a bead scanner, and/or a confocal fluorescent laser scanning module 373. In some embodiments, the immunoassay module 370 comprises an immunoassay wash module 600. In some embodiments, the immunoassay detection tool 373 comprises a laser alignment fixture 371 configured to align beam 372 with one or more mirrors 374 through lens 377 to a bottom of one or more wells.

In some aspects, the clinical chemistry module 380 is described herein in relatively succinct mode. Module 380 can include or otherwise use several main components, namely, a sample, sample transfer tool (e.g., system 400), first prepare instrument (e.g., multi-well plate 340), second prepare instrument (e.g., service pack 230), and a measurement tool (e.g., camera 442 and absorbance module 383). In some embodiments, the absorbance module 383 comprises laser alignment fixture 381 to focus beam 382 for excitation on one or more wells, and an emission fiber 382a In some aspects, electrochemistry module 390 is described herein in relatively succinct mode and can include or otherwise use several main components, namely, a sample, sample transfer tool (e.g., system 400), first prepare instrument (e.g., electrochemical cartridge 391) located on the service pack 230 and/or on the disc 340, and an electrochemical measurement tool (e.g., absorbance module 383 or electrical sensor 3313). Electrochemical analytes, namely, sodium, potassium, chloride, and bicarbonate can be detected by clinical chemistry methods and/or electrochemical methods. Electrochemical methods are more widely accepted in the medical community. Nevertheless, the electrochemistry module 240 contemplates detection of electrochemistry analytes by both methods (the absorbance module 383 or electrical sensor 3313). An electrical sensor can take several forms of electrical measurement (voltage, current, resistance, etc.)

In some embodiments, disclosed is a first module, second module, third module, fourth module and combinations thereof. The first module detects hematology assays, immunoassays, clinical chemistry assays, electrolyte assays, and combinations thereof. The second module detects hematology assays. The second module detects immunoassays. The second module detects electrochemistry assays.

During operations, system 100 can be configured to receive a sample received by a support pack 230 of a support pack tray module 220 and system 400 can distribute sample and other contents of pack 230 such as diluent or reagents to a multi-well plate (e.g., a disc) 340 that is loaded in module 500 as well as to other portions of the support pack 230.

Once prepared by system 100, modules 370, 380 can each measure optical performance of one or more wells of plate 340 that contain at least a portion of the patient sample and one or more reagents to render one or more detection results. Pack 230 can also include a monolayer assay device 170 that operates as a hematology slide, such as the device shown and described in U.S. Pat. Pub. 2022/0088583 A1, also by Truvian Sciences, Inc. and incorporated by reference herein. Pack 230 can also include an electrochemistry cartridge 391 that resides on the support pack 230. System 400 can prepare device 170 by distributing at least a portion of the separated patient sample from plate 340 and one or more reagents and/or diluents from pack 230. Once prepared, a cell imaging system 243 of module 240 can analyze device 170 to render one or more detection results. In some aspects, a preparer module (e.g., system 400) does not comprise a camera.

Figure 1B:
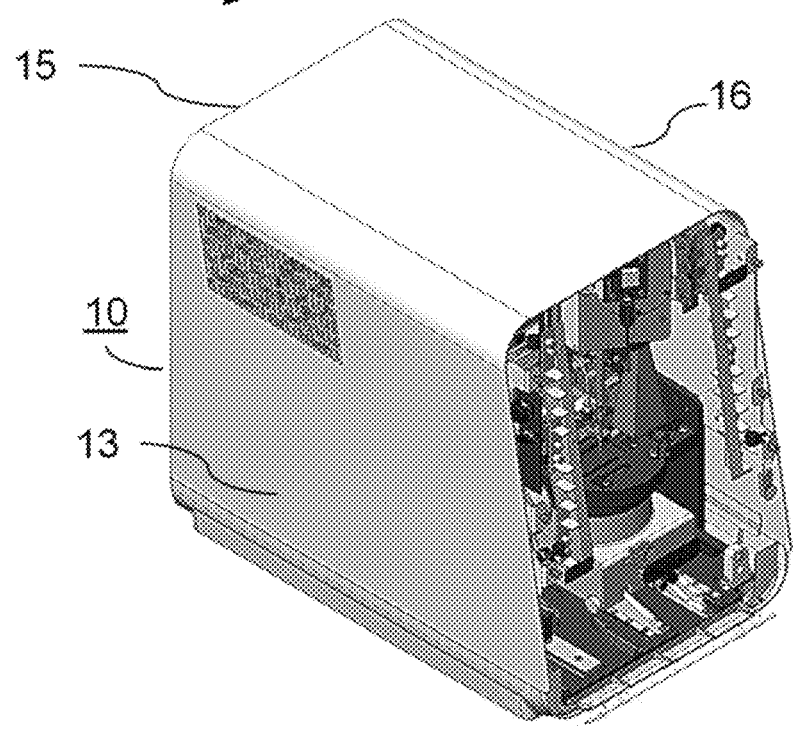
FIG. 1B shows a perspective view of the exemplary multi-modality processing platform system of FIG. 1A with the forward housing panel removed strictly for viewing purposes, in accordance with an exemplary embodiment.

System housing 10 can include a forward panel 17, a rear panel 15, and one or more lateral panels 13, 16 therebetween. A graphical user interface (GUI) 20 can be positioned on panel 17 and/or elsewhere externally accessible on housing 10. GUI 20 can be connected to a computing system (e.g., results processor system 360) that includes communication subsystem, device memory, data storage subsystem, and input/output (I/O) subsystem configured to process input from one or more users and present information analyzed by the computing system on a display panel of GUI 20. FIG. 1B shows a perspective view of system 100 with panel 17 removed strictly for viewing purposes. In one operation, the instrument can receive a user input via GUI 20 so as to cause a drawer 22 of panel 17 to transition to an open position (e.g., to receive a sample) associated with a load state and a closed position as shown in FIG. 1A associated with an operational state.

Figure 2:
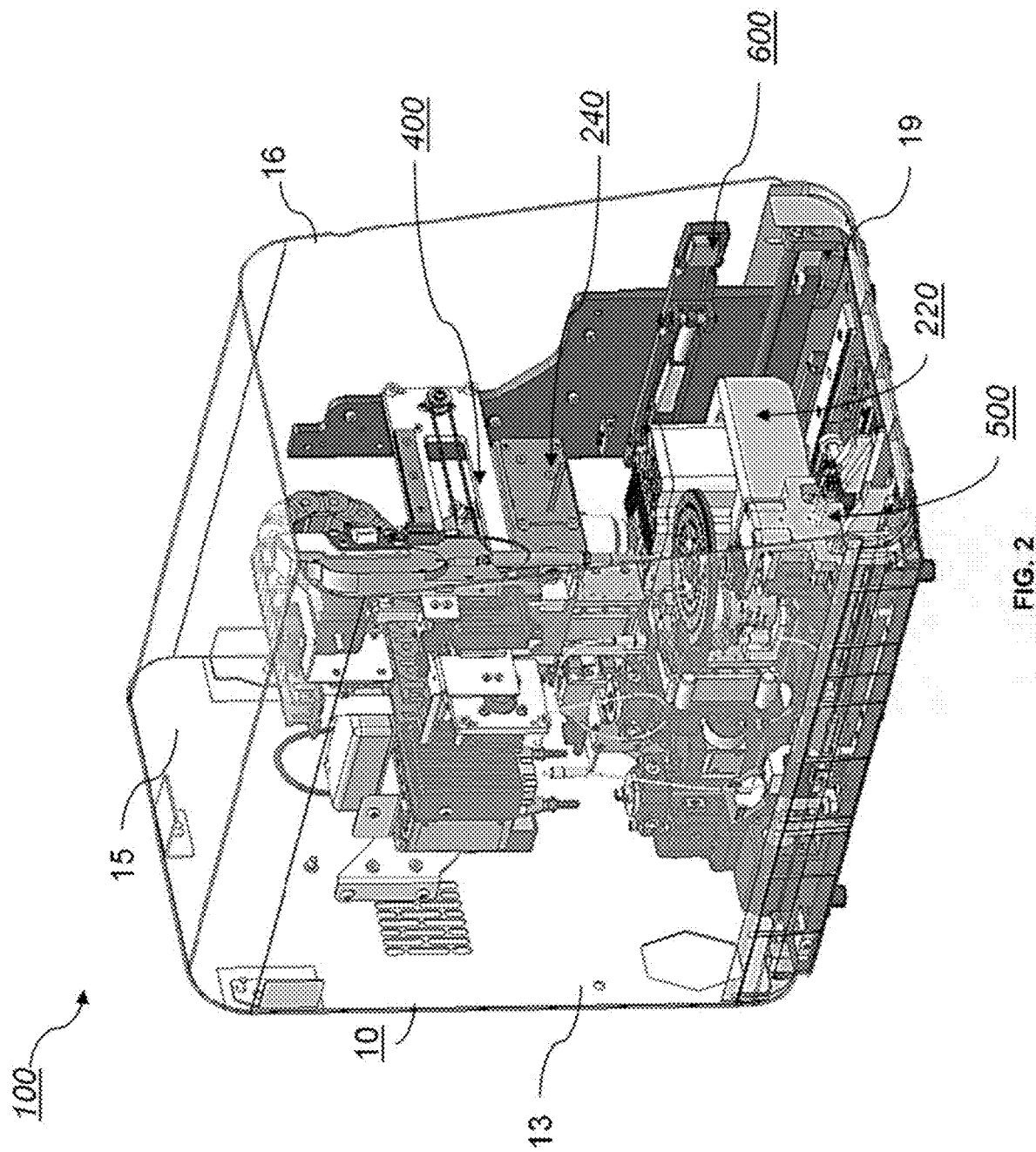
FIG. 2 shows a forward perspective view of the exemplary multi-modality processing platform system of FIG. 1A with the forward housing panel removed and outer housing generally translucent strictly for viewing purposes, in accordance with an exemplary embodiment.

FIG. 2 shows a forward perspective view of system 100 with panel 17 removed and outer housing 10 generally translucent strictly for viewing purposes. As can be seen, a base plate 19 can be positioned along a lower surface of housing 10. Plate capture module 500 and tray module 220 can be coupled directly to plate 19 and be capable of sliding forward and backward (e.g., in the direction between panels 13 and 17) in response to operations by system 100 and as run in the load state and/or operational state. For example, if system 100 receives input at GUI 20 (e.g., to load a sample at drawer 22 and then perform one or more modality operations such as running a first panel associated with the patient sample loaded in pack 230), then module 500 with plate 340 and tray module 220 with support pack 230 can be caused to slide along plate 19 in the direction of panel 15 until aligned with modules 240, 370, 380, respectively, of system 100 for each respective module to perform measurement and result detection operations. Module 500 with plate 340 and tray module 220 with support pack 230 are aligned with modules 240, 370, 380, even if a detection result from one or two modules will not be reported. In some aspects, GUI 20 can be communicatively coupled to a results processor system 360 that causes drawer 22, in response to input at GUI 20, to move to an opened configuration whereby support pack 230 with the patient sample can be loaded into tray module 220.

Figure 3:
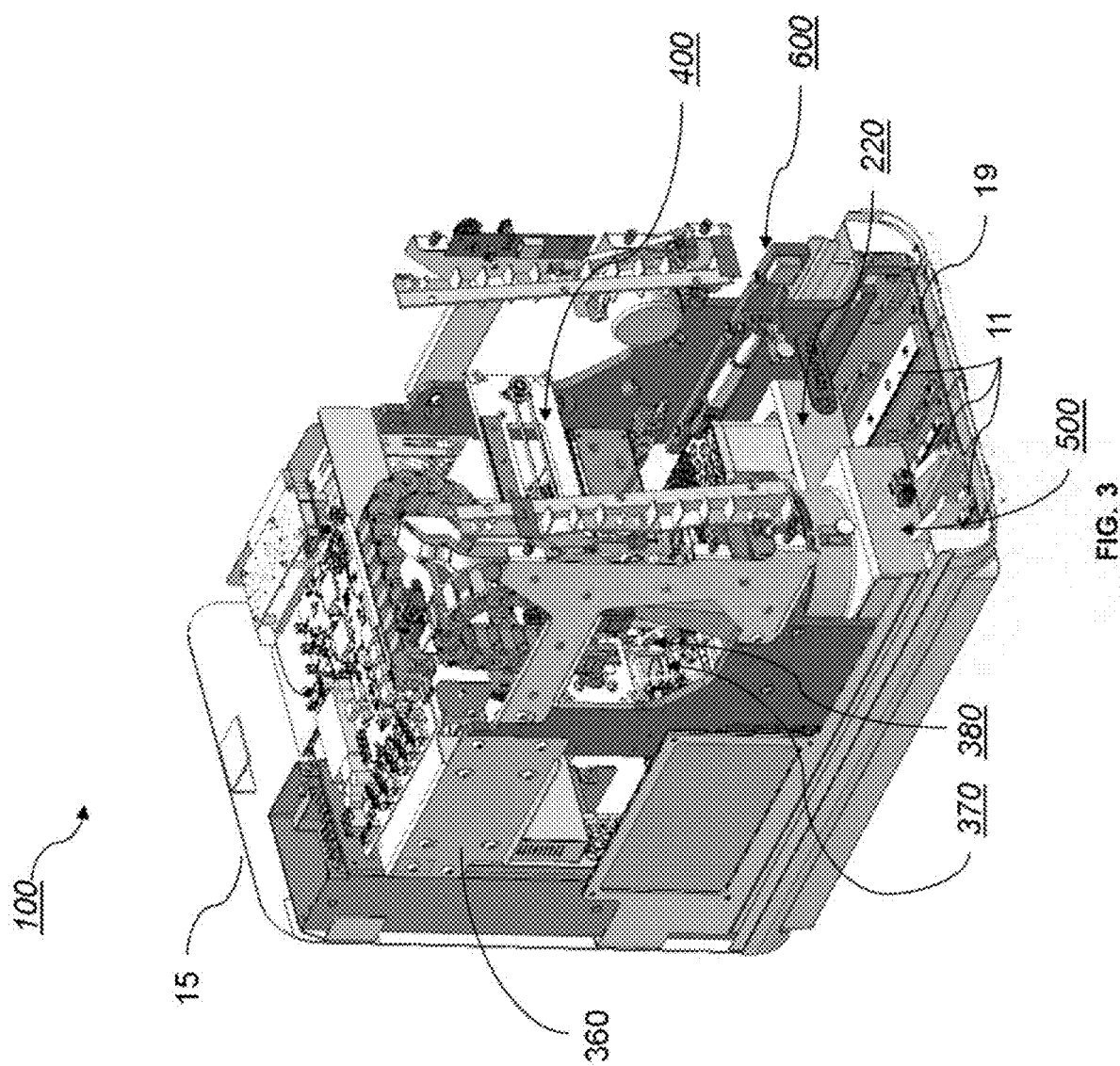
FIG. 3 shows a forward perspective view of the exemplary multi-modality processing platform system of FIG. 1A with the housing removed strictly for viewing purposes, in accordance with an exemplary embodiment.
Figure 4:
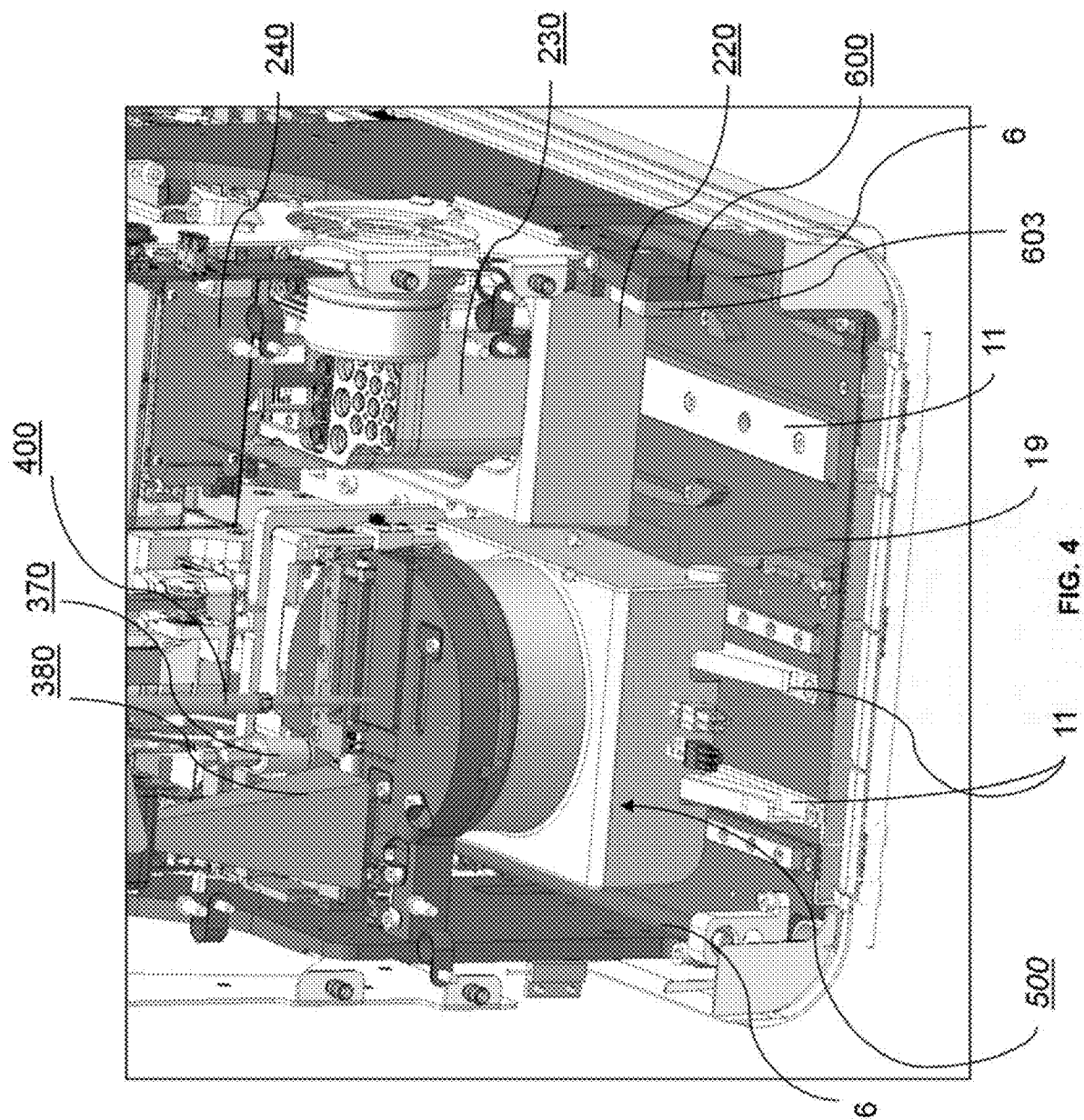
FIG. 4 shows a close-up perspective view of a forward portion of the exemplary multi-modality processing platform system of FIG. 1A with the housing removed strictly for viewing purposes, in accordance with an exemplary embodiment.
Figure 5:
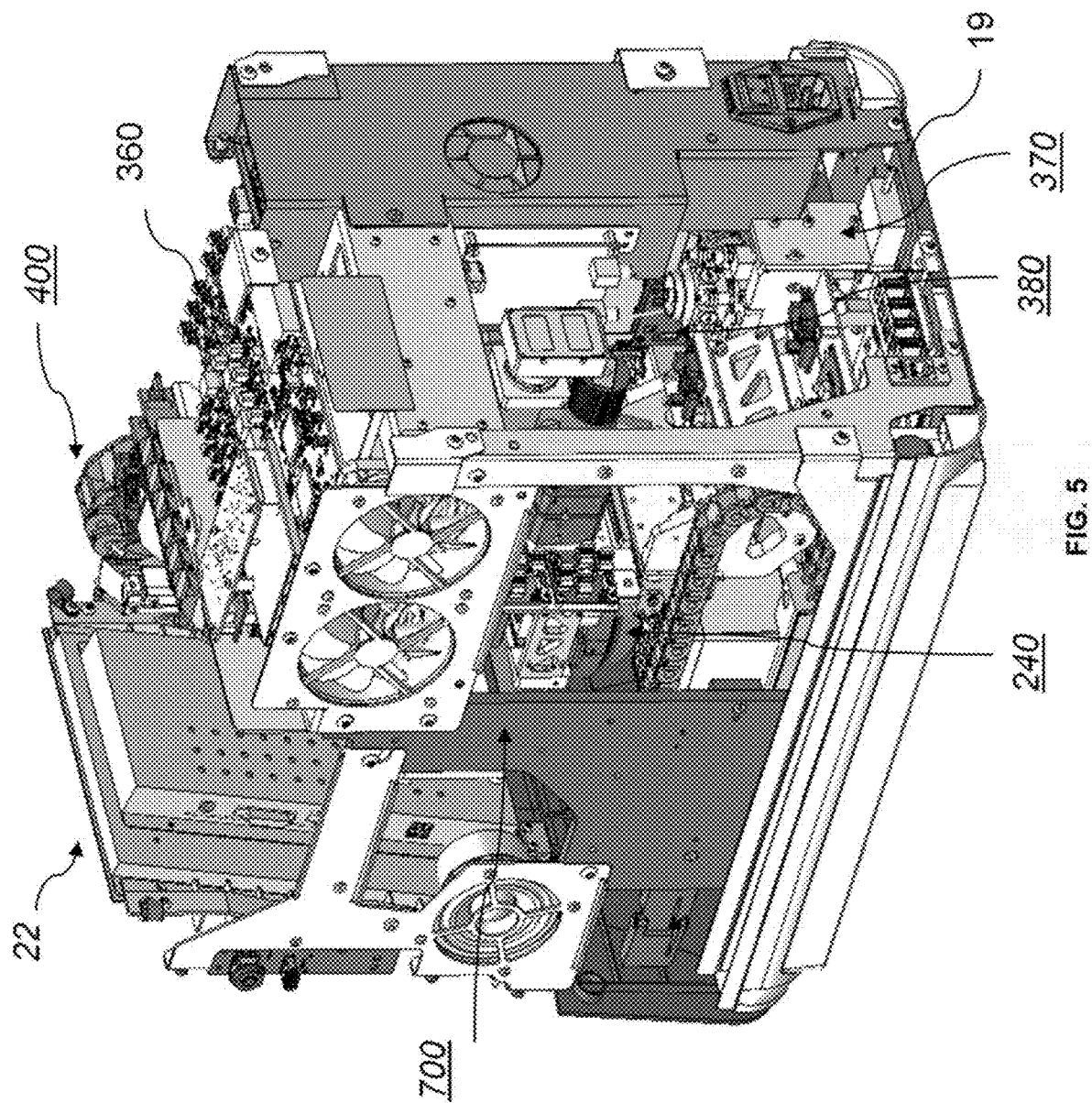
FIG. 5 shows a rear view of the exemplary multi-modality processing platform system of FIG. 1A with the housing removed strictly for viewing purposes, in accordance with an exemplary embodiment.

FIG. 3 shows a forward perspective view of system 100 with housing 10 partially removed strictly for viewing purposes. FIG. 4 shows a close-up forward perspective of system 100, similar to FIG. 3. FIG. 5 shows a rear perspective view of system 100 with housing 10 removed strictly for viewing purposes. Plate 19 is also shown in FIGS. 3-4 with a plurality of guide rails 11 configured to guide module 500 and tray module 220 when sliding plate 19 from the loading state to the operational state within housing 10. In some embodiments, the only physical connection between modules 240, 370 and 380 is the plate 19. In some embodiments, the only operational connection between modules 240, 370 and 380 is pipette system 400. While module 500 is shown with a pair of rails 11 running thereunder and module 220 with only one rail 11 thereunder, any number of rails 11 can be used, as needed or required. In some aspects, to facilitate alignment of modules 220 and 240 when moving from the loading state to the operational state, one end of rail 11 can be tightened to the rest of module 240 thereby creating at least a partially floating first end of rail 11 and creating at least a partially tight second end of rail 11. This looseness allows the rail 11 associated with modules 220 and 240 to move a small amount, which allows it to self-parallelize with a second rail 11 associated with modules 500 and 370/380, which is securely tightened at both ends. In some embodiments, there is at least two rails wherein the first rail is securely tightened at both ends and the second rail is securely tightened at only one end. In operation, during the load state the first rail and second rail are not aligned. During the operational state module 220 the first rail and second rail are aligned. In some embodiments, the first rail and second rail are both associated with modules 220 and 240. In some embodiments, the first rail is associated with modules 220 and 240 and the second rail is associated with modules 500 and 370/380.

As illustrated in FIGS. 3-6, a results processor system 360 is provided to control operations of the system based on data received from each module of system 100 and/or other components of system 100 (e.g., thermistors internal to housing 10 measuring temperature, cameras capturing images, barcode scanners scanning labels and other items germane to result detection related to the patient sample, etc.), can be positioned stationary adjacent panel 15 and above modules 370, and 380. System 360 can include a single-board computer (SBC) system having a memory (e.g., non-transitory computer readable storage medium), at least one processor, and instructions for data collection and results processing across multiple modalities, such as from modules 240, 370, 380 and 390. In some aspects, system 360 can be configured to operate locally (e.g., without any network access and/or connectivity to one or more remote servers) and process in real time data during analytical operations by modules 240, 370, 380 and 390 to reduce any one-point-in-time computer processing load. Further aspects of system 360 are described in FIGS. 15-17.

In some aspects, all the modules in system 100 share communication hardware. In some aspects, all the modules in system 100 share power hardware. In some aspects, all the modules in system 100 share communication and power hardware. In some aspects, the shared communication hardware comprises or consists of an electronics board (e.g., a PCB mounted to or otherwise in electrical communication with plate 19) for mechanical movement, a power supply, a single-board computer (SBC) (e.g., system 360) for data collection and results processing, and combinations thereof.

Figure 6:
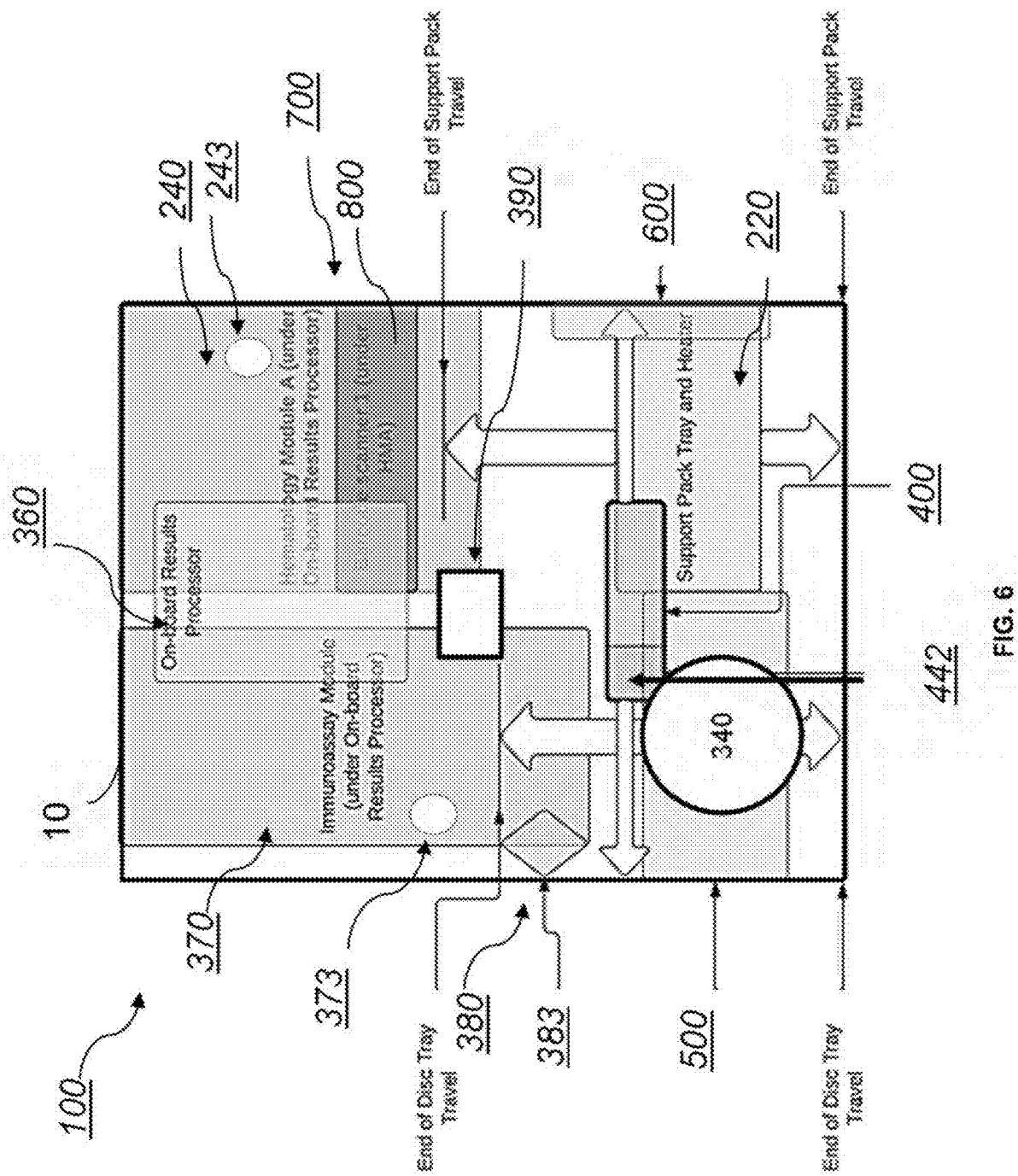
FIG. 6 is a top plan schematic view of the system of FIG. 1A, in accordance with an exemplary embodiment.

FIG. 6 is a top plan schematic view of system 100 showing exemplary movement of certain modules and sub-systems within housing 10 during operation, such as transition from the loading state to the operational state when respective modules are aligned to carry out multi-modal processing operations. In some aspects, module 500 can transition along plate 19 inside housing 10 from a foremost position shown by the end of disc tray travel arrow to a rearmost position shown by the end of disc tray travel arrow when aligned with immunoassay module 370. In some embodiments, module 500 is aligned with immunoassay module 370 and clinical chemistry module 380 in the operational state. In some aspects, tray module 220 can transition along plate 19 inside housing 10 from a foremost position shown by the end of support pack travel arrow to a rearmost position shown by the end of support pack travel arrow when aligned with hematology module 240 and/or electrochemistry module 240 in the operational state. In some aspects, modules 500, 220 can slide in unison at the same rate and slide the same distance. In some aspects, modules 500, 220 can slide at different rates and/or slide different distances (e.g., module 500 traveling further than module 220 or vice versa). In some aspects, system 400 as well as barcode scanner 442 can slide laterally between each side of housing 10. Though not shown, systems 400, and 442 can move both laterally as shown in FIG. 6, as well as up-and-down. In some embodiments, barcode scanner 800 can move laterally and/or up and down and/or forward in back in order to align with the tags on the support pack, 230, monolayer 170 and/or electrochemistry module 391. Specifically, system 400 moves laterally and up and down as it distributes resources (sample, a diluting agent, and/or reagents) from pack 230 to plate 340 and centrifuged sample from plate 340 to pack 230. Modules 500 and 220 can only move in and out of the system, they cannot move left to right or up and down. As such, system 400 moves sample from the support pack to the disc and vice versa. System 400 can access the full area of plate 340 and pack 230. System 400 is connected to a pipetting mount, a camera (e.g., camera 442) is also connected to the pipet mount. Camera 442 forms part of a vision system. The vision system contains onboard image analysis, data logic and capabilities specific to plate 340, so that the camera 442 can "home" in on the plate 340, i.e., identifying the location of fiducial protrusions 348 so that plate 340 can be loaded in any orientation. In some embodiments, barcode scanner 800 is aligned to read the barcode on the support pack 230 and monolayer 170. In some embodiments, camera 442 is aligned to read the barcode on the support pack 230 and monolayer 170. In some embodiments, barcode scanner 800 is a laser scanner, pen wand, CCD (charge-coupled device) scanner, slot scanner, or image scanner.

Figure 7:
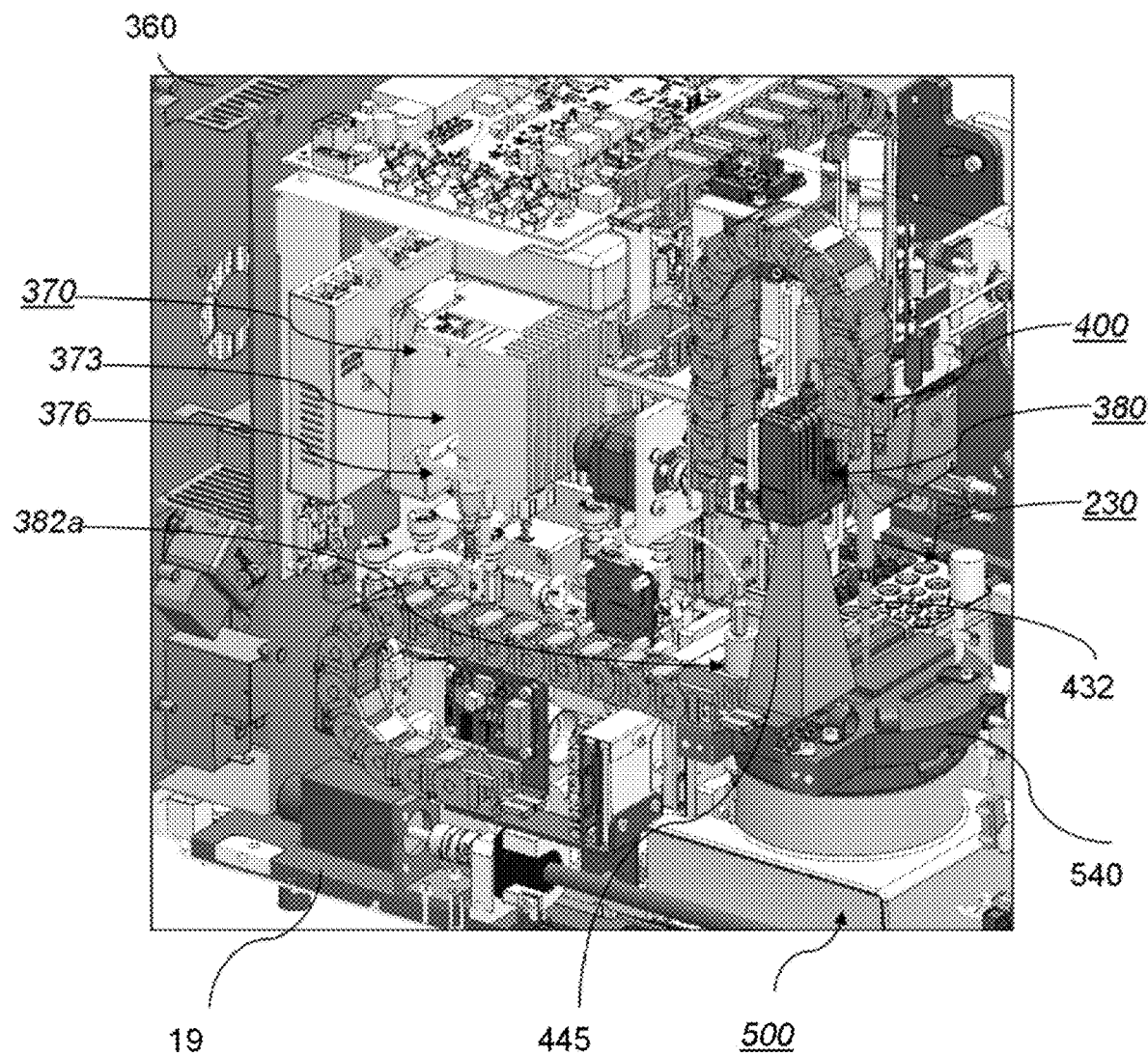
FIG. 7 shows a close-up perspective view of a lateral portion of the exemplary multi-modality processing platform system of FIG. 1A with the housing removed strictly for viewing purposes, in accordance with an exemplary embodiment.

FIG. 7 shows a close-up perspective view of a lateral portion of system 100 with housing 10 for viewing purposes. Here, pipette system 400 is shown with its pipette member 432 above plate receiving housing 540 of module 500, which contains plate 340 assembled therein. Module housing 376 of module 370 is also shown positioned below system 360. Emission fiber 382a of module 380 is also positioned so beam 382 of module 380 can pass through a respective well of plate 340 assembled in housing 540. In some aspects, housing 540 can include an openable door in an upper surface configured to swing open to give system 400, including member 432, access and access for camera 442 to view one or more wells 342 of plate 340 and any other features thereof (e.g., protrusions 348).

Based on measured characteristics of beam 382 with respect to the respective well of plate 340, which can include at least a portion of the patient sample and at least one reagent, module 380 can measure optical characteristics to render a detection result across multiple modalities, including but not limited to electrochemical, clinical chemistry, immunoassays and hematology. In FIG. 7, module 500 has already slid into housing 10 and is aligned with modules 370, 380 in an example operational state so that the field-of-view 445 of the camera of system 400 can acquire one or more images and modules 370, 380 can perform their respective analytical operations. In some embodiments, system 700 comprises a barcode scanner 800 and/or a camera 442. In some embodiments, system 700 is just a camera which also functions as a barcode scanner. In some embodiments, system 700 is the barcode detection system for modules 240, 370, 380, and 390.

Consumables

Figure 12A:
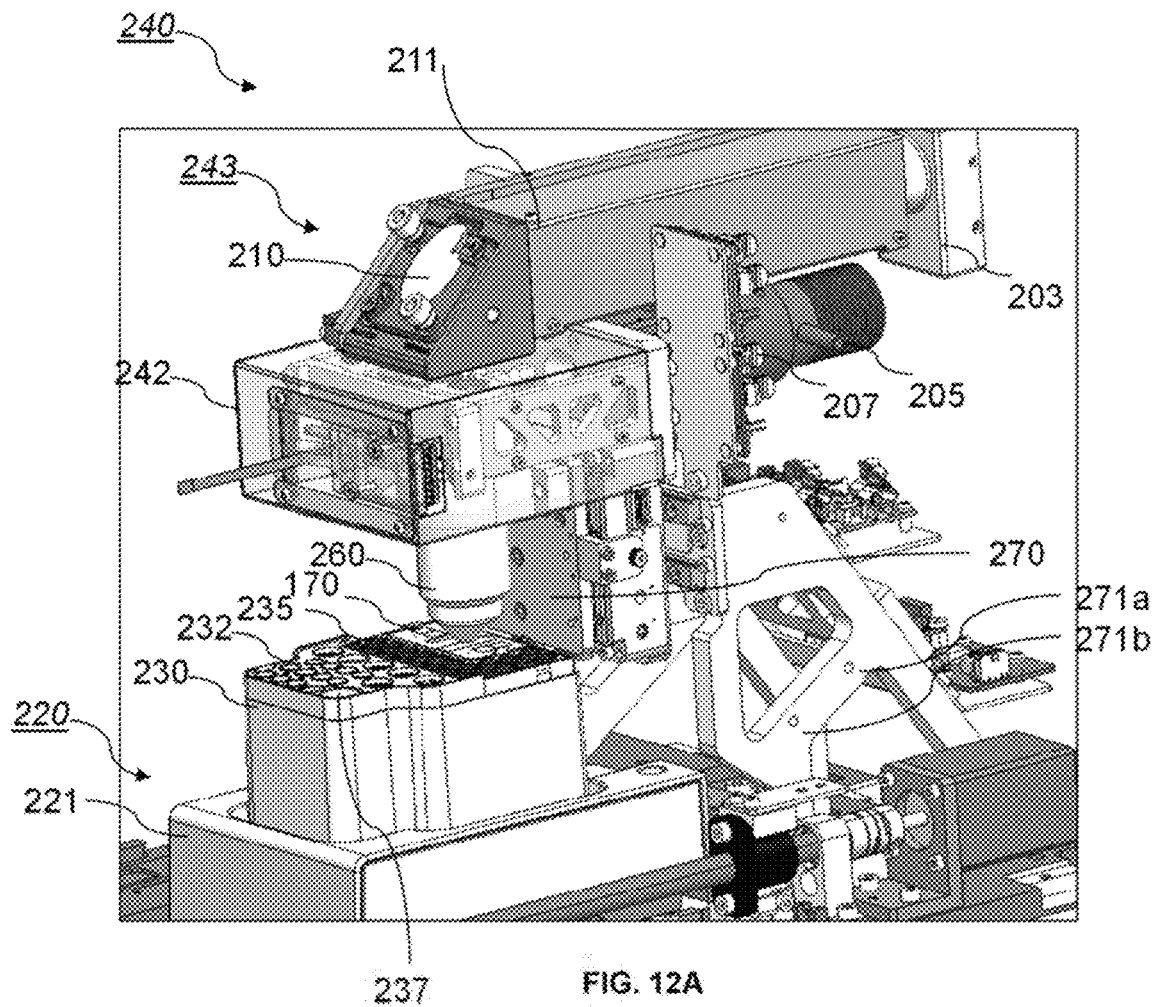
FIG. 12A shows a drawing of an exemplary close-up of the hematology module of FIGS. 1A and 1i, in accordance with an exemplary embodiment.
Figure 12B:
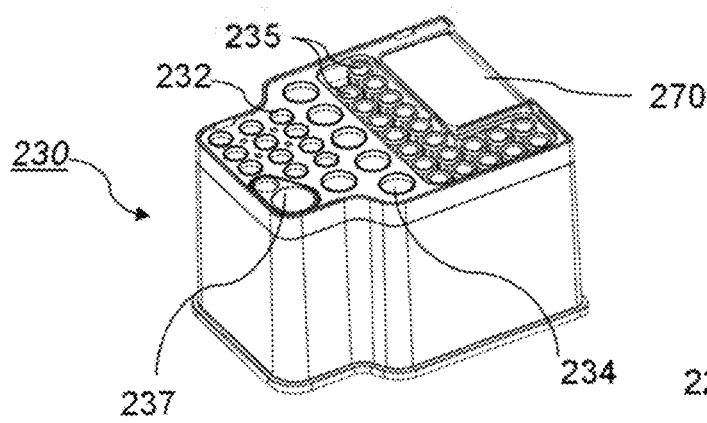
FIG. 12B shows an exemplary close-up of the support pack of FIG. 12A, in accordance with an exemplary embodiment.
Figure 12C:
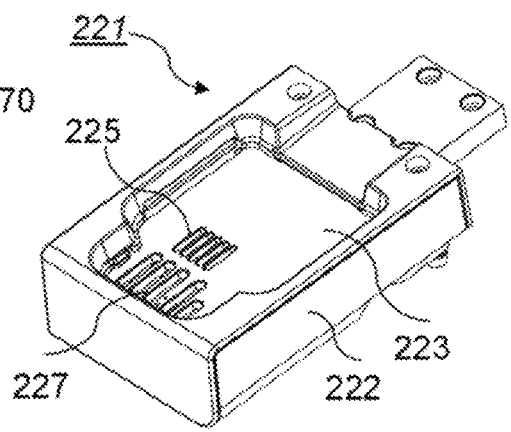
FIG. 12C shows an exemplary close-up of the support pack capture module of FIG. 12A, in accordance with an exemplary embodiment.

The diagnostic instrument uses two unique, single-use consumables, a disc (FIGS. 10A and 10B) and a support pack (FIG. 12B-C). These disposables provide all the necessary reagents and materials to perform all assays for each panel on each of the four modalities (electrochemistry, hematology, clinical chemistry, and immunoassay). The disc contains a plasma separation feature, hematocrit channel and universal microwells where chemistry reagents are dried and stabilized for room temperature storage. The disc can also contain reagents for detecting electrolytes such as sodium, potassium, chloride, and bicarbonate, which are dried and stabilized for room temperature storage. The support pack includes a blood sample holder, pipette tips, buffers, reagent preparation wells, and a monolayer for hematology analysis. The support pack can also include an electrochemical cartridge 391 for electrochemical analysis.

In some aspects, the assay measurement vessels (e.g., wells of plate 340 and pack 230) are agnostic to the assay executed within. In some aspects, the assay measurement vessel is specifically designed to execute a specific assay. For example, the hematocrit channel of the plate 340 is specially designed to execute the hematocrit assay. However, wells 342 of plate 340 can be configured to accept any reagent.

In some aspects, the multi-well plate includes at least an outer row of measurement vessels 342b and an inner row of measurement vessels 342a. As used herein, the outer row of measurement vessels 342b and the inner row of measurement vessels 342a is made up of any number of measurement vessels 342n. In some aspects, clinical chemistry assays can only be run in the outer row of measurement vessels 342b. In some aspects, the outer row of measurement vessels 342b can be used for any measurement of optical absorbance, and/or scattering of the clinical chemistry module 380. In some aspects, clinical chemistry detection module (such as the camera 442) is only aligned with the outer row of measurement vessels 342b. In some aspects, any assay measurement vessel (inner and outer) can be measured by the immunoassay module 370. The outer row of measurement vessels 342b can be rotated into the optical path of the clinical chemistry module 380, and any vessel (e.g., one of vessels 342a) can be rotated into the optical path 372 of the immunoassay module 370.

In some aspects, immunoassays can only be run in the inner-row of measurement vessels 342a, in the outer-row of measurement vessels 342b or both. In some aspects, the inner-row of measurement vessels 342a can be measured by a confocal fluorescent laser scanning module 373 for bead-based immunoassays of the immunoassay module 370. In some aspects, the outer row of measurement vessels 342b can be used for any measurement of optical absorbance, and/or scattering of the clinical chemistry module 380 to measure immunoassays. In some aspects, immunoassay detection module (confocal fluorescent laser scanning module 373) is only aligned with the inner row of measurement vessels 342a. In some aspects, any assay measurement vessel (inner and outer) can be measured by the immunoassay module 370 using the confocal fluorescent laser scanning module 373 and camera. The inner row of measurement vessels 342a can be rotated into the path of the immunoassay module 370.

In some aspects, the multi-well plate 340 includes microwells 342. In some aspects, all of the microwells 342 have the exact same size, shape, and material finish, such that they can accept any assay reagent. In some aspects, a portion of the microwells 342 have a different size, shape, and/or material finish, such that they can accept a single assay reagent. In some aspects, only the outer row of microwells 342b can be rotated into the optical path 382 of the clinical chemistry module 380, and any well (inner and outer) can be rotated into the optical path 372 of the immunoassay module 370. In some aspects, only the outer row of microwells 342b can be rotated into the optical path 382 of the clinical chemistry module 380, and only the inner well 342a can be rotated into the optical path 372 of the immunoassay module 370. In some aspects, the outer row 342b and inner row 342a of microwells 342 can be rotated into the optical path 382 of the clinical chemistry module 380. In some aspects, only the inner row of microwells 342a can be rotated into the optical path 372 of the immunoassay module 370.

In some aspects, a hemoglobin assay is part of the hematology panel, but its reagent is contained in an outer row microwell 342b of the multi-well plate 340 and is measured by the clinical chemistry module 380 detection device (camera 442). In some aspects, the multi-well plate 370 runs a hematology assay and clinical chemistry assay(s). In some aspects, the multi-well plate 370 runs a hematology assay, immunoassay, and clinical chemistry assay(s). In some aspects, the multi-well plate 370 runs a hematology assay, immunoassay, electrochemistry, and clinical chemistry assay(s). In some aspects, the multi-well plate 370 runs a hematocrit assay, and at least one clinical chemistry assay each detected by the clinical chemistry assay detection device (camera 442). In some aspects, the multi-well plate 370 runs a hematocrit assay, and a metabolic panel or lipid panel each detected by the clinical chemistry assay detection device (camera 442). In some aspects, the multi-well plate 370 runs a hematocrit assay, a HbA1c assay, and a metabolic panel or lipid panel each detected by the clinical chemistry assay detection device (camera 442). In some aspects, the multi-well plate 370 runs a hematocrit assay, hemoglobin measurement assay, a HbA1c assay, and a metabolic panel or lipid panel each detected by the clinical chemistry assay detection device (camera 442). In some aspects, the multi-well plate 340 runs a hematocrit assay, hemoglobin measurement assay, a HbA1c assay, a metabolic panel or lipid panel, and takes electrolyte measurements each detected by the clinical chemistry assay detection device (camera 442). In some aspects, the multi-well plate 370 takes electrolyte measurements each detected by the clinical chemistry assay detection device (absorbance module 383).

The disc structure with many reaction wells allows flexibility for future test panel expansion, i.e., new tests can be easily added to the disc and/or support pack.

In some aspects, first and second prepare instruments can be formed of two separate carrier devices, such as multi-well plate 340 and service pack 230. In some aspects, each of first and second prepare instruments can be part of a single carrier device, where the device can include a first portion configured to rotate for centrifuging and/or to carry out detection results with a plurality of modules, such as the clinical chemistry module 380 and/or immunoassay module 370 of this disclosure. The single carrier device can also include a second portion configured to include at least some of the structural aspects of service pack 230, including a sample receiving well, one or more removable pipette tips, one or more reagent vessels and a monolayer.

In some aspects, clinical chemistry assays measured by module 380 can only be run in wells 342b. In some aspects, the outer row of wells 342b can be used for any measurement of optical absorbance, and/or scattering of the clinical chemistry module 380 to generate a detection result. In some aspects, clinical chemistry assays measured by module 380 can be run in any wells (342a and 342b) of plate 340. In some aspects, the inner row of wells 342a can be used for any measurement of optical absorbance, and/or scattering of the module 370 to generate a detection result. In some aspects, immunoassays measured by module 370 can only be run in wells 342a or 342b. In some aspects, module 240 measures reactions run in wells 342a, 342b or combinations thereof and transferred to pack 230. In some aspects, wells 342a, 342b are configured to contain a plurality of reagents for tests such as complete blood count with differential, comprehensive metabolic panel, lipid panel, hemoglobin A1c, TSH, and/or the like. In some aspects, wells 342a, 342b are configured to contain a plurality of reagents for a plurality of assay modalities such as chemistry assays, immunoassays, hematology assays, nucleic acid assays, receptor-based assays, cytometric assays, colorimetric assays, enzymatic assays, electrophoretic assays, electrochemical assays, electrolyte assays, spectroscopic assays, chromatographic assays, microscopic assays, topographic assays, calorimetric assays, turbidmetric assays, agglutination assays, radioisotope assays, viscometric assays, coagulation assays, clotting time assays, protein synthesis assays, histological assays, culture assays, osmolarity and combinations thereof.

The consumables of plate 340 can be better understood by the following numbered paragraphs:

Paragraph 1. An analyte analysis system, comprising:
a disc comprising a plurality of microwells arranged in at least an inner circle and an outer circle;
a clinical chemistry detection instrument aligned to read the microwells in the outer circle; and
an immunoassay detection instrument aligned to read the microwells in the inner and outer circle.

Paragraph 2. The analyte analysis system of paragraph 1 further comprising a hematocrit channel wherein the clinical chemistry detection instrument is aligned to read the hematocrit channel.

Waste

The plate 340 and pack 230 employ a pack-in/pack-out strategy like responsible hiking and camping.

In some aspects, the plate 340 contains all the waste generated during the analysis of a sample. In some aspects, the support pack 230 contains all the waste generated during the analysis of a sample. In some aspects, the plate 340 and pack 230 contain all the waste generated during the analysis of a sample. This means that no periodic management of liquids, waste, or other consumables must be performed by the user—the only necessary user interaction with the system occurs when running a sample. In some embodiments, a pipet tip is picked up from a first location in the support pack, used to deliver reagent, diluent, sample, and then returned back to the first location in the support pack. In some embodiments, a pipet tip is picked up from a first location in the support pack, used to deliver reagent, diluent, sample, and then returned back to a second location in the support pack wherein the first location and second location are different.

In some aspects, the user only interacts with the hardware via the power button, touchscreen (GUI 20), and loading of consumables (e.g., pack 230, plate 340, etc.). The door 22 opens and closes automatically. The user performs no maintenance on system 100.

Clinical Chemistry Module and Immunoassay Module

Figure 8:
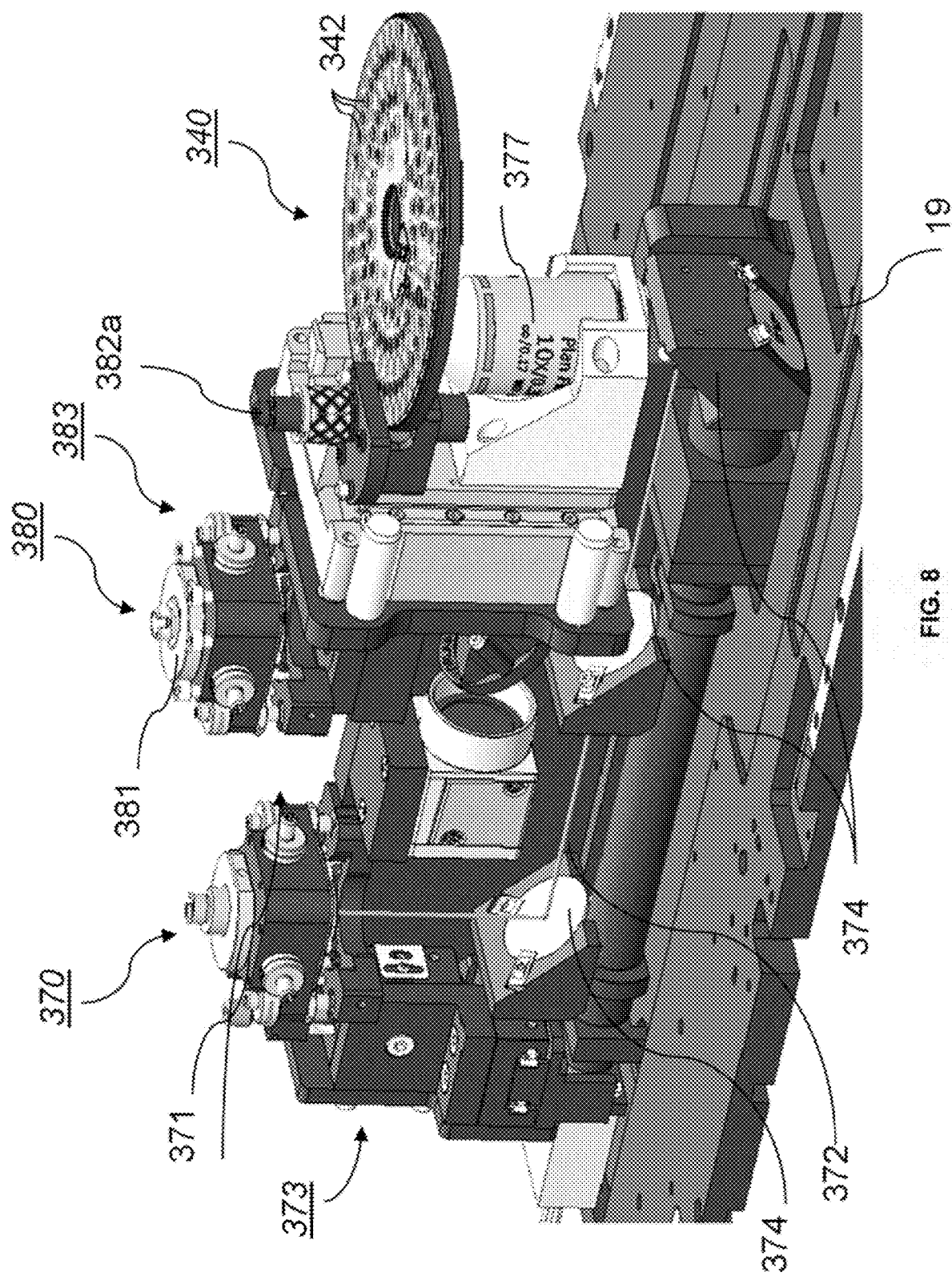
FIG. 8 shows a drawing of an exemplary close-up of clinical chemistry and immunoassay (IA) modules of the system of FIGS. 1A and 1B interacting with a multi-well plate. Not shown is the loading tray of the clinical chemistry and IA modules; the clinical chemistry and IA modules share a loading tray.
Figure 9:
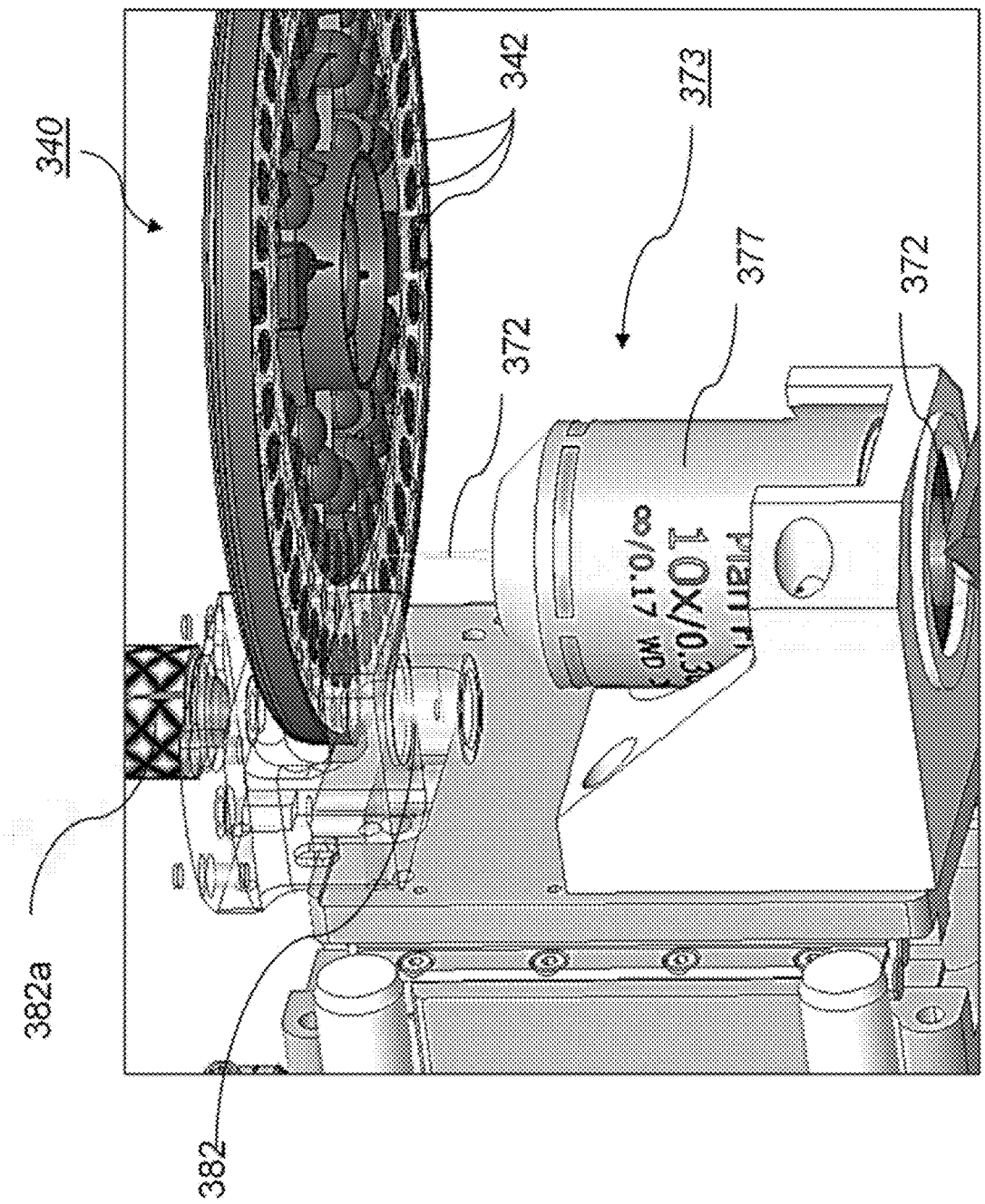
FIG. 9 shows a perspective view of an exemplary close-up of optical interactions of the clinical chemistry and immunoassay modules interacting with an exemplary multi-well plate (again not shown is the loading tray of the clinical chemistry and IA modules).

FIG. 8 shows a perspective view of aspects of modules 370, 380 assembled with plate 19. FIG. 9 shows a perspective view of an exemplary close-up of optical interactions of subcomponents of modules 370, 380 interacting with an exemplary plate 340. Accordingly, while plate 340 is shown floating in FIGS. 8-9 to demonstrate optical paths of respective beams 372, 382 of respective modules 370, 380, during analytical operations, plate 340 would actually be positioned with plate receiving housing 540 shown in FIG. 7. Operations of modules 370, 380 rely upon focusing excitation of respective beams 372, 382 on wells 342 (e.g., wells 342*a*, 342*b* shown in FIG. 10A more particularly), respectively, on the bottom of plate 340 (e.g., at layer 349) to a tolerance of approximately 1-100 μm and in some embodiments, to a tolerance of about 10 μm. In this respect, each of modules 370, 380 can include one or more lasers, photomultipliers (PMT), and associated control electronics. Detailed aspects of wells 342*a*, 342*b* of plate 340 are discussed more particularly in FIGS. 10A to 10B.

Immunoassay Module

Module 370 is configured to separate plasma from blood cells, implement precise thermal control for consistent antibody/antigen binding progression, and adjust plasma concentration for each assay's antibody/antigen ratio. It is understood that plate 340 forms part of module 370 and module 380. In some aspects, module 370 can include a laser alignment fixture 371 configured to align beam 372 with one or more mirrors 374 through lens 377 to a bottom of one or more wells 342*a*. In operation, once beam 372 has gone down through one or more wells 342*a*, beam 372 gets collected by a second fiber and goes into a spectrometer, hits a diffraction grading, absorbance is measured from all light in wavelengths of approximately 340 to 850 nanometers. It is understood that each assay absorbs light at a specific wavelength and that absorbance is directly proportional to the amount of analyte present. In some aspects, lens 377 is coated with a film so that shorter wavelengths of light are affected the same way as longer wavelengths as the light goes through lens 377. In order for module 370 to scan one or more wells 342 of plate 340, module 370 includes precision location control and constant speed of movement at the micron level.

In some aspects, module 370 can include a directional spring to ensure consistent speed during scanning. Module 370 can also include precise thermal control (e.g., approximately +/−1 deg C) for consistent antibody/antigen binding progression. For example, system 360 can monitor temperature and other thermal characteristics relevant to module 370, such as thermal characteristics of plate 340, pack 230, and based on detected thermal characteristics adjust one or more heat management mechanisms, such as one or more circulating fans, rotation of plate 340, one or more resistive heating elements of module 500 or module 220, etc.

In some aspects, during the operational state, plate 340 can be rotated around and then moved in and out while scanning with lens 377 to read each of wells 342*a* for independent fluorescent reading of each well 342*a*. In some aspects, an autofocus operation is performed where assays of wells 342*a* are read for every single run based on comparative locations of wells 342*a* to protrusions 348 to determine a focal point into a correct location of each well 342*a*.

In some aspects, module 370 can be configured to adjust the plasma concentration for each assay's sample-to-reagent ratio. For example, module 370 can include a first assay with a first sample-to-reagent ratio and a second assay with a second sample-to-reagent ratio wherein the first sample-to-reagent ratio and second sample-to-reagent ratio are different. This is accomplished without changing the hardware or consumable. This is also accomplished for new assays added to the system without changing the hardware or consumable. In some aspects, module 370 adjusts the plasma concentration for each assay's sample-to-reagent ratio by re-programming the hardware operation (e.g., volume in the pipette member 432 of system 400). In some aspects, the same motor used for measuring clinical chemistry and immunoassays are required to separate plasma and move system 400.

In some aspects, module 370 measures, based on detected optical characteristics of beam 372 with respect to one or more wells of plate 340, the fluorescence of the bead-antigen-fluorescent complex. In some aspects, module 370 measures, based on detected optical characteristics of beam 372 with respect to one or more wells of plate 340, the fluorescence of the bead-antigen-fluorescent complex and the fluorescence of free-floating fluorescent antibodies. In some aspects, the fluorescence of the free-floating antibodies increases the background noise in the assay, making it harder to detect bead-antigen fluorescence when the sample has low concentrations of analyte present.

Module 370 can also include and/or be in communication with a wash module 600. During a wash operation, the system 400 distributes the reaction from 340 to support pack 230 where member 603 washes the reaction media, and then the washed reaction media (e.g., washed bead-antigen-fluorescent complex) is distributed by system 400 back to plate 340. Module 370 can then measure the fluorescence of the washed reaction media. In some aspects, module 370 can be configured to measure the fluorescence of free-floating fluorescent antibodies (wash transferred back to 340 and analyzed) and the bead-antigen-fluorescent complex (reaction). In some aspects, module 370 can be configured to measure the fluorescence of the unwashed reaction (free-floating fluorescent antibodies and bead-antigen-fluorescent complex) before the reaction is moved to by system 400 to support pack 230 where it is washed by module 600, system 400 then moves the washed reaction back to plate 340, and then module 370 measures the fluorescence of the bead-antigen-fluorescent complex a second time.

Hemoglobin A1c is an immunoassay that operates via immunoturbidimetry and is detected by the absorbance module 383. TSH is the only assay performed using the Fluorescent Laser scanning module 373.

The absorbance module 383 can detect assays from all three modalities (IA, clinical chemistry and hematology), these include but not limited to Hemoglobin A1c, Glucose, and hemoglobin.

Clinical Chemistry Module

In some aspects, module 380 is configured to identify, based on detected optical characteristics of beam 382 with respect to one or more wells of plate 340, the presence of analyte. In some aspects, module 380 is configured to identify, based on detected optical characteristics of beam 382 with respect to one or more wells of plate 340, the presence of endogenous interference. Assay results can be adversely impacted if the sample contains too much of any of three types of material—lipids, bilirubin (a product of hemoglobin breakdown), and/or punctured red blood cells.

The Sample Quality Assessment uses the clinical chemistry module to obtain background optical absorbance of plasma across all wavelengths used for the individual assays. This background absorbance provides semi-quantitative information on the presence of three different substances that can interfere with individual assays: (1) Hemolysis—ruptured red blood cells. Hemoglobin optically absorbs at a range of wavelengths, and if these overlap with absorbance wavelengths of assay(s), it could falsely elevate the reported measurement of the assay(s). Ruptured blood cells can also result in the elevation of certain analytes in plasma. For instance, AST is present in high concentration in RBCs, so hemolysis would result in extra AST being present in the plasma and lead to a falsely high AST result; (2) Icteric interference—high bilirubin presence. Bilirubin absorbs light at ~460 nm, and if any assays have optical measurements around this wavelength, it could falsely elevate the reported measurement of the assay(s); and (3) Lipemia—high lipid presence. Lipemic interference scatters light across all wavelengths, which is interpreted as higher absorbance. If not accounted for, or if too significant, it could falsely elevate the reported measurement of the assay(s).

Each assay can tolerate different amounts of each of these materials. In some aspects, when processing a sample, module 380 can be configured to emit beam 382 through well 342b (e.g., one of the wells of the outer row of plate 340), bounce the light off a mirror, and send beam 382 through the well 342b a second time, before detecting the beam 382. In some aspects, when processing a sample, module 380 can be configured to only emit beam 382 through well 342b once before detecting it. In some aspects, the lens is not coated with a film since the light source is a laser that has very limited wavelength range output. In some aspects, the lens is coated with a film so that shorter wavelengths of light are affected the same way as longer wavelengths as the light goes through the lens.

Module 380 can be configured to measure in all four modalities (electrochemistry, clinical chemistry, IA and hematology) and similarly utilize laser alignment fixture 381 to focus beam 382 for excitation on one or more wells 342b. Module 380 can be configured to provide dual collimation (parallel) of beam 382 (e.g., focused to infinity) on aspects of plate 340 with an emission fiber 382a and an emission doublet lens on one side of wells 342b (e.g., above well 342b) and a collection fiber and a collection doublet lens on the opposite side of wells 342b (e.g., below well 342b). In some aspects, module 380 can include emission fiber 382a as well as an emission lens, a collection fiber, and a collection lens. During operation, module 380 is configured to separate plasma from blood cells, implement precise thermal control for consistent assay reaction progression, adjust plasma concentration for each assay's sample-to-reagent ratio, measure optical absorbance at specific wavelengths spanning UV to NIR, and identify the presence of endogenous interference. During operation, module 500 is configured to separate plasma from blood cells and implement precise thermal control for consistent assay reaction progression.

In some aspects, module 380 can be configured to measure optical absorbance at specific wavelengths spanning UV to NIR-I. In some aspects, the module 380 can be configured to measure optical absorbance at specific wavelengths spanning UV to NIR-I with and without using absorbance.

Plate 340 can also be configured to run more than 1 type of modality assays such as 1-3, 1-4 or 1-10 modalities. Plate 340 can be configured to run electrochemistry assays, hematology assays, immunoassays and/or clinical chemistry assays. Plate 340 can also be configured to run electrochemistry assays, hematology assays, immunoassays and clinical chemistry assays from a single blood sample, i.e., a sample taken from a single blood tube type. In some embodiments, plate 340 measures hemoglobin. Plate 340 can include a kinetic assay, endpoint assay, immunoassay, hematology (hematocrit) assay, electrochemistry assays and/or combinations thereof.

Module 380 can include precise (e.g., approximately +/−1 deg C) thermal control for consistent assay reaction progression. In some embodiments, module 500 and module 540 comprise the components for thermal control of the disc. Module 380 can include assays wherein the change in optical absorbance over time is measured at a constant temperature (e.g., approximately +/−1 deg C). Module 380 can include assays wherein the assay reaction reaches completion at a constant temperature (e.g., approximately +/−1 deg C).

In some aspects, module 380 is configured to adjust the plasma concentration for each assay's sample-to-reagent ratio. For example, module 380 can include a first assay with a first sample-to-reagent ratio and a second assay with a second sample-to-reagent ratio wherein the first sample-to-reagent ratio and second sample-to-reagent ratio are different. In some aspects, module 380 is configured to adjust the plasma concentration for each assay's sample-to-reagent ratio (for assays on the system and new assays added to the system). This is achieved by pipette system 400, thus the sample-to-reagent ratio can be changed without changing the hardware or consumable, such as plate 340 or pack 230. As new assays are added to the system the optimal sample-to-reagent ratio can be achieved by changing the system 400 settings, new hardware or a new consumable are not needed. In some aspects, module 380 is configured to adjust the plasma concentration for each assay's sample-to-reagent ratio by automatically updating a hardware operation for system 400. In some aspects, module 380 adjusts plasma concentration based on detected blood levels from support pack 230, then based on this information, plasma concentration requirements by module 380 is adjusted. In this way, future panels could include a majority of the immunoassays as an example, with a few or no chemistry assays. In this way, future panels could include a majority of the clinical chemistry assays as an example, with a few or no immunoassays. This highlights the flexibility, versatility and extensibility of the platform. Module 380 can include precise (e.g., approximately +/−1 deg C) thermal control for consistent assay reaction progression. In some embodiments, module 500 and module 540 comprise the components for thermal control of the disc. Module 380 can include assays wherein the change in optical absorbance over time is measured at a constant temperature (e.g., approximately +/−1 deg C). Module 380 can include assays wherein the assay reaction reaches completion at a constant temperature (e.g., approximately +/−1 deg C). In some aspects, module 500 is configured to adjust the plasma concentration for each assay's sample-to-reagent ratio.

Module Descriptions

In some aspects, all four modules 240, 370, 380, and 390 operate dependently. In some aspects, all four modules 240, 370, 380, and 390 operate independently. In some aspects, all four modules can operate in parallel (run at the same time). In some aspects, all four modules cannot operate in parallel (cannot run at the same time). In some aspects, the clinical chemistry and immunoassay modules cannot operate in parallel. In some aspects, the clinical chemistry and electrochemistry modules operate in parallel. In some aspects, the IA and electrochemistry modules operate in parallel. In some aspects, the hematology and electrochemistry modules operate in parallel. In some aspects, the clinical chemistry and hematology modules cannot operate in parallel. In some aspects, the immunoassay and hematology modules cannot operate in parallel. In some aspects, the electrochemistry and hematology modules cannot operate in parallel. For example, the clinical chemistry and immunology modules both measure assays in the plate 340. The clinical chemistry module requires the plate 340 to remain stationary (e.g., approximately 0.25s) at some time points for the clinical chemistry detection instrument to take measurements of the reaction in the well(s), while the immune assay module requires constant motion (e.g., rotation of plate 340) in order to take measurements of the reaction in the well(s). Thus, the module 370 and module 380 cannot take detection measurements at the same time. Thus, in some embodiments, immunoassay module is stopped while the clinical chemistry module obtains detection results. In some embodiments, the both the clinical chemistry module and immunoassay module can operate under constant motion during preparation, reaction and/or detection. In some embodiments, the electrochemistry and hematology modules both measure assays in the support pack 230 using the hematology detection instrument (cell imager 243) to measure hematology analytes and using the electrical sensor 3313 to measure electrolytes. Electrochemical sensors convert the information associated with electrochemical reactions (the reaction between an electrode and analyte) into an applicable qualitative or quantitative signal.

In some embodiments, an ion-selective electrode (ISE) consists of a thin membrane across which only the intended ion can be transported. In some embodiments, the electrochemical sensors are made up of bead-based electrochemical immunoassays. In some embodiments, electrochemical sensors are made up of three essential components: a receptor that binds the sample, the sample or analyte, and a transducer to convert the reaction into a measurable electrical signal. In the case of electrochemical sensors, the electrode acts as the transducer. Electrochemical sensors include potentiometric, amperometric and conductometric. Electrochemical sensors can be used to detect neurotransmitters, catecholamines, aminoglycosides, carbohydrates, thiols and phenols. The hematology detection instrument (cell imager 243) cannot measure analytes for the electrochemistry module. The clinical chemistry detection instrument (absorbance module 383) can measure analytes for the electrochemistry module.

In some aspects, a module cannot operate in parallel with a specific operation of another module. In some aspects, the immunoassay wash 600 and hematology module 240 cannot operate in parallel. In some aspects, the immunoassay wash 600 and hematology processing module and/or hematology detection module cannot operate in parallel. In some aspects, the immunoassay wash 600 and hematology module 240 can operate in parallel. In some aspects, the immunoassay wash 600 and hematology processing module and/or hematology detection module can operate in parallel. In some aspects, the immunoassay wash 600 and electrochemistry processing module and/or electrochemistry detection module (electric sensor) can operate in parallel. In some aspects, the immunoassay wash 600 and electrochemistry processing module and/or electrochemistry detection module (electric sensor) cannot operate in parallel.

The system operation can be better understood by the following numbered paragraphs:

Paragraph 1. A method for analyzing a sample, the method comprising:
  loading a sample into the instrument;
  detecting by a first detection instrument in a clinical chemistry module a first analyte;
  washing by an immunoassay (IA) module a reaction comprising a second analyte;
  detecting by a second detection instrument in the IA module the second analyte wherein
  detecting the first analyte and second analyte cannot happen at the same time;
  detecting by a third detection instrument in a hematology module a third analyte wherein washing the reaction comprising the second analyte and detecting the third analyte cannot happen at the same time; and
  detecting by a fourth detection instrument in an electrochemistry module a fourth analyte.

Shared Resource Location

In some aspects, two modules share a resource, but the shared resource is positioned differently for each module. For example, the immunoassay wash module 600 and hematology modules 240 both utilize the support pack tray but can require the tray 221 to be in different positions. For example, the tray 221 when loaded and in use with module 240 (e.g., processing and detection by module 240), tray 221 is in the operational state shown in FIG. 4. When module 600 utilizes the support pack tray 221 (e.g., by causing the magnetic member 603 to pivot away from the side panel of FIG. 4 and couple to the forward face of tray 221 shown in FIG. 4), then tray 221 will move (e.g., slide along plate 19) forward to maintain a coupling with member 603 (washing state).

In this respect and advantageously, system 100 provides for a dynamic platform where modules 240, 370, 380 and 390 actively share resources. In some aspects, the shared resources can include a pulsed xenon arc lamp, fiber optics, UV-VIS-NIR detector, achromatic collimating lens, system 400, and combinations thereof. In some aspects, one resource is shared across all modalities. For example, system 400 is used with modules 240, 370, 380 and 390. In some aspects, one resource is shared across a subset of modalities present on the system such as 240, 370, and 380. In some aspects, the shared resources share the same function. In some aspects, the shared resources have a different function. For example, sometimes (in modules 240, 370, 380 and 390)

the pipette module 400 functions to extract, transport and dispense sample, reagent and/or diluent. For example, sometimes (in module 390) the pipette module 400 functions (without a pipette tip) to create an electrical connection with the electrochemistry cartridge and pins (such as pogo pins or H-Pin) on the instrument to create an electrical connection with the detection instruments.

Clinical chemistry module measures assays across all modalities

In some aspects, the measurement of hemoglobin is part of the hematology panel, but it cannot be measured by the hematology module 240 detection instrument, e.g., a microscope comprising a lens 264 of module 240. The measurement of hemoglobin requires the same detection instrument as the clinical chemistry module, e.g., a camera 442.

The A1C test also known as the hemoglobin A1C or HbA1c test—is a blood test that measures your average blood sugar levels over the past 3 months. In some aspects, the assay for HbA1c is an immunoassay, but also requires the same detection instrument as the clinical chemistry module, e.g., a camera. Hence, the clinical chemistry module measures assays across all modalities: clinical chemistry assays, immunoassays and hematology assays.

Electrolytes (part of the electrochemistry module) can also be measured by the same detection instrument as the clinical chemistry module, e.g., absorbance module 383 (380).

Non-Shared Resources: Immunoassay Module

In some aspects, the multi-modality diagnostic system comprises a clinical chemistry module, an immunoassay module and a hematology module which share certain resources. In some embodiments, the multi-modality diagnostic system further comprises an electrochemistry module. In some aspects, the multi-modality diagnostic system comprises a clinical chemistry module, an immunoassay module, electrochemistry module and a hematology module which do not share certain resources. In some aspects, those IA module non-shared resources comprise or consist of a green laser source, a red laser source, a PMT detector, a collimating optics, and combinations thereof (not shared with the hematology module, electrochemistry module, or clinical chemistry module; unique to the IA module). In some aspects, those IA module shared resources comprise or consist of a high-speed camera (shared with the clinical chemistry module), a focusing objective (shared with the hematology module) and/or a Z-stage motor to move focusing objective up and down (shared with the hematology module). In some aspects, those IA module shared resources comprise or consist of the pipette module 400 (shared with the clinical chemistry module, hematology module, and electrochemistry module).

In some aspects, the IA module non-shared resources comprise or consist of a 532 nm green laser, a 660 nm red laser, a PMT detector, a high speed camera, a collimating optics, a focusing objective, a Z-stage motor to move focusing objective up and down, and combinations thereof; and the shared resources comprise or consist of a pulsed xenon arc lamp, fiber optics, UV-VIS-NIR detector, an achromatic collimating lens, and combinations thereof (shared with the hematology module and/or clinical chemistry module; not unique to the IA module).

Non-Shared Resources: Hematology Module

In some aspects, the multi-modality diagnostic system comprises a clinical chemistry module, an immunoassay module, electrochemistry module and a hematology module which share some resources and do not share certain resources. In some aspects, those non-shared resources of the hematology module comprise or consist of a white light source, a movable filter complex, a focusing objective, a Z-stage motor to move focusing objective up and down, an image transmission focusing optics, a monochromatic image sensor, a X-stage motor to move optics left-to-right, and combinations thereof (not shared with the IA module, electrochemistry module, or clinical chemistry module; unique to the hematology module). In some embodiments, the hematology module shares the focusing objective, and Z-stage motor to move focusing objective up and down with the IA module.

In some aspects, the hematology module non-shared resources comprise or consist of a white light source, a movable filter complex, a focusing objective, a Z-stage motor to move focusing objective up and down, an image transmission focusing optics, a monochromatic image sensor, a X-stage motor to move optics left-to-right, and combinations thereof; and the shared resources with the clinical chemistry module comprise or consist of a pulsed xenon arc lamp, fiber optics, UV-VIS-NIR detector, an achromatic collimating lens, and combinations thereof (shared with the IA module and/or clinical chemistry module; not unique to the hematology module).

In some aspects, the movable filter complex comprises or consists of a brightfield filter and reflection optics, a blue-excitation/green-emission filter and reflection optics, a blue-excitation/red-emission filter and reflection optics, a linear actuator motor and support rail for movement, and combinations thereof. In some aspects, operations of the movable filter can include use of brightfield light source (e.g., a high-resolution camera 442) that goes from the UV into the infra-red for emission so the system can determine measuring in brightfield or one of the two fluorescent channels. The brightfield bright light source goes from the UV into the infra-red for emission and by moving a filter into the light path of this white light the system is able to get both brightfield and fluorescent through the detection instrument. The filter determines if what is being measured is in brightfield or one of the two fluorescent channels.

Below is Table 1 detailing assays on the system, the module they are a part of and the detection instrument they are detected by:

TABLE 1

| Panel | Assays | Module | Detection Instrument |
|---|---|---|---|
| Complete Blood Count | WBC | Hematology module | Cell imager 243 |
| | RBC | Hematology module | Cell imager 243 |
| | Hemoglobin | Clinical Chemistry module | Absorbance module 383 |
| | Hematocrit | Hematology module | Camera |
| | MCV | Hematology module | Cell imager 243 |
| | Platelets | Hematology module | Cell imager 243 |

TABLE 1-continued

| Panel | Assays | Module | Detection Instrument |
|---|---|---|---|
| | Neutrophils (%) | Hematology module | Cell imager 243 |
| | Lymphocytes (%) | Hematology module | Cell imager 243 |
| | Other (%) | Hematology module | Cell imager 243 |
| | Neutrophils (Absolute) | Hematology module | Cell imager 243 |
| | Lymphocytes (Absolute) | Hematology module | Cell imager 243 |
| | Other (Absolute) | Hematology module | Cell imager 243 |
| | MCH | Calculated from hemoglobin and RBC count | |
| | MCHC | Calculated from hemoglobin and RBC count | |
| | RDW | Hematology module | Cell imager 243 |
| | MPV | Hematology module | Cell imager 243 |
| | PDW | Hematology module | Cell imager 243 |
| Metabolic Panel | Glucose | Clinical Chemistry module | Absorbance module 383 |
| | BUN | Clinical Chemistry module | Absorbance module 383 |
| | Creatinine | Clinical Chemistry module | Absorbance module 383 |
| | eGFR | Calculated from creatinine, age, and gender | |
| | Calcium | Clinical Chemistry module | Absorbance module 383 |
| | Protein, Total | Clinical Chemistry module | Absorbance module 383 |
| | Albumin | Clinical Chemistry module | Absorbance module 383 |
| | Bilirubin, Total | Clinical Chemistry module | Absorbance module 383 |
| | Alkaline Phosphatase | Clinical Chemistry module | Absorbance module 383 |
| | AST (SGOT) | Clinical Chemistry module | Absorbance module 383 |
| | ALT (SGPT) | Clinical Chemistry module | Absorbance module 383 |
| | Sodium | Clinical Chemistry module and/or electrochemistry module | Electrochemistry sensor and/or absorbance module 383s |
| | Potassium | Clinical Chemistry module and/or electrochemistry module | Electrochemistry sensor and/or absorbance module 383s |
| | Chloride | Clinical Chemistry module and/or electrochemistry module | Electrochemistry sensor and/or absorbance module 383s |
| | Bicarbonate | Clinical Chemistry module and/or electrochemistry module | Electrochemistry sensor and/or absorbance module 383s |
| | Anion gap | Calculated from Sodium, Potassium, Chloride, and Bicarbonate | |
| Lipid Panel | Cholesterol, Total | Clinical Chemistry module | Absorbance module 383 |
| | Triglycerides | Clinical Chemistry module | Absorbance module 383 |
| | HDL Cholesterol | Clinical Chemistry module | Absorbance module 383 |
| | Non-HDL Cholesterol | Calculated from Total and HDL Cholesterol | |
| | VLDL Cholesterol | Calculated from Triglycerides | |
| | LDL Cholesterol | Calculated from Total and HDL Cholesterol | |
| | Cholesterol/HDL Ratio | Calculated from Total and HDL Cholesterol | |

TABLE 1-continued

| Panel | Assays | Module | Detection Instrument |
|---|---|---|---|
| Hemoglobin A1c Panel | Hemoglobin A1c | Clinical Chemistry module | Absorbance module 383 |
| Thyroid Panel | TSH (Thyroid Stimulating Hormone) | Immunoassay module | Fluorescent laser scanning module 373 |

Multi-Well Plate

FIG. 10A shows a perspective view of an exemplary plate 340 while FIG. 10B shows an exploded view of plate 340. As shown in FIG. 10B, plate 340 can be multi-layered and include a layer 345, a central layer 343, and a lower ring-like layer 349. Layer 343 can be an opaque layer attached to layer 345 (e.g., by laser welding or ultrasonic welding). Layer 349 can be "translucent." As used herein, "translucent" is used to describe a material that at least partially transmits light of a wavelength of interest in an ultraviolet or visible range, e.g., between 220 nm and 850 nm, between 300 nm-850 nm, between 400 nm-800 nm, or between 300 nm-700 nm. By contrast, a material referred to herein as "opaque" or "solid" (e.g., solid black or solid white) is a material that transmits essentially no light of a wavelength of interest in the ultraviolet or visible range. Layer 349 can be "transparent." Transparent implies being so clear that objects can be seen distinctly. In some aspects, the bottoms of some or all wells 342a, 342b include the transparent and or translucent material of layer 349 (e.g., allowing transmission of light in 300-700 nm range).

Plate 340 is configured to facilitate the parallel performance of two or more different modalities (assay formats e.g., a fluorescence and absorbance-based format), to facilitate the performance of different assays for two or more different analytes (e.g., a high-abundance and a low-abundance analyte), and/or the like. In some aspects, plate 340 can include a plurality of wells 342n comprising outer wells 342b aligned in an outer row, a plurality of inner wells 342a aligned in an inner row, and a central aperture 347 to align with and be driven by module 500. Wells 342a, 342b can be arranged in concentric circles around aperture 347 and can have a diameter of between 0.5 mm and 3.0 mm (e.g., 1.5 mm). In some aspects, geometry of wells 342a, 342b can be the same or different and can be in one or more shapes, such as cubed, cylindrical, or any shape to contain solution or dimension (e.g., volume) as well as well surface property (e.g., high protein-binding or cell adhesion promoting), or with respect to any other property affecting the performance of an assay for an analyte (e.g., assay reagents).

System Loading

Plate 340 can include one or more alignment fiducial protrusions 348. In some aspects, planarity of plate 340 can be limited to approximately 200 μm and can be different between respective plates 340. During initializing scanning by scanner system 700 upon loading plate 340 with module 500 and moved into a load configuration, system 700 can determine a load orientation of a plurality of plate orientations with respect to module 500 by analyzing orientation and location information related to/by protrusions 348. In some embodiments, the portion of scanner system 700 that interacts with plate 340 is camera 442.

In some aspects, during an initialization calibration operation of plate 340, beams 372, 382 can reflect off the bottom of wells 342a, 342b, and related reflections can be captured by a high-speed camera (e.g., camera 442 of system 400).

Captured images are then transmitted to and analyzed by system 360 to calculate a distance between protrusions 348 in the image that corresponds to a distance of the focusing objective to the bottom of each well 342a, 342b. Once this focusing objective distance is known, the objective can be selectively placed, by module 370 (in some embodiments, this is achieved or partially achieved via module 500 which puts the disc in the correct position) and controlled by system 360, at that distance when emitting beam 372 through respective well 342a, 342b for assay measurements. In some aspects, all of wells 342a, 342b have the exact same size, shape, and material finish, such that they can accept any assay reagent (e.g., delivered by pipette system 400 from support pack 230 during load operations). In some aspects, a portion of the wells 342a, 342b have a different size, shape, and/or material finish, such that they can accept a single assay reagent. In some embodiments, all the wells 342a and 342b or a portion of the wells 342a and 342b have been manufactured to be pre-loaded (contain) reagents prior to loading into the detection instrument. Sometimes wells are pre-loaded with a single reagent or a plurality of reagents. In some embodiments, the sample does not require washing prior to adding to a pre-loaded well. In some embodiments, the sample requires washing prior to adding to a pre-loaded well. In some aspects, the outer row of wells 342b can be rotated into aperture 543 of module 500 so as to align with the camera 442 of clinical chemistry module 380, and any well 342a, 342b can be rotated into the optical path of beam 372 of module 370. In some aspects, a first plurality of wells 342b can be rotated into aperture 543 of module 500 so as to align with the clinical chemistry module 380, and a second plurality of wells 342a, 342b can be rotated into the optical path of beam 372 of module 370. In some embodiments, the first plurality of wells and second plurality of wells are different, in some embodiments, the first plurality of wells and second plurality of wells are the same, in some embodiments, the first plurality of wells and second plurality of wells overlap (some different, some the same).

In some aspects, once protrusions 348 are recognized by system 700 (e.g., via pattern recognition), system 442 (via a component within module 500 such as an encoder reader) reads the position of an encoder on the theta motor that spins plate 340, thereby learning the rotational position of every disc feature relative to the theta motor encoder. In some aspects, if specific features are not identified in the image of plate 340, the system will continue to rotate plate 340, record, and analyze another image until the desired plate features are found, at which point the orientation of plate 340 is confirmed. System 700 can function as a barcode scanner of a detectable barcode on plate 340 as well as measure diagnostic aspects of plate 340. System 700 can function as a barcode scanner of a detectable barcode on plate 340, support pack 230, monolayer 170 and/or electrochemistry consumable 391. In some aspects, plate 340 can be loaded in any orientation. In some aspects, system 700 (via camera 442) also scans and interprets two-dimensional barcodes, and collects the image used to quantify the hematocrit of a blood sample. System 700 (via processor 360) is configured to analyze this image to detect specific features in a column of centrifuged blood to calculate the hematocrit. In some embodiments, system 700 operates in both module 370 and module 380. In some embodiments, system 700 (via camera 442 and barcode scanner 800) operates in modules 240, 370, 380 and/or 390. In some embodiments, system 700 (via camera 442) can detect if the view window of the disc has failed to open. If it fails to open, system 700 will not allow any pipetting or further action to take place and will eject any cartridges in the instrument.

Turning back to the transition between the loading state and the operational state, system 100 can begin operations by determining a load orientation of plate 340. In some aspects, system 360 determines the load orientation of plate 340 based on fiducial protrusions 348. Upon determining the load orientation based on protrusions 348, then pipette system 400 can prepare to run one or more panels and causing resource sharing between support pack 230 and plate 340. For example, using at least one pipette member 432 of system 400, a portion of a patient sample can be distributed from pack 230 to one or more wells 342b, 342a of plate 340 to prepare an associated assay and perform a clinical analysis of at least one of clinical chemistry characteristics and/or immunoassay characteristics or hematology characteristics (hemoglobin measurement) of that portion of the patient sample. In some aspects, though contents thereof are distributed by system 400, the patient sample tube of a sample well 237 of support pack 230 does not move from support pack 230 during analysis. Though as described, assets of plate 340 are also distributed by system 400 from plate 340 to pack 230 during operation. For example, a TSH assay can be present in one or more wells 342 at the start of the operational state and system 400 can cause sample from pack 230 to be moved to plate 340 to the sample well comprising TSH reagent. The TSH reagent and sample can be transferred back to pack 230 for magnetic washing by wash module 600. After washing, the TSH reagent and sample can be transferred back to plate 340 for analysis module 370. In some aspects, blood from the patient sample in pack 230 is present in the sample tube of well 237 at the start of the operational state then is transferred by system 400 to plate 340 for plasma isolation then is transferred by system 400 back to pack 230 for plasma dilution. Upon completion of a plasma dilution operation, it is transferred by system 400 back to plate 340 for analysis operations by modules 370 and 380.

Theta Motor

In some aspects, the theta motor that rotates plate 340 can be a single motor to enable sample delivery to reaction vessels, to enable reagent or diluent delivery to reaction vessels, to move the plate 340 to optically read it as part of the clinical chemistry module and/or immunoassay module and to centrifuge the plate 340.

In some embodiments, the same motors are used for measuring clinical chemistry assays and immunoassays, to separate plasma and prepare these assays. For example, the same mechanics that spin a multi-well plate at 7,000 RPM to separate plasma in blood also rotates down to ~1 RPM for measuring immunoassays and stops in specific locations as part of liquid handling for sample and assay preparation, as well clinical chemistry and hematology measurements. In some embodiments, the system uses more than one motor to spin the multi-well plate, and to move the plate into the correct location within the system.

In some aspects, the same motors used to measure hematology assays are also used for the sample and assay preparation for clinical chemistry and immunoassays modules. The motor that moves the support pack within the system to enable sample and assay preparation is also used to move the microscope slide 170 for imaging blood cells.

The theta motor can be better understood by the following numbered paragraphs:

Paragraph 1. A method of detecting an analyte in a sample, the method comprising:
receiving by the detection instrument a disc comprising a sample wherein the detection instrument comprises a first motor and wherein the disc comprises a first reaction vessel and a second reaction vessel;
rotating by the first motor the disc to a first load position to load a first sample portion into the first reaction vessel;
rotating by the first motor the disc to a second load position to load a second sample portion into the second reaction vessel;
centrifuging the disc by the first motor;
rotating by the first motor the disc to detect a first detect position to detect the presence of a first analyte in the first reaction vessel; and
rotating by the first motor the disc to a second detect position to detect the presence of a second analyte in the second reaction vessel, thereby detecting an analyte in a sample.

Paragraph 2, the method of paragraph 1 wherein the first motor is capable of spinning at speeds which allow for plasma separation in less than about 5 min, stopping at specific positions with rotational precision of less than about 0.5 mm, when stopped, hold location with precision of less than about 0.5 mm, and combinations thereof.

Paragraph 3, the method of paragraph 1 or 2 wherein the first load position and first detect position are different and wherein the second load position and second detect position are different.

Barcode Scanner

In some aspects, a barcode scanner system 800 is mounted to or otherwise fixedly coupled to module 240. In some aspects, a barcode scanner system 800 is not mounted to or otherwise fixedly coupled to module 240. System 800 is configured as a consumable locator system (CL) that images tray module 220 and/or pack 230. In some aspects, the CL system can include both system 800 to image pack 230 and system 442 to image plate 340. In some aspects, the CL system also detects that the housing 540 that receives plate 340 has been cleared of the plate 340 at the completion of a run. In some aspects, the CL system detects that the tray module 220 has been cleared of the pack 230 at the completion of a run. In some aspects, the CL system also detects that modules 500 and 220 have been cleared at the completion of a run. In some aspects, modules 500, 220 can slide at different rates and/or slide different distances (e.g., module 500 traveling further or different rates than module 220 or vice versa) while movement of the CL system is also separate from movement of modules 500, 220.

Plate Capture Module

Figure 11:
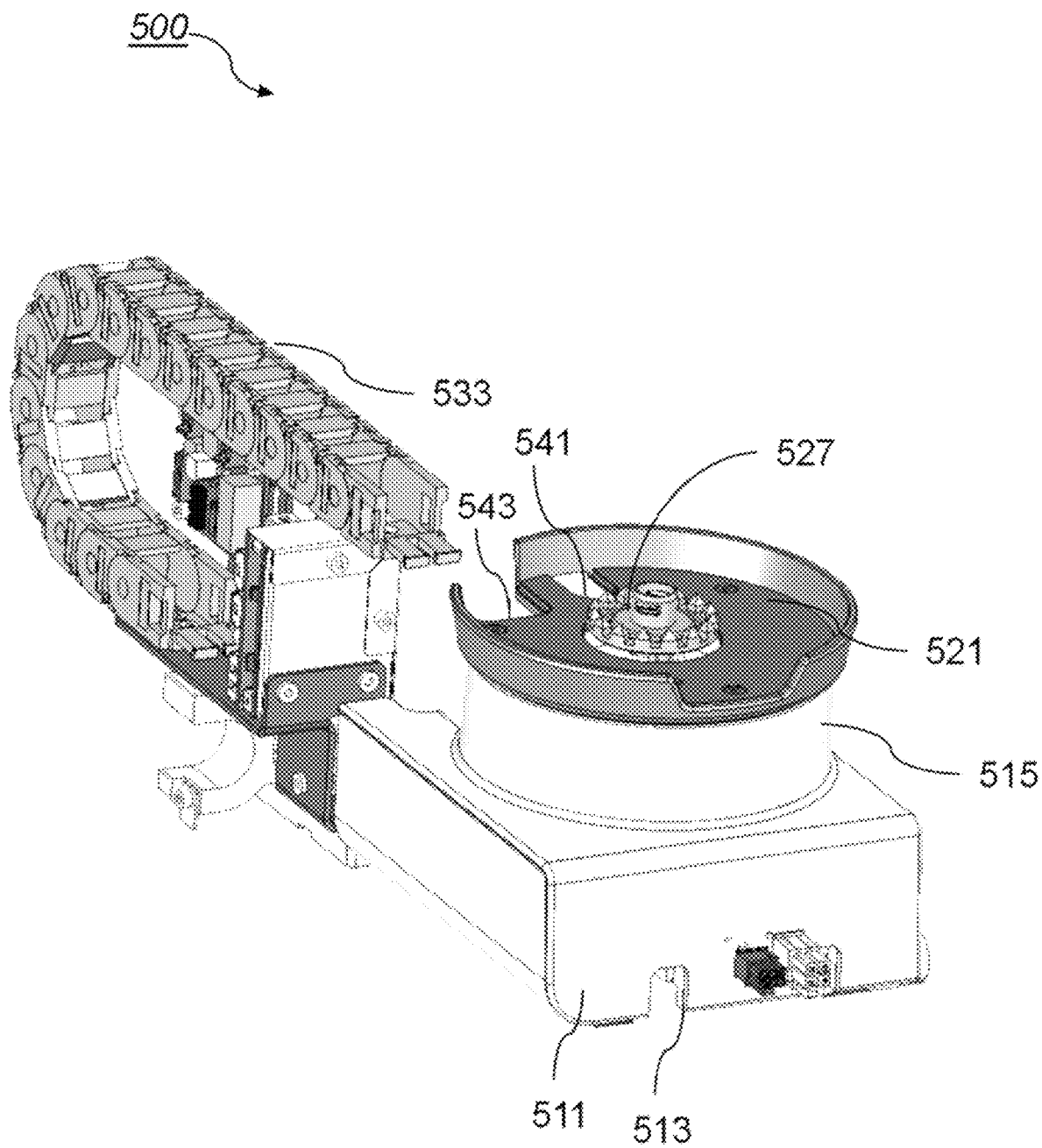
FIG. 11 shows a perspective view of an exemplary multi-well plate capture module of the system of FIGS. 1A and 1B, in accordance with an exemplary embodiment. Not shown is the lid 540 to the multi-well plate capture module.

FIG. 11 shows a perspective view of plate capture module 500. A disc tray 521 can include one or more connectors (e.g., alignment pins, magnetic connectors, etc.) to engage corresponding receivers to align plate 340 and tray 521. In some aspects, module 500 can include a housing 511 with guide chain 533 and one or more guide apertures 513 formed in a lower surface of the housing. Apertures 513 are formed and positioned so that as a motor (e.g., motor 6 shown in FIG. 4) pulls or pushes chain 533, guide rails 11 positioned along plate 19 of housing 10 can guide housing 511 of module 500 to slide along plate 19 forward and backwards between open and load configuration. A tray portion 515 of housing 511 can extend upwards to receive tray 521. A plate coupler 527 can extend through tray 521 and is rotatably connected to the theta motor within housing 511. In operations, the theta motor within housing 511 can rotatably drive coupler 527 that in turn can cause plate 340 to be rotated during operations, such as centrifugation. In some aspects, the motor of module 500 can be a servo motor that can reach approximately 7,000 RPM with no gearing. Plate 340 is configured to engage with coupler 527 of tray 521 so that the motor can rotate the tray 521 and rotate the wells 342a, 342n of plate 340 relative to beams 372, 382. Tray 521 can include a clinical chemistry aperture 543 configured so that one or more corresponding emission and/or collector fibers of module 380 can be aligned with aperture 543 and corresponding wells 342b of plate 340. Tray 521 can include an IA aperture 541 configured so that one or more corresponding emission and/or collector fibers of module 370 can be positioned aligned with aperture 541 and corresponding wells 342a of plate 340. In some embodiments, the IA aperture 541 and clinical chemistry aperture 543 are the same.

All electrically powered componentry will, as a byproduct, generate heat. In some aspects, each modality is housed within an instrument housing. Housing multiple modalities within a single instrument housing requires deliberate thermal management so as to not overheat assays or any component to the point of failure.

In some aspects, one or more resistive heating elements can be positioned underneath tray 521 and within housing 511. The one or more resistive heating elements can include one or more respective thermistors in communication with system 360. During thermal management operations, system 360 can actively detect and predict heating states of plate 340 based on feedback received from the one or more respective thermistors of module 500. Thermal management operations can include controlling current transmitted to the one or more resistive elements so as to increase or decrease the applied thermal load to plate 340 by tray 521. In some aspects, rotating plate 340 by coupler 527 causes to distribute heat and thermal management operations can include causing coupler 527 to adjust rotational parameters of plate 340 based on detected thermal state of plate 340 (e.g., rotational velocity increase or decrease or pause). In some aspects, the plate 340 is rotated for thermal management when it is not being used for plasma separation, optical measurement, or liquid handling, to ensure even heat distribution.

Hematology Module

FIG. 12A shows module 240 with an exemplary cell imaging system 243. In some aspects, module 240 is configured to measure aspects related to the sample loaded in support pack 230, including measuring absorbance for blood cells (typically PLT, WBC, and RBC) generally. In some aspects, module 240 is configured to measure aspects related to the sample loaded in disc 340, including measuring absorbance for hemoglobin. In some aspects, module 240 is configured to measure aspects related to the sample loaded in support pack 230 and the disc 340. Barcode scanner 800 (not shown) is aligned to read the barcode on the support pack 230 and monolayer 170. Barcode scanner 800 (not shown) align with pins 271a and 271b on the hematology rack mount.

In some aspects, module 240 can tolerate thermal swings (about +/−1 deg C. to +/−10 deg C). Tray module 220 can be positioned thereunder and configured to store support pack 230. Pack 230 is more particularly shown in FIG. 12B. In some aspects, the support pack 230 can be loaded into the instrument in any direction. Pack 230 can be a consumable tube holder that includes a plurality of tube receiving wells 232 to receive one or more reagents, diluents, and/or the like. Pack 230 can include a sample receiving well 237 configured to receive a sample in a sample tube loaded by a user. Pack 230 can include a plurality of removable pipette tips 235 configured to be releasably controlled by pipette system 400 after pack 230 is loaded in module 220 and module 220 is translated to the operational state. Once in the operational state, pack 230 is scanned and verified by barcode scanner system 800. Pack 230 can include an assay device recess 270 sized to receive device 170 so that aspects of device 170 are selectively aligned with the lens 260 of module 240.

FIG. 12C shows an exemplary close-up of the support pack tray 221 of module 200. Tray 221 can include one or more outer walls that form a housing 222. In some embodiments, the support pack comprises structural features so that the support pack can only be loaded into the instrument in one orientation. A tray recess area 223 can be formed within an interior portion of an outer surface of housing 222. Area 223 can be shaped so that pack 230 can only be inserted therein in a single orientation (e.g., pack 230 is prevented structurally by area 223 from being loaded misaligned with area 223). Though not shown, one or more circulating fans and resistive heating elements can be included within housing 222. A plurality of inlet apertures 225 can be formed in area 223 and a plurality of larger outlet apertures 227 can be formed adjacent thereto. The one or more resistive heating elements can include one or more respective thermistors in communication with system 360. During thermal management operations of module 220, including contents of pack 230 thereon, system 360 can actively detect and/or predict heating states of pack 230 based on feedback received from the one or more respective thermistors of module 220. Thermal management operations can include controlling operations of a fan so as to draw air through apertures 225 and cause the area to circulate and egress out through apertures 227. Thermal management operations can also control current transmitted to the one or more resistive elements so as to increase or decrease the applied thermal load to pack 230.

In some aspects, the multi-modality diagnostic system comprises a clinical chemistry module, an immunoassay module, electrochemistry module, and a hematology module wherein the hematology module and/or electrochemistry module comprise or consist of a Y-motor to move a support pack comprising a hematology slide and/or electrochemistry cartridge back and forth for assay preparation, hematology slide imaging and/or electrochemistry detection, a support pack tray comprising a recirculating fan and thermal element to heat and recirculate air within the front underside of the support pack, and combinations thereof.

Module 240 is configured to analyze assays as well as be communicatively coupled to a barcode scanner system 800. System 800 can be positioned within housing 10 underneath module 240 relatively fixed and positioned so that once pack 230 is loaded in module 220 and module 220 has been moved from the loading state to the operational state (e.g., by motor 6 shown in FIG. 4, which can be a stepper motor moving a chain connected to module 220), then once in the operational state system 800 can scan a barcode of pack 230 to verify pack related characteristics and determine whether and how to adjust certain analytical aspects (such as adjust plasma concentration, calibrating the system based on data in the barcodes) related to panels on pack 230.

Hematology module 240 is configured to measure absorbance for hemoglobin (in the disc via 383, absorbance module) as well as measure blood cells in the support pack in module 170 via 243 (cell imager). In some aspects, module 240 can capture images of white blood cells, red blood cells, and platelets from whole blood that are distributed by system 400 in device 170 loaded in support pack 230. In some aspects, module 240 can include an imaging configuration comprising epi-illumination fluorescence microscopy (e.g., with Koehler illumination that generates an even illumination of the sample and ensures that an image of the illumination source can be captured). In some aspects, module 240 can include a condenser lens 207 that focuses the illumination source 205 on a rear portion of a focal plane of the imaging objective so that illumination source 205 is defocused at the subject plane. In some embodiments, the illumination source is fluorescent tubes, optical fibers or LEDs.

During operations of module 240, fluorescence microscopy is achieved by passing light from light source 205 through narrow band filters within filter housing 242 to provide wavelength selectivity. Module 240 in some aspects can also include a beam splitter to turn the beam to device 170 (e.g., which is underneath objective lens 260 in the operational state) and allow transmission of collimated reflected and fluorescent light from device 170 to a series of selectable emission filters. A broadband reflecting turning mirror 210 is used to align the image onto a digital camera 203 via a tube lens 211 that can be disposed within the housing between mirror 210 and camera 203. In some aspects, mirror 210 is configured to align an imaging field of view with a center of a field of view of camera 203. In some aspects, the X/Y area of the field of view of camera 203 can be wide (e.g., approximately 750×500 um) and substantially planar for all cells in the field of view to be in focus.

During analytical operations of the depicted operational state, illuminated device 170 can be scanned by moving a Y-axis of the loaded support pack 230, and the X-axis of lens 260. The Z-axis of lens 260 can be used to focus device 170. In some aspects, lens 260 can focus light down to a minimum spot size and collected light by device 170 from the sample plane can be collimated between device 170 and tube lens 211. In some aspects, lens 260 is configured so that the image performance is optimized when the object is one focal length away from a principal plane producing the collimated beam.

In some aspects, a first portion of reagents or diluents necessary to perform the assays in plate 340 are in wells 342 in plate 340 and a second portion of the reagents or diluents necessary to perform the assays in plate 340 are in wells 232 in support pack 230 and must be moved by system 400 to the wells of plate 340. In some embodiments the first portion of reagents are moved to wells 342 in plate 340 which do not have any reagents in them and in some embodiments the first portion of reagents are moved to wells 342 in plate 340 which have any reagents already in them. In some aspects, all or most reagents necessary to perform the assays of system 100 are in support pack 230 and assays of plate 340 are only performed after pipette system 400 automatically transfers aspects of reagent and the sample, and diluent and the sample from support pack 230 to selective locations of plate 340.

In some aspects, a consumable locator operation can be initiated upon drawer 22 closing with support pack 230 loaded in module 220. In the consumable locator operation, one or more images are acquired of aspects of both pack 230 and plate 340. The acquired images are then sent to system 360 where they are processed to provide a determined sample tube presence (e.g., True/False), plate 340 orientation, pack 230 orientation, rotational position of every feature of plate 340 (e.g., wells, fiducial protrusions, etc.) relative to a theta motor encoder, and/or the like. Based on the information output from the consumable locator operation, pipette system 400 can automatically begin the processing of the patient sample from sample well 237 and placing aspects thereof in a reaction well of pack 230 and/or reaction well of plate 340.

In some aspects, module 240 is configured to tolerate some degree of alignment error by light source 205. In some aspects, during operations even if the light source 205 is off in translation by approximately 1 mm, the illumination center of light source 205 relative to the field of view of camera 203 can remain unaffected. In some aspects, during operations even if the light source 205 is off in angle of alignment by approximately 2 degrees, an illumination area of light source 205 can still cover the field of view of camera 203.

Figure 13:
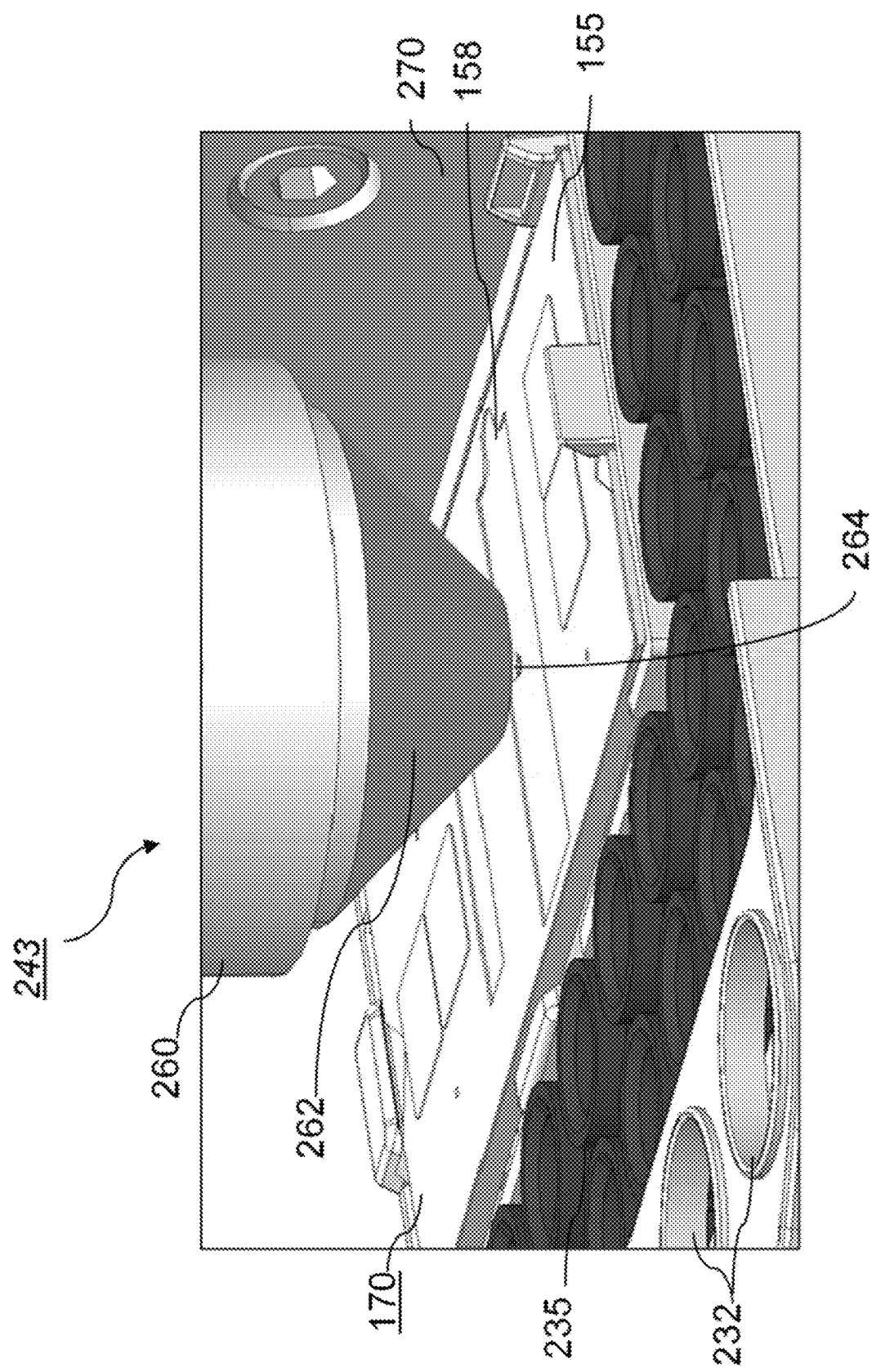
FIG. 13 shows an exemplary close-up of the cell imaging system of FIG. 12A focusing on an exemplary assay device, in accordance with an exemplary embodiment.

FIG. 13 shows an exemplary close-up of aspects of distal portion 262 of the lens 260, including specifically lens tip 264 focusing on exemplary device 170, in accordance with an exemplary embodiment. Device 170 can be substantially flat and include a planar substrate 155 with one or more flow channels 158 extending along a dimension of substrate between top and bottom surfaces. Each flow channel 158 can include an inlet and a vent so that a respective channel 158 can receive a liquid sample deposited in the inlet and allow flow of the liquid sample within flow channel 158 toward the vent whereby analytes of the liquid sample are distributed within flow channel 158. In the depicted example of FIG. 12, the analytes are distributed within the flow channel 158 as a monolayer. Due to part-to-part variation in the production and assembly of both device 170 and pack 230, module 240 is configured to locate the three-dimensional position of each device 170 at the outset of the operational state. In some aspects, the three-dimensional position of device 170 is determined via a "homing" process that locates a plurality of fiducials embedded in the device 170 in all three dimensions. Based on scanning areas of each fiducial, an exact three-dimensional position of the device 170 is obtained so that module 240 can then capture high quality cell images of cells from the sample in device 170.

Pipet System

Figure 14:
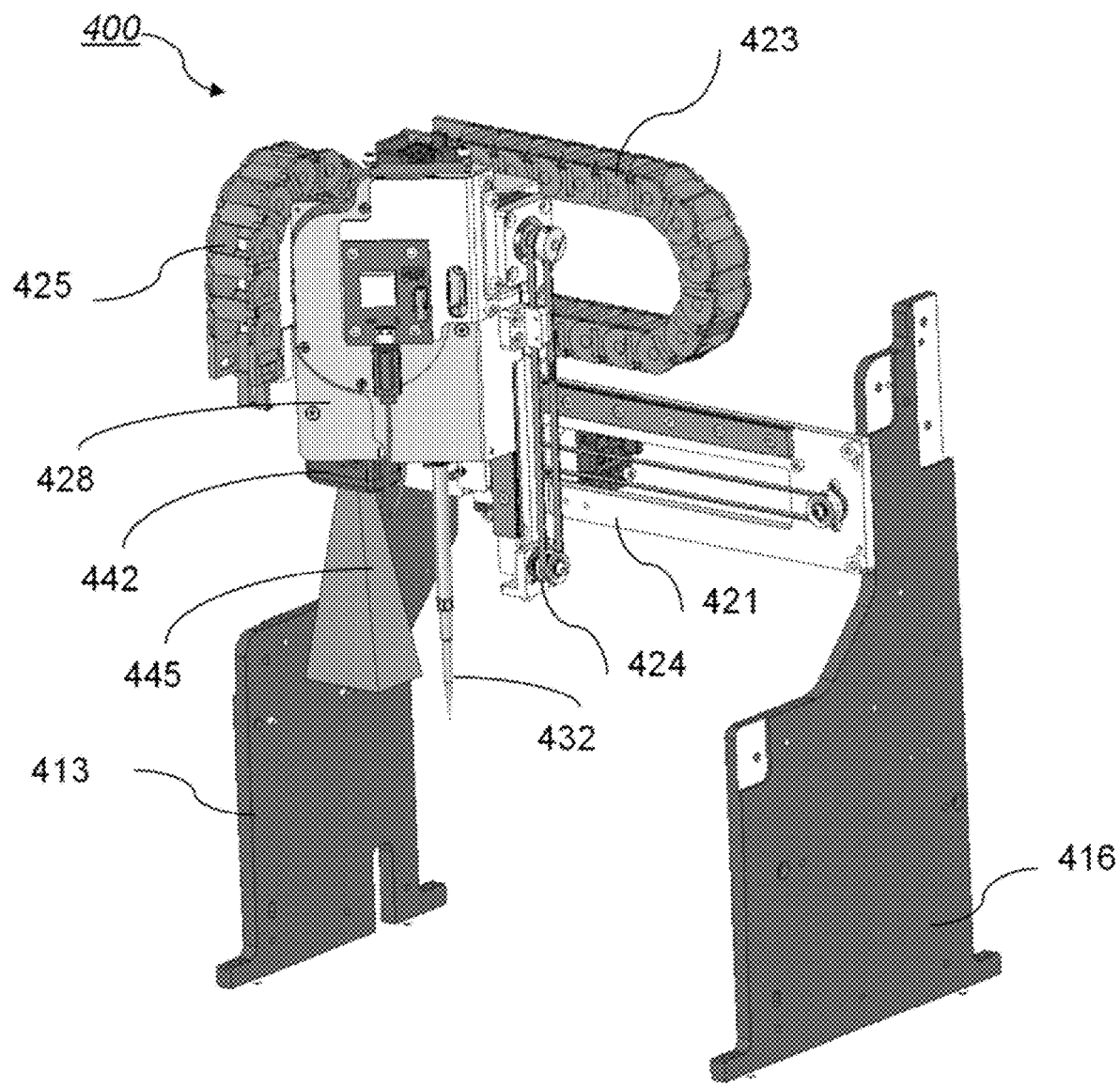
FIG. 14 shows a perspective view of an exemplary multi-axis pipette system of the system of FIGS. 1A and 1B, in accordance with an exemplary embodiment.

FIG. 14 is a perspective view of automatic pipette system 400 with multi-axis guide rails 421, 424. System 400 can include lateral support panels 413, 416 with a lateral guide rail 421. Rail 421 is configured so that housing 428, on which pipette camera 442 and pipette member 432 are mounted, can move side-to-side. Pipette member 432 can be used for assay preparation for all modalities, including with modules 370, 380, and 240. FIG. 14 shows an exemplary field of view 445 of camera 442 used during operations of system 400. Housing 428 can also move up-and-down via guide rail 424. Each of rails 421, 424 can include pulleys driven by one or more motors and used with Z-axis chain 425 and X-axis chain 423. System 400 is configured to directly interact with and distribute resources between support pack 230 and plate 340 so that one or more assays can be analyzed by the respective modules 240, 370, 380. System 400 is configured to directly interact with and distribute resources within support pack 230 (i.e., from the support pack 230 to the device 170 so that one or more assays can be analyzed by the 240 module.

In some aspects, system 400 is used for assay preparation for all modalities, including for modules 240, 370, 380. For example, system 400 can initiate staining operations while also simultaneously initiating blood centrifuging operations (e.g., by spinning of tray 521 to rotate plate 340 loaded therewith). In some aspects, system 400 can directly interact with the immunoassay wash module 600 positioned adjacent panel 16 and aligned with module 240. In some aspects, magnetic member 603 of module 600, shown in FIG. 4, can be caused to pivot away from side panel 416 until parallel with a forward face of support pack 230 causing magnetic washing by module 600. In some aspects, magnetic member 603 of module 600 is in a first position parallel with panel 416 at a first time point (non-operational position) and is in a second position perpendicular with panel 416 at a second time point (operational position). In some aspects, module 240 and module 600 both use module 220 during operation. An imaging device (e.g., camera 203) of module 240 images device 170 on the top of the support pack 230 (near the back of the pack), before/after/during the immunoassay wash module 600 places member 603 on the front face of pack 230. In operation, member 603 attracts magnetic beads, so that excess fluorescent antibody can be removed and replaced with non-fluorescent liquid. In some aspects, the same motor(s) can be used to measure hematology assays as well as sample and assay preparation for modules 370, 380, 390, and/or 240.

Processor System

Figure 15:
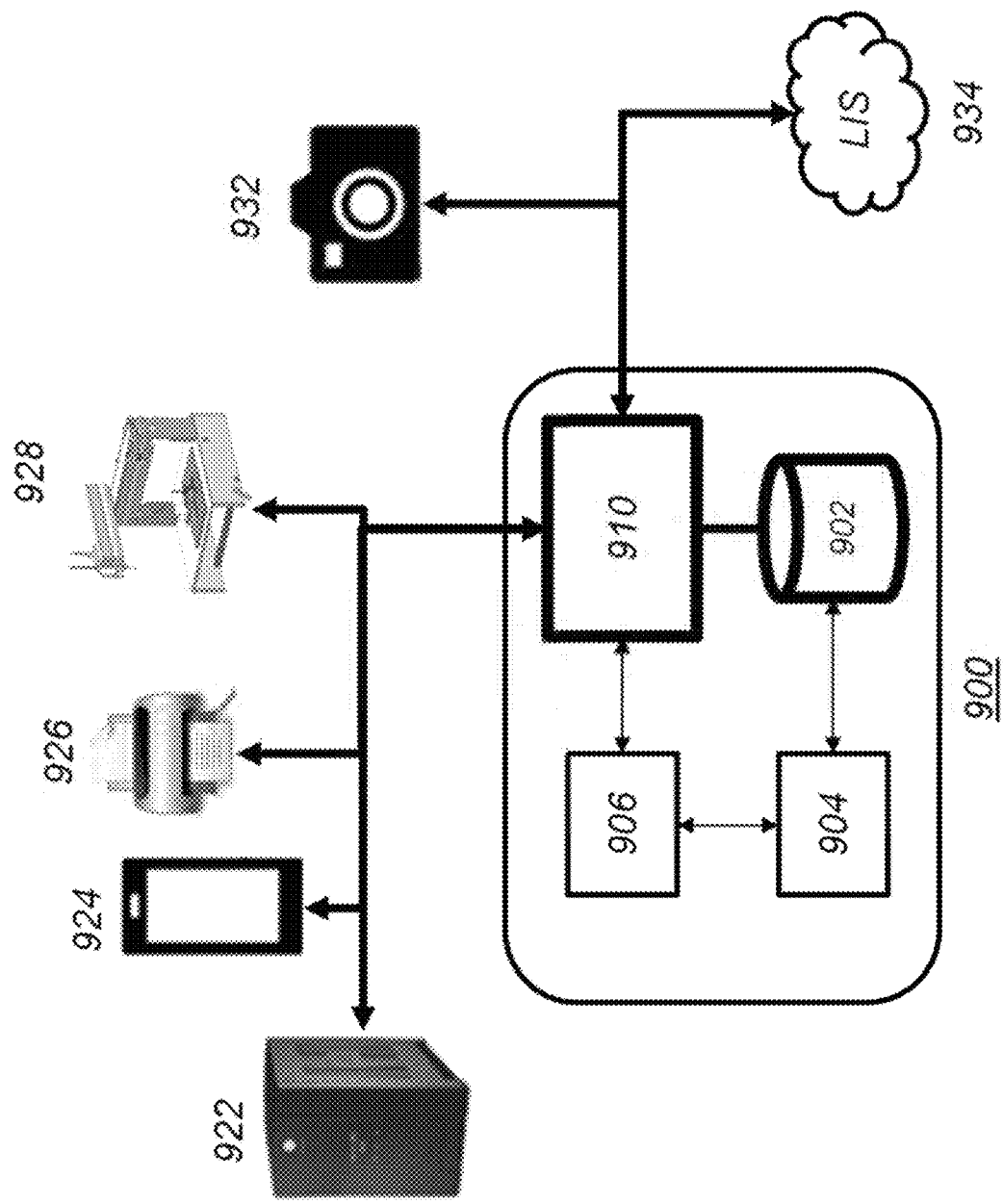
FIG. 15 is a block diagram of an exemplary results processor system, in accordance with an exemplary embodiment.

Turning to FIG. 15, a block diagram environment 900 of previously described results processor system 360 is provided. Environment 900 can include a central control module 910 communicatively coupled to a launcher utility module 906, a database restore utility module 904 (in some embodiments a database restore utility module 904 is absent) and one or more server databases 902. Control module 910 can in turn actively receive data from one or more devices external to environment 900, wired data connections and/or wireless data connections, such as, for example, a local area network (LAN), wide area network (WAN), Ethernet, wireless fidelity (Wi-Fi), IEEE 802.11, Bluetooth or other short-range radio communication, near field communication, or any combination thereof. For example, an uninterrupted power supply (UPS) 922, printer 926, instrument hardware 928 (e.g., system 400), and one or more imaging devices 932 (e.g., cameras of system 100) can be connected directly to control module 910. One or more library information systems (LIS) 934 as well as GUI 924 (e.g., GUI 20 of system 100) can be bidirectionally coupled wirelessly to control module 910. LIS 934 can include aspects such as download test order, release results, and host query(ies). GUI 924 is configured to receive, store, and transmit data such as user login, user management, sample run setup, sample workflow, assay definition file import, result and report management, system configuration, troubleshooting, maintenance, etc.

In some aspects, to run a sample, the user logs into the system and is immediately shown a screen with the menu of assays and/or panels shown as tiles. The user selects the assay and/or panel to be run by touching it on the screen of GUI 921. In some aspects, the user may select one or more assay and/or panel. The user then enters the patient information and can use a barcode scanner to scan in a patient ID if desired. The user touches a button on the GUI 924 to open one or more sample receiving drawers, which extends the disc tray and support pack trays out for loading. The GUI displays on-screen directions on how to load the sample (i.e., by inverting it eight times [no sample pre-processing—no washing, additional mixing, pipetting, plasma isolations, dilutions, etc.] and then removing the blood tube cap) and presents a single button to close the drawer after loading the consumables. If a disc and/or support pack are not loaded into the diagnostic instrument, the instrument will retract the disc tray and support pack tray and close the sample receiving drawer.

The GUI can be better understood by the following numbered paragraphs:

Paragraph 1. A method for loading a sample into a diagnostic instrument, the method comprising:
  extending by the diagnostic instrument a drawer comprising a disc tray and support pack tray;
  receiving by the disc tray a disc and receiving by the support pack tray a support pack wherein the support pack comprises at least a portion of the sample;
  closing by the diagnostic instrument the drawer thereby loading a sample into a diagnostic instrument.

Paragraph 2. The method of paragraph 1 wherein the diagnostic instrument further displays on a graphical user interface a button to open the drawer; and receiving by the diagnostic instrument the user's selection of the button to open the single drawer.

Paragraph 3. The method of any preceding paragraph wherein the diagnostic instrument further displays on a graphical user interface a button to close the single drawer; and receiving by the diagnostic instrument the user's selection of the button to close the single drawer.

Control Module

Figure 16:
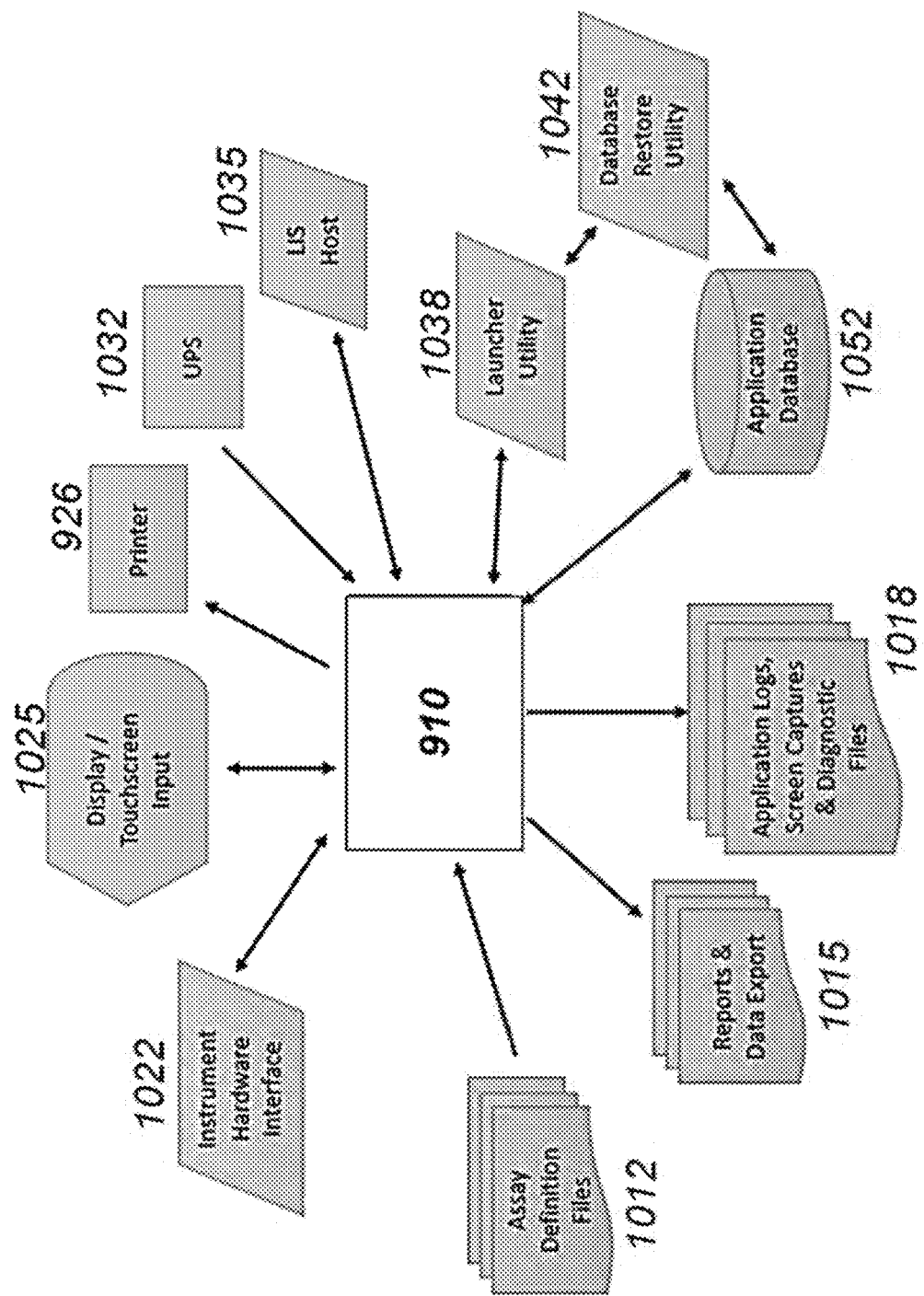
FIG. 16 is a block diagram of an application context system for operations of the control module of the system of FIG. 15, in accordance with an exemplary embodiment.

FIG. 16 is a block diagram of an application context system for operations of module 910. In some aspects, module 910 can unidirectionally receive data from one or more assay definition files 1012, and UPS 1032. In some aspects, module 910 can bidirectionally receive data from instrument hardware interface 1022, GUI input 1025, LIS host 1035, a launcher utility 1038, and an application database 1052. In some situations, the launcher utility 1038 displays a splash screen on the GUI with error code in case of instrument software fatal error/INI file (initialization file) not being present or correct. In some embodiments, the launcher utility 1038 for manages instrument software and software upgrades. In some aspects, utility 1038 can bidirectionally exchange data with database restore utility 1042, which similarly bidirectionally exchanges data with application database 1052. In some aspects, the database restore utility 1042 is absent and utility 1038 can bidirectionally exchange data with application database 1052. In some aspects, based on received data, module 910 can send data (e.g., data packets, instructions for one or more operations, etc.) to reports/data export module 1015, application logs, screen captures, diagnostic files 1018, and printer 926.

Figure 17:
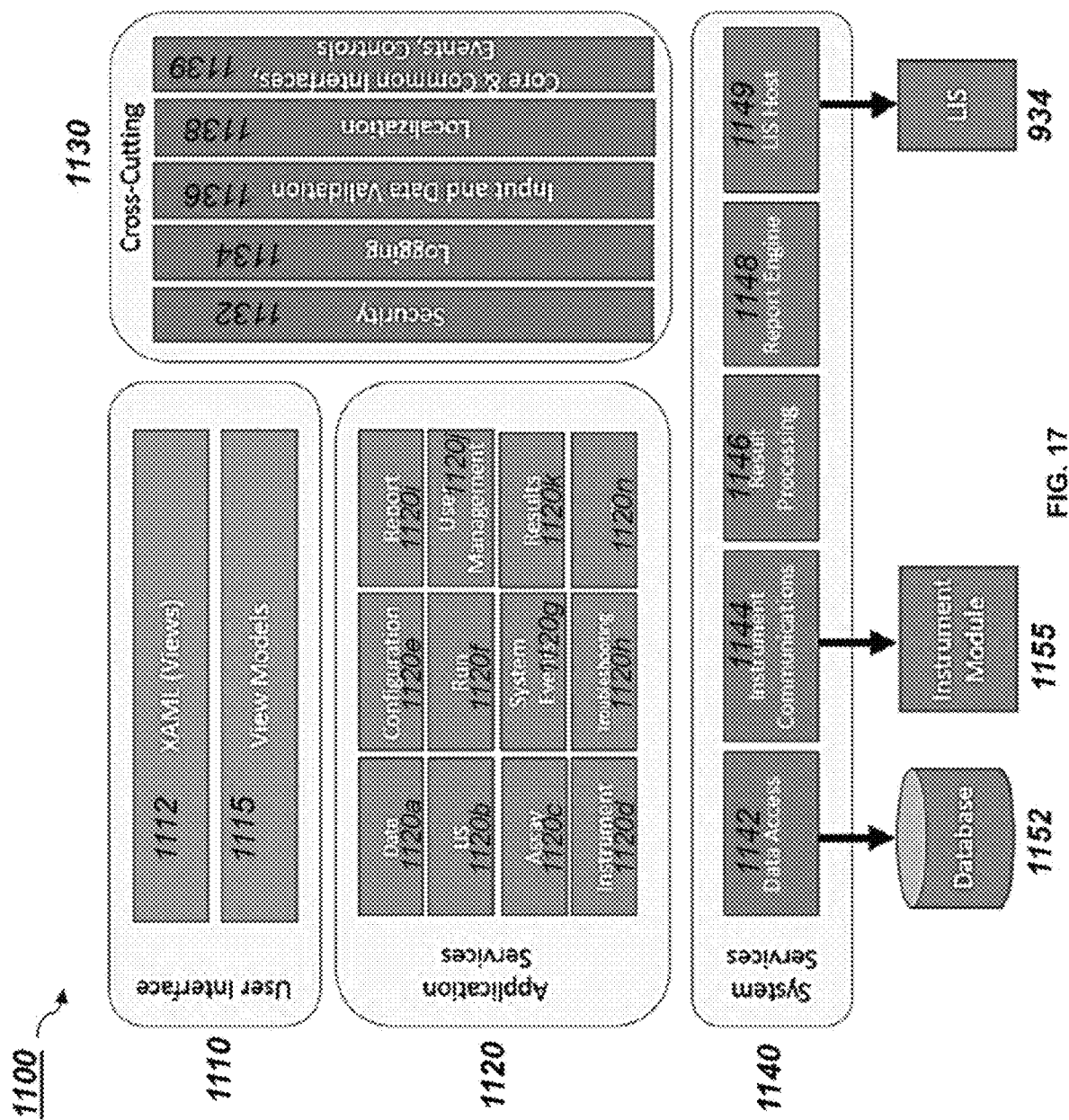
FIG. 17 is a block diagram of a logical composition system for operations of an exemplary results processor system, in accordance with an exemplary embodiment.

FIG. 17 is a block diagram of a logical composition system for operations of an exemplary results processor system 1100 (e.g., previously described system 360), in accordance with an exemplary embodiment. System 1100 can include a plurality of layers, such as a user interface layer 1110, an application services layer 1120, a cross cutting layer 1130, and a system services layer 1140. In some aspects, layer 1110 can include XAML (views) logic 1112 and view models logic 1115. In some aspects, layer 1120 can contain applications from among a pre-determined set of applications, including data, configuration, reporting, LIS, run, user management, assay, system events, results, instrument, troubleshooting, etc. In some aspects, layer 1130 can include security 1132, logging 1134, input and data validation 1136, localization 1138, and core and common interfaces, events, and controls 1139. In some aspects, layer 1140 can include data access 1142 communicatively coupled to one or more databases 1152. Layer 1140 can include an instrument communications module 1144 communicatively coupled to instrument module 1155. Layer 1140 can include LIS host 1149 communicatively coupled to LIS 934, from FIG. 15. Layer 1140 can also include result processing 1146 and a report engine 1148.

In some aspects, all the modules in the diagnostic instrument share software, firmware, and combinations thereof. In some aspects, all mechanical components are controlled via firmware and CANBus communication lines, which in turn is controlled by software. In some aspects, all optical components are controlled via software housed on the single board computer (SBC) of the results processor system. In some aspects, all optical components are not controlled via the same software. In some aspects, all optical components are controlled via software housed on the SBC except the PMT detector in the immunoassay module which is controlled via firmware housed on the SBC.

Optical Module

In some embodiments, the diagnostic instrument comprises one, two, three, four, five, six, seven, eight, nine, or ten detection modules. In some embodiments, the diagnostic instrument comprises four optical modules. The four optical modules include: 1. a cell imager 243 to collect high resolution brightfield and fluorescent images for hematology tests. 2. an absorbance module 383 with a spectrophotometer to measure the light absorbance through the microwells for endpoint, kinetic, and immunoturbidimetric clinical chemistry tests. 3. A confocal fluorescent laser scanning module 373 for bead-based immunoassays. 4. A CCD camera for collecting assay readings in addition to quality control images. In some embodiments, the diagnostic instrument comprises optical module(s) and an electrical sensor. In some embodiments, the diagnostic instrument comprises four optical module(s) and an electrical sensor. As such, the system comprises four optical modules to detect analytes from three, four or more modules (electrochemistry, IA, clinical chemistry or hematology). As such, the system comprises four optical modules to detect analytes from three, four or more modules (electrochemistry, IA, clinical chemistry or hematology) and an electrical sensor to detect analytes from the electrochemistry module.

In some embodiments, the optical signal is transmitted via optical fiber to the receiver, who then converts the optical signal back into an electrical signal. In some embodiments, the optical signal is not transmitted via optical fiber. In some embodiments, the hematology module, IA module, the clinical chemistry module, electrochemistry module or combinations thereof do not transmit the optical signal via an optical fiber.

Process

Figure 18:
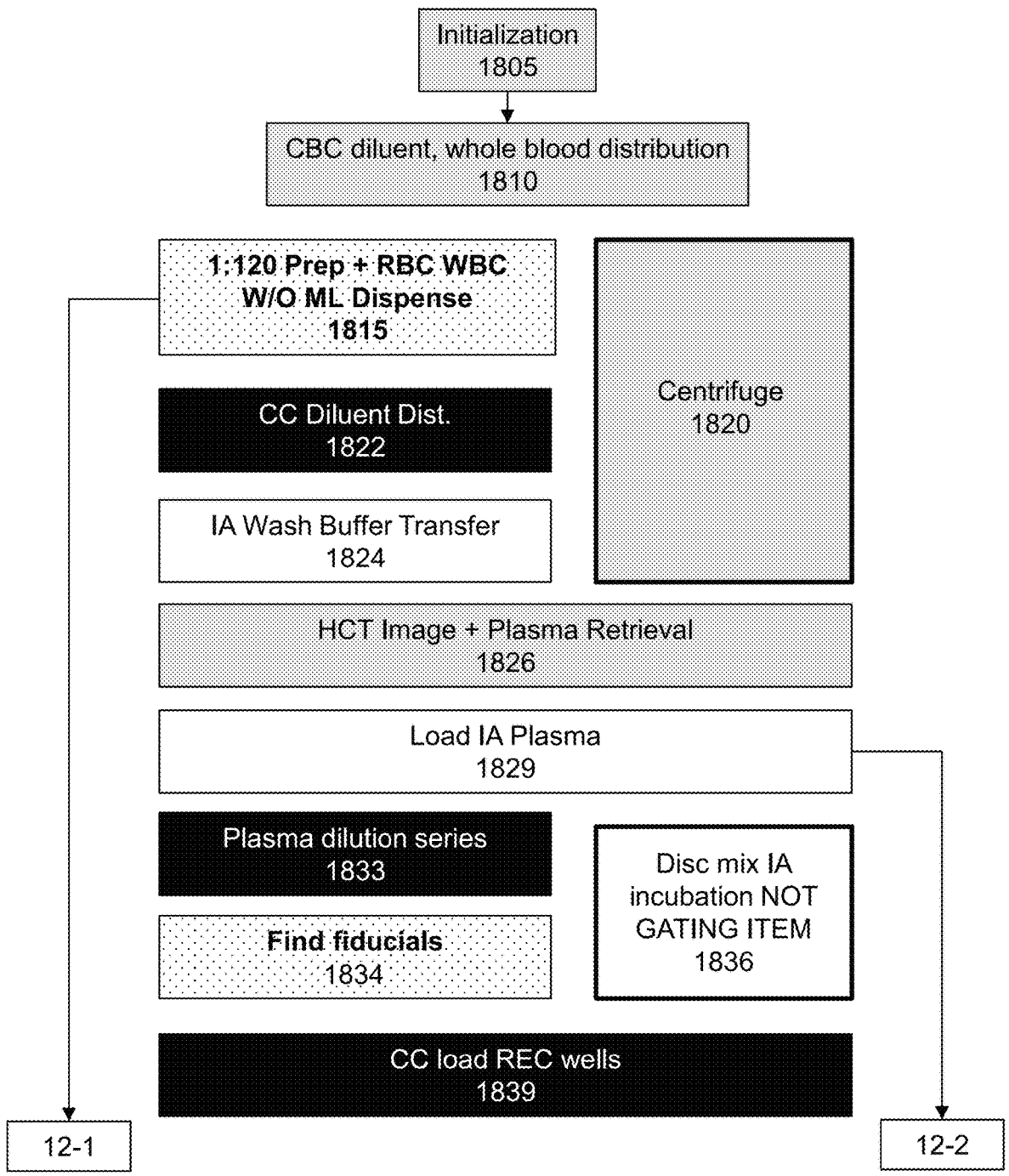
FIGS. 18-19 show a flow chart for a sequence of events of operations of the system of FIGS. 1A to 1B in a plurality of different modes, in accordance with an exemplary embodiment.
Figure 19:
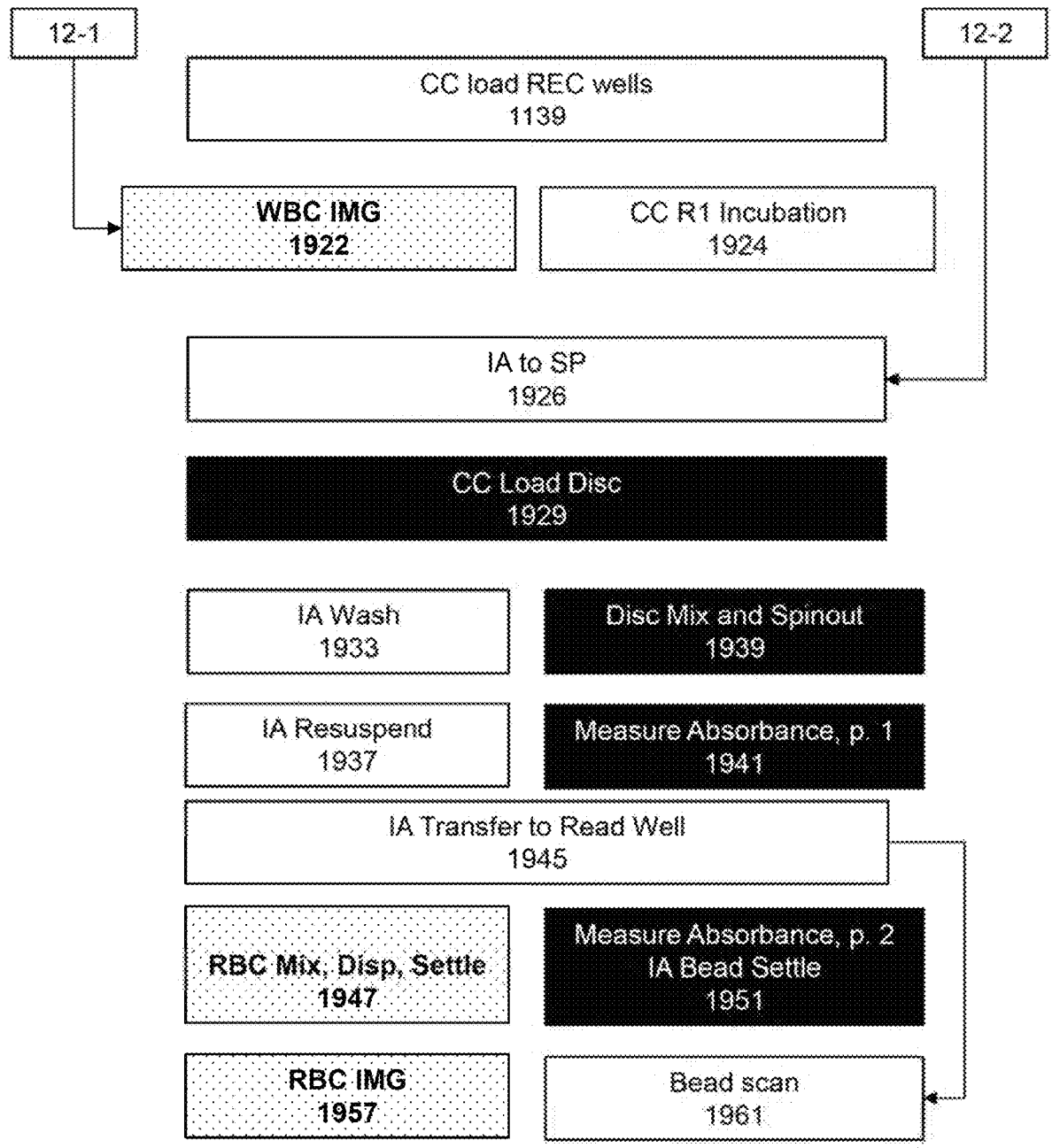

FIGS. 18-19 show a flow chart for an exemplary sequence of events of system 100 having a plurality of different modalities, in accordance with an exemplary embodiment, beginning from initialization step 1805 through one or more steps of sample preparation, carrier orientation diagnostics, and ultimately optical measurements and/or electrochemical measurements by respective modules. Going through the depicted steps of the sequence illustrated, it is understood that blocks in gray show events that are shared between assay modalities, blocks with dots show events for using the hematology module and processing hematology assays, blocks in black show events for using the clinical chemistry module and processing clinical chemistry assays, and blocks in white show events for using the IA module and processing immunoassays. Going through the depicted steps of the sequence illustrated, it is understood that blocks on the left take place in the support pack while blocks on the right take place in the disc; blocks that span both take place in both the support pack and the disc. The sequence shown in FIGS. 18-19 is merely one exemplary sequence and to one of ordinary skill in the art, it will be readily apparent that any step or operation of FIGS. 18-19 may be modified and one or more of the procedures, processes, or activities of FIGS. 18-19 may include different procedures, fewer procedures than depicted, different processes, and/or activities and be performed by some different modules, in some different orders. In some embodiments, the sample does not require upfront pre-analytical processing. The diagnostic instrument is designed to be plug-and-play and is factory calibrated. As shown in FIG. 18, initialization 1805 comprises homing of one or more of the consumables, scanning all (3) barcodes, integrity check for barcodes, calibrating the system based on data in the barcodes and combinations thereof. Step 1810 of FIG. 18 comprises distributing the whole blood to tubes in the support pack and wells in the disc and diluting a portion of the whole blood in the support pack with saline and fluorescent stain for WBC imaging as part of the hematology module. Steps 1815, 1822 and 1824 take place in the support pack, at the same time whole blood in the disc is centrifuged 1820. In step 1815, a second dilution 1:120 is made in the support pack for RBC imaging. In step 1822, diluent (water) is distributed to clinical chemistry tubes in the support pack. In step 1824, immunoassay wash buffer is transferred to tubes in the support pack. At step 1826, the hematocrit (hematology assay) image is taken in the disc by the camera (clinical chemistry imager) and plasma from the whole blood is distributed back to the support pack. In step 1829, plasma for an immunoassay is moved back to the disc, but to a different location than where it was taken from in step 1826. Steps 1833, and 1834 take place in the support pack, at the same time an immunoassay incubation takes place in the disc 1836. In step 1833, undiluted plasma in the support pack is diluted for clinical chemistry assays. In step 1834, the hematology module (cell imager 243) locates the fiducials in the monolayer. In step 1836, the disc mixes the immunoassay by rotating clockwise and counterclockwise to mix the plasma and immunoassay reagent. In step 1839, diluted plasma is moved from the support pack back to the disc and loaded into the reaction wells. In FIG. 19 at step 1922, WBC imaging is taken by the hematology module (cell imager 243) at the same time the clinical chemistry reactions are incubating in the disc. In step 1926, the immunoassay reaction (plasma plus immunoassay reagent) is moved back to the support pack. In step 1929, plasma is loaded into the disc in the outer wells for clinical chemistry assays. Steps 1933, washing the IA reaction in the support pack with the wash module takes place at the same time as step 1939 the disc mixes (rotates clockwise and counterclockwise) to mix the clinical chemistry reactions in the reaction wells. In step 1937, the pipet module resuspends the beads in the IA reaction at the same time as step 1941, the clinical chemistry detection instrument (absorbance measurer) measures a first portion of the clinical chemistry assays in the outer circle of the disc. In step 1945, the IA reaction is transferred back to a read well in the disc. Step 1947 (the RBC is mixed, dispensed into a different tube in the support back and allowed to settle) takes place at the same time as step 1951 (the clinical chemistry detection instrument [absorbance measurer] measures a second portion of the clinical chemistry assays in the outer circle of the disc.) and the beads in the IA reaction are allowed to settle. Steps 1957 (imaging the RBC with the hematology module (cell imager 243) at the same time as step 1961 (imaging the beads in an immunoassay with the immunoassay imager (fluorescent laser scanning module 373). Electrochemical detection steps are not shown. Generally speaking, the electrochemistry cartridge 391 can be loaded with sample simultaneously with steps 1820, 1826, 1829, 1834, 1836, 1922, 1924, 1937, 1939, 1941, 1947, 1957, 1951 or 1961. Generally speaking, the electrochemistry cartridge 391 can be detected simultaneously with steps 1820, 1826, 1829, 1834, 1836, 1922, 1924, 1937, 1939, 1941, 1947, 1957, 1951 or 1961. Generally speaking, the electrochemistry cartridge 391 cannot be loaded or analytes detected during step 1933 (IA wash).

FIG. 21 is a flow chart of an exemplary method 2100 for multi-modal method for multianalyte detection. In some aspects, the method 2100 can include step 2105 of scanning, by a detection instrument of a multi-modality blood analysis system, user-related information of a sample into a computer system. The method 2100 can include step 2110 receiving, by the detection instrument, a cartridge comprising a single sample. The method 2100 can include step 2115 measuring, by the detection instrument in a clinical chemistry mode, by the computing system controlling a clinical chemistry module of the multi-modality blood analysis system, at least one of an optical absorbance and a scattering value. The method 2100 can include step 2120 measuring in an immunoassay mode, by the computing system controlling an immunoassay (IA) module of the multi-modality blood analysis system, one or more vessels of the cartridge to measure fluoresce. The method 2100 can include step 2125 measuring in a hematology mode, by the computing system controlling a hematology module of the multi-modality blood analysis system, one or more hematology assays (e.g., by cell imaging) of a general cartridge well. Not shown, the method 2100 can include an additional step of measuring in an electrochemistry module, by the computing system controlling an electrochemistry module of the multi-modality blood analysis system, one or more electrochemistry assays (e.g., by the electrical sensor or absorbance module 383) of a general cartridge well. In this example, a single cartridge is capable of detecting an analyte by the electrochemical module, hematology module, IA module, and clinical chemistry module. Detection of these analytes from the electrochemical module, hematology module, IA module, and clinical chemistry module can also be performed on 2, 3, 4, 5, 6, 7, 8, 9, 10, or 1-50 separate cartridges.

In some embodiments, to begin the operation a user opens the single-use consumables (e.g., plate 340 and pack 230) which can be shipped together or separate. When shipped together, the disc can be on top of the support pack. Next, the user can enter patient information (e.g., at the GUI, which is received by the instrument), and loads a patient sample into the support pack. Then the user loads the consumables into the instrument (which is received by the instrument). Next the user selects an assay panel to run (which is received by the instrument), and the instrument processes the sample which takes about 10-75 minutes, or 20-45 minutes. Different assays take different amounts of time to run. The diagnostic instrument obtains results and displays them on a GUI, prints them, reports them to a hospital LIS or combinations thereof. Once the run is done and the cartridges come out, and the touch screen displays the results on the system, results outside of the normal range are flagged.

Once the run is complete, the user removes the cartridges and disposes of them in the biohazard waste. The system has no support liquids such as reagents, buffers, or diluents. The instrument is not plumbed into a house line. The only supporting materials to run the assays are contained in the cartridges. In this way, if new assays are added to the panel that have different reagent, buffer, or diluent requirements, they can be added to the disc, the sample pack or both.

Computer Architecture Diagram

Figure 20:
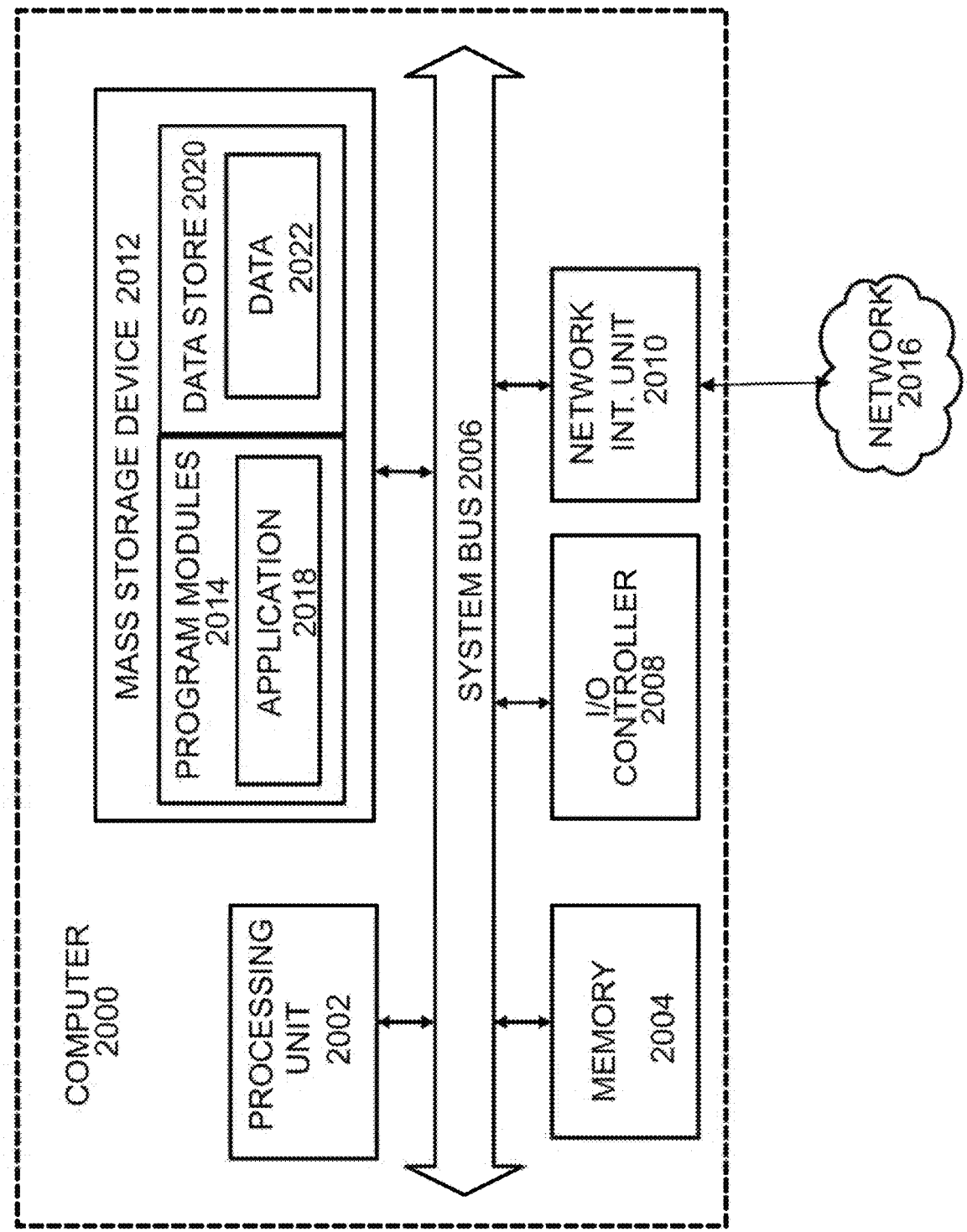
FIG. 20 is a computer architecture diagram showing a general computing system for implementing aspects of the present disclosure in accordance with one or more embodiments described herein.

FIG. 20 is a computer architecture diagram showing a general computing system capable of implementing aspects of the present disclosure in accordance with one or more embodiments described herein, such as the computing systems and related operations for each heretofore module discussed in connection with systems, such as system 100. In any of these example implementations, computer 2000 of the aforementioned may be configured to perform one or more functions associated with embodiments of this disclosure. For example, the computer 2000 may be configured to perform operations in accordance with those examples shown in FIGS. 1A to 19. It should be appreciated that the computer 2000 may be implemented within a single computing device or a computing system formed with multiple connected computing devices. The computer 2000 may be configured to perform various distributed computing tasks, in which processing and/or storage resources may be distributed among the multiple devices. The data acquisition and display computer 2050 and/or operator console 2010 of the system not shown in FIG. 20 may include one or more systems and components of the computer 2000.

As shown, the computer 2000 includes a processing unit 2002 ("CPU"), a system memory 2004, and a system bus 2006 that couples the memory 2004 to the CPU 2002. The computer 2000 further includes a mass storage device 2012 for storing program modules 2014. The program modules 2014 may be operable to analyze data from any herein disclosed data feeds, determine responsive actions, and/or control any related operations. The program modules 2014 may include an application 2018 for performing data acquisition and/or processing functions as described herein, for example to acquire and/or process any of the herein discussed data feeds. The computer 2000 can include a data store 2020 for storing data that may include data 2022 of data feeds (e.g., data from modules 240, 370, 380 as well as any aspects of systems shown in FIGS. 15-17). In some aspects, the device manages the used hard drive capacity automatically. In some aspects, when reaching full use, the system deletes the oldest results to clear up drive space for new records. In some aspects, the system does not store results, when the cartridge is removed, the result is deleted. In some aspects, when a new cartridge is loaded a prior result is deleted.

The mass storage device 2012 is connected to the CPU 2002 through a mass storage controller (not shown) connected to the bus 2006. The mass storage device 2012 and its associated computer-storage media provide non-volatile storage for the computer 2000. Although the description of computer-storage media contained herein refers to a mass storage device, such as a hard disc or CD-ROM drive, it should be appreciated by those skilled in the art that computer-storage media can be any available computer storage media that can be accessed by the computer 2000.

By way of example and not limitation, computer storage media (also referred to herein as "computer-readable storage medium" or "computer-readable storage media") may include volatile and non-volatile, removable, and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile discs ("DVD"), HD-DVD, BLU-RAY, or other optical storage, magnetic cassettes, magnetic tape, magnetic disc storage or other magnetic storage devices, or any other medium which can be used to store the desired information, and which can be accessed by the computer 2000. "Computer storage media", "computer-readable storage medium" or "computer-readable storage media" as described herein do not include transitory signals.

According to various embodiments, the computer 2000 may operate in a networked environment using connections to other local or remote computers through one or more wired connections (e.g., USB, ethernet, etc.) as well as a network 2016 via a network interface unit 2010 connected to the bus 2006. The network interface unit 2010 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems.

The computer 2000 may also include an input/output controller 2008 for receiving and processing input from any of a number of input devices. Input devices may include one or more of keyboards, mice, stylus, touchscreens, microphones, audio capturing devices, and image/video capturing devices. An end user may utilize the input devices to interact with a user interface, for example a graphical user interface, for managing various functions performed by the computer 2000. The bus 2006 may enable the processing unit 2002 to read code and/or data to/from the mass storage device 2012 or other computer-storage media.

The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology. The computer storage media may also represent secondary storage, whether implemented as hard drives or otherwise. Hard drive implementations may be characterized as solid state or may include rotating media storing magnetically encoded information. The program modules 2014, which include the data feed application 2018, may include instructions that, when loaded into the processing unit 2002 and executed, cause the computer 2000 to provide functions associated with one or more embodiments illustrated in the figures of this disclosure. The program modules 2014 may also provide various tools or techniques by which the computer 2000 may participate within the overall systems or operating environments using the components, flows, and data structures discussed throughout this description.

In general, the program modules 2014 may, when loaded into the processing unit 2002 and executed, transform the processing unit 2002 and the overall computer 2000 from a general-purpose computing system into a special-purpose computing system. The processing unit 2002 may be constructed from any number of transistors or other discrete circuit elements, which may individually or collectively assume any number of states. More specifically, the processing unit 2002 may operate as a finite-state machine, in response to executable instructions contained within the program modules 2014. These computer-executable instructions may transform the processing unit 2002 by specifying how the processing unit 2002 transitions between states, thereby transforming the transistors or other discrete hardware elements constituting the processing unit 2002.

Encoding the program modules 2014 may also transform the physical structure of the computer-storage media. The specific transformation of physical structure may depend on various factors, in different implementations of this description. Examples of such factors may include but are not limited to the technology used to implement the computer-storage media, whether the computer storage media are characterized as primary or secondary storage, and the like. For example, if the computer storage media are implemented as semiconductor-based memory, the program modules 2014 may transform the physical state of the semiconductor memory, when the software is encoded therein. For example, the program modules 2014 may transform the state of transistors, capacitors, or other discrete circuit elements constituting the semiconductor memory.

As another example, the computer storage media may be implemented using magnetic or optical technology. In such implementations, the program modules 2014 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

Shared Results

In some aspects, each module reports results for assays on that module. In some aspects, a first module shares assay results with a second different module. In some aspects, assay results from a first module are combined with assay results from a second module. For example, the hematology assay, hemoglobin, and hematology assay, hematocrit, are detected on the disc by the shared resources between the hematology module and clinical chemistry module, i.e., the camera 442, to generate hematology results. The hematology assay, WBC count, is detected on the support pack by the cell imager 243 absorbance module 383 to generate a hematology result. The hemoglobin and hematocrit assay results are shared and combined with results from the results obtained by the cell imager 243. The hematology module reports the final combined hematology result (hemoglobin, hematocrit, and WBC).

In some embodiments, the electrochemistry module via the electrical sensor measures some electrolytes and the clinical chemistry via the absorbance module 383 measures some electrolytes and reports them to the electrochemistry module. In some embodiments, the electrochemistry module via the electrical sensor measures all the electrolytes. In some embodiments, the clinical chemistry module via the absorbance module 383 measures all the electrolytes.

The method 2100 can include step 2125 measuring in a hematology mode, by the computing system controlling a hematology module of the multi-modality blood analysis system, one or more hematology assays (e.g., by cell imaging) of a general cartridge well.

The shared results can be better understood by the following numbered paragraph:

Paragraph 1. A method of diagnosing a patient, comprising:
  receiving a disc by a multi-modality blood analysis system, the disc comprising patient sample and reagents;
  receiving a support pack by the multi-modality blood analysis system, the support pack comprising reagents;
  processing, by the multi-modality blood analysis system, a clinical chemistry assay using reagents from the disc to obtain clinical chemistry assay results;
  processing, by the multi-modality blood analysis system, an immunoassay (IA) assay using reagents from the disc to obtain IA results;
  processing, by the multi-modality blood analysis system, a hematology assay using reagents from the disc to obtain a first hematology assay result; and
  processing, by the multi-modality blood analysis system, a hematology assay using reagents from the support pack to obtain second hematology assay results;
  wherein the second hematology assay results will not be reported if the first hematology assay results are not obtained thereby diagnosing a patient.

Tags

In some aspects, the assay definition file (ADF) contains all the instructions to run at least one an assay on the system. The ADF is loaded onto the instrument prior to use. In some aspects, the plate 340 contains plate information necessary to run at least one assay on the plate on the system. In some aspects, the support pack contains support pack information necessary to run at least one assay on the support pack on the system. In some aspects, the support pack contains support pack information necessary to run at least one assay on the disc on the system. In some aspects, the plate 340 and support pack 230 contain plate information and support pack information necessary to run at least one assay on the system. In some embodiments, this plate information is located on a plate label and the support pack information is located on a support pack label and a hematology label is on the monolayer. In some embodiments, the electrochemistry cartridge comprises a label. In some aspects, each label can include calibration information (e.g., calibration coefficients). In some aspects, the label on the support pack includes calibration information (e.g., calibration coefficients) for assays run on the disc and assays run on the monolayer. In some aspects, the label on the electrochemistry cartridge includes calibration information (e.g., calibration coefficients) for assays run on the electrochemistry cartridge. In some aspects, assay device 170 can include a label, support pack 230 can include a label, electrochemistry cartridge 391 can include a label, and the plate 340 can include a label. In some embodiments, the electrochemistry cartridge does not have a label. In some aspects, each of these labels can be linked so that upon scanning each respective label during operations, the system 100 can detect if plate 340, pack 230, device 170, electrochemistry cartridge 391, and/or the like are compatible for working. If determined to be incompatible, the system 100 will prevent further analytical operations from occurring. The processor receives data from the assay device 170 label, electrochemistry cartridge 391, support pack 230 label, and the plate 340 label and the data received from all three labels (or from 1, 2, or 3 μlabels) is used to calibrate the system and/or configure execution instructions to perform operations on the system. In this way, the diagnostic instrument can run even if it is not connected to the internet. All of the processing instructions used to process a sample are preloaded on the instrument processor 360 and included in one or more label. In some embodiments, only the support pack label and disc label comprise instructions for calibration the monolayer label does not have calibration instructions. In some embodiments, only the support pack label comprises instructions for calibration the monolayer label and disc labels do not have calibration instructions.

Island Mode

In some aspects, the diagnostic instrument functions in the absence of internet connectivity. In some aspects, all information required to convert raw optical data into reportable assay results is contained within the barcodes read within the device at the beginning of a sample run. In some aspects, all processing data rules are loaded into the system as part of the system operating software. The barcodes included in each consumable kit, which are automatically read by the system, contain all necessary data to convert raw optical data into assay results calculated via the results processing data rules. In some embodiments, assay calibration coefficients to go from optical signals to sample concentration are contained in the barcodes.

The island mode can be better understood by the following numbered paragraphs:

Paragraph 1. A method for analyte detection, the method comprising:
  receiving by a diagnostic instrument a cartridge comprising a sample and a barcode;
  reading by the diagnostic instrument the barcode on the cartridge wherein the barcode comprises result processing rules;
  processing the patient sample to obtain raw optical data;
  converting by the diagnostic instrument the raw optical data based on the result processing rules from on the barcode on the cartridge into reportable results;
  reporting by the diagnostic instrument the reportable results.

Paragraph 2. A method for measuring the percentage of red blood cells in a blood sample, the method comprising:
  receiving by a diagnostic instrument a support pack comprising a first blood sample and a blood channel;
  receiving by a disc in the diagnostic instrument a first portion of a first blood sample wherein the disc comprises first and second plasma separation chambers;
  moving by the diagnostic instrument the first portion of a first blood sample into the blood channel in the disc;
  moving by the diagnostic instrument a second portion of a first blood sample into the first and second plasma separation chambers;
  centrifuging by the diagnostic instrument the disc;
  imaging by the diagnostic instrument the blood channel;
  identifying by the diagnostic instrument the blood/channel barrier, the blood/plasma barrier, and the plasma/air barrier in the blood channel;
  calculating by the diagnostic instrument a hematocrit value based on the blood/channel barrier, the blood/plasma barrier, and the plasma/air barrier thereby measuring the percentage of red blood cells in a blood sample.

The system can be better understood by the following numbered paragraphs:

Paragraph 1. A blood analysis system, comprising:
  a disc holder comprising a disc;
  a support pack holder comprising a support pack; and
  a sample processing module.

Paragraph 2. The blood analysis system of paragraph 1 wherein the sample processing module is selected from the group comprising an electrochemistry module, clinical chemistry module, a hematology module, an immunoassay module, and combinations thereof.

Errors

As is appreciated, sometimes errors occur when the system is running. In the case of errors, the device performs a "clean-up" process so that it can ready itself for further use. In some aspects, if an error is detected, the system first detects if a pipette tip is attached to the pipettor. If so, the system will eject the pipette tip back in the pipet tip's original location in the support pack from where it picked up the tip. In some aspects, if an error is detected, the system will mechanically move all axes of motion to their home locations. In some aspects, if an error is detected the system will eject the consumables and allow another sample run to occur.

Thermal Requirements

Disclosed is a diagnostic platform comprising multiple modalities wherein each modality has different thermal requirements to execute assays simultaneously. In some aspects, the clinical chemistry and immunoassay modules require approximately 37 (+/−1) deg C. In some aspects, the hemoglobin assay (hematology panel) require approximately 37 (+/−1) deg C. In some aspects, other hematology assays do not have strict thermal requirements. In some aspects, the DNA amplification module requires different thermal needs from the clinical chemistry and immunoassay modules.

In some aspects, the different thermal requirements to execute assays in different modalities is accomplished by (1) splitting the assay reaction and/or the assay measurement vessels between multiple consumables that reside in separate mechanical modules, (2) designing consumables such that heat flow is directed to specific assay reaction and/or measurement vessels and (3) combinations thereof. For example, the microscope slide used for hematology does not have thermal requirements and can actually benefit from less heat exposure as it will minimize sample evaporation. For example, the electrochemistry cartridge 391 used for the electrochemistry module does not have thermal requirements and can actually benefit from less heat exposure as it will minimize sample evaporation. In contrast, the cartridge requires an approximately 37+/−1 deg C. environment. By splitting these assays onto different locations around the disc, heat can be directed locally where needed. In another example, the support pack is heated via airflow underneath it. The underside of the support pack is hollow but comprises a wall in the middle of the pack that stretches from top to bottom, blocking all airflow from reaching the microscope slide.

In some aspects, all thermal requirements are satisfied without the use of cooling equipment. In some aspects, all assays are performed without the use of refrigerated storage of reagents. In some aspects, the analyzer does not include any reagent carriers, i.e., reagents separately loaded from the reaction carriers. The reaction carriers contain all of the reagents necessary to perform all of the assays.

The thermal requirements can be better understood by the following numbered paragraphs:

Paragraph 1. A multi-modality blood analysis system, comprising:
  a disc holder comprising a disc tray;
  a support pack tray;
  a clinical chemistry module having a first thermal requirement;
  an immunoassay (IA) module having a second thermal requirement; and
  a hematology module and/or an electrochemistry module without a thermal requirement,
  wherein the first thermal requirement and second thermal requirement are the same.

Optical Interference

In some aspects, the diagnostic instrument optically isolates each module. Optical isolation can be achieved through physical barriers between modules. In some aspects, optically isolation is achieved though physical barriers, moveable physical barriers, optical design, and combinations thereof.

Different assays on the various modules can be impacted by optical interference. To reduce optical interference for certain assays hardware barriers, assay scheduling and combinations thereof techniques are utilized. In some aspects, the cartridge is used as a physical barrier that blocks any stray light from reaching hematology module detection instrument (cell imager 243), and vice versa. In some aspects, the assays are read in a particular order such that if stray light from one module were to reach another, the module generating stray light is not used when recording data for assays with which it would interfere.

Optical interference is also caused by vibration. In some aspects, in order to achieve volume- and time-practical plasma separation, centrifugation is needed, which requires high speed rotation and the risk of vibration generation, which can disrupt optical alignment. For example, if one system is imaging blood cells and a neighboring system is centrifuging the disc, the vibrations could transmit through the countertop to the system imaging cells. In some aspects, optical interference caused by vibration is reduced by adding adhesives to lock optical elements in place. In some aspects, optical interference caused by vibration from another nearby machine is reduced by vibration-isolation feet on the system. The vibration-isolation feet reduce the transfer of vibrations between neighboring units, allowing detection devices to be placed within about two feet from one another. In some aspects, the vibration-isolation feet are made of rubber that absorb vibrations rather than transmit them.

Results Processing

Real-Time Data Collection

Disclosed is a diagnostic instrument comprising at least two modalities wherein each modality comprises at least one assay wherein data from each assay is processed during collection. Processing data during collection reduces the chances of processing overload at any one point in time.

Over-Collection/Exclusion of Data

In some aspects, the diagnostic instrument comprising at least two modalities over collects data for at least one assay on the instrument. By over collect, it is meant that more data is collected than is relied upon to generate a detection result. For example, to count red and white blood cells images are collected. However, not all images collected must be used to generate a result. Images of lesser optical quality can be excluded so they do not skew the results, and still generate accurate results. In some aspects, every optical image collected is used to generate a result. In some aspects, not every optical image collected is used to generate a result. In some aspects, optical images collected with an optical quality below a threshold are not used to generate a result.

In some aspects, some data collected is excluded from the result. In some aspects, data caused by variations is subtracted from raw assay optical data to provide accurate and precise assay results.

Disclosed is a diagnostic instrument comprising at least two modalities wherein the two modalities are selected from the group comprising clinical chemistry assays, immunoassays, hematology assays, nucleic acid assays, receptor-based assays, cytometric assays, colorimetric assays, enzymatic assays, electrophoretic assays, electrochemical assays, electrolyte assays, spectroscopic assays, chromatographic assays, microscopic assays, topographic assays, calorimetric assays, turbidmetric assays, agglutination assays, radioisotope assays, viscometric assays, coagulation assays, clotting time assays, protein synthesis assays, histological assays, culture assays, or osmolarity assays. Disclosed is a diagnostic instrument comprising three modalities wherein the three modalities are clinical chemistry, immunology, and hematology. Disclosed is a diagnostic instrument further comprising an electrochemistry module. Disclosed is a diagnostic instrument comprising an electrochemistry module. Disclosed is a diagnostic instrument comprising four modalities wherein the four modalities are electrochemistry, clinical chemistry, immunology, and hematology. Disclosed is a diagnostic instrument comprising three modalities wherein the three modalities are clinical chemistry, electrochemistry, and hematology. Disclosed is a diagnostic instrument comprising three modalities wherein the two modalities are clinical chemistry and hematology. Disclosed is a diagnostic instrument comprising one modality wherein the one modality is selected from the group comprising electrochemistry, clinical chemistry, immunology, and hematology.

In some embodiments, disclosed is a diagnostic instrument capable of processing a sample in at least two assays selected from the group consisting of an endpoint clinical chemistry assay or kinetic clinical chemistry assay, immunoturbidimetry assay, and cell counting assay. In some embodiments, disclosed is a diagnostic instrument capable of processing a sample in at least two assays selected from the group consisting of AST, ALP, HbA1c, TSH, Cholesterol, HGB, WBC, PLT, and RBC.

In some embodiments, the clinical chemistry module's clinical chemistry detection instrument is an optical instrument. In some embodiments, the immunoassay modules' immunoassay detection instrument can detect fluorescence, radiolabeled antigens, ELISA, and/or chemiluminescence. In some embodiments, the immunoassay modules' immunoassay detection instrument can detect fluorescence, radiolabeled antigens, ELISA, and/or chemiluminescence and the immunoassay modules' immunoassay detection instrument can be a bead scanner. In some embodiments, the immunoassay modules' immunoassay detection instrument is a spectrometer, can detect fluorescence, radiolabeled antigens, ELISA, or chemiluminescence, a bead scanner, and/or is an optical instrument such as a camera. In some embodiments, the hematology modules' hematology detection instrument is a microscope. In some embodiments, the hematology modules' hematology detection instrument is a microscope and an optical instrument such as a camera. In some embodiments, the electrochemistry module's detection instrument is an electrical sensor. In some embodiments, the electrochemistry modules' detection instrument is an electrical sensor and/or an absorbance module 383.

In one embodiment, a results processor system (e.g., system 360) of this disclosure is used in an in vitro diagnostics (IVD). The system can include a sample handler module configured to accept a plurality of sample reaction carriers wherein at least a first reaction carrier (e.g., support pack 230) includes at least one patient sample tube and at least a second reaction carrier (e.g., plate 340) does not comprises a patient sample tube. The sample is directly loaded into the second reaction carrier after loading the first reaction carrier and second reaction carrier into the system.

In some aspects, the assay reagents and diluents are preloaded into reaction wells in the second reaction carrier. In some aspects, the reagents and/or diluent are preloaded into reaction wells in the first reaction carrier. In some aspects, a first portion of reagents and/or diluent are preloaded into reaction wells in the first reaction carrier and a second portion of reagents and/or diluent are preloaded in reagent wells in the second reaction carrier and must be moved from the first reaction carrier to the second reaction carrier during processing. The reaction carriers can be loaded via one or more drawers located at a front of the sample handler module that is accessible to a human operator, and one or more analyzer modules configured to aspirate, using at least one pipette, a portion of a patient sample from the first reaction carrier (but not the second reaction carrier) and perform a clinical analysis of at least one of clinical chemistry characteristics and immunoassay characteristics, hematology characteristics or electrolyte characteristic of that patient sample. In some aspects, the patient sample tube does not move from the first reaction carrier during analysis. In some aspects, there is only a single patient sample tube and sample from that tube can be used in electrolyte assays, immunoassays, hematology assays and clinical chemistry assays. In some aspects, there is only a single patient sample tube and sample from that tube can be used in immunoassays, clinical chemistry assays and capture images of white blood cells, red blood cells, and platelets from whole blood.

In one embodiment, a method for analyzing patient samples includes steps of receiving, at a sample handler module, a plurality of reaction carriers wherein the first reaction carrier holds a single patient sample tube and patient sample is loaded directly into the second reaction carrier by the user and all of the reagents necessary to perform the assays are in the first reaction carrier and second reaction carrier. In some aspects, the first reaction carrier comprises reagent vessels and reaction vessels. In some aspects, the second reaction carrier comprises reagent/diluent vessels and reaction vessels. In some aspects, the second reaction carrier only comprises reaction vessels which comprise reagents/diluent. In some aspects, a first portion of reagents necessary to perform the assays are in reaction vessels in the second reaction carrier and a second portion of the reagents necessary to perform the assays in reaction vessels in the second reaction carrier are in reagent vessels in the first reaction carrier and must be moved to the reaction vessels in the second reaction carrier during operation.

The first and second reaction carriers are loaded via one or more drawers located at a front of the analyzer. Steps further include positioning, the first reaction carrier at a first reaction carrier location within the analyzer that is accessible to a sample preparer module, removing a first sample portion from the patient sample tube housed in the first reaction carrier using the sample preparer module, and placing the first sample portion in the first reaction carrier reaction vessel. Steps further include positioning, the second reaction carrier at a first, second reaction carrier location within the analyzer that is accessible to the sample preparer module, removing a second sample portion from the patient sample tube housed in the first reaction carrier using the sample preparer module, and placing the second sample portion in the second reaction carrier reaction vessel. In some aspects, first reaction carrier does not move to a second location during operation. In some aspects, second reaction carrier does not move to a second location during operation. Additionally, steps include performing, by a second analyzer module, a clinical analysis of at least one of clinical chemistry characteristics, immunoassay characteristics, electrolyte characteristics, hematology characteristics and combinations thereof of that patient sample and performing, by a first analyzer module hematology characteristics of that patient sample.

Although systems and methods have been described with reference to specific embodiments, it will be understood by those skilled in the art that various changes may be made without departing from the spirit or scope of the disclosure. Accordingly, the disclosure of embodiments is intended to be illustrative of the scope of the disclosure and is not intended to be limiting. It is intended that the scope of the disclosure shall be limited only to the extent required by the appended claims. For example, to one of ordinary skill in the art, it will be readily apparent that any element of FIGS. 1A-21 may be modified, and that the foregoing discussion of certain of these embodiments does not necessarily represent a complete description of all possible embodiments. For example, one or more of the procedures, processes, or activities of FIG. 21 may include different procedures, processes, and/or activities and be performed by some different modules, in some different orders.

Figure 22:
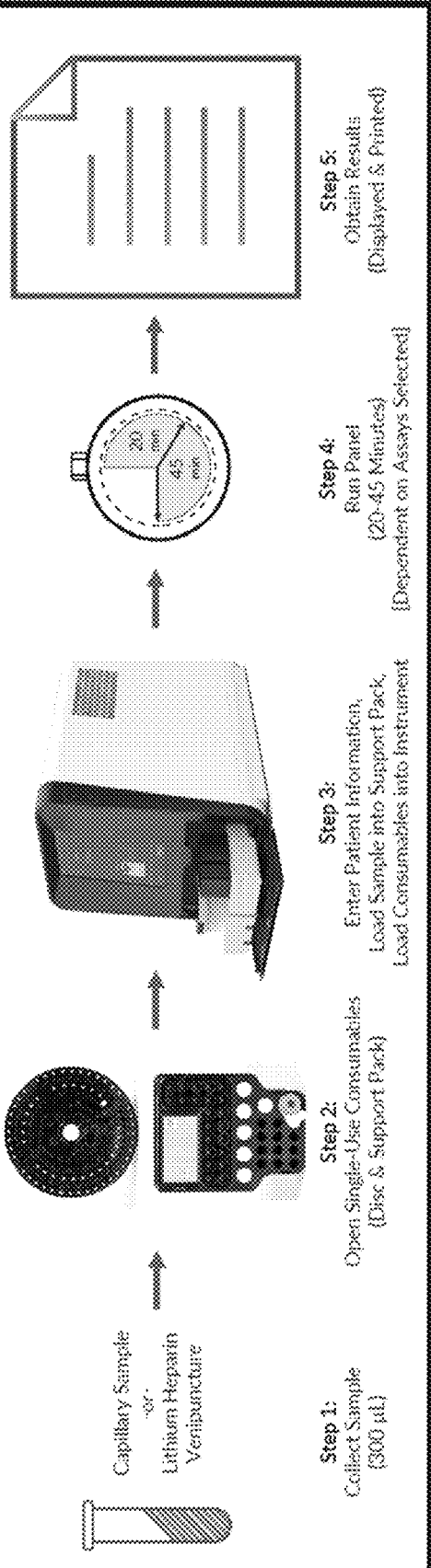
FIG. 22 illustrates a method, according to an embodiment. The diagnostic instrument is fully integrated and automated with no upfront processing or pipetting steps required. Step 1: Insert the sample (~300 μL tube of Li-Hep blood) into the support pack, Step 2: Place single-use disc and support pack into the device, Step 3: Start the panel which comprises a hematology assay, an immunoassay and clinical chemistry assays. At the end of the run, panel results are displayed on the device and can be printed. The consumables are then ejected to be disposed.
Figure 24A:
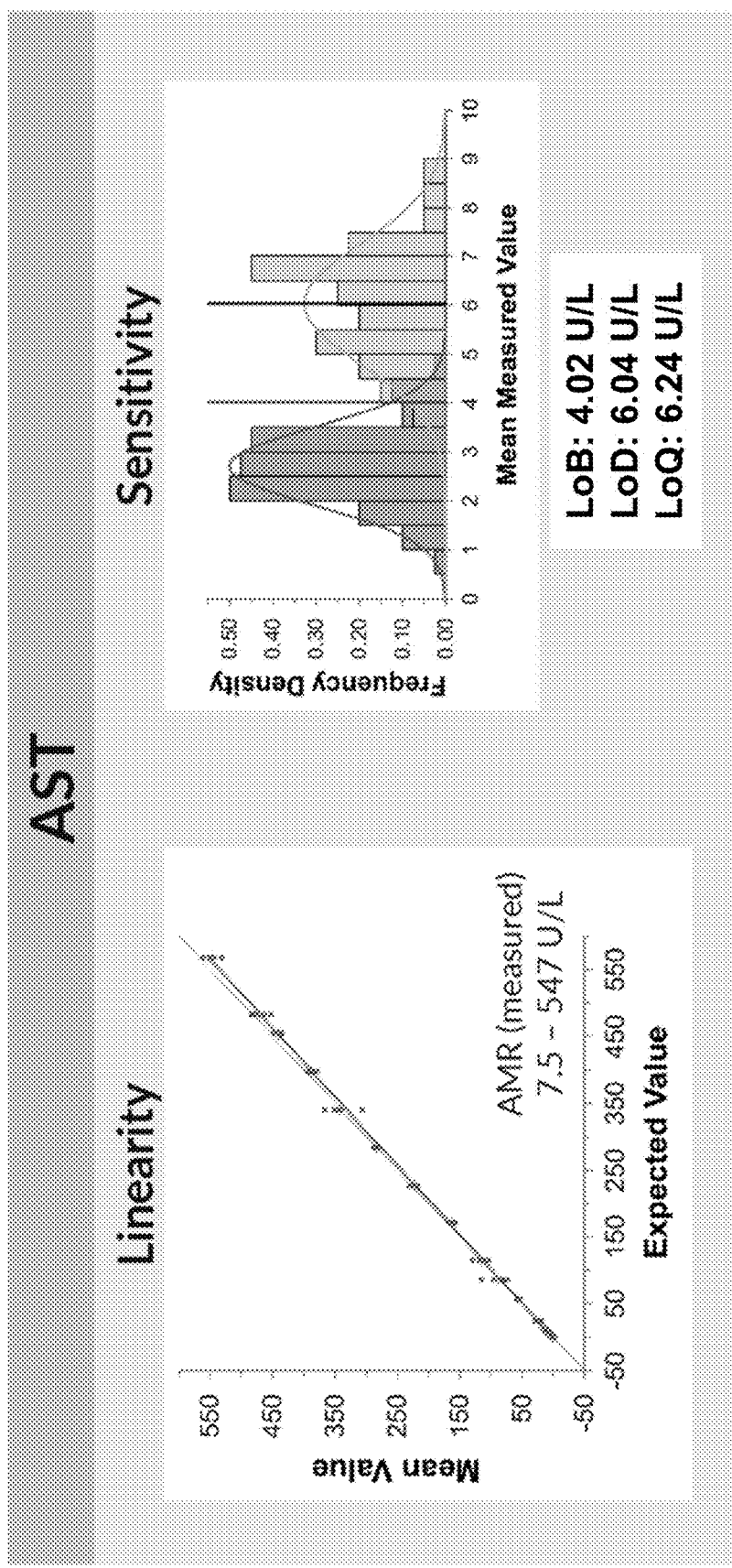
Figure 24B:
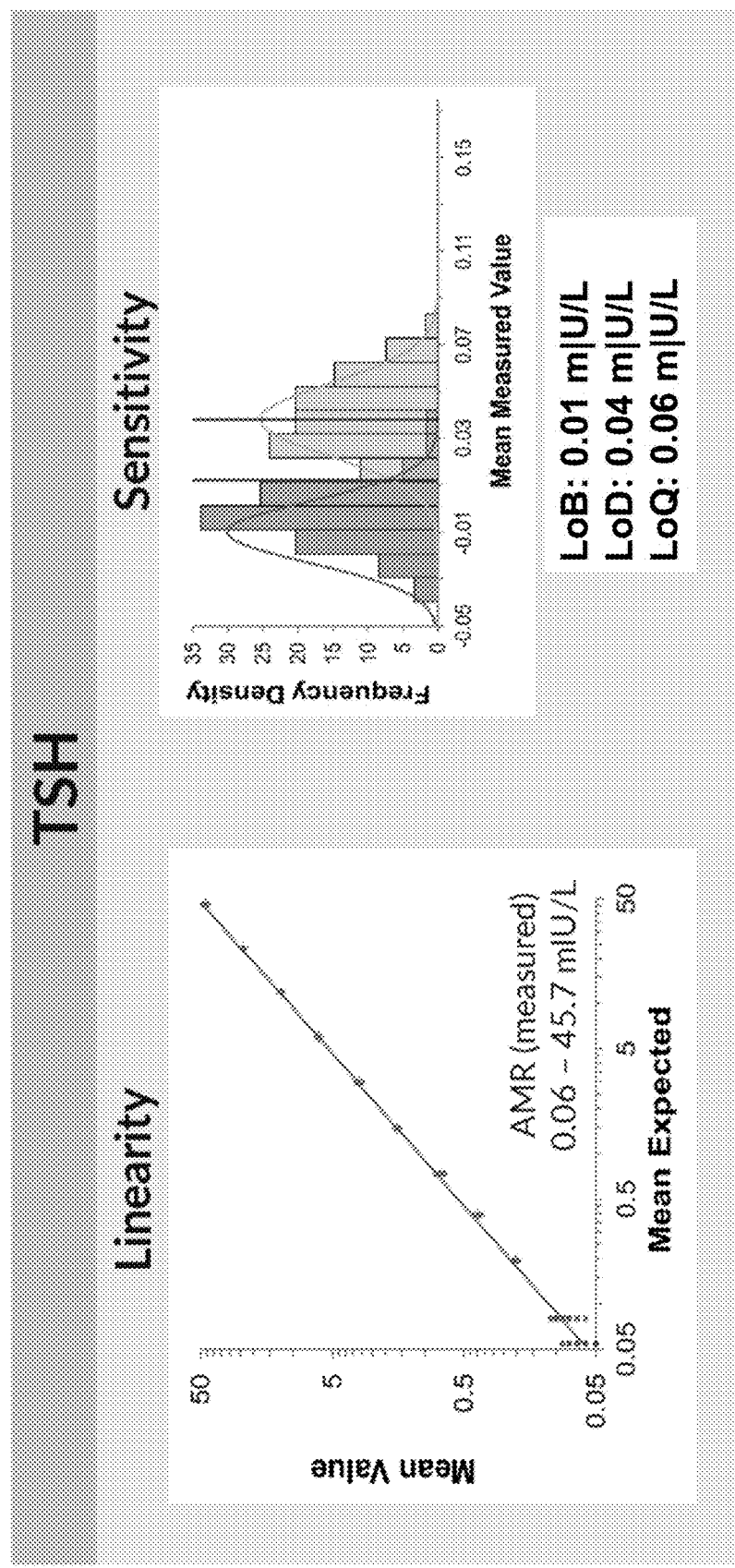
Figure 24C:
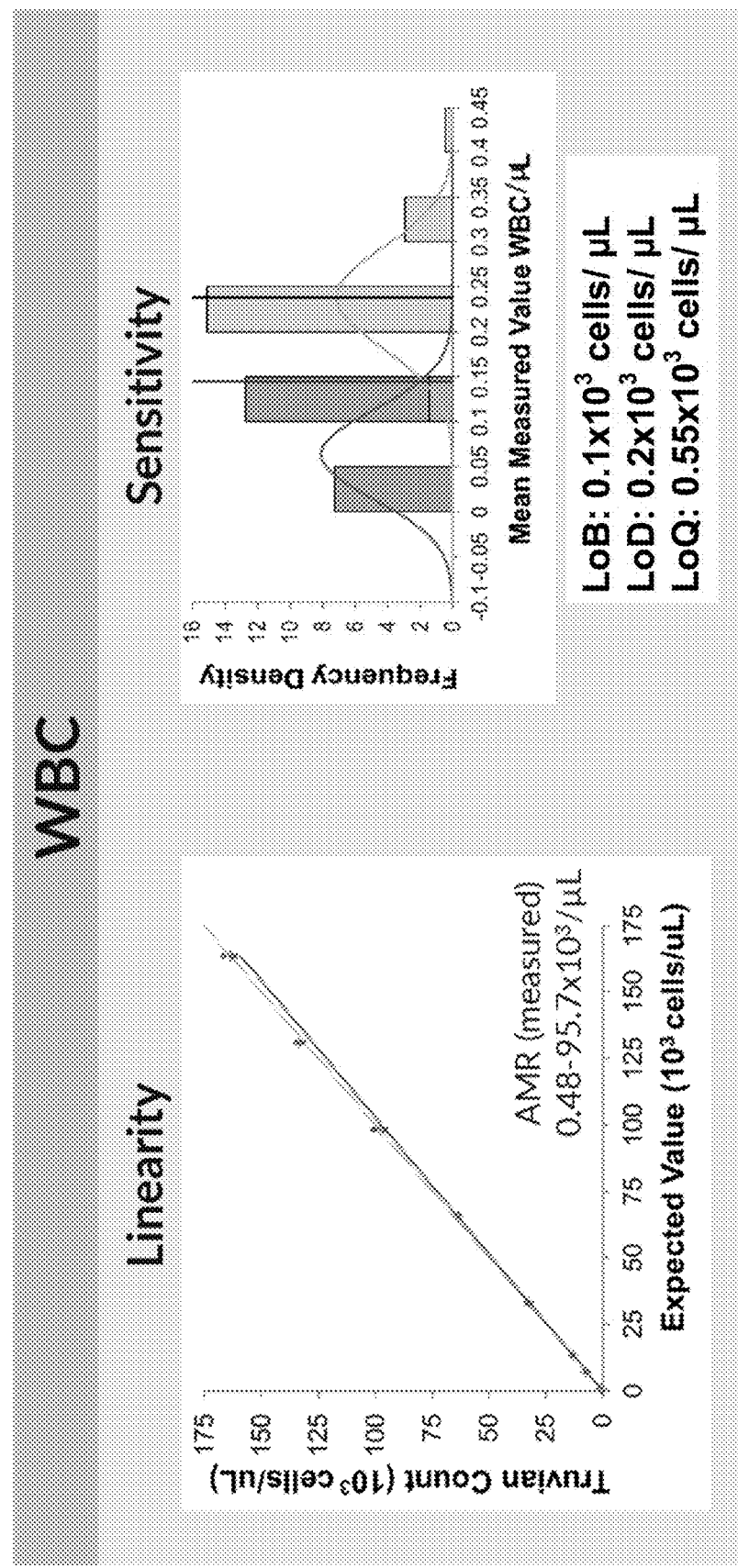
Figure 25A:
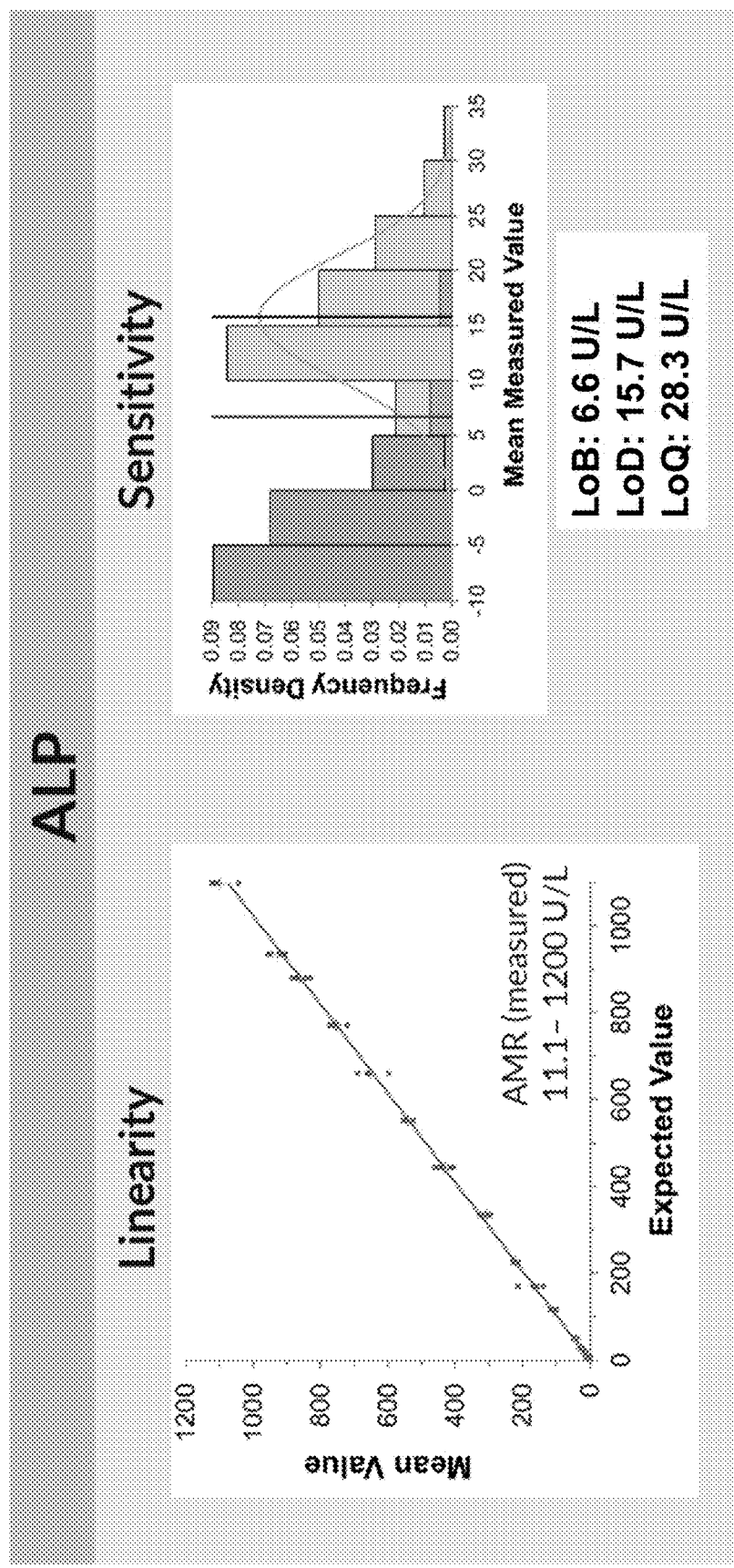
FIGS. 25A-25C show performance data.
Figure 25B:
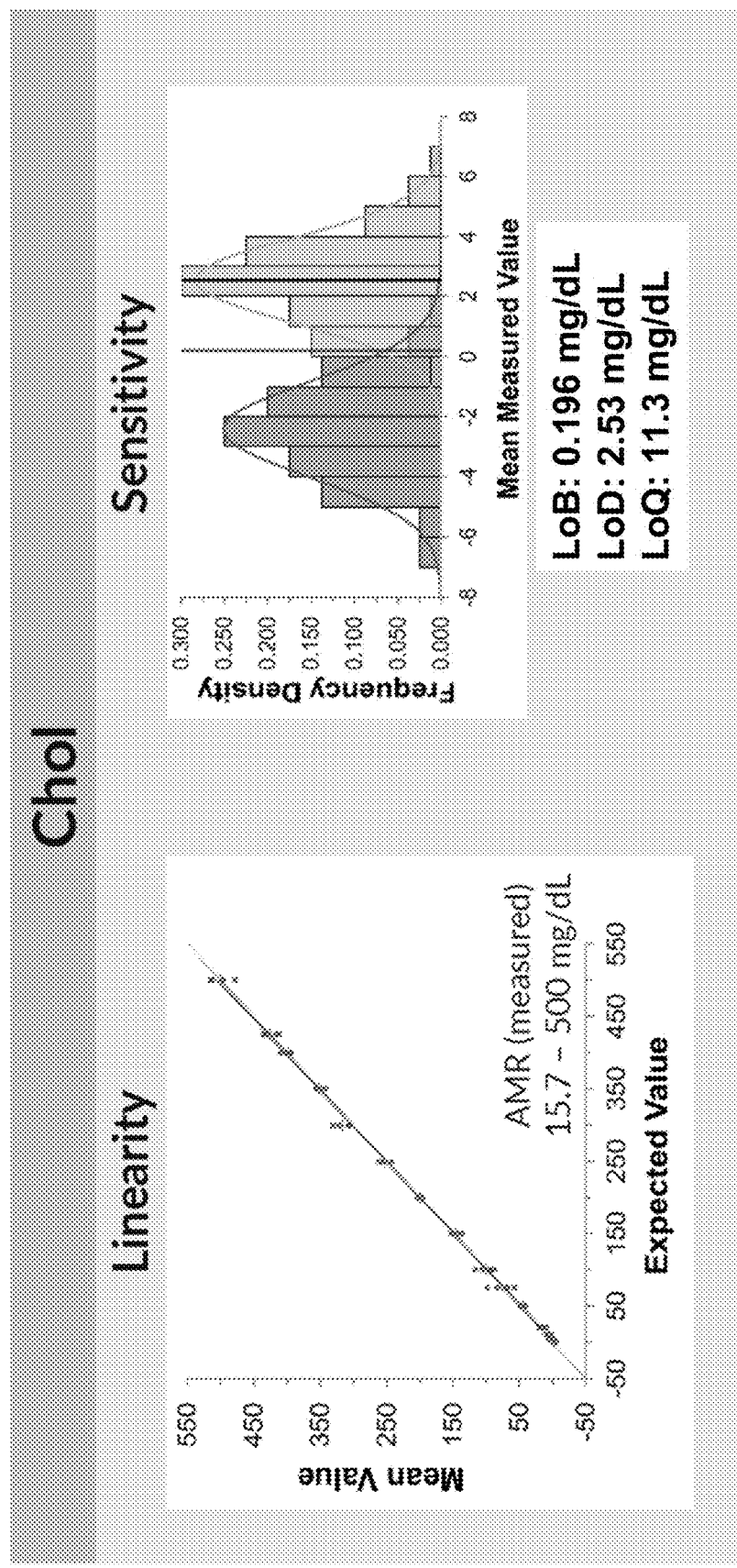
Figure 25C:
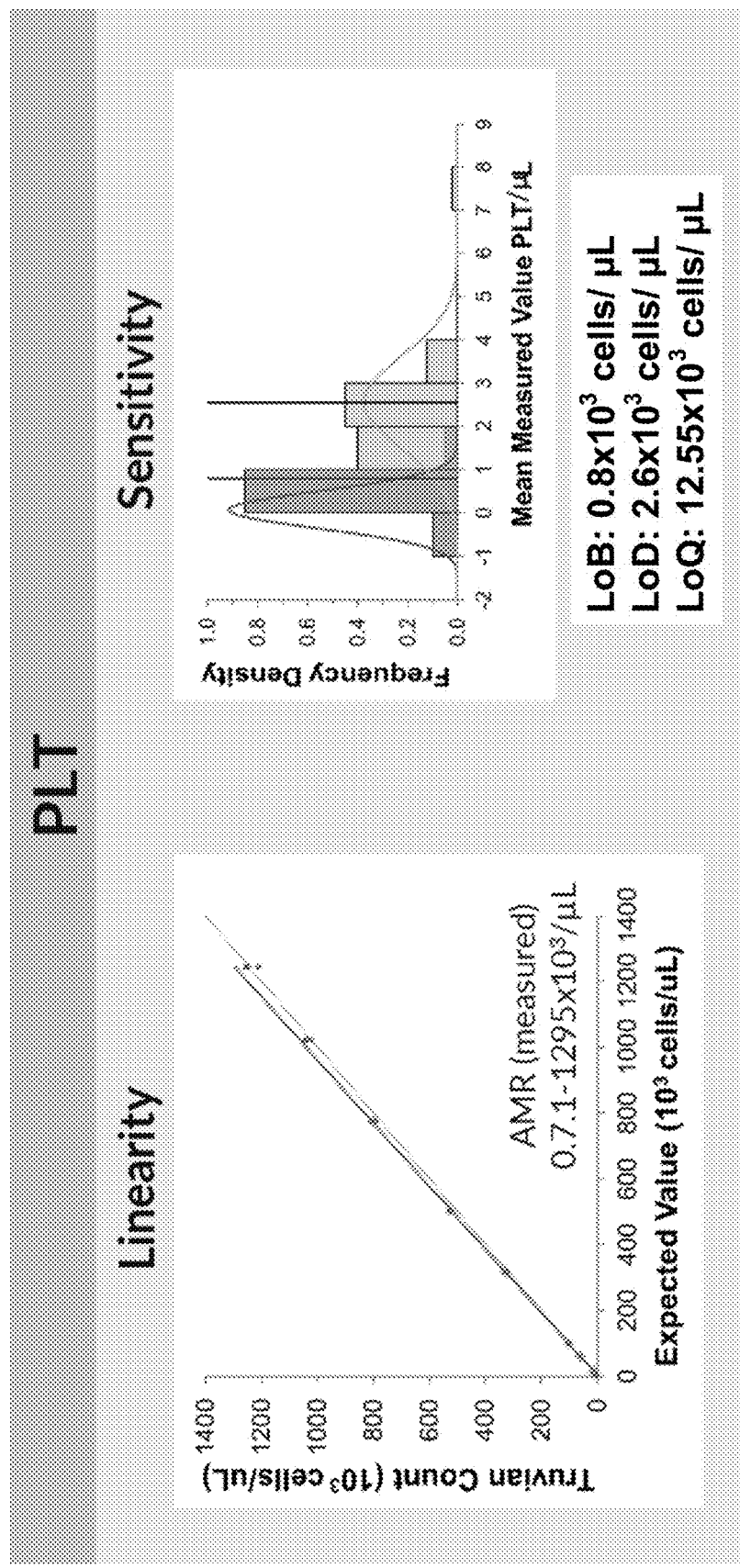
Figure 26A:
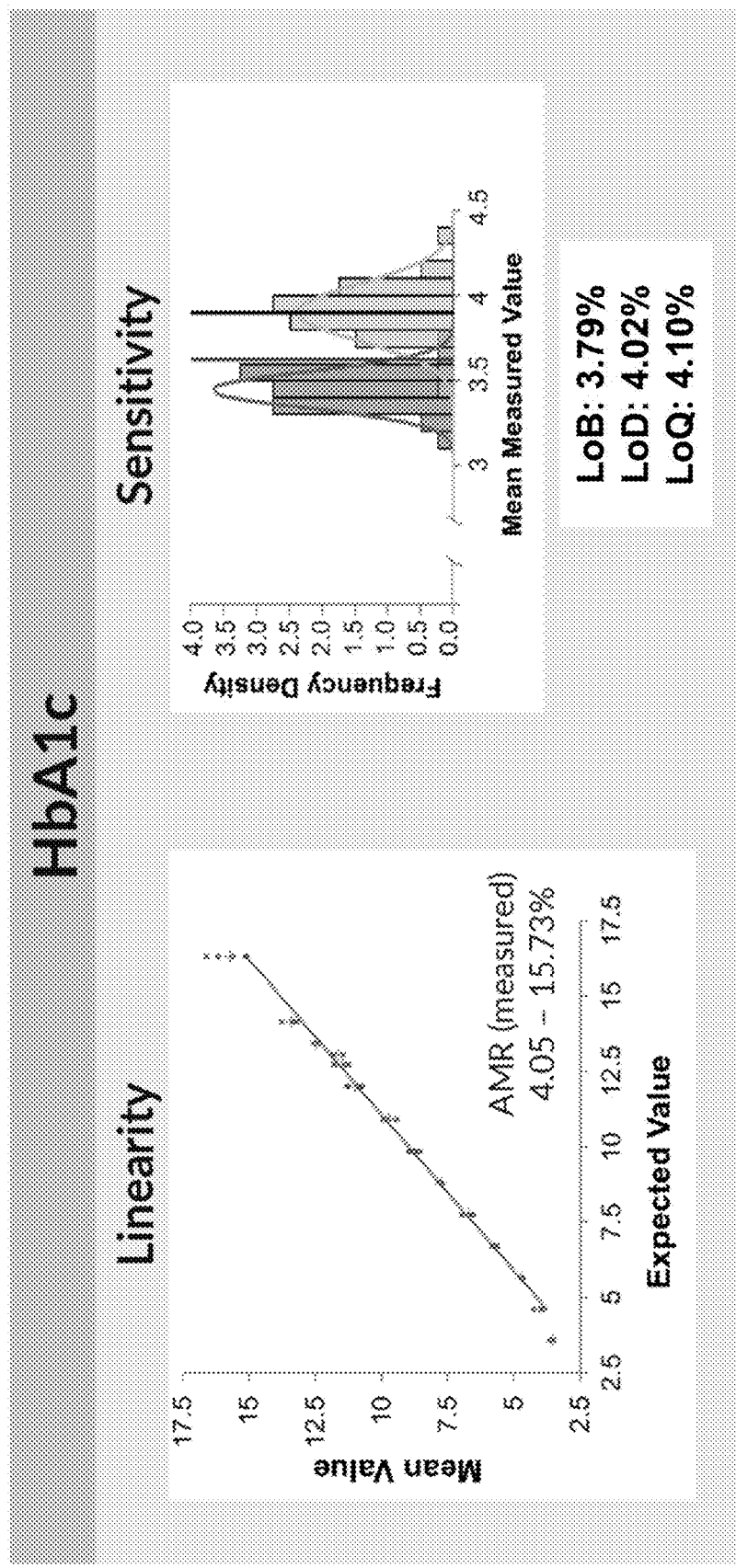
FIGS. 26A-26C show performance data.
Figure 26B:
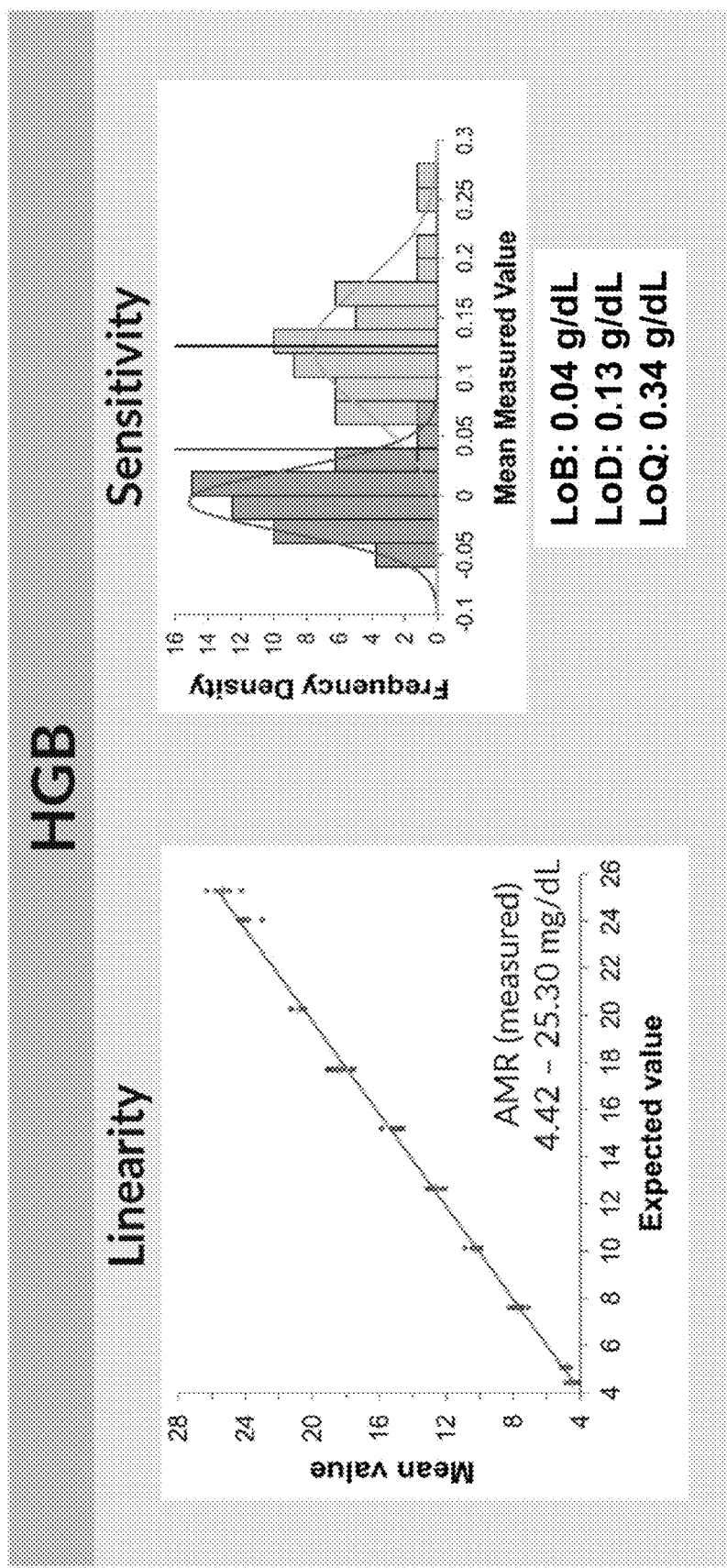
Figure 26C:
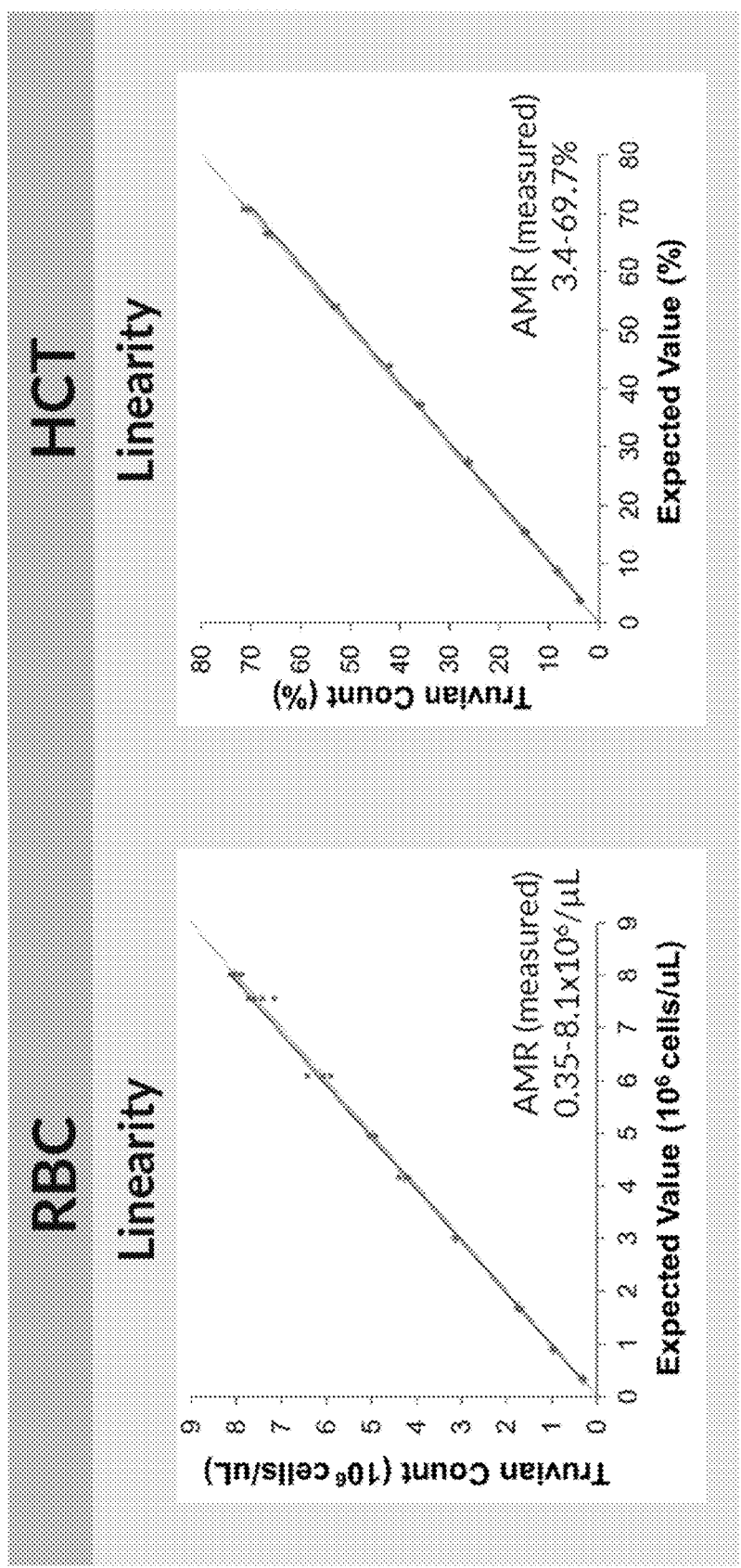
Figure 28:
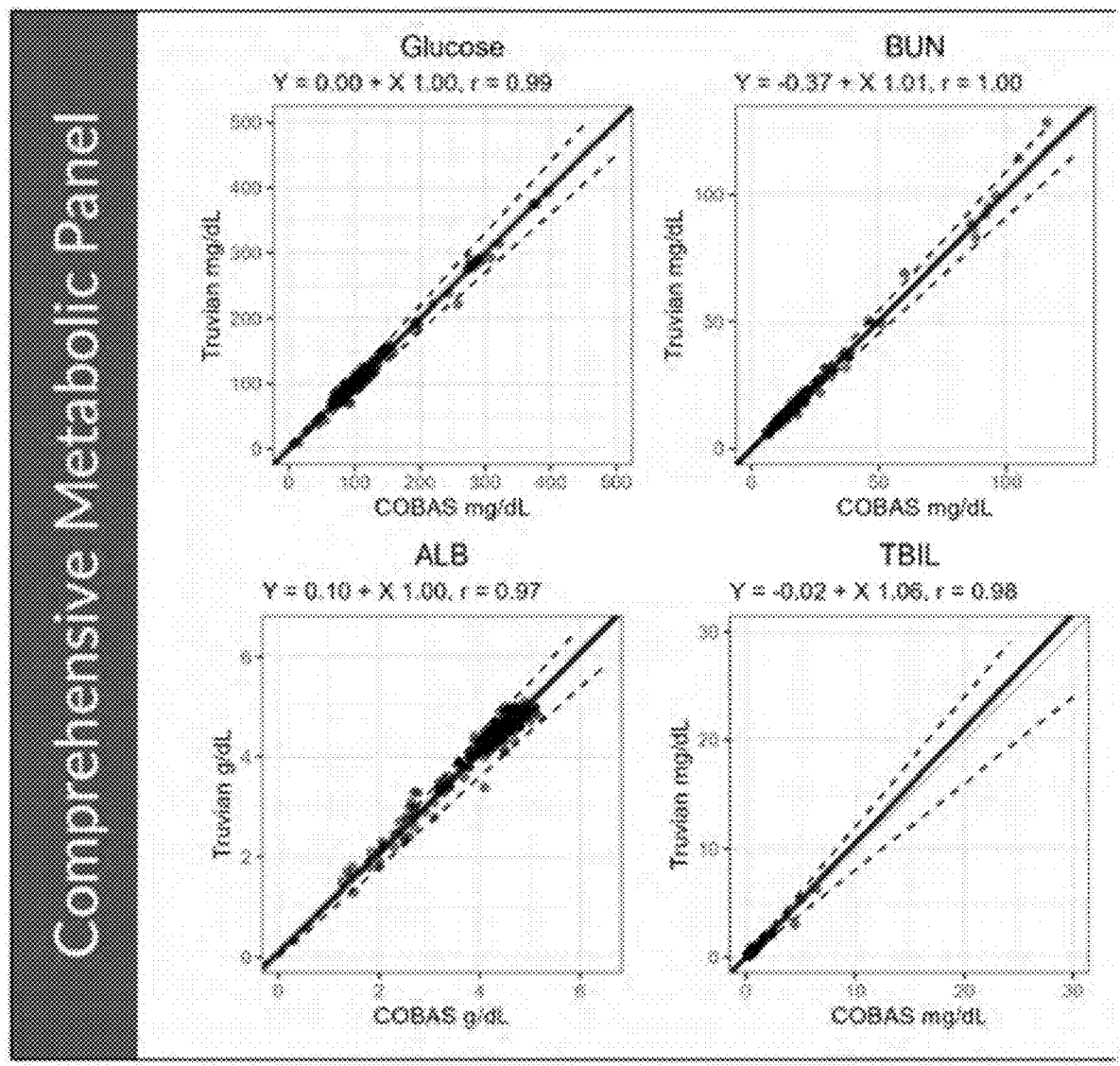
Figure 29:
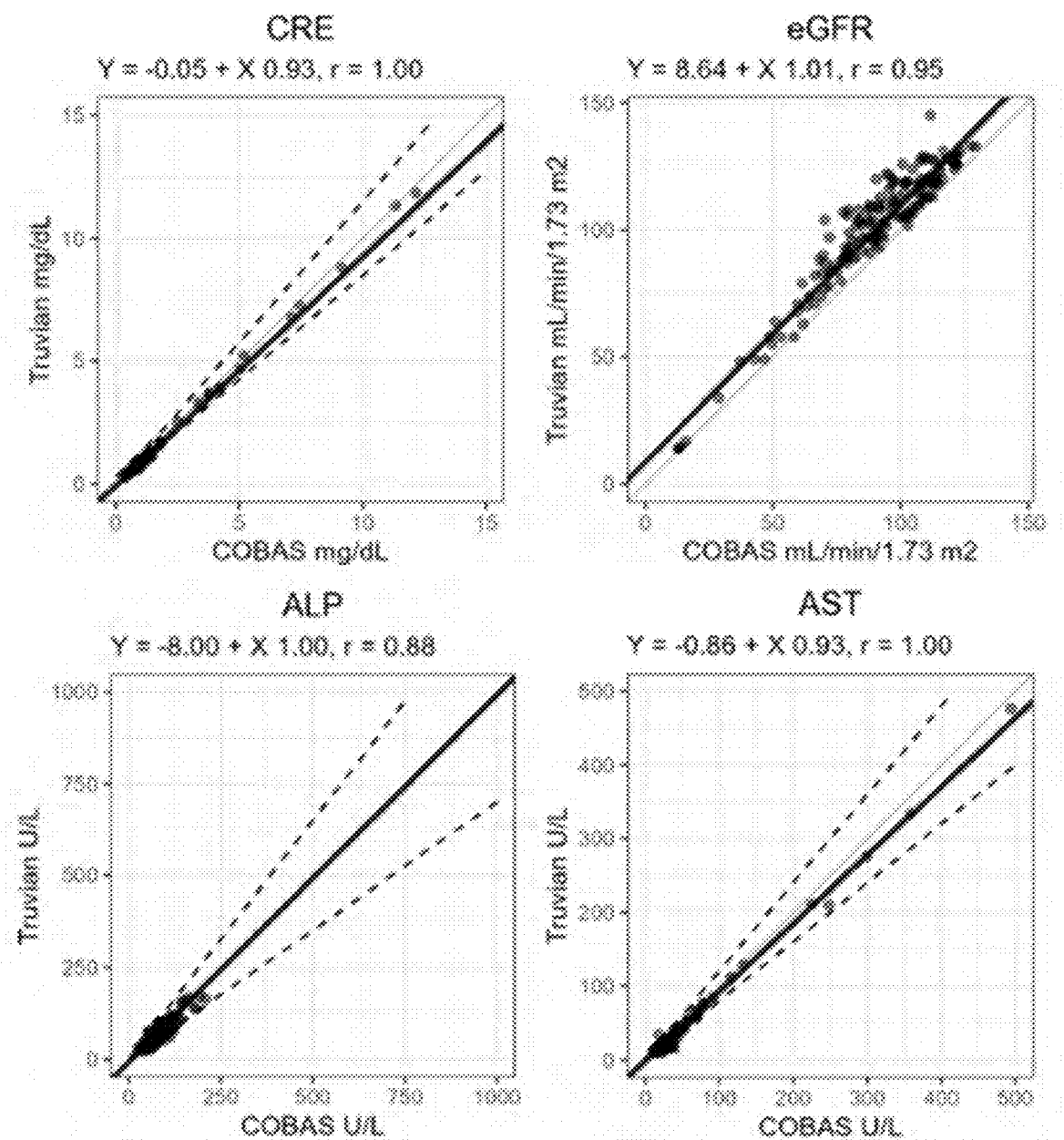
Figure 30:
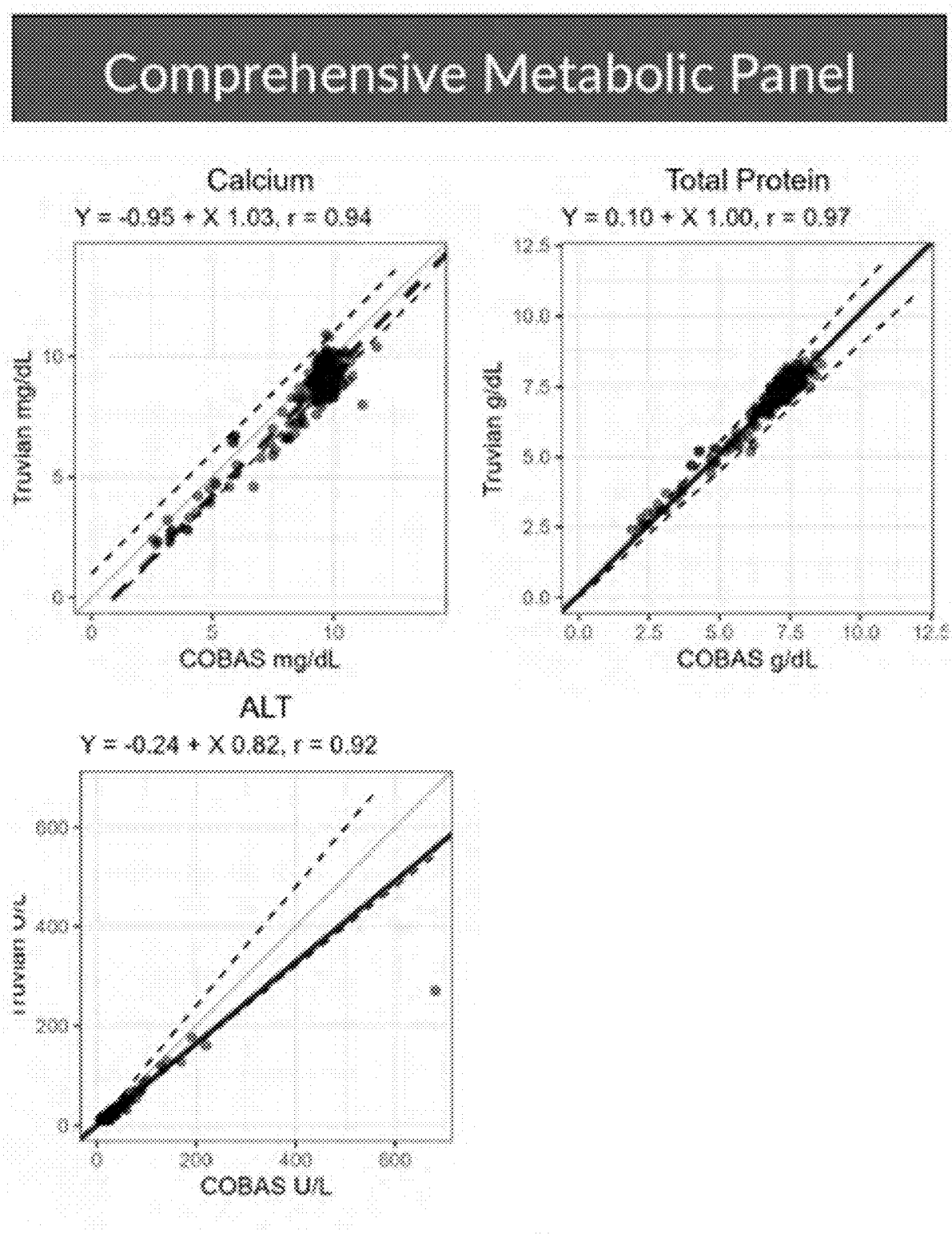

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein Study Overview This disclosure is more clearly understood with a corresponding study discussed more particularly below with respect to performance of system 100. It is understood that data is presented herein for purposes of illustration and should not be construed as limiting the scope of the disclosed technology in any way or excluding any alternative or additional embodiments. FIG. 22 illustrates a method, according to an embodiment of the study. FIG. 23 shows performance acceptance criteria of the study. FIGS. 24A-24C, FIGS. 25A-25C, FIGS. 26A-26C, and FIGS. 32A-32EE show performance data.

Example 1

Introduction

The diagnostic instrument is designed with the aim to decentralize and streamline routine blood testing, replacing traditional send-outs to a central laboratory with a compact, easy-to-use benchtop instrument at point-of-care to ensure timely and actionable results. Using only a small amount of blood from a single heparinized sample, the diagnostic instrument can simultaneously provide results for a full panel of routine blood tests spanning clinical chemistry, hematology, and immunoassays. Evaluation of the diagnostic instrument in an independent external study is important to understand its performance in a real world setting and to identify areas for improvement. To assess the performance of the diagnostic instrument for a comprehensive wellness panel, a two-site study was completed. The study evaluated the diagnostic instrument's precision and accuracy against central laboratory instruments.

Precision and accuracy studies were performed with a wellness panel for clinical chemistry and hematology tests on the diagnostic instrument. The precision study assessed repeatability and reproducibility for each test in the panel across multiple days and instruments. The method comparison study compared the diagnostic instrument to best-in-class FDA cleared central laboratory instruments—the Roche Cobas and Sysmex analyzers—in 258 patients. Bland-Altman and Passing-Bablok regression analyses were used to determine agreement for each analyte in the panel.

Results

In the precision study, the tests evaluated demonstrated good repeatability and reproducibility. The method comparison study showed strong concordance between in-house and central laboratory instruments with no significant differences between the internally and externally collected data or between the diagnostic instrument and central laboratory results.

Conclusions

This first two-site study demonstrated clinical feasibility and promising performance for the diagnostic instrument, which is still under development. The diagnostic instrument showed good precision and accuracy compared to central clinical laboratory instruments for the majority of evaluated tests and the study provided additional areas of focus.

Precision Study

The precision study, based on CLSI EP05-A3 guidelines, was used to evaluate repeatability and reproducibility using commercially available controls for clinical chemistry and hematology. Fresh vials of control material (BioRad and R&D Systems) were used on each of three testing days, to collect five replicate runs on each of three instruments, to produce 45 measurements in total per analyte.

Method Comparison Study

The method comparison study compared the diagnostic instrument's results to those obtained from Roche Cobas (for chemistry) and Sysmex XN and pocH-100i (for hematology) in 258 patients (75 enrolled in San Diego, CA, and 183 enrolled in Seattle, WA).

Donors were consented under IRB approved protocols PS-2023-0001 and 0012022 (IRB Registration: IRB00000533), with each participant donating three tubes of blood. One tube of EDTA anticoagulated blood was collected for analysis on the Sysmex hematology analyzer. One lithium heparin anticoagulated blood (Li-Hep) in a gel-separator tube was collected and centrifuged to isolate plasma for the Roche Cobas. The third tube contained Li-Hep anticoagulated blood, which was run on the diagnostic instrument within one hour of collection.

The EDTA and Li-Hep samples were either analyzed in-house on comparator devices or sent to a central laboratory for testing. Samples sent to the central laboratory were processed following central laboratory instructions and stored at 2-8° C. until courier collection. The study included samples from 208 normal patients and 50 pathological samples from patients with chronic diseases such as Type 1 and Type 2 diabetes, kidney disease, high blood pressure, hypertension, renal failure, and COPD as well as contrived samples to assess the diagnostic instrument's performance across an extended analytical measuring range and around medical decision points.

Contrived samples were prepared for selected analytes found to have inadequate coverage of the measuring range.

High and low samples were contrived for ALB, TP, CA, and ALT by spiking fresh donor whole blood with concentrated analyte stocks or diluting the whole blood sample with saline, respectively. These samples were included for other assays when found to be commutable with donor samples.

Data Analysis

Software was used to assess the precision study data per CLSI EP05-A3 guidelines. Measurement system analysis was performed using a 2-factor model in which testing day was nested within each instrument. A 2-sided confidence interval of the standard deviation was determined for each analyte at the 95% level. Repeatability, within-instrument precision, and reproducibility were calculated for each analyte as standard deviation and % CV.

For the method comparison study, Passing-Bablok regression was used to estimate intercept and slope, as well as the 95% confidence intervals using the bootstrap approach. Bland-Altman analysis was used to assess the mean difference or % difference along with the limits of agreement with 95% confidence. Method agreement was also evaluated for each analyte by comparing the observed differences against CLIA, NCEP, or NGSP allowable total error using two one-sided Student's t-test (TOST) and a significance level of 5%. Additionally, Pearson's Correlation Coefficient (r) and mean % bias were calculated. Percent bias, assuming y as the value from the diagnostic instrument, and x as the value from Roche Cobas or Sysmex, was calculated as: % bias=$100*((y-x)/((y+x)/2))$. For CBC analytes, to account for the difference in approaches, calibration factors were determined based on the Passing-Bablok intercept and slope estimates. Assuming Passing-Bablok regression as y=alpha+beta*x, where y is the value from the diagnostic instrument, and x is the value from Sysmex, the disclosed instrument's analyte was calibrated using the following methodology: a*y+b, where a=1/beta and b=negative alpha. These calibration factors were developed based on the existing clinical studies only. They may be further trained or applied to future studies for validation.

Results

All The diagnostic instruments performed similarly at both in-house and the Seattle clinical trial site with >95% run reliability and <2% invalid rates. The system reliability and assay performance measured at the clinical trial site were consistent with data collected in-house.

Precision Study

The precision study demonstrated good to acceptable repeatability and reproducibility with 19 tests for measured analytes evaluated for precision performance. Results are summarized in Table 2.

All tests evaluated showed consistent repeatability and within instrument CV, demonstrating stable performance across the testing period. Reproducibility was also comparable to within instrument CV across all tests, showing minimal inter-instrument variability, indicating the instruments performed similarly.

The directly measured tests on the CBC and lipid panel, HbA1c, along with ALB, BUN, CRE, GGT, GLU and TP in the chemistry panel had acceptable precision performance. Notably, ALP and TBIL each had a single outlier, determined by statistical analysis, that significantly increased imprecision. When this outlier is removed, reproducibility CV was 6.1% for ALP and 2.7% for TBIL. Continuing development efforts, including formulation, algorithm and workflow optimizations are underway for ALT, TBIL and CA and will be implemented in upcoming studies.

TABLE 2

Precision Study Results

| Test | N | Mean | Repeatability SD | Repeatability CV | Within Instrument SD | Within Instrument CV | Reproducibility SD | Reproducibility CV |
| --- | --- | --- | --- | --- | --- | --- | --- | --- |
| Complete Blood Cell Count Tests | | | | | | | | |
| RBC | 45 | 4.0 | 0.1 | 1.5% | 0.1 | 1.8% | 0.1 | 1.8% |
| WBC | 45 | 7.4 | 0.2 | 2.2% | 0.2 | 2.2% | 0.2 | 2.2% |
| PLT | 45 | 289.0 | 3.5 | 1.2% | 3.5 | 1.2% | 4.4 | 1.5% |
| HCT | 45 | 34.5 | 0.5 | 1.4% | 0.6 | 1.8% | 0.6 | 1.8% |
| HGB | 45 | 13.1 | 0.5 | 3.8% | 0.5 | 3.8% | 0.6 | 4.3% |
| Lipid Panel Tests | | | | | | | | |
| HDL | 45 | 48.8 | 1.7 | 3.4% | 1.7 | 3.5% | 2.7 | 5.5% |
| TC | 45 | 187.7 | 4.4 | 2.3% | 5.2 | 2.8% | 5.7 | 3.1% |
| TRIG | 45 | 136.8 | 2.0 | 1.5% | 2.8 | 2.0% | 4.0 | 2.9% |
| HbA1C | | | | | | | | |
| HbA1c | 45 | 6.5 | 0.2 | 2.9% | 0.2 | 2.9% | 0.2 | 2.9% |
| Chemistry Panel Tests | | | | | | | | |
| ALB | 45 | 3.7 | 0.1 | 1.5% | 0.1 | 1.6% | 0.1 | 2.9% |
| ALP | 45 | 139.9 | 13.9 | 9.9% | 13.9 | 9.9% | 13.9 | 9.9% |
| BUN | 45 | 40.7 | 2.2 | 5.4% | 2.2 | 5.4% | 2.2 | 5.4% |
| CRE | 45 | 1.4 | 0.1 | 4.2% | 0.1 | 4.4% | 0.1 | 4.5% |
| GGT | 45 | 75.4 | 2.3 | 3.1% | 2.4 | 3.2% | 3.0 | 4.0% |
| GLU | 45 | 112.6 | 3.3 | 2.9% | 3.3 | 2.9% | 4.4 | 3.9% |
| TP | 45 | 5.7 | 0.1 | 1.7% | 0.1 | 1.7% | 0.1 | 2.1% |
| ALT | 45 | 76.7 | 5.0 | 6.6% | 5.2 | 6.8% | 8.5 | 11.0% |
| CA | 45 | 10.3 | 0.5 | 4.7% | 0.5 | 4.7% | 0.6 | 6.2% |
| TBIL | 45 | 2.9 | 10.3 | 9.5% | 0.3 | 9.7% | 0.3 | 10.0% |

Method Comparison Study

In the method comparison study, results from a total of 258 donors, 208 normal and 50 donors with chronic diseases were evaluated for concordance and equivalency using Passing-Bablok regression and Bland-Altman analyses, comparing results from the diagnostic instrument to those from either the Roche Cobas (chemistry) or Sysmex XN or pocH-100i (hematology). Bland-Altman analyses showed that the majority of tests exhibited acceptable differences between the diagnostic instrument and central laboratory results except for ALT (data not shown), which is currently undergoing formulation optimization to improve assay stability and performance.

Figure 32A:
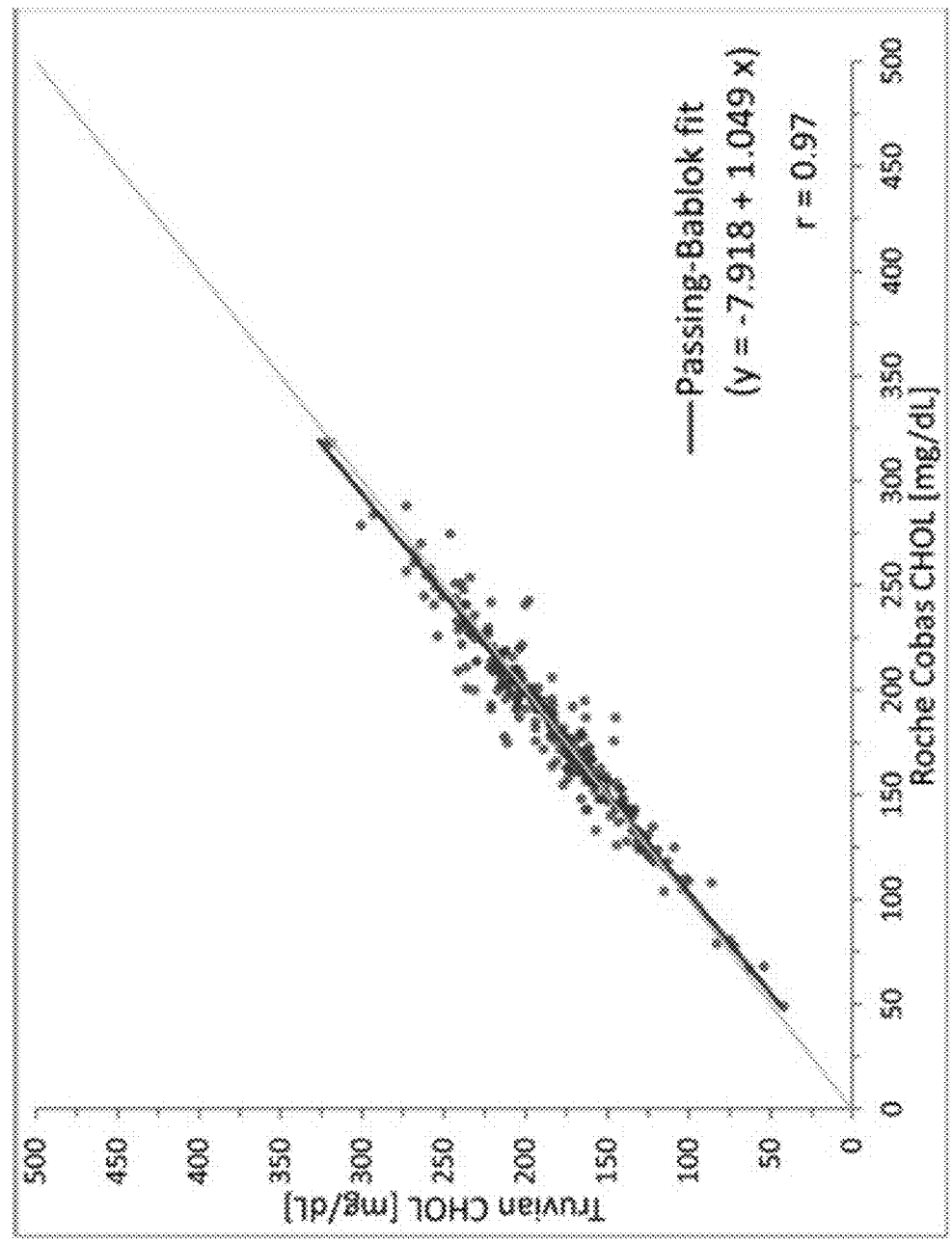
FIGS. 32A-32EE show method comparison data. Results from the diagnostic instrument disclosed showed strong concordance with central laboratory comparator results. Passing-Bablok regression plots were generated for a) lipid panel against Roche Cobas (FIGS. 32A-G), b) hematology CBC panel against Sysmex (FIGS. 32H-S), and c) chemistry panel and HbA1c against Roche Cobas (FIGS. 32T-EE). Slope, intercept and correlation coefficient (Pearson's r) are included within each graph.
Figure 32B:
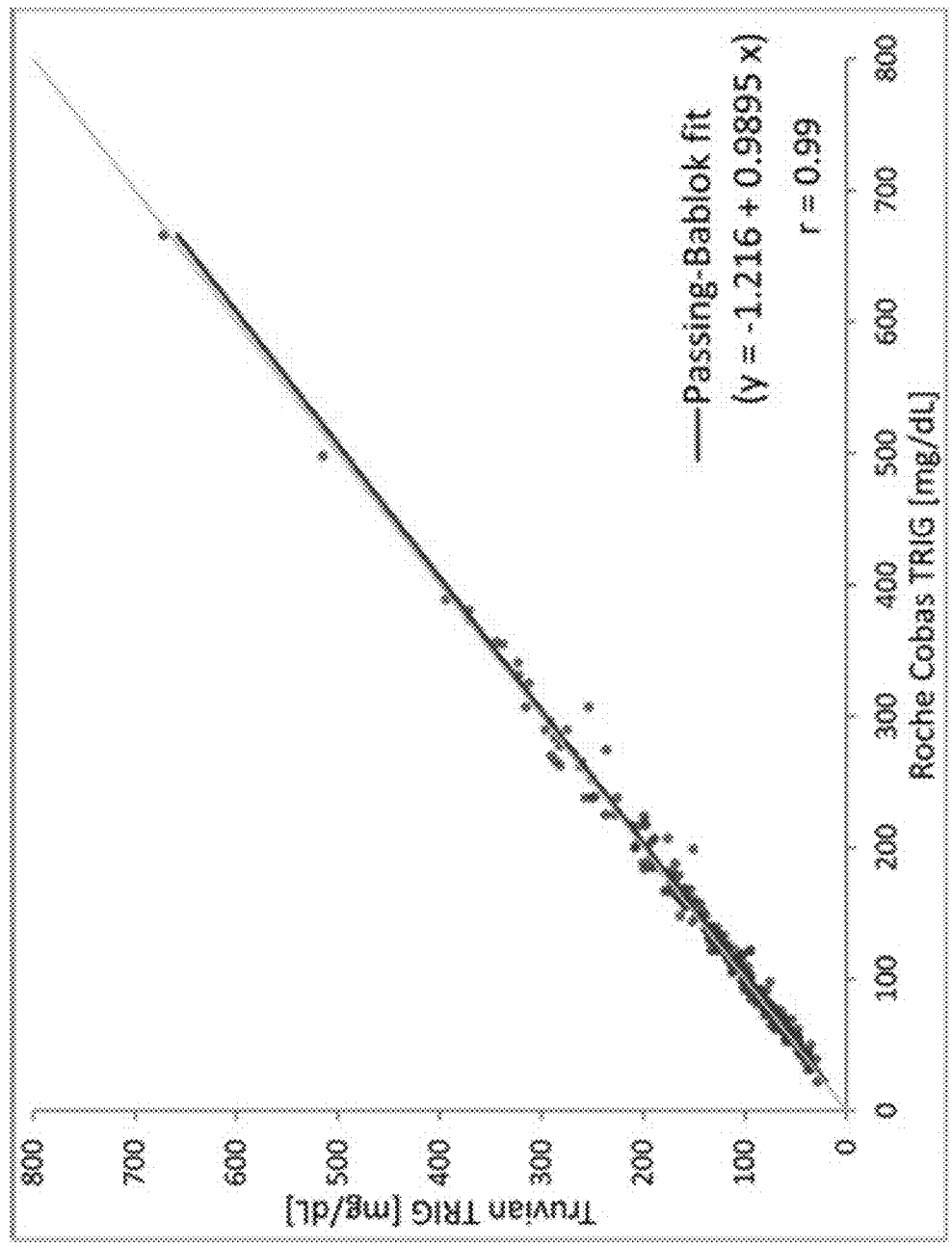
Figure 32C:
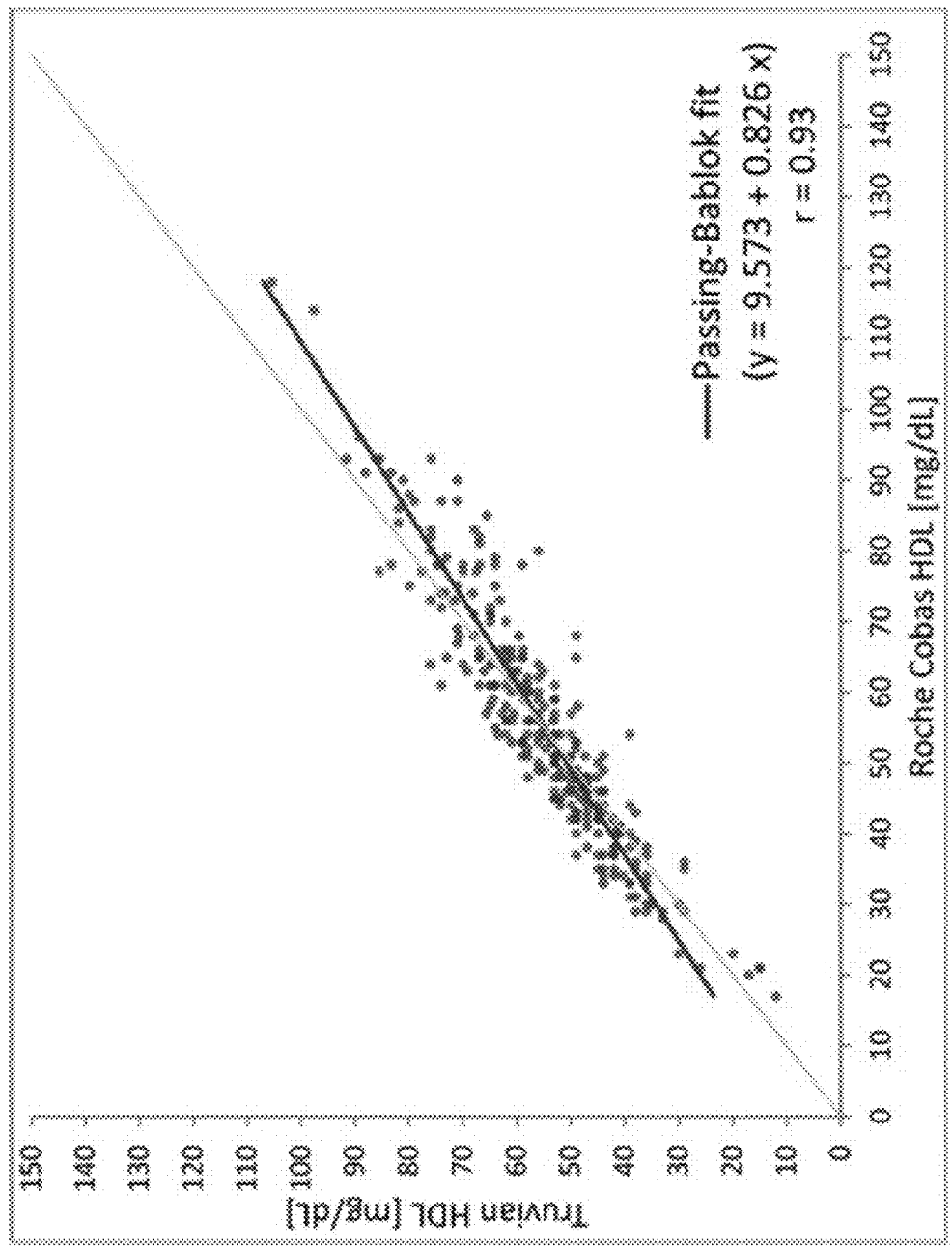
Figure 32D:
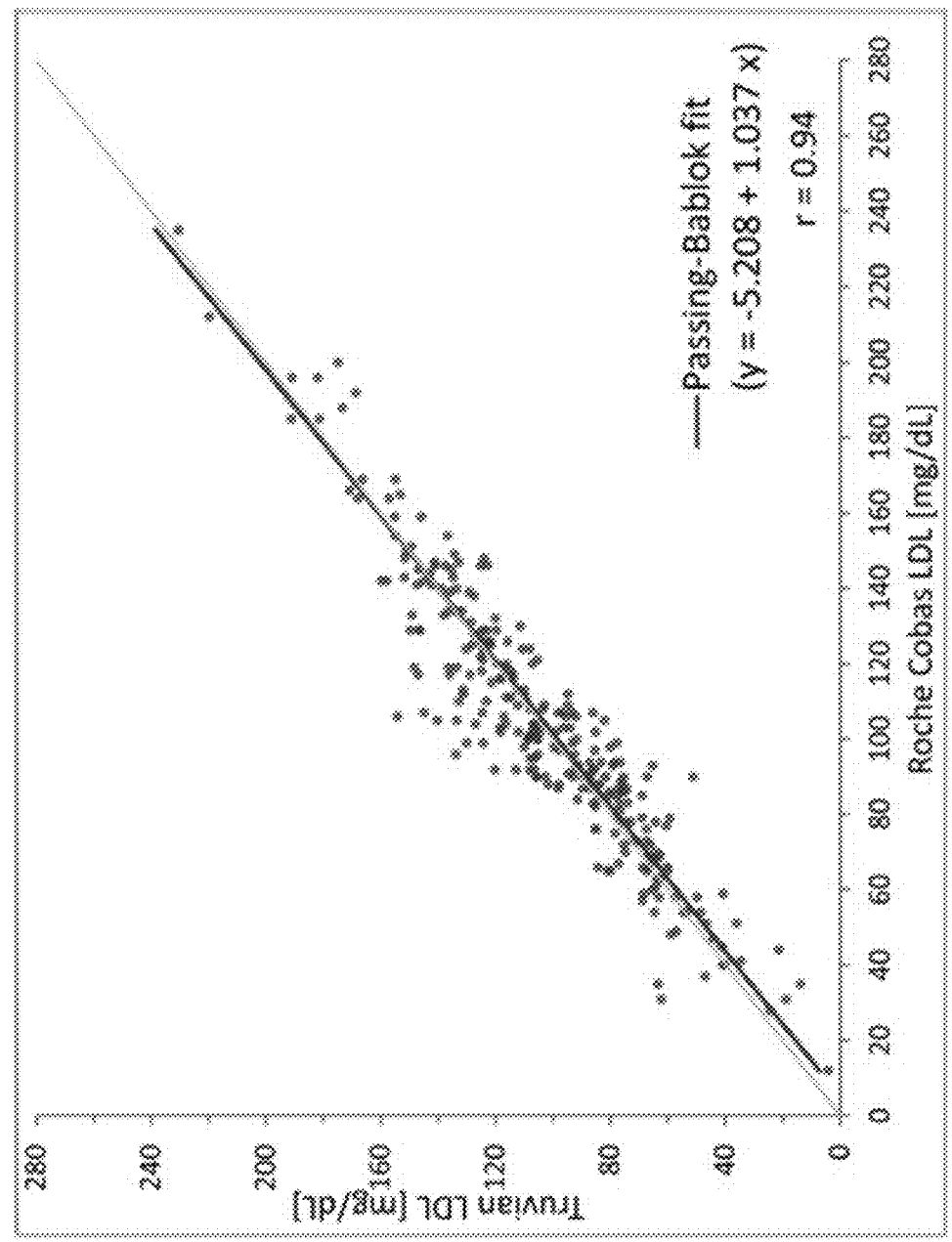
Figure 32E:
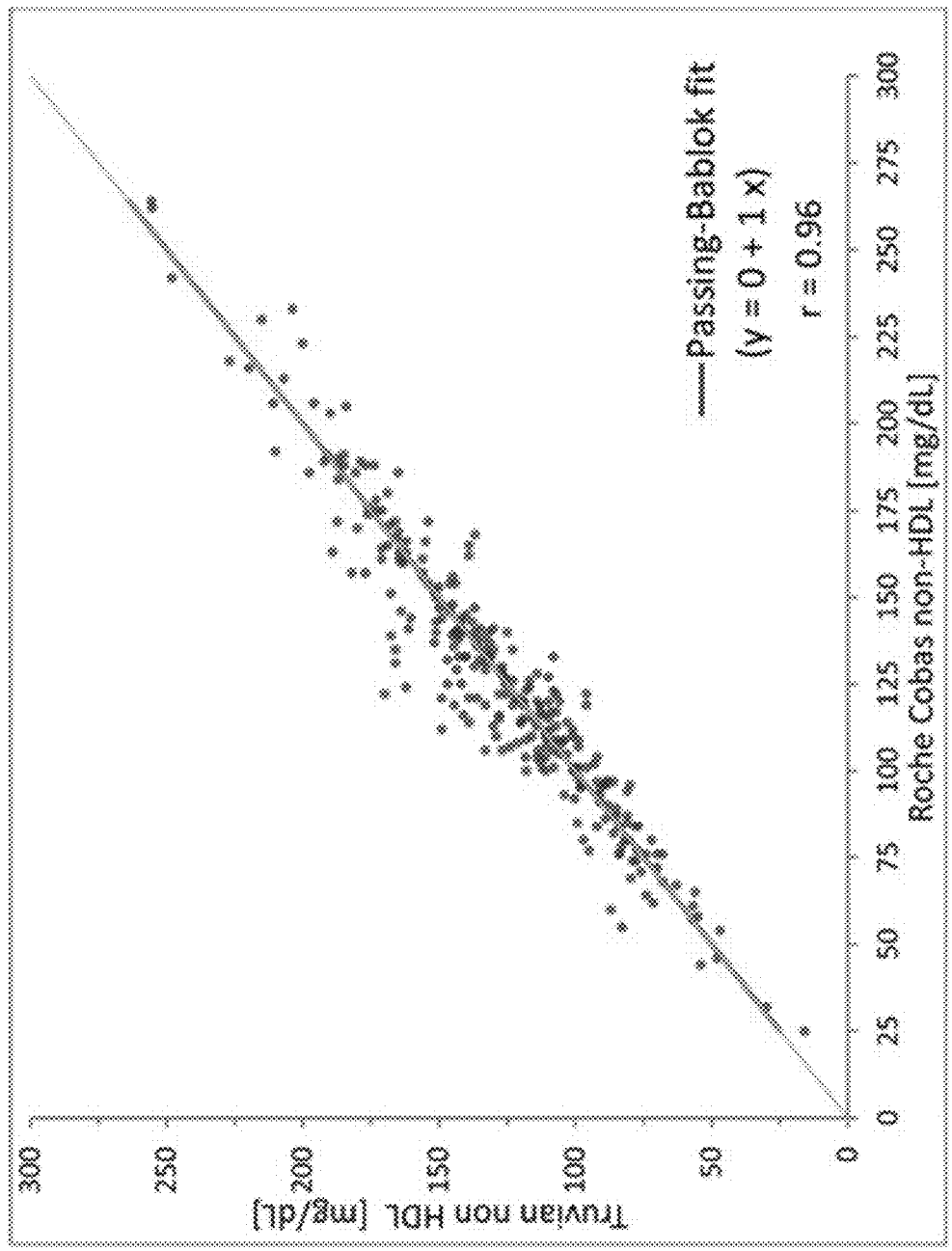
Figure 32F:
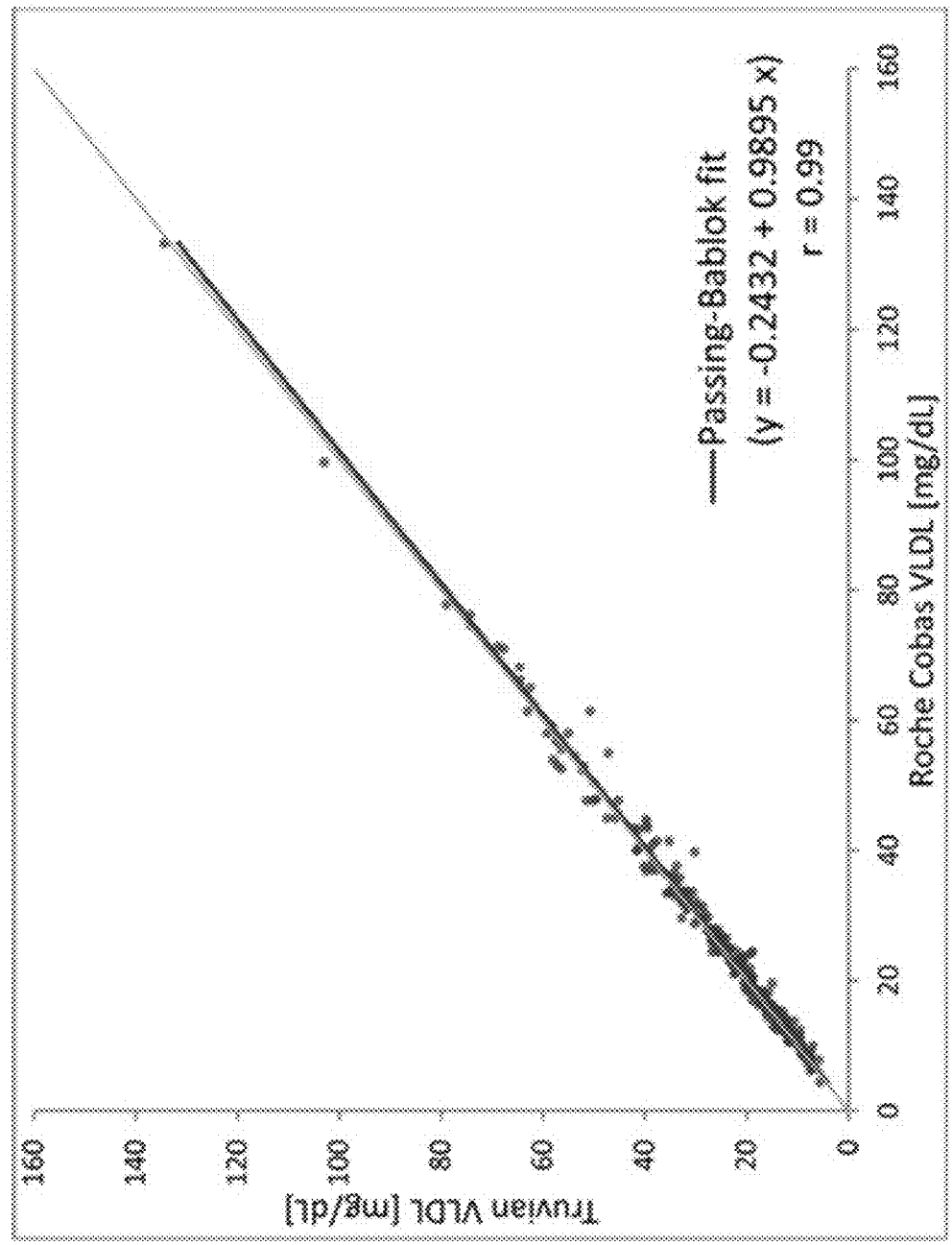
Figure 32G:
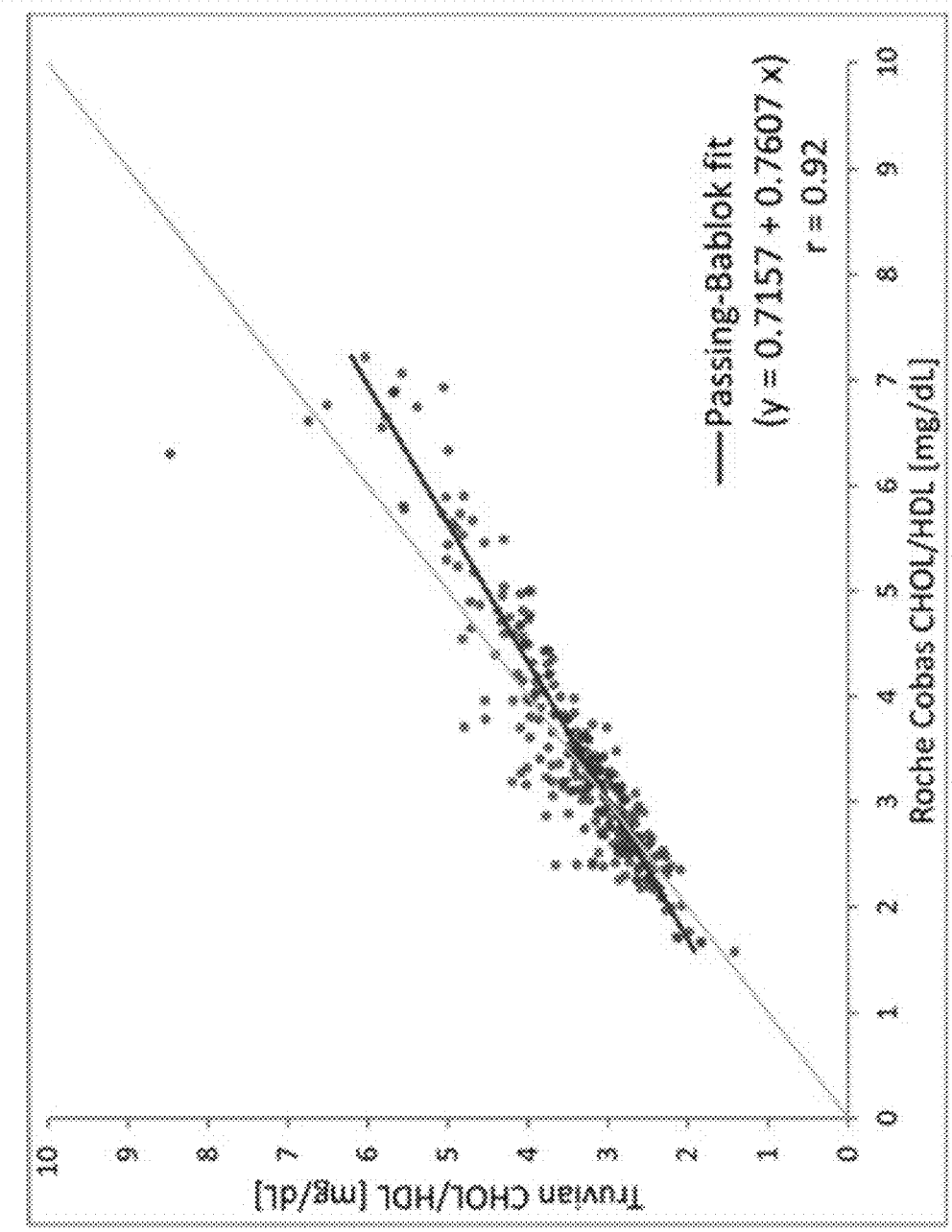
Figure 32H:
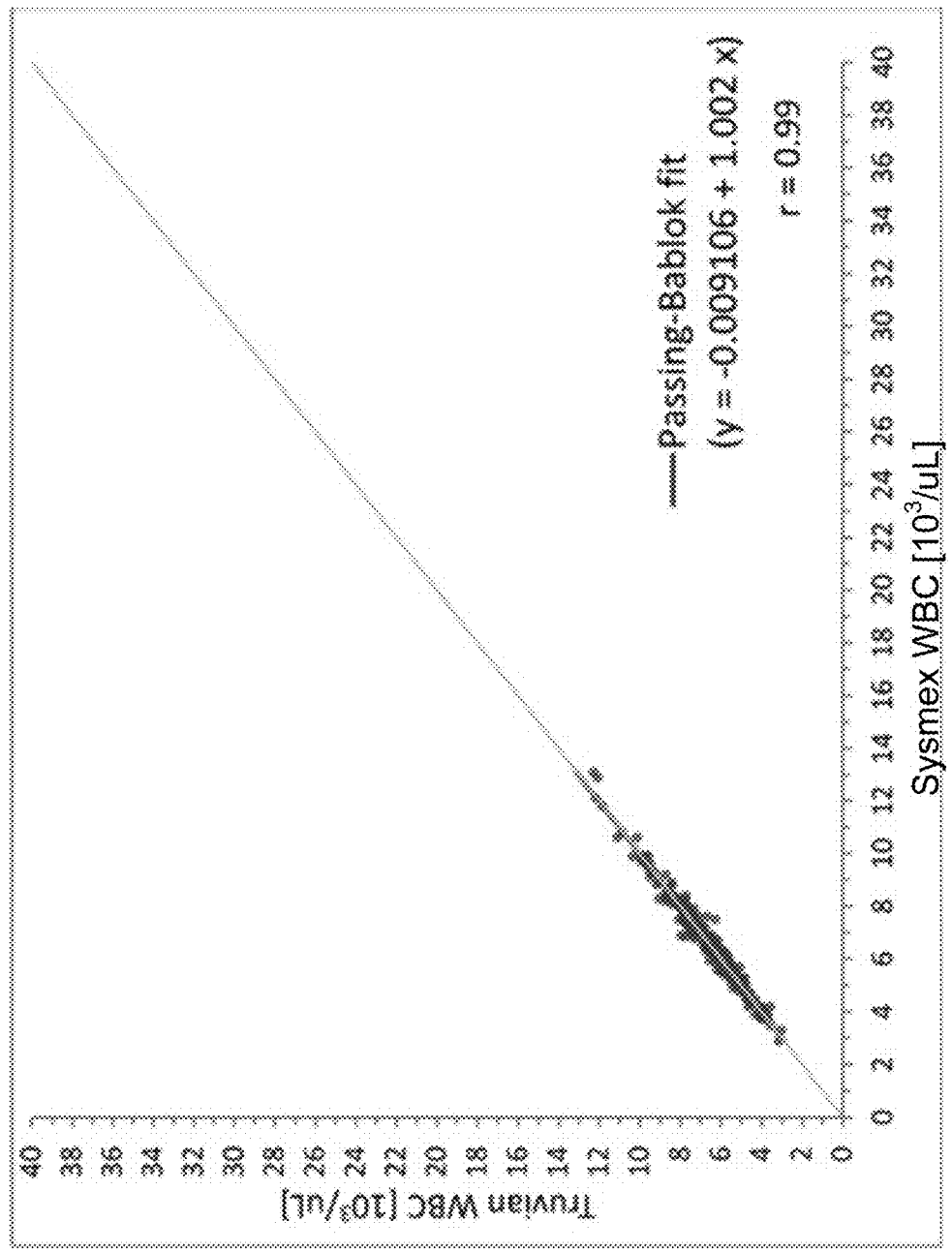
Figure 32I:
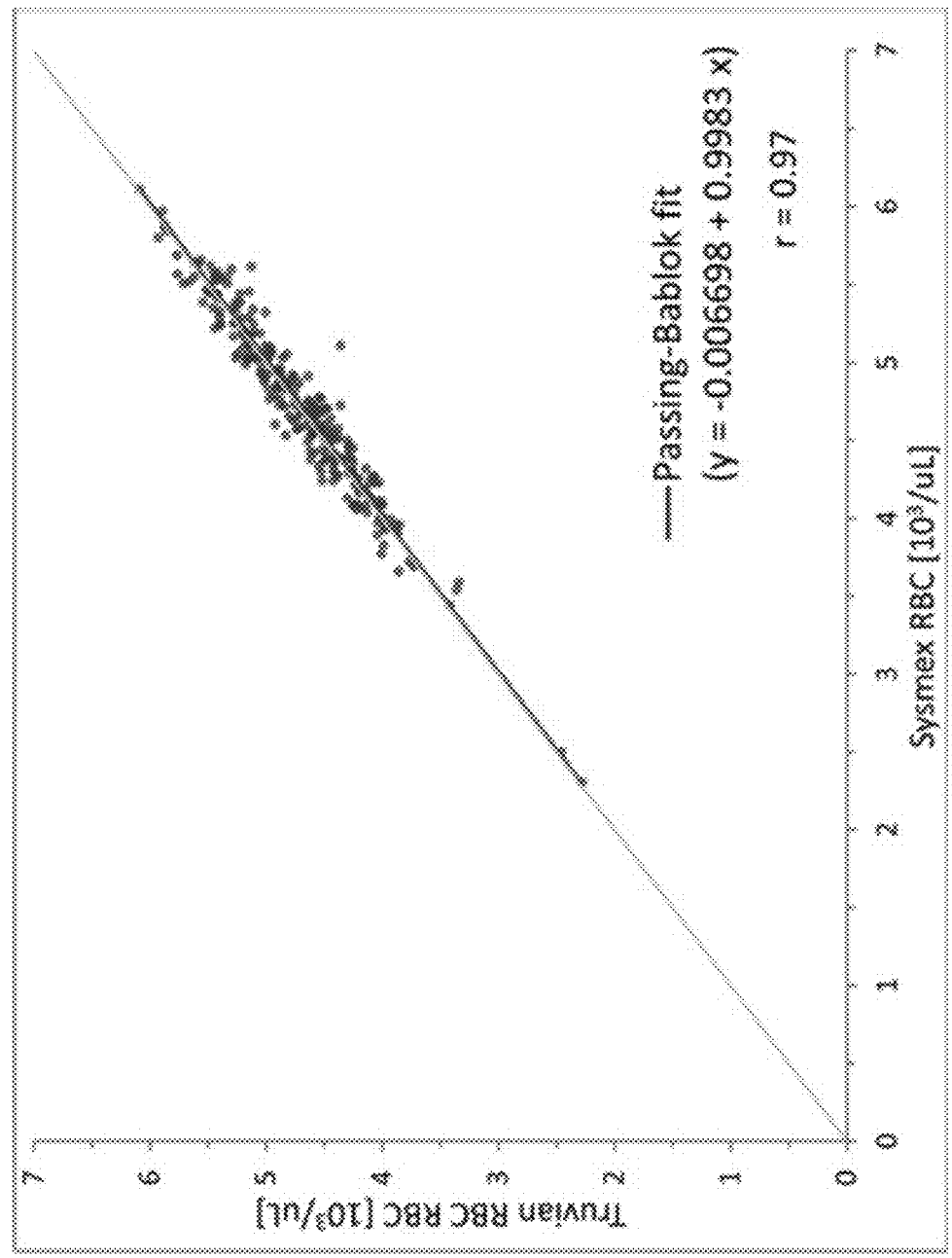
Figure 32J:
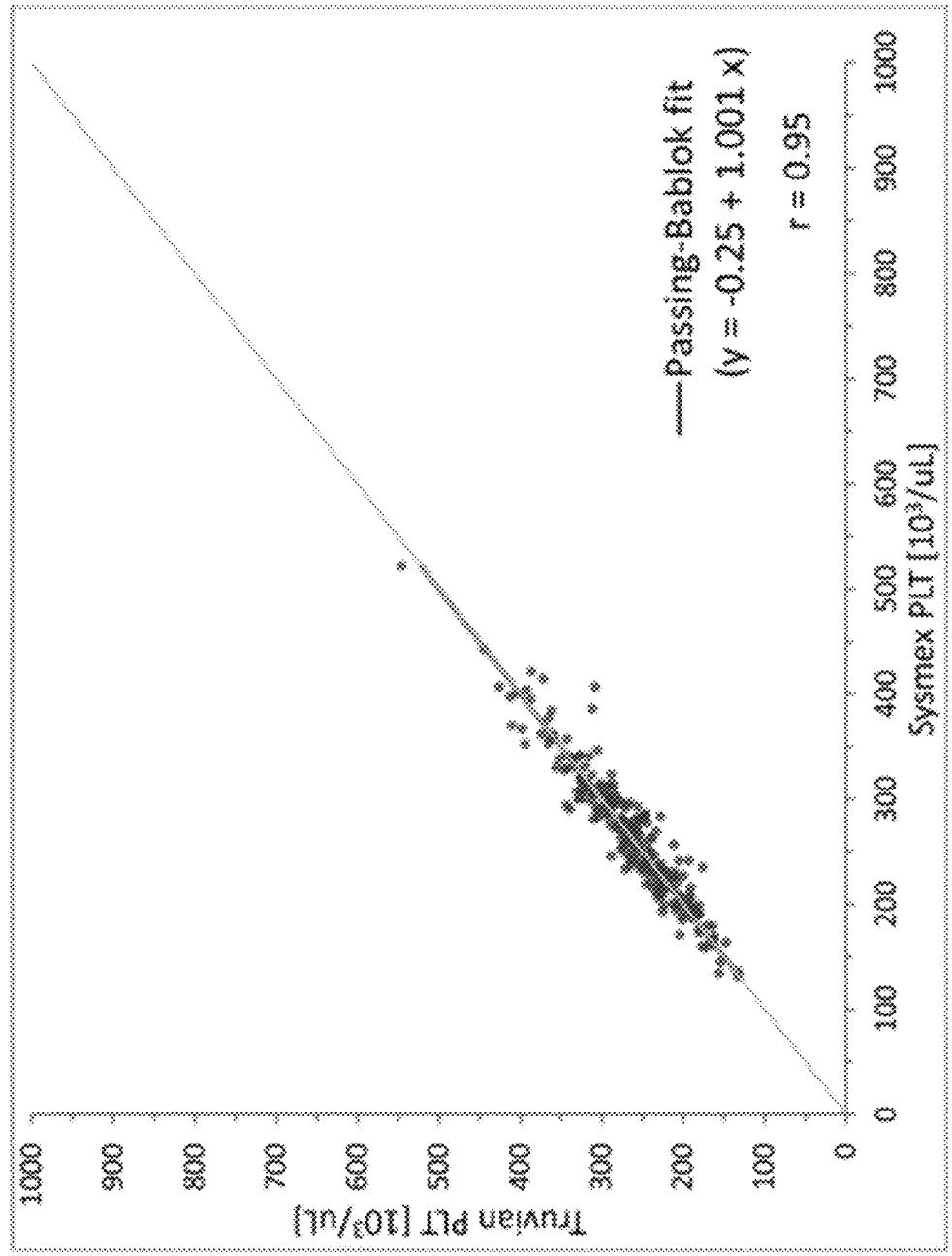
Figure 32K:
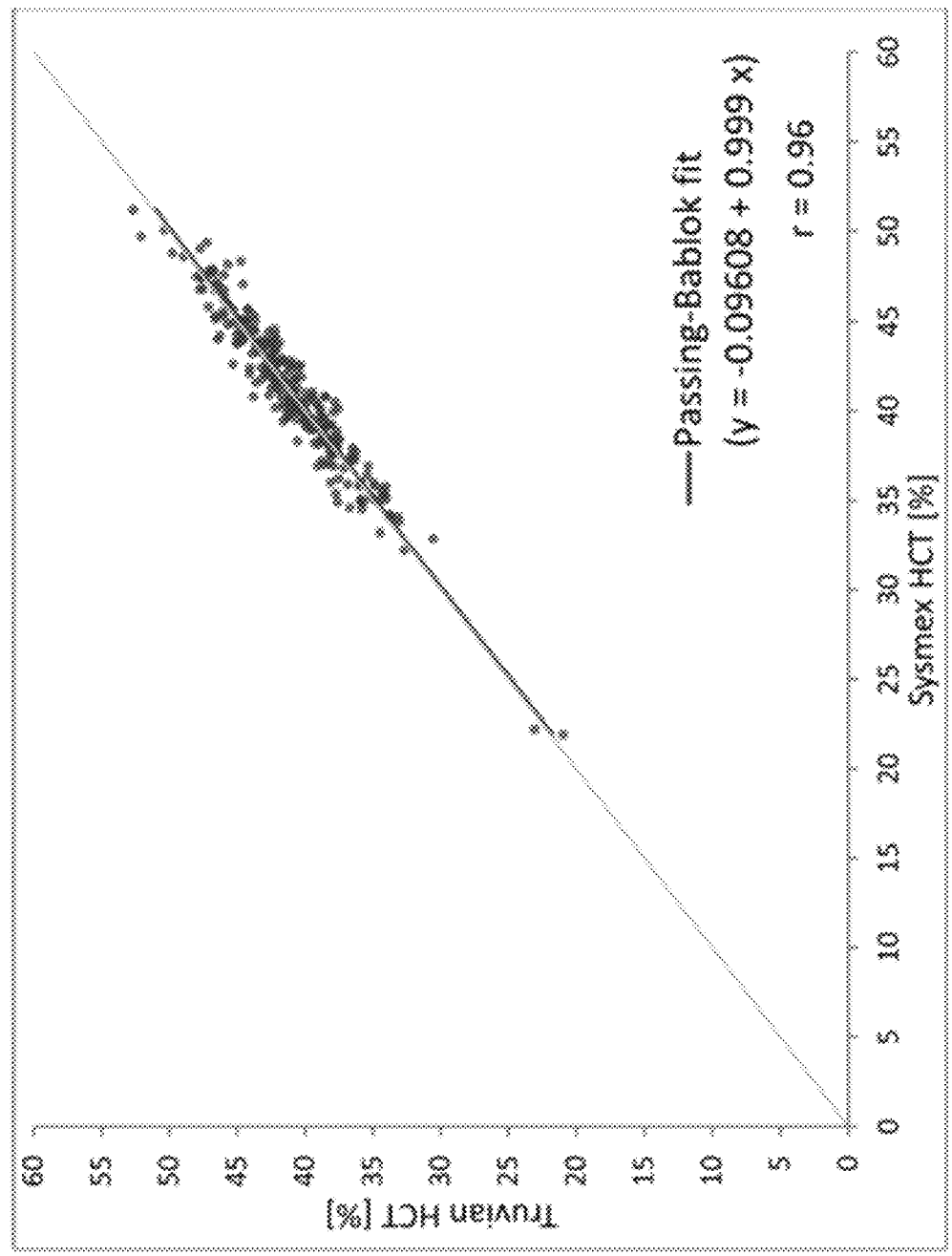
Figure 32L:
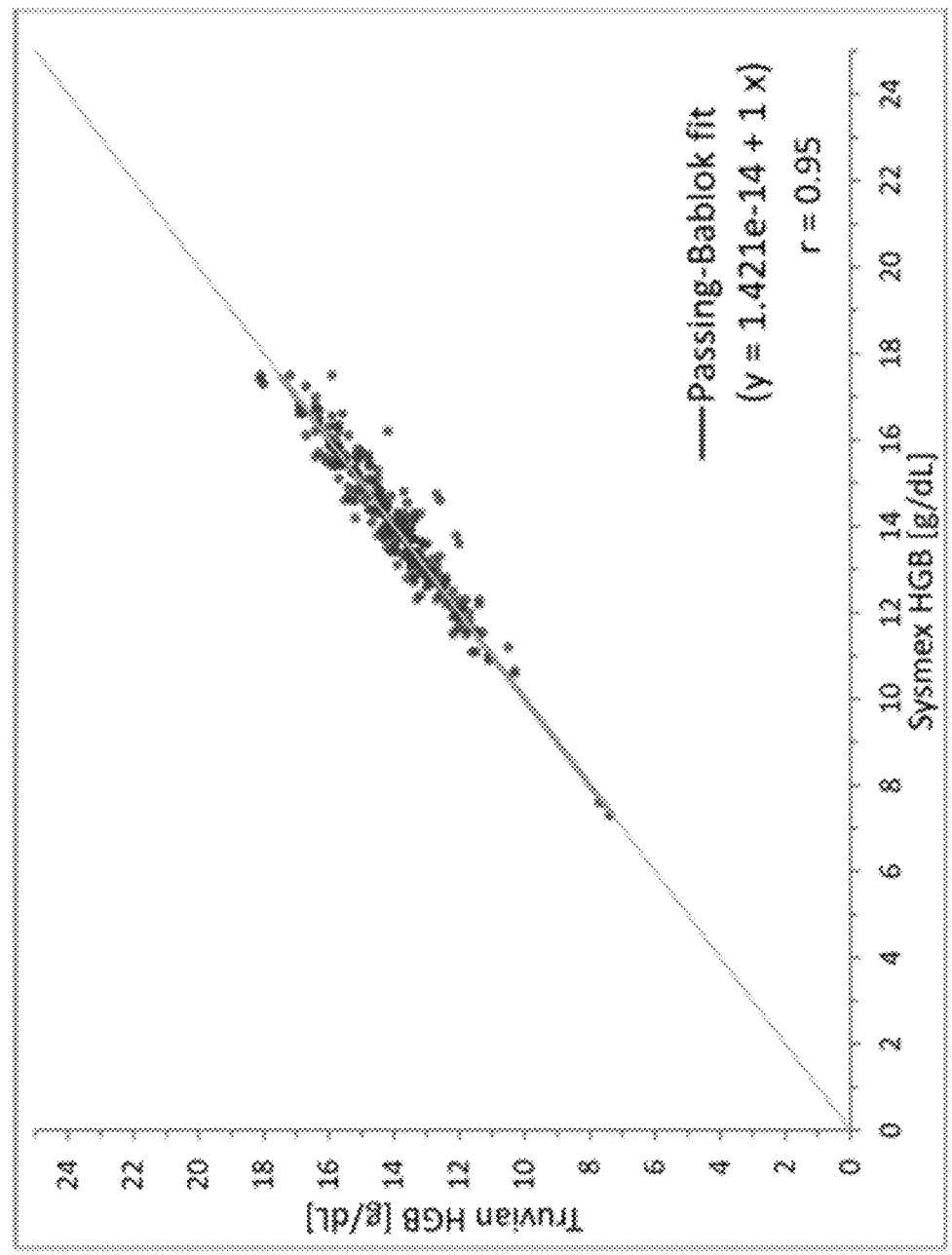
Figure 32M:
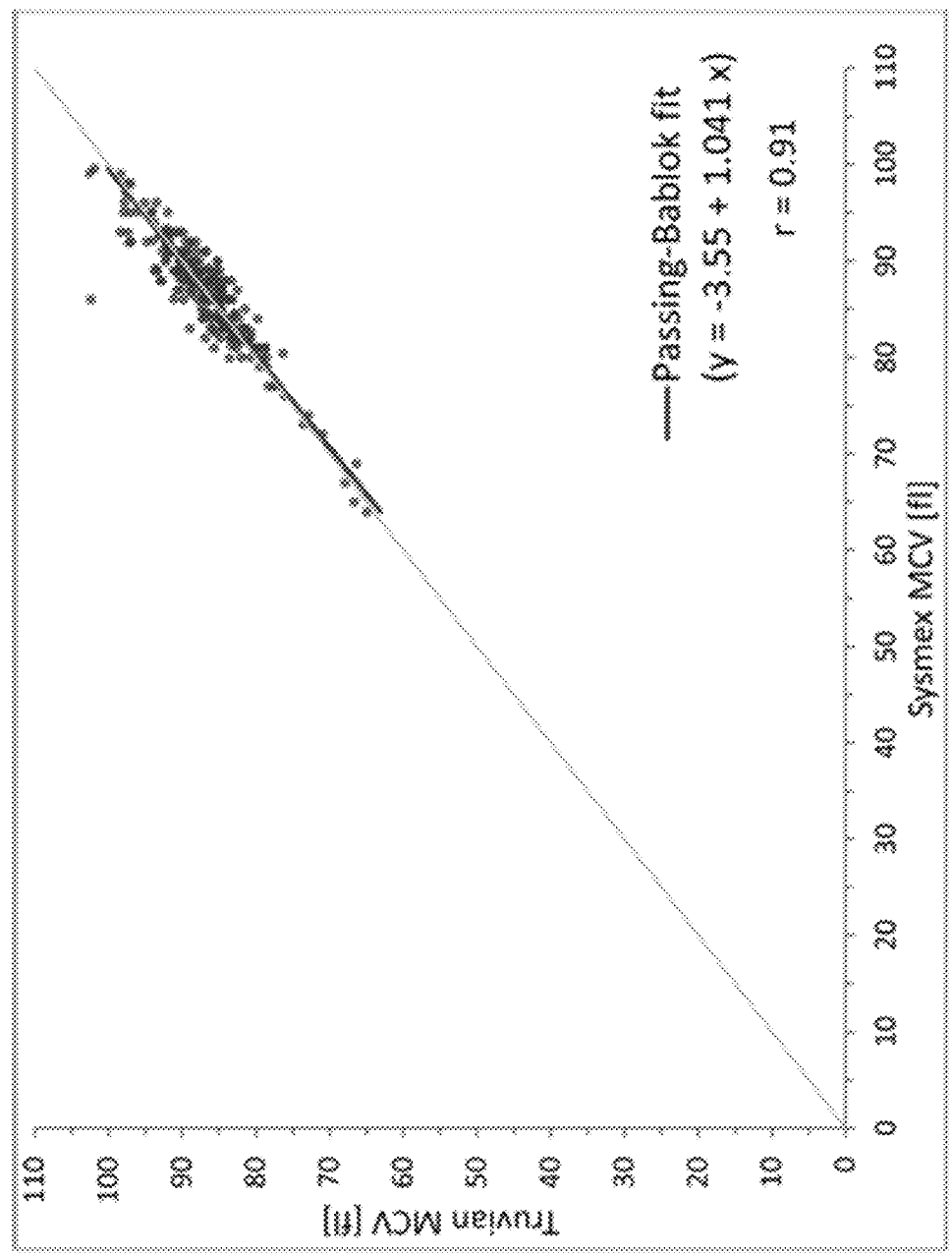
Figure 32N:
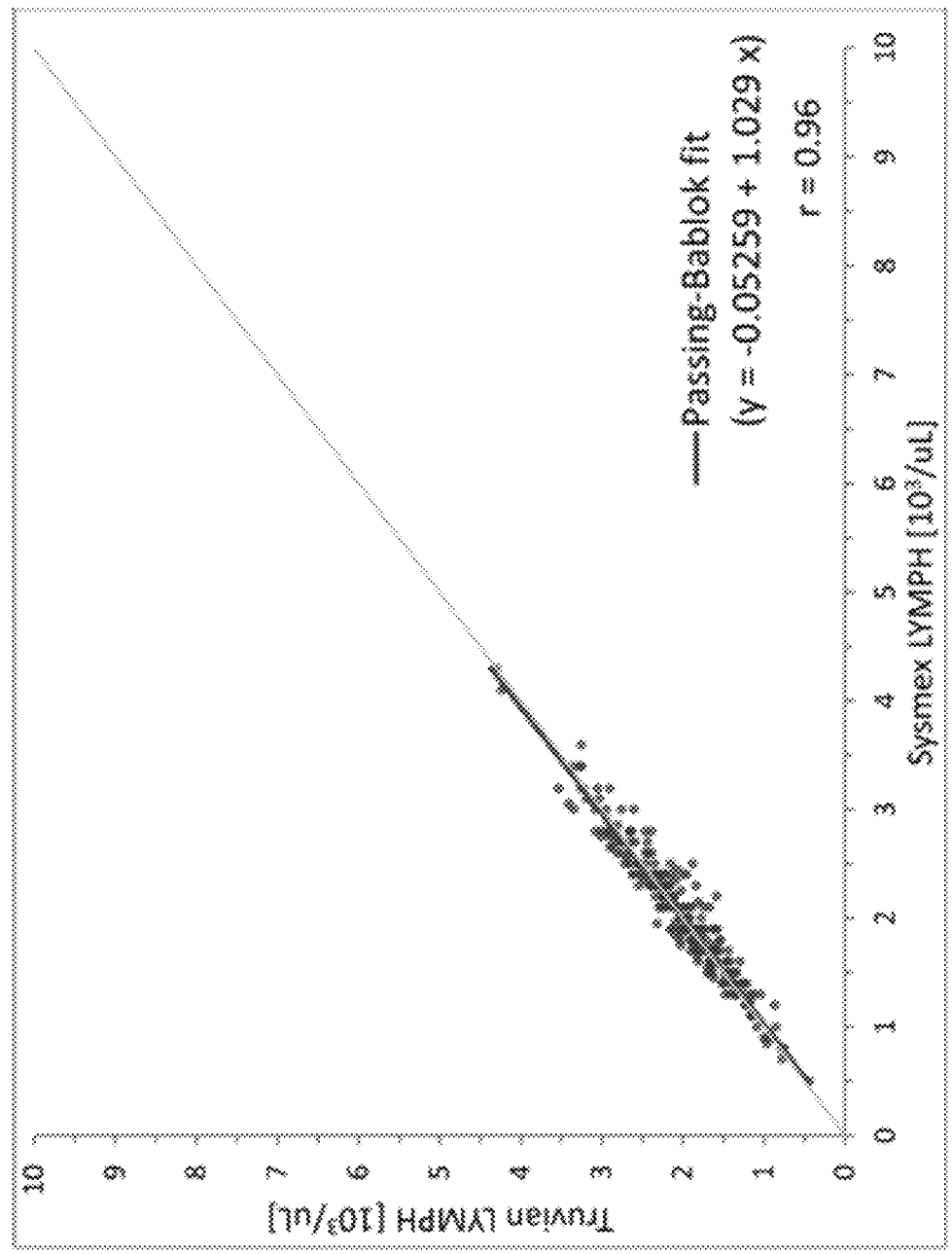
Figure 32O:
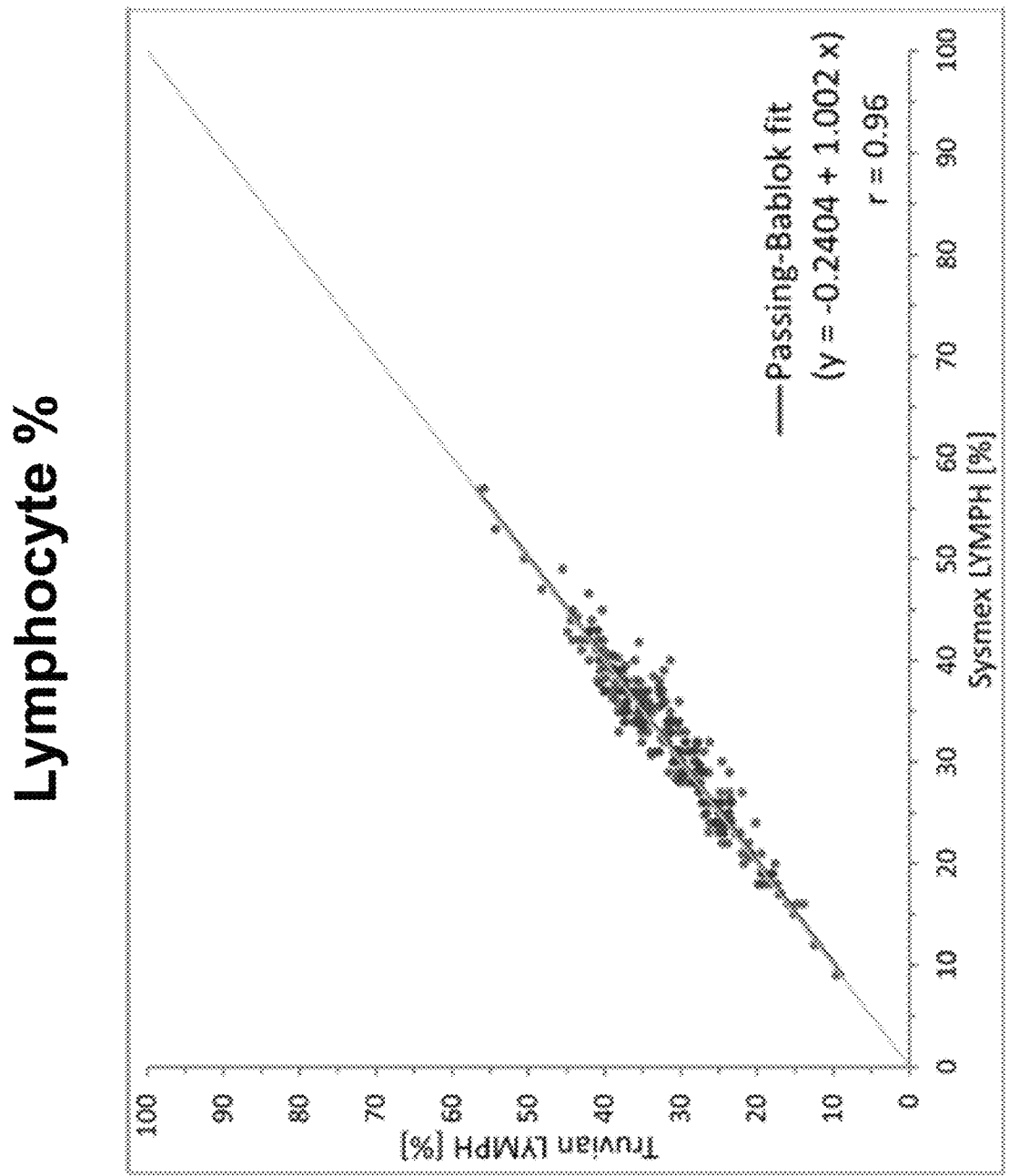
Figure 32P:
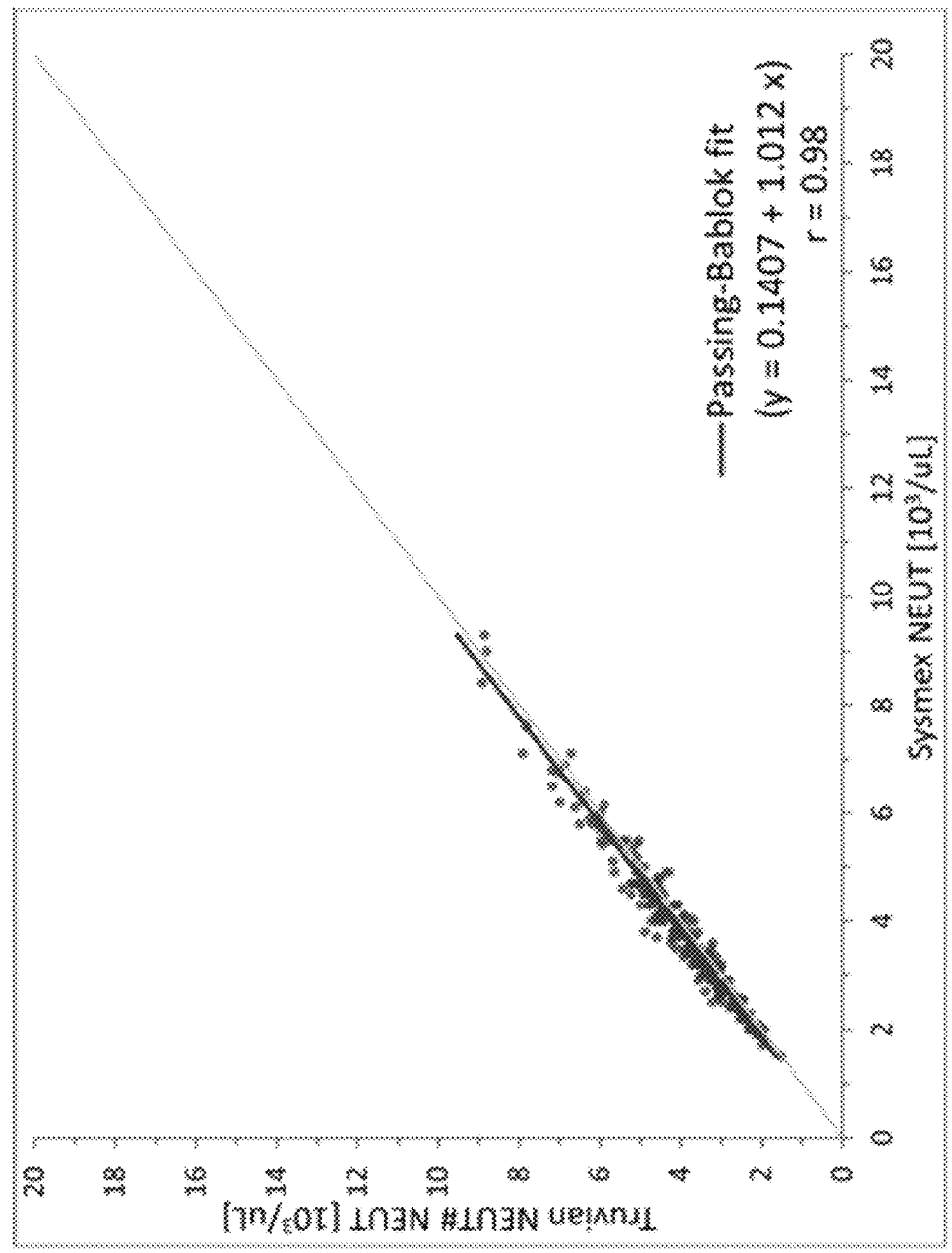
Figure 32Q:
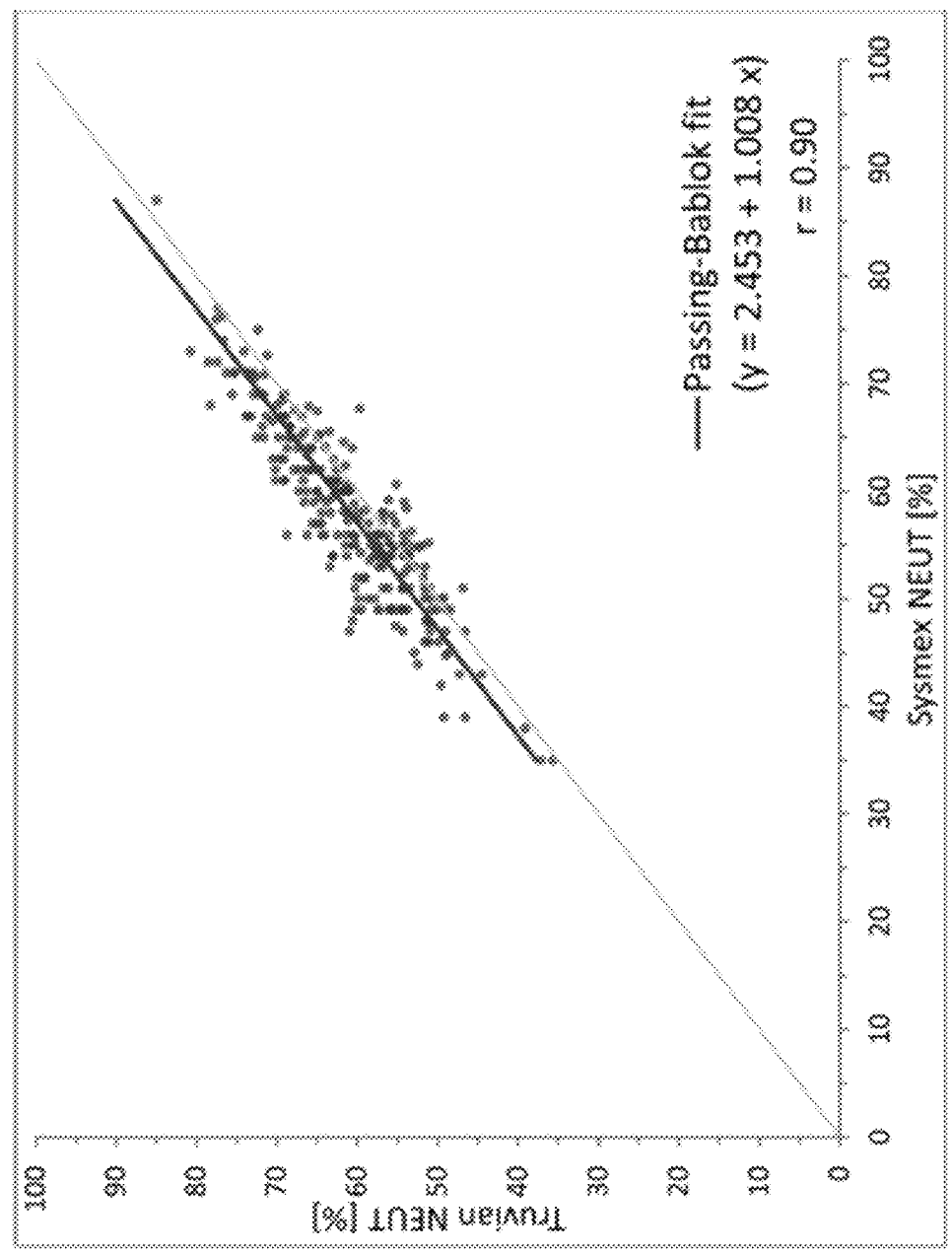
Figure 32R:
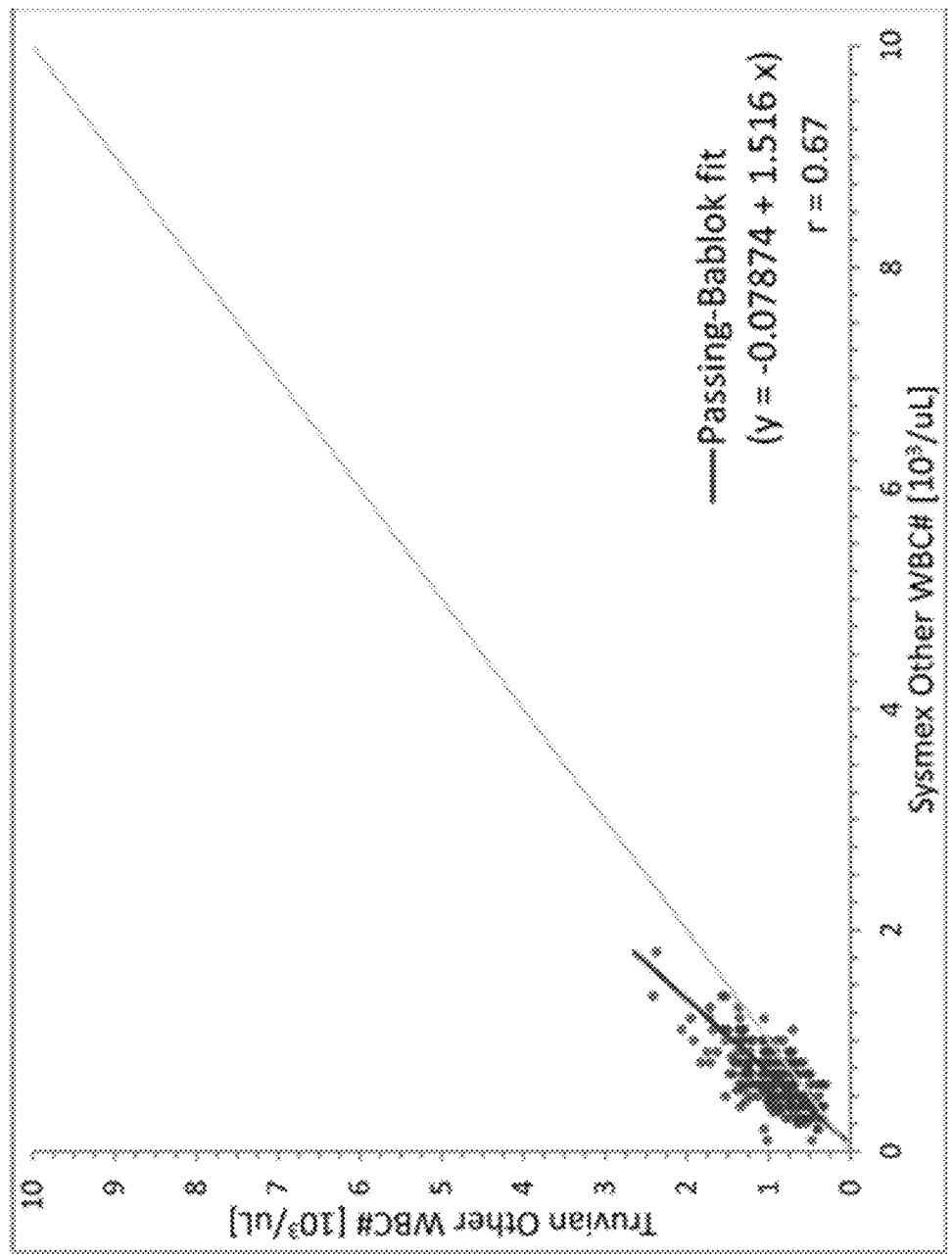
Figure 32S:
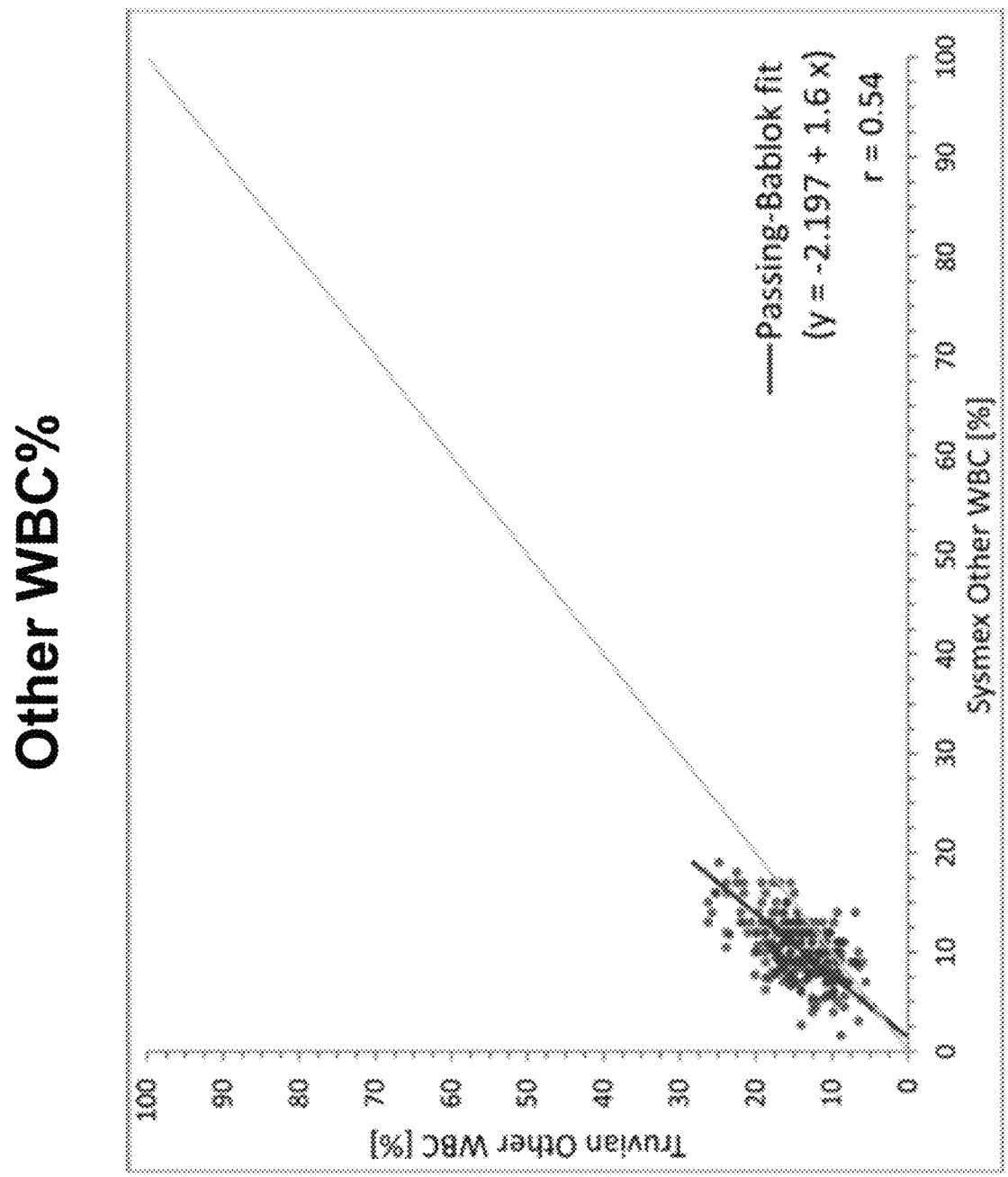
Figure 32T:
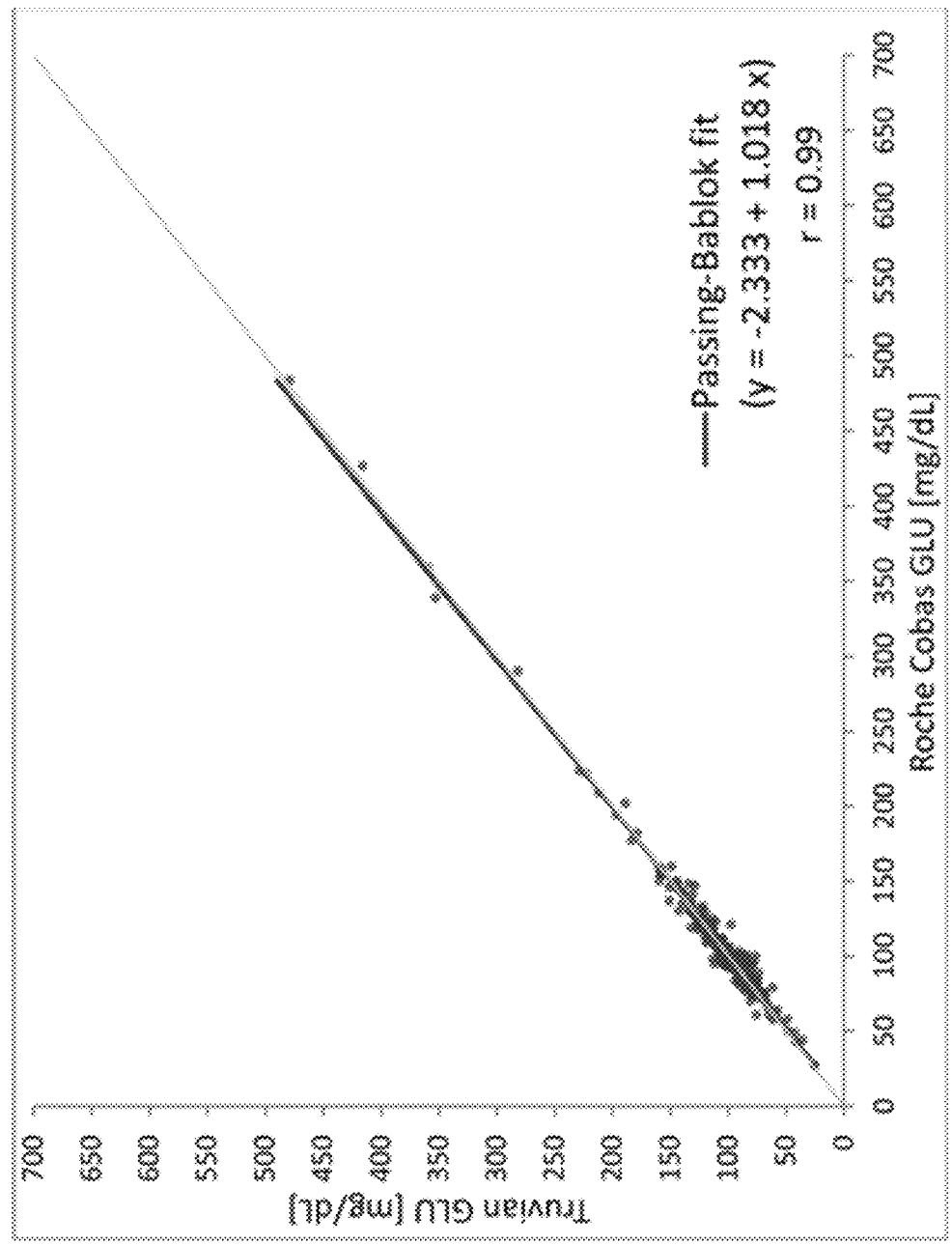
Figure 32U:
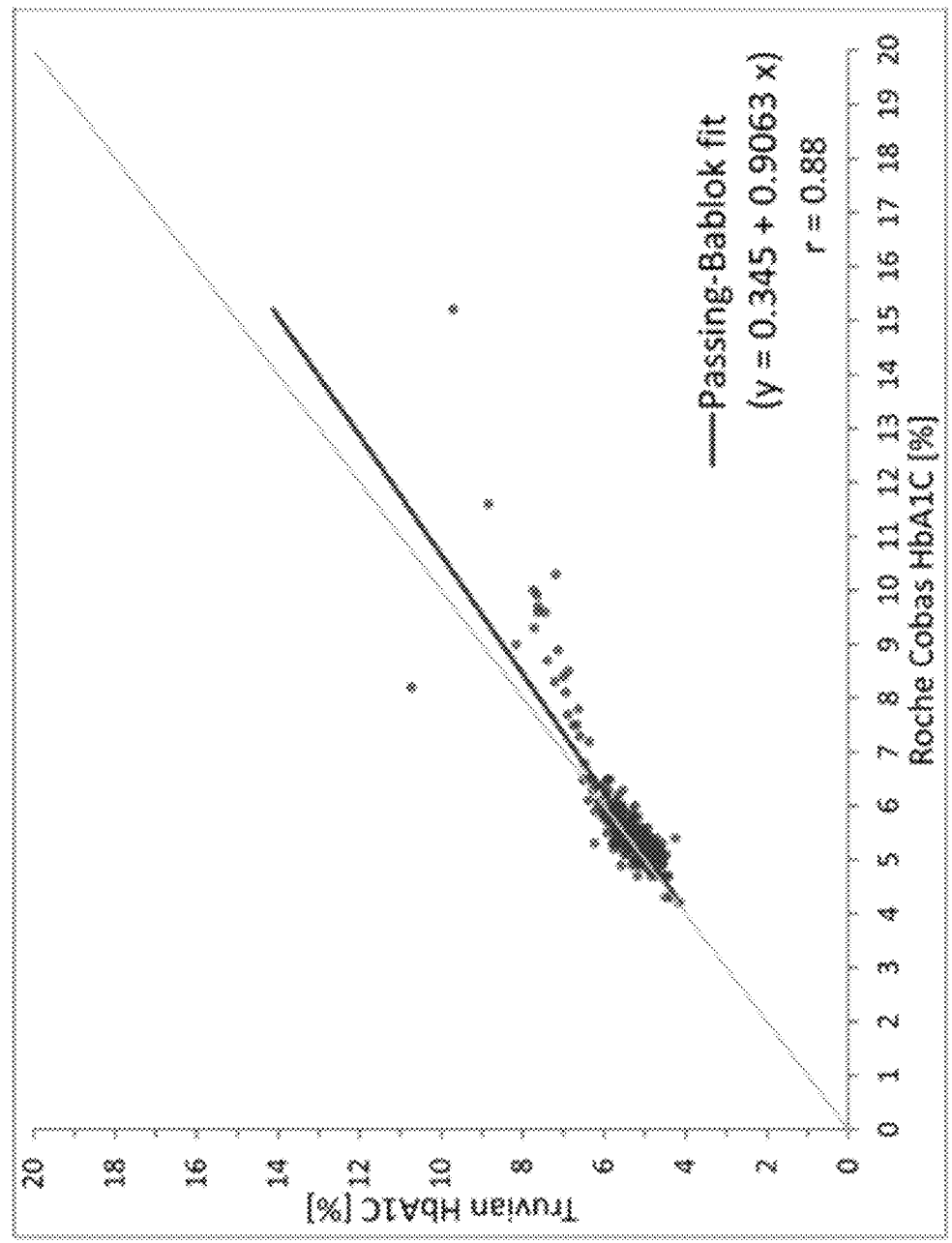
Figure 32V:
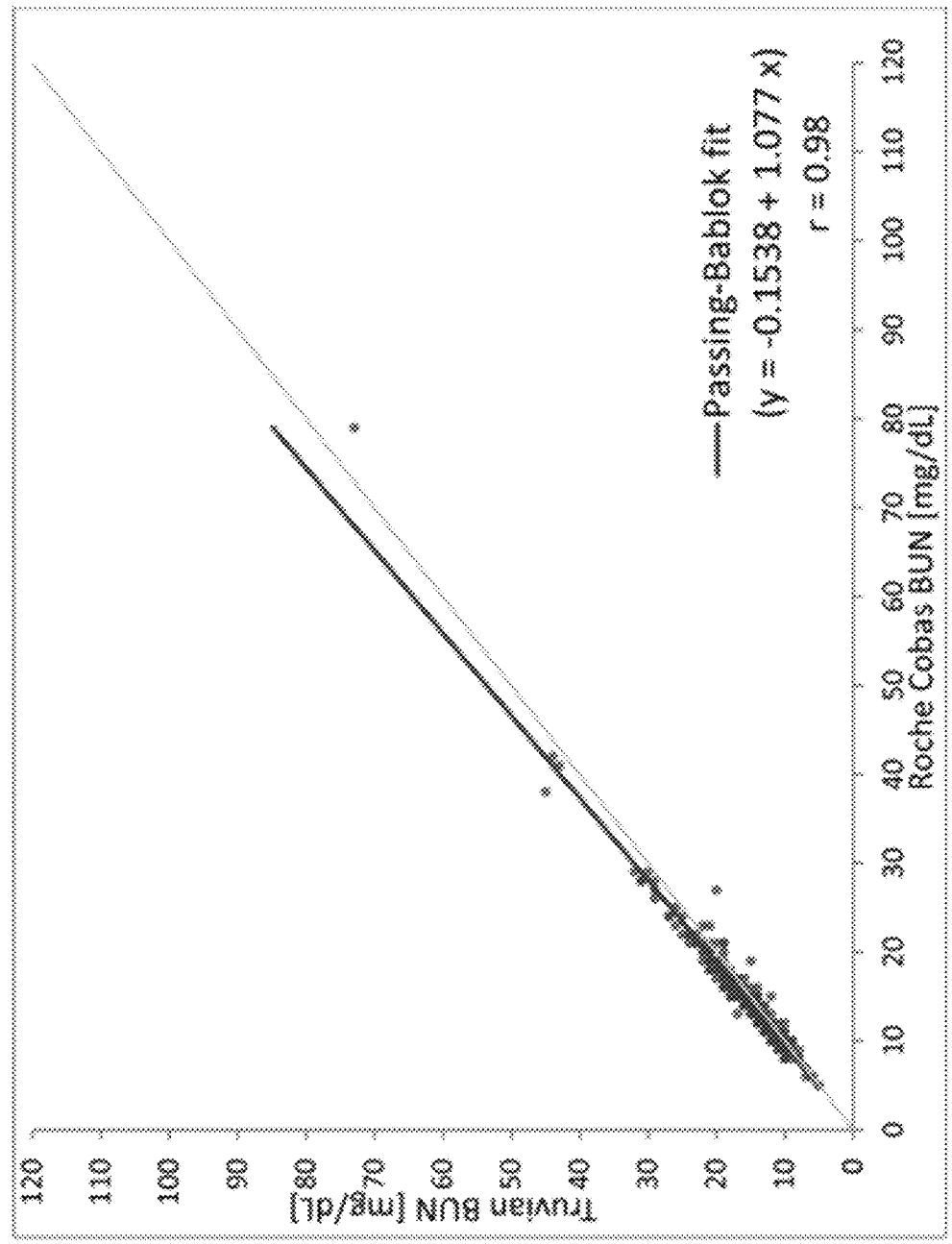
Figure 32W:
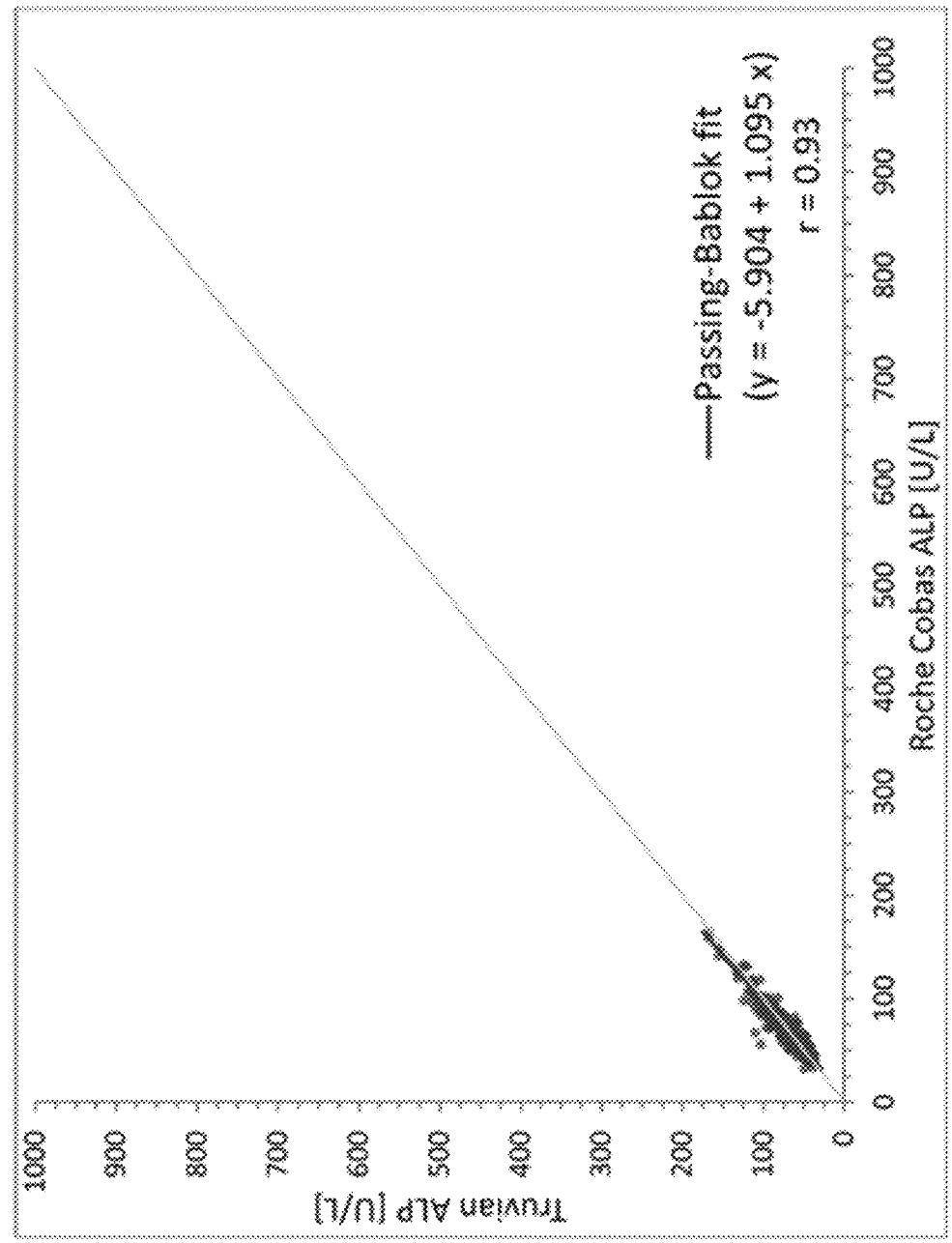
Figure 32X:
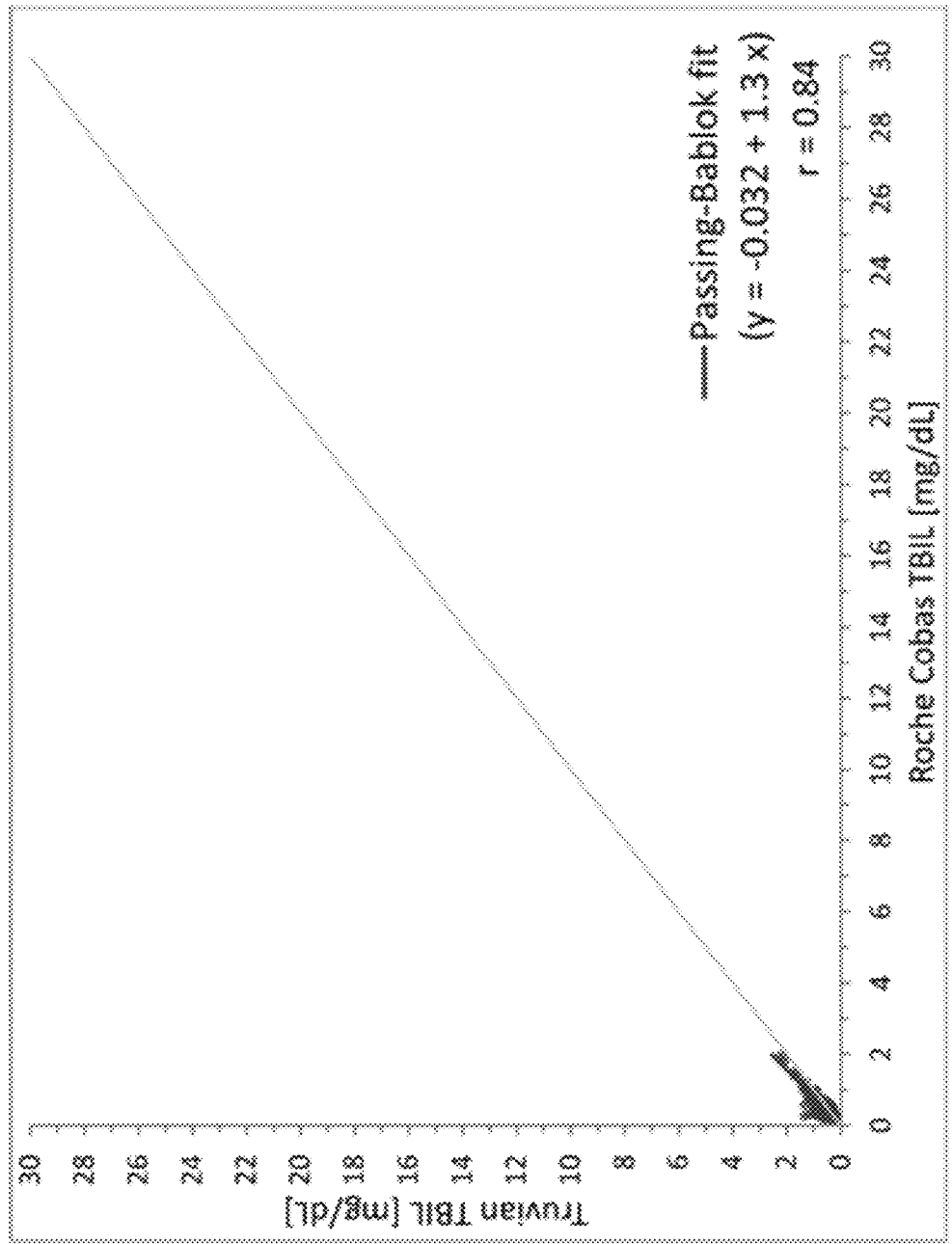
Figure 32Y:
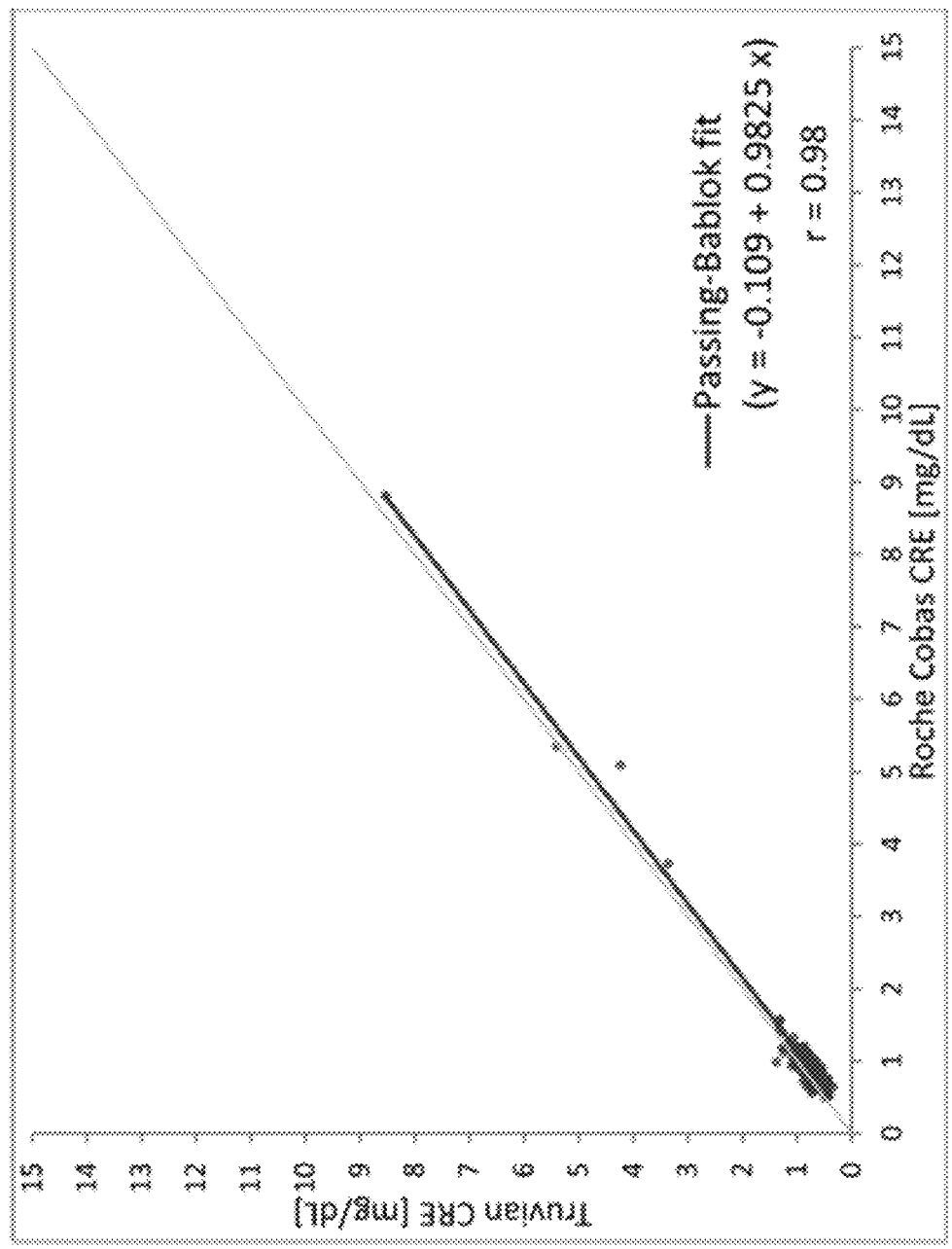
Figure 32Z:
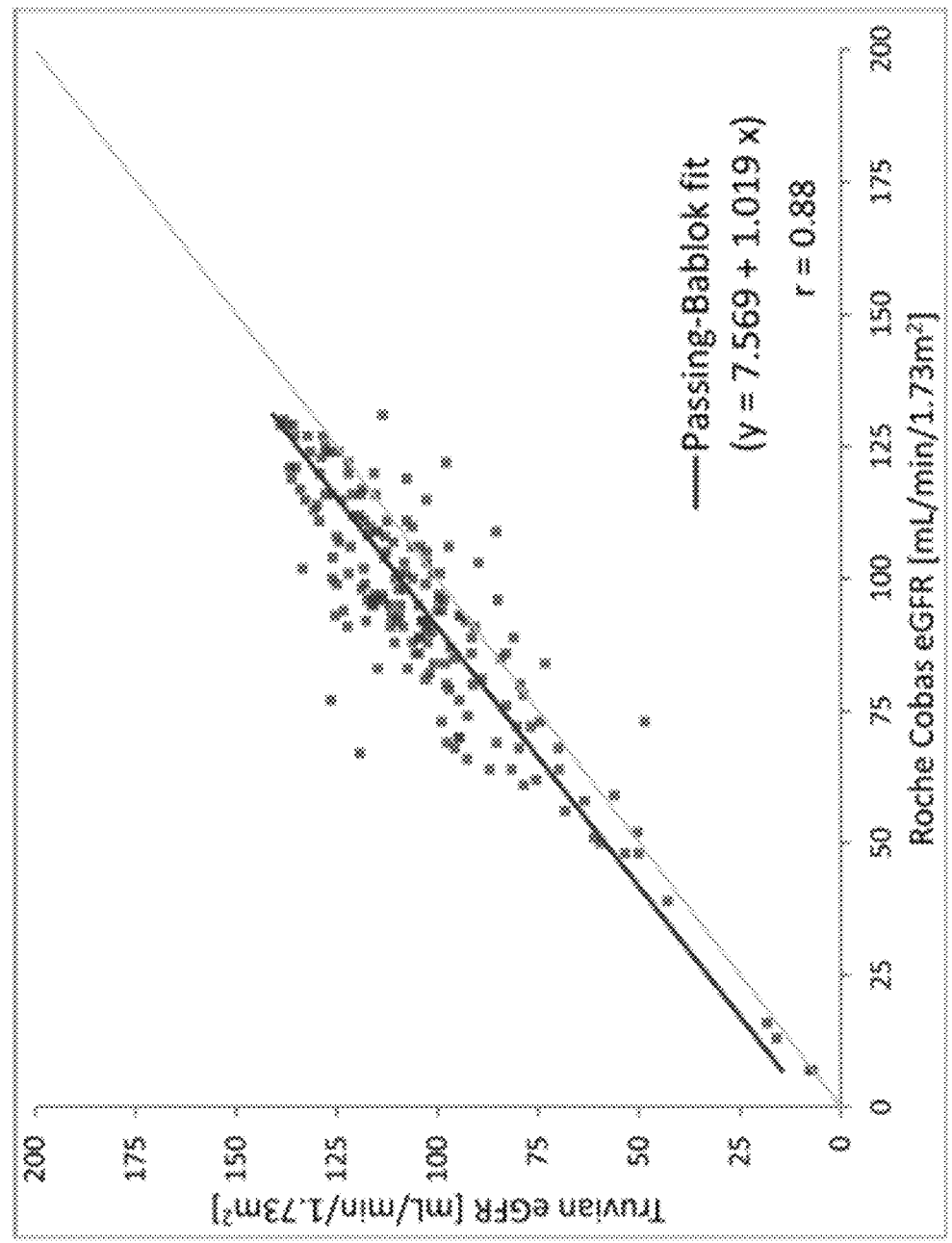
Figure 32A:
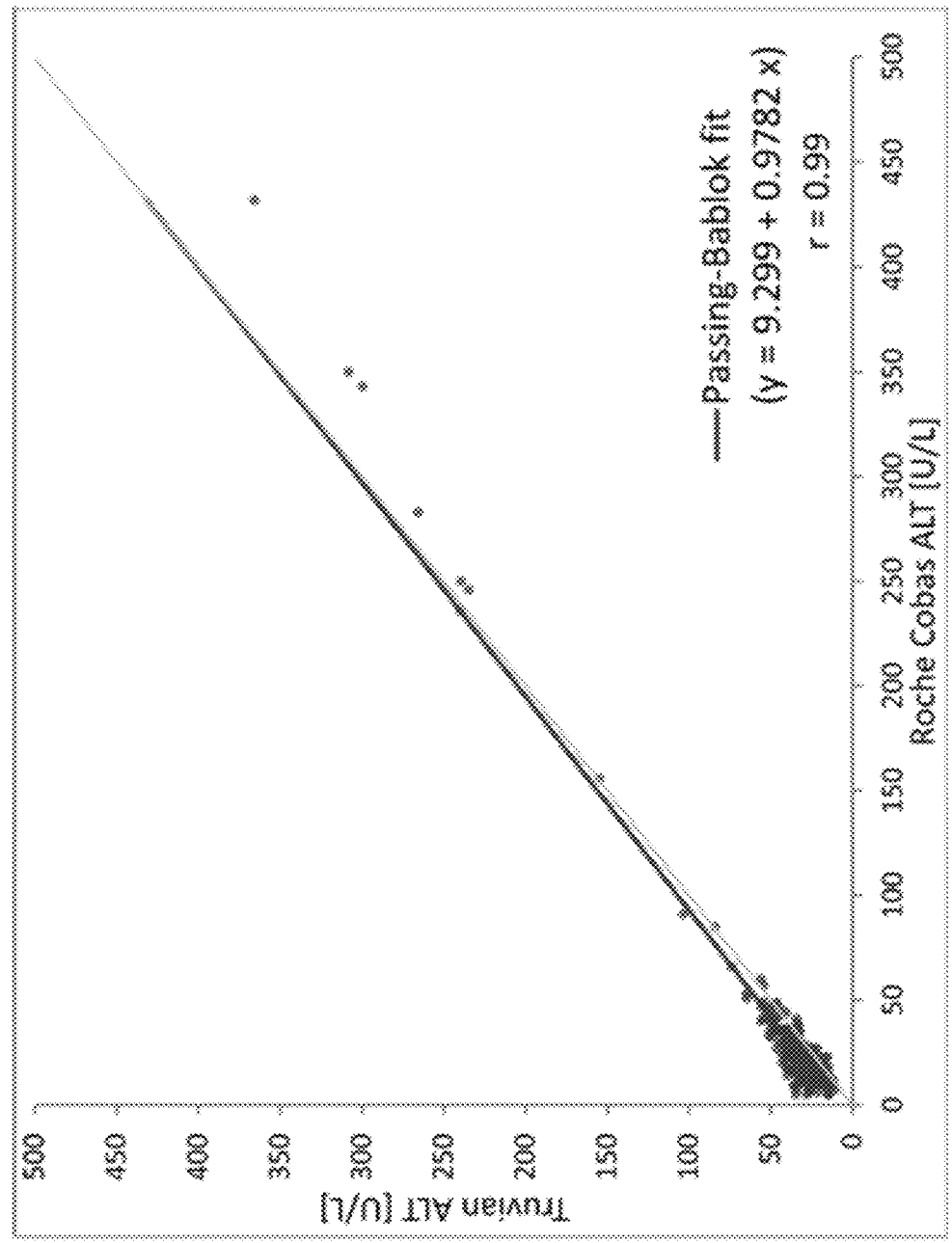
Figure 32B:
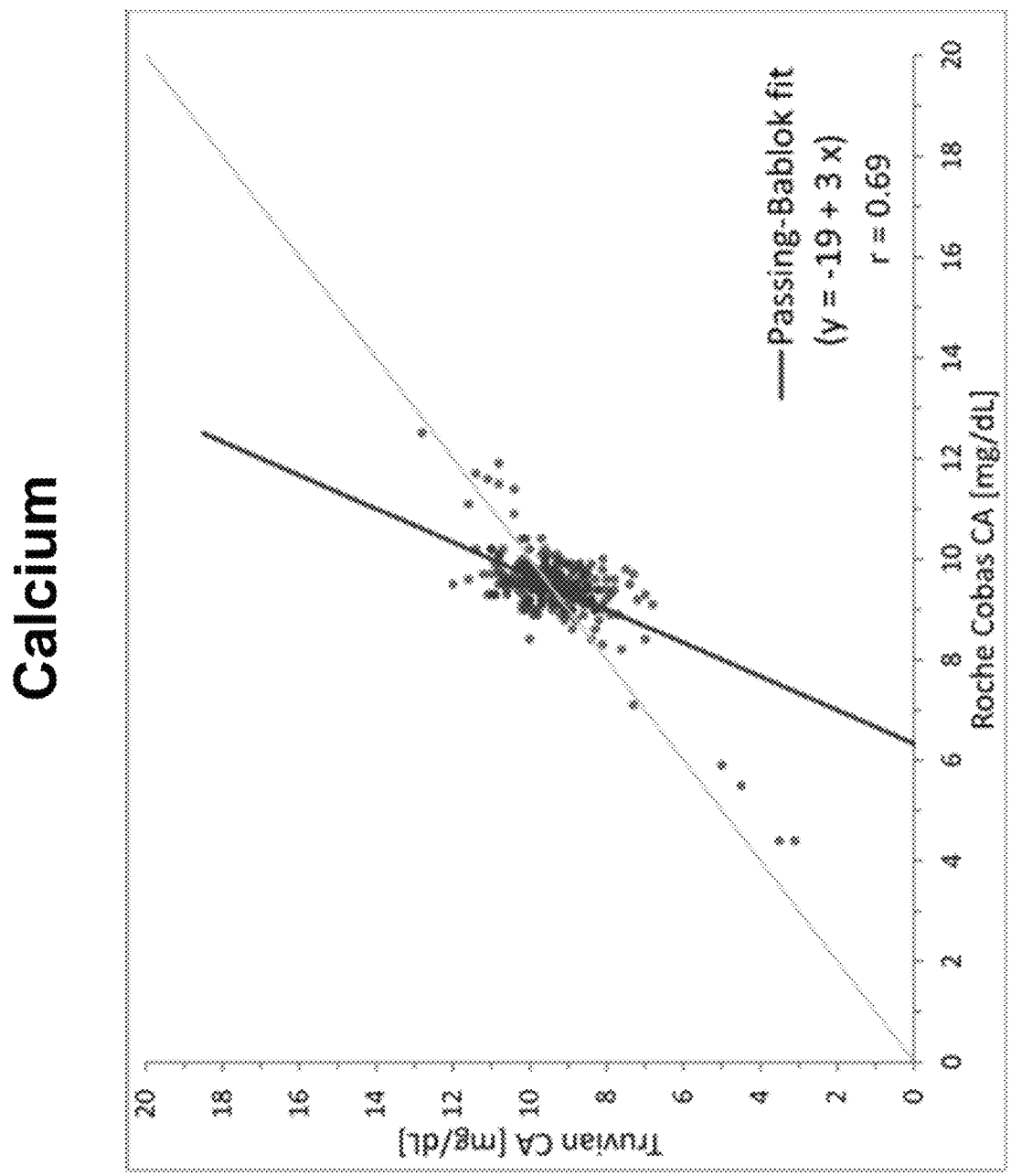
Figure 32C:
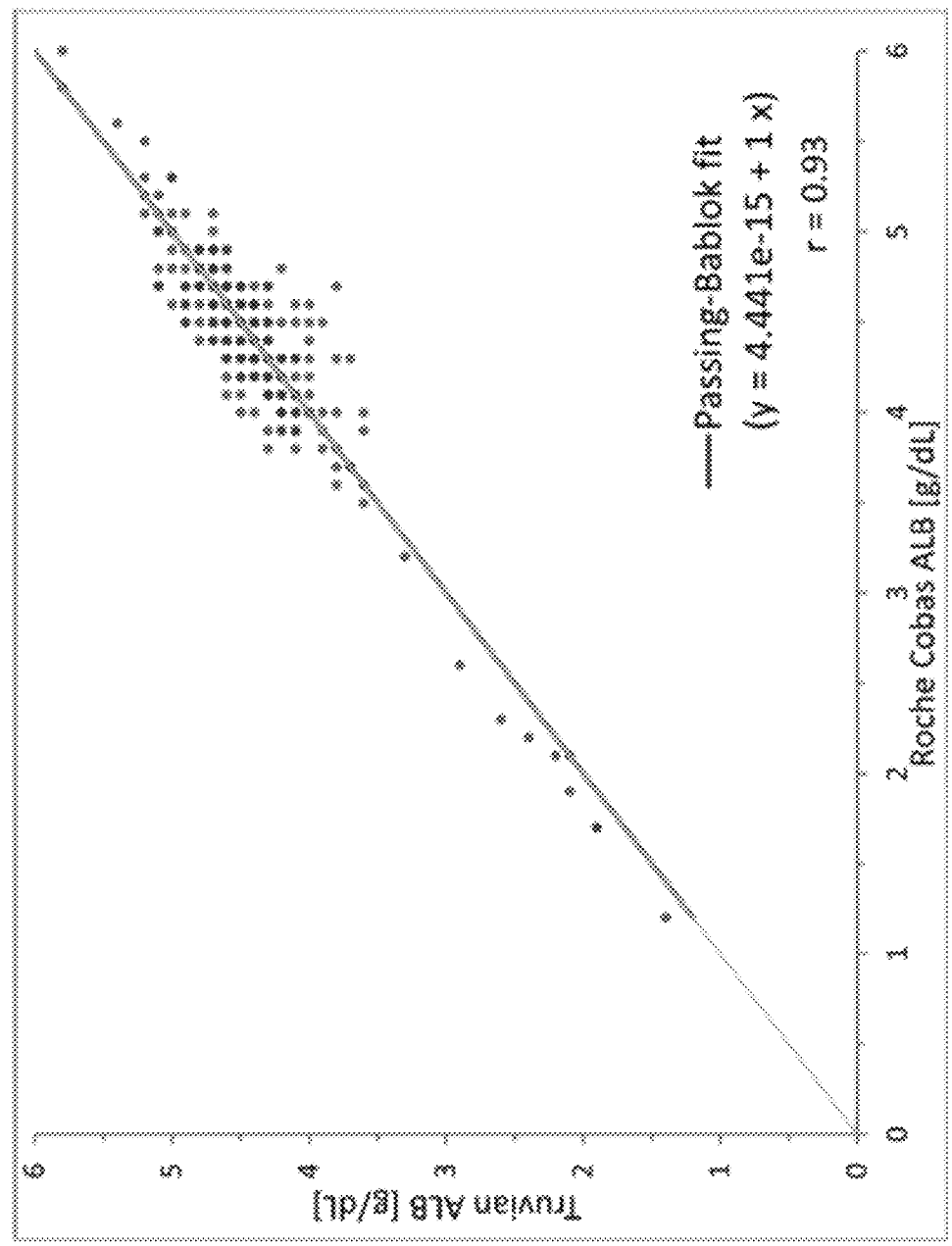
Figure 32D:
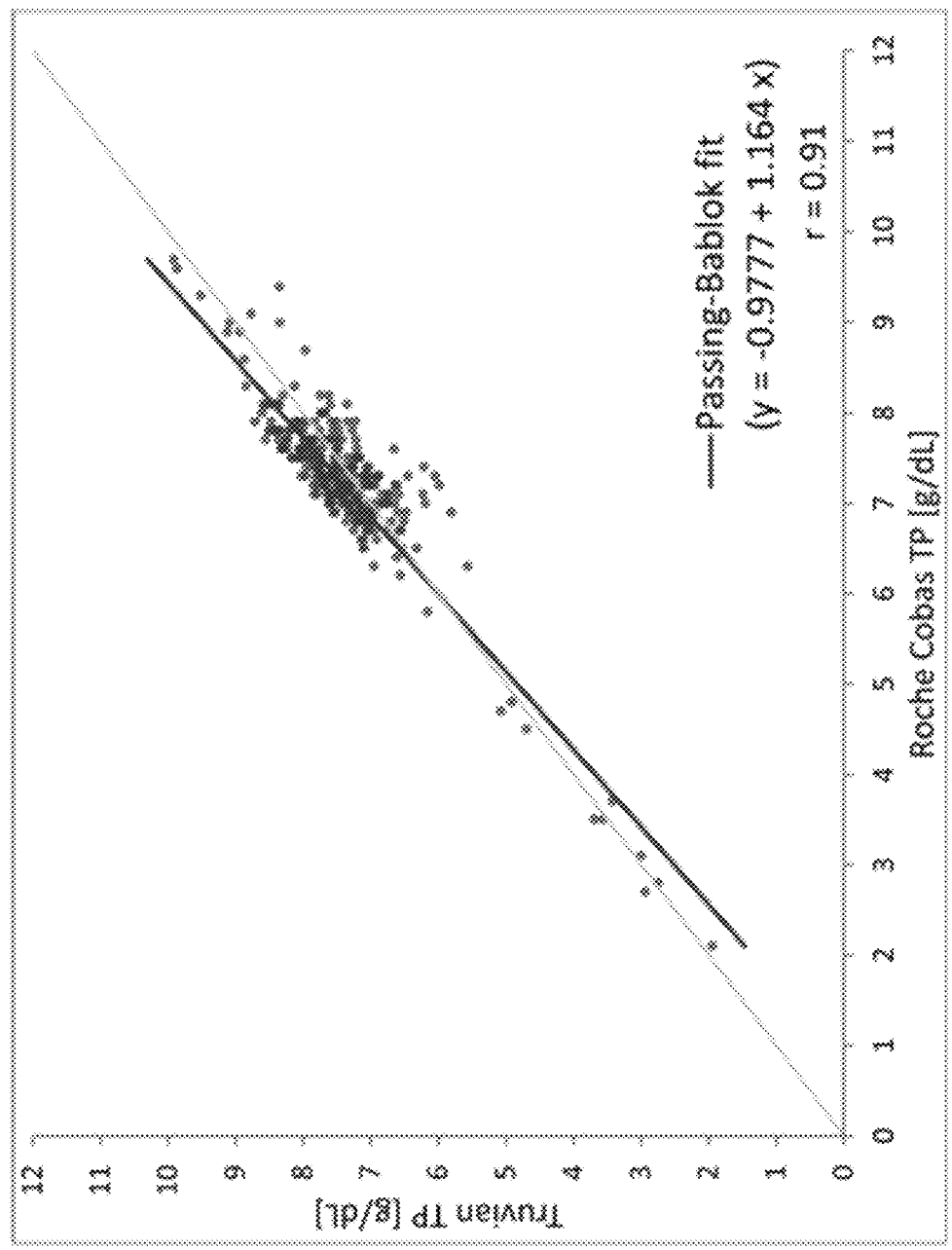
Figure 32E:
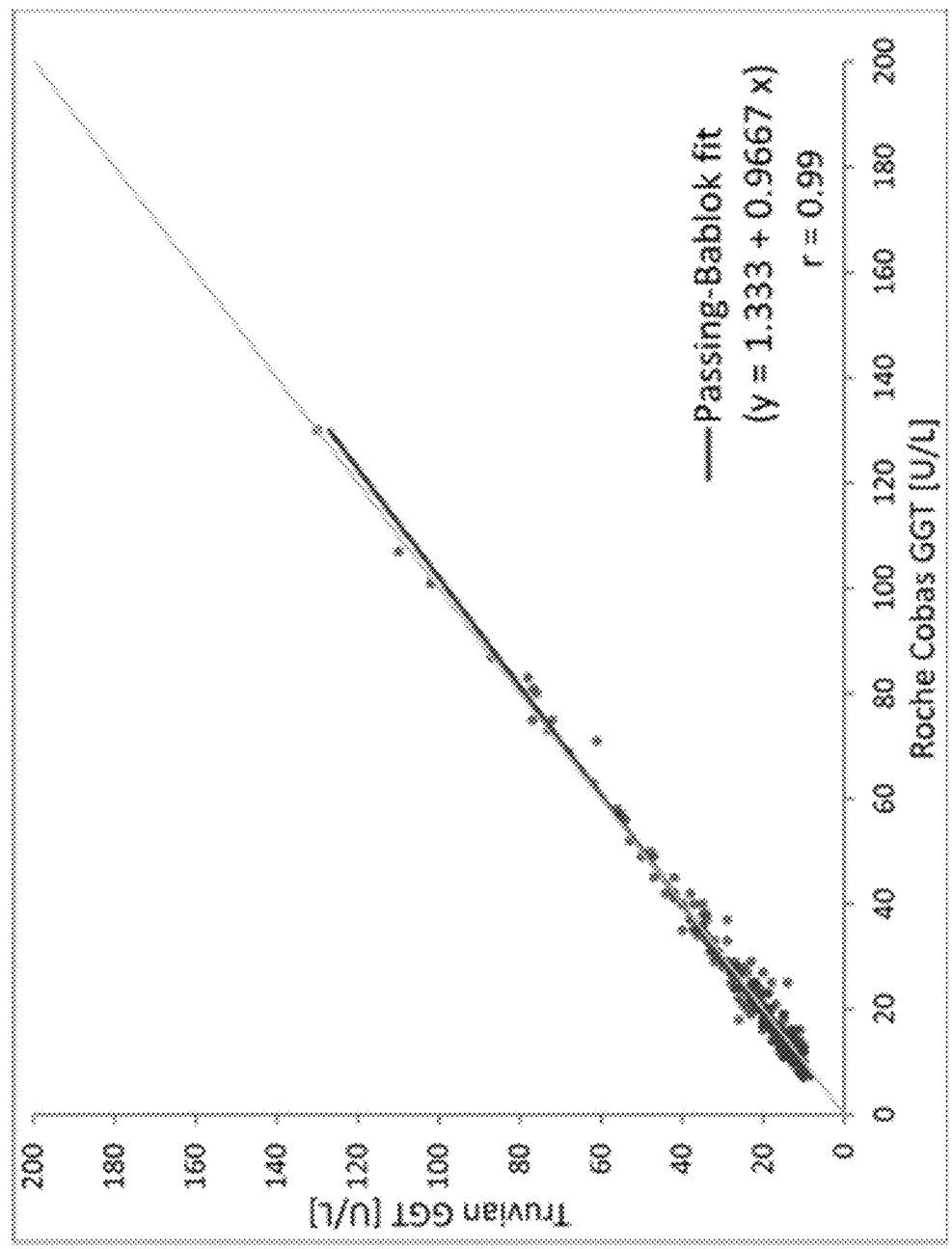

As shown in FIG. 32A (Method Comparison of the disclosed diagnostic instrument and Roche for Lipid Panel), 32B-C (Method Comparison of the disclosed diagnostic instrument and Sysmex for CBC), and 32D-EE (Method Comparison of the disclosed diagnostic instrument and Roche for Chemistry & HbA1C), regression analyses showed strong concordance between the diagnostic instrument and central laboratory results for the majority of clinical chemistry tests with no observed differences between internally and externally collected data. All Hematology tests, lipid panel tests except HDL and Chol/HDL ratio, and chemistry panel tests except CA, TBIL, A1c and TP demonstrated excellent agreement with the comparator across the measurement range. A number of tests had insufficient samples outside the reference range, preventing full comparative assessment. For these assays—ALB, ALP, BUN, GGT, TBIL, and TP—efforts were made to contrive samples to expand measurement range coverage. These efforts will continue in future performance evaluations, along with efforts to source native samples outside the reference interval. Lastly, ALT, CA, HbA1c, and HDL are undergoing formulation optimization and workflow updates to improve performance across the measurement interval.

DISCUSSION

This two-site study evaluated the precision and accuracy of the diagnostic instrument, which is in late-stage development. The main goals for conducting this study, were to understand the performance of the diagnostic instrument in a real-world setting and to identify areas of improvements necessary for a future FDA submission. Performance was evaluated across multiple assay types and by external untrained operators.

The high run reliability (>95%) and low invalid rates (<2%) during the course of the study demonstrated the feasibility and reliability of the core hardware design. The precision study showed that the diagnostic instrument produced repeatable and reproducible results for the majority of tests, demonstrating the interoperability of multiple diagnostic instruments. The method comparison study showed encouraging results with good concordance between the diagnostic instrument and the central laboratory results as assessed by Passing-Bablok regression and Bland-Altman analyses in 258 patients.

While this study provides strong evidence of the core viability of the diagnostic instrument, these results will be strengthened by including additional pathological and contrived samples to cover the entire measuring range, especially for tests such as calcium, total bilirubin, creatinine, ALP, ALT, BUN, HbA1c, and total protein. This will be a key focus for internal efforts and future studies. Additional improvements are being developed for selected assays including formulation, algorithm, and workflow optimization. Sample quality check to detect endogenous interference (i.e., hemolysis, lipemia and icterus) will also be implemented. In conjunction with testing pathological and contrived samples, calibration and value assignment strategies will be further refined and validated using international standards. Furthermore, as these improvements are incorporated, optimizations in the test panel workflow will be implemented to shorten run time.

In addition to the favorable assay performance in precision and method comparison, the system reliability of 95% with <2% invalid rate are acceptable for late-stage development and will be improved for launch. Along with achieving lab-accurate performance, a key benefit of the diagnostic instrument is simplifying the pre-analytical and sample handling process. The value of this goal was exemplified during the method comparison study, where 6 samples were lost in transit to the comparator central laboratory.

The diagnostic instrument is a novel, fully automated, device which aims to disrupt how blood testing is performed and experienced in today's healthcare system. Although under development, the data presented here suggest that accurate results, comparable to FDA cleared devices used in central laboratories, are achievable from a single sample type on this multi-modal platform. The diagnostic instrument is a first-in-class technology that will make central lab performance possible at the point of care. The learnings mentioned above, as well as the known limitations in the study that are currently being addressed along with an expanded wellness panel, will be incorporated into upcoming studies.

Example 2

Reproducibility

The reproducibility study, based on CLSI EP05-A3 guidelines, was used to evaluate repeatability and reproducibility using commercially—available controls for clinical chemistry and hematology. Fresh vials of control material (Bio-Rad and R&D Systems) were used on each of five testing days, to collect 4 Replicates/Level/Day on each of three instruments, to produce 180 measurements (with low, normal, and high controls) in total per analyte.

CV represents the sum of repeatability (within-run), between-day and between-instrument variances Reproducibility Summary:

The diagnostic instrument is performing well across all levels on multiple machines over multiple days. Met CV acceptance criteria for 74/75 (99%) of all levels (See FIG. 23). 100% of all levels meet the CV acceptance criteria if single RBC normal level outlier is excluded from analysis.

Linearity and Sensitivity

The diagnostic instrument achieved linearity and sensitivity across clinically relevant ranges. Representative data in FIGS. 24A-24C, FIGS. 25A-25C, and FIGS. 26A-26C demonstrate various detection methods including immunoassay, endpoint, and kinetic clinical chemistry, immunoturbidimetry, and cell counting assays within the panels on the diagnostic instrument. The diagnostic instrument achieved suitable thresholds for HIL interferences. The diagnostic instrument features integrated sample quality assessment (SQA) to determine levels of HIL in samples. Tolerance to HIL interferences is established for all assays and is comparable to FDA-cleared predicate methods (see FIG. 27A and FIG. 27B).

Method Comparison Study

Similar to Example 1, a multi-site method comparison study was performed. the multi-site method comparison study demonstrates the diagnostic instrument's results are concordant with central lab testing.

Method Comparison Study Design:

In the central lab comparison matched samples from 237 donors were run on the diagnostic instrument and compared to central laboratory analyzers. Donors are estimated to be 49% healthy donors, 43% donors with chronic disease, and 8% contrived samples. Samples were run across 5 diagnostic instruments at 2 sites. Regression analysis (Passing Bablok or Deming) was used to determine concordance for each assay (see FIGS. 28-31).

Method Comparison Summary:

Results from the panels run on the diagnostic instrument demonstrates central laboratory quality results are possible at the point of care.

Numbered Paragraphs

The system can be further understood by the following numbered paragraphs.

1. A multi-modality blood analysis system, comprising:
 a housing containing:
  a support pack with a sample;
  a multi-well plate with a plurality of wells;
  a computing system comprising at least one memory storing instructions and at least one processor configured to execute the instructions to perform operations;
  a clinical chemistry module controlled by the instructions of the computing system to collect data from at least one vessel of the multi-well plate that received at least a portion of the sample from the support pack based on optical measurements of an optical absorbance and/or a scattering value of a beam emitted by the clinical chemistry module; an immunoassay (IA) module controlled by the instructions of the computing system to collect data from the multi-well plate from another at least one vessel of the multi-well plate that received at least a portion of the sample from the support pack based on measurements of a beam emitted by the IA module; and
  a hematology module comprising a cell imager controlled by the instructions of the computing system to measure one or more hematology assays of the support pack.

2. The system of Paragraph 46, further comprising: a multi-well plate housing comprising a tray configured to receive the multi-well plate at any orientation.

3. The system of Paragraph 1, further comprising an immunoassay wash module configured to retain a plurality of beads in a well of the support pack while a liquid wash operation of the immunoassay wash module is performed.

4. The system of Paragraph 1, wherein the clinical chemistry module, the IA module, and the hematology module are fixed coupled directly to the base plate but not directly coupled to each other.

5. The system of Paragraph 1, further comprising an automated pipetting system within the housing for distributing resources between the multi-well plate and the support pack within the housing.

6. The system of Paragraph 1, wherein the support pack and the multi-well plate are in thermal communication with respective active heating systems controlled by the computing system based on thermal feedback detected by one or more onboard thermistors.

7. The system of Paragraph 1, further comprising: an automated pipetting system in communication with the immunoassay module, the clinical chemistry module, and the hematology module during a sample preparation operation.

8. The system of Paragraph 7, wherein the pipetting system is in communication with an immunoassay wash module.

9. The system of Paragraph 1, wherein the clinical chemistry module is configured to measure hemoglobin.

10. The system of Paragraph 1, wherein the clinical chemistry module and the immunoassay module are incapable of operating in parallel.

11. The system of Paragraph 1, wherein an immunoassay wash module and the hematology module are incapable of operating in parallel.

12. The system of Paragraph 1, wherein each of the modules are physically separated from one another within the housing only being interconnected via a baseplate of the system.

13. The system of Paragraph 1, wherein the clinical chemistry module is configured to separate plasma from blood cells, implement precise thermal control for consistent assay reaction progression, adjust plasma concentration for each assay's sample-to-reagent ratio, measure optical absorbance at specific wavelengths spanning UV to NIR, identify the presence of endogenous interference and combinations thereof.

14. The system of Paragraph 13, wherein the clinical chemistry module is configured to uniformly control a path of a wide spectrum of light wavelengths and wavelength-specific interactions of the light path and a lens.

15. The system of Paragraph 1, wherein the IA module is configured to separate plasma from blood cells, implement precise thermal control for consistent antibody/antigen binding progression, adjust plasma concentration for each assay's antibody/antigen ratio and combinations thereof.

16. The system of Paragraph 1, wherein the disc tray is configured to move along a base of the housing away from a forward end of the housing towards the IA module of an aft end of the housing.

17. The system of Paragraph 1, wherein heat transfer is at least semi-isolated between assay vessels.

18. The system of Paragraph 1, wherein the support pack tray and the support pack are configured so that when a sample is loaded in the support pack, the support pack can only be loaded in a load orientation.

19. The system of Paragraph 18, wherein the support pack is configured to move along a base of the housing away from a forward end of the housing towards the hematology module of an aft end of the housing.

20. The system of Paragraph 1, wherein the multi-well plate and the support pack comprise all materials necessary to run all tests, and contain all waste generated during the analysis of a blood sample.

21. The system of Paragraph 1, wherein the hematology module is configured to locate a three-dimensional position of a monolayer assay device via a homing process that locates features embedded in the monolayer assay device in all three dimensions of the three-dimensional position, wherein the monolayer assay device comprises a planar substrate and a flow channel disposed within the planar substrate, an inlet, and a vent.

22. The system of Paragraph 21, wherein a cell imaging system of the hematology module is configured to analyze one or more analytes within the flow channel, the one or more analytes comprising WBC, RBC, MCV, Platelets, Neutrophils (%), Lymphocytes (%), Neutrophils (Absolute), or Lymphocytes (Absolute).

23. A multi-modal method for multianalyte detection, comprising:
  scanning, by a detection instrument of a multi-modality blood analysis system, user-related information of a sample into a computer system;
  receiving, by the detection instrument, a disc comprising one or more samples in one of a plurality of orientations into a disc tray;
  measuring, by the detection instrument in a clinical chemistry mode, by the computing system controlling a clinical chemistry module of the multi-modality blood analysis system, at least one of an optical absorbance and a scattering value;
  measuring in an immunoassay mode, by the computing system controlling an immunoassay (IA) module of the multi-modality blood analysis system, one or more vessels of the disc; and
  measuring in a hematology mode, by the computing system controlling a hematology module of the multi-modality blood analysis system, one or more hematology assays of a general disc well in a support pack.

24. The method of Paragraph 23, further comprising:
  receiving, by a detection instrument a user selection of a run operation.

25. The method of Paragraph 23, further comprising:
  distributing, by an automatic multi-axis pipetting system, one or more reagents in a plurality of vessels of the disc.

26. The method of Paragraph 23, wherein the at least one of optical absorbance and the scattering value is of one or more outer-row vessels of the disc.

27. The method of Paragraph 23, further comprising:
  measuring, by the clinical chemistry module, a hemoglobin level of the one or more samples.

28. The method of Paragraph 23, further comprising:
  upon loading the disc into the tray, then causing the disc tray to move away from a forward end of the housing towards the IA module of an aft end of the housing and causing the support pack to move away from the forward end of the housing towards the hematology module of the aft end of the housing.

29. The method of Paragraph 23, wherein the clinical chemistry module and the immunoassay module are incapable of operating in parallel.

30. The method of Paragraph 23, wherein an immunoassay wash module and the hematology module are incapable of operating in parallel.

31. The method of Paragraph 23, further comprising:
  retaining, by an immunoassay wash module, a plurality of beads in a well of the disc while a liquid wash operation of the immunoassay wash module is performed.

32. The method of Paragraph 23, wherein a pipettor module is in communication with the immunoassay module, the clinical chemistry module, and the hematology module during a sample preparation operation.

33. The method of Paragraph 23, further comprising:
  separating, by the clinical chemistry module, plasma from blood cells;
  adjusting, by the clinical chemistry module, plasma concentration for each assay's sample-to-reagent ratio;
  measure, by the clinical chemistry module, optical absorbance at specific wavelengths spanning UV to NIR;
  identifying, by the clinical chemistry module, a presence of endogenous interference.

34. The method of Paragraph 23, further comprising:
  uniformly controlling, by the clinical chemistry module, a path of a wide spectrum of light wavelengths and wavelength-specific interactions of the light path and a lens.

35. The method of Paragraph 23, further comprising:
  separating, by the IA module, plasma from blood cells; and
  adjusting, by the IA module, plasma concentration for each assay's antibody/antigen ratio.

36. The method of Paragraph 23, wherein the step of measuring, by the IA module of the multi-modality blood analysis system, one or more vessels of the disc comprises focusing excitation on a bottom of the disc to a tolerance of approximately 10 µm.

37. The method of Paragraph 23, further comprising locating, by the hematology module, a three-dimensional position of each monolayer assay device via a homing process that locates features embedded in the monolayer assay device in all three dimensions of the three-dimensional position, wherein the monolayer assay device comprises a planar substrate and a flow channel disposed within the planar substrate, an inlet, and a vent.

38. The method of Paragraph 37, further comprising:
  analyzing, by a cell imager 243 of the hematology module, one or more analytes within the flow channel, the one or more analytes comprising a pre-diabetes panel, a cholesterol/lipid analyte panel, a nutrition panel, a fertility panel, a sexually transmitted disease (STD) panel, a thyroid panel, an electrolyte panel, a complete metabolic panel (CMP), and a complete blood cell (CBC) panel of analytes.

39. The method of Paragraph 23, wherein the step of loading the disc in one of a plurality of orientations comprises:
  imaging, by a consumable locator system, a disc image comprising a portion of the disc in the one of the plurality of orientations
  analyzing, by a consumable locator imaging logic, the disc image so that if a plurality of disc features are not identified in the image, then causing the disc to rotate to a second orientation of the plurality of orientations; and
  imaging, by the consumable locator system, a disc image comprising a portion of the disc in the second of the plurality of orientations until the plurality of disc features are detected.

40. The method of Paragraph 39, further comprising:
  scanning and interpreting, by the consumable locator system, a plurality of two-dimensional barcodes;
  collecting, by the consumable locator system, an image used to quantify a hematocrit of the blood sample; and
  analyzing, by a hematocrit analyzer, the collected image to detect specific features in a column of centrifuged blood to calculate the hematocrit.

41. The method of Paragraph 39, further comprising:
  detecting, by the consumable locator system, an orientation of the support pack to determine if the support pack has been properly loaded.

42. The method of Paragraph 39, further comprising:
  detecting, by the consumable locator system, the disc tray is clear of consumables at the completion of a run.

43. The method of Paragraph 23, wherein the step of scanning user-related information of the sample comprises scanning by a barcode scanner a patient identifier associated with the sample in an island defined by an absence of network connectivity.

44. A multi-modality blood analysis system, comprising:
a disc holder comprising a disc tray;
a support pack holder comprising a support pack tray;
a clinical chemistry module;
an immunoassay (IA) module; and
a hematology module, wherein the clinical chemistry module and IA module collect data from a disc in the disc tray and wherein the hematology module and IA module use reagents in a support pack in the support pack tray.

45. A method of diagnosing a patient, comprising:
loading a disc into a multi-modality blood analysis system, the disc comprising reagents;
loading a support pack into a multi-modality blood analysis system, the support pack comprising reagents and a patient sample;
processing, by the multi-modality blood analysis system, a clinical chemistry assay using reagents from the disc to obtain clinical chemistry assay results;
processing, by the multi-modality blood analysis system, an immunoassay (IA) assay using reagents from the disc;
processing, by the multi-modality blood analysis system, a hematology assay using reagents from the disc to obtain hematology assay results; and
processing, by the multi-modality blood analysis system, a hematology assay using reagents from the support pack to obtain hematology assay results thereby diagnosing a patient.

46. A multi-modality blood analysis system, comprising:
A housing
A sample handler module in the housing wherein the sample handler module comprises a sample carrier configured to store a single blood tube;
a sample preparation unit in the housing configured to interact with the sample handler module; and
a sample detection unit in the housing wherein the sample detection unit comprises a hematology detection tool, an immunoassay detection tool, and a clinical chemistry detection tool.

47. The multi-modality blood analysis system of Paragraph 46, wherein the blood tube contains sodium heparin or lithium heparin.

47a. The multi-modality blood analysis system of Paragraph 46, wherein if the system includes electrochemical detection the blood tube contains only lithium heparin.

47b. The multi-modality blood analysis system of Paragraph 46, wherein if the system includes hematology, IA, clinical chemistry, and electrochemical detection the blood tube contains only lithium heparin.

47c. The multi-modality blood analysis system of Paragraph 46, wherein if the system includes hematology, IA, or clinical chemistry the blood tube contains sodium heparin or lithium heparin.

48. The multi-modality blood analysis system of Paragraph 46, wherein the sample handler module further comprises a disc tray and a support pack tray.

49. The multi-modality blood analysis system of Paragraph 48, wherein the disc tray loaded with a disc and support pack tray loaded with a support pack comprise all materials necessary to run:
a. a hematology assay selected from the group comprising or consisting of red blood cell count (RBC), white blood cell count (WBC), platelet count (PLT), hematocrit (HCT), hemoglobin (HGB), mean corpuscular volume (MCV), lymphocyte count (LYMPH), lymphocyte percentage (LYMPH %), neutrophil count (NEUT), neutrophil percentage (NEUT %), other WBC count (OTHER), other WBC percentage (OTHER %) and combinations thereof,
b. an immunoassay selected from the group comprising or consisting of TSH (Thyroid Stimulating Hormone), glycated hemoglobin A1c and combinations thereof; and
c. a clinical chemistry assay selected from the group comprising or consisting of sodium (NA), potassium (K), chloride (CL), bicarbonate (CO2), albumin (ALB), alkaline phosphatase (ALP), alanine aminotransferase (ALT), blood urea nitrogen (BUN), calcium (CA), creatinine (CRE), estimated glomerular filtration rate (eGFR)*, gamma-glutamyl transferase (GGT), glucose (GLU), glycated hemoglobin A1c (HbA1c), high density cholesterol (HDL), low density cholesterol (LDL), non-HDL cholesterol (non-HDL), total cholesterol (CHOL), total cholesterol/HDL ratio (CHOL/HDL), total bilirubin (TBIL), total protein (TP), triglycerides (TRIG), very low density cholesterol (VLDL) and combinations thereof.

Wherein a clinical chemistry module measures the CBC, lipid panel, HbA1c, HGB, ALB, BUN, CRE, GGT, GLU and TP assays.

50. The multi-modality blood analysis system of Paragraph 48, wherein the disc and support pack are configured to contain all waste generated during the analysis of a blood sample.

51. The multi-modality blood analysis system of claim 3, wherein the support pack tray and the hematology detection tool are aligned by a rail resting on the hematology detection tool module thereby creating at least a partially floating first end of the rail.

52. The multi-modality blood analysis system of Paragraph 46, wherein the hematology detection tool is cell imager 243 callable of collecting high resolution brightfield and fluorescent images, the immunoassay detection tool is a laser-based detector, and a clinical chemistry detection tool is a spectrophotometer and a camera.

53. A multi-modality blood analysis system, comprising:
A housing
a sample preparation system in the housing comprising a sample receiving station, a monolayer, and a plurality of reagent vessels; and
a sample detection unit in the housing wherein the sample detection unit comprises a first detection station comprising an absorbance detection tool, a second detection station comprising a laser-based detector, a third detection station comprising a cell imager 243 and a fourth detection station comprising a camera.

54. The multi-modality blood analysis system of Paragraph 53, wherein the sample preparation system comprises a bead wash module.

55. The multi-modality blood analysis system of Paragraph 53, wherein the sample receiving station comprises a first reaction carrier and second a second reaction carrier wherein a blood tube is in the first reaction carrier.

56. The multi-modality blood analysis system of Paragraph 55, wherein the first reaction carrier comprises a first scannable code and a second scannable code and the second reaction carrier comprises a third scannable code and the sample receiving station comprises a barcode scanner to read the first scannable code and the second scannable code and a camera to read the third scannable code.

57. A point of care biological sample processing system for performing assays on a first biological sample obtained from a subject comprising:

a first cartridge and a second cartridge wherein the first cartridge comprises reagents for performing assays on the second cartridge, diluents for performing assays on the second cartridge, the first biological sample and a monolayer;

the second cartridge comprising reagents wherein the second cartridge comprising a first reaction vessel for performing a first assay on a first portion of the first biological sample to detect a first analyte, wherein the first assay comprises a kinetic assay or an end point assay; a second reaction vessel for performing a second assay on a second portion of the first biological sample to detect a second analyte, wherein the second assay is a florescent based assay; a third reaction vessel for performing a third assay on a third portion of the first biological sample to detect a third analyte, wherein the third assay is a hematology based assay; and wherein the second cartridge does not comprise all the reagents necessary for performing the first and second assays.

A sample processing device comprising a cartridge receiving location for receiving the first cartridge and second cartridge, a pipet module for moving sample from the first cartridge to the second cartridge, a centrifuge, an absorbance detection module, a cell imaging module, fluorescent laser scanning module 373, and a camera.

58. The point of care biological sample processing system of Paragraph 57, wherein the point of care biological sample processing system is not connected to the internet.

59. The point of care biological sample processing system of Paragraph 57, wherein the processing system comprises a first motor operatively coiled to the clinical chemistry detection instrument, the immunoassay detection instrument a disc tray to separate plasma and the pipet module.

Electrochemistry Module

In some embodiments, the detection system comprises an electrochemistry module 390. Electrolyte measurement entails measuring the concentration of electrolytes such as sodium, potassium, chloride, and bicarbonate in whole blood or plasma. While these measurements could be performed using chemical reagents and the clinical chemistry module 380, this is not the generally accepted measurement method within the medical community. The medical community almost exclusively prefers electrochemical measurement. As such, the disclosed instrument further comprises an electrochemistry module that utilizes the electrochemical measurement modality for these assays. Ion-selective electrodes (ISEs) are electroanalytical sensors whose signals depend on the activities of ions in solution and exhibit a certain degree of selectivity for particular ionic species. The operation of classical ISEs is based on direct measurement of a single membrane potential at zero net current. The three main components of making a measurement at an ISE are an inner reference, or standard, solution and an outer analyte, or sample, solution separated by a thin membrane.

Figure 33:
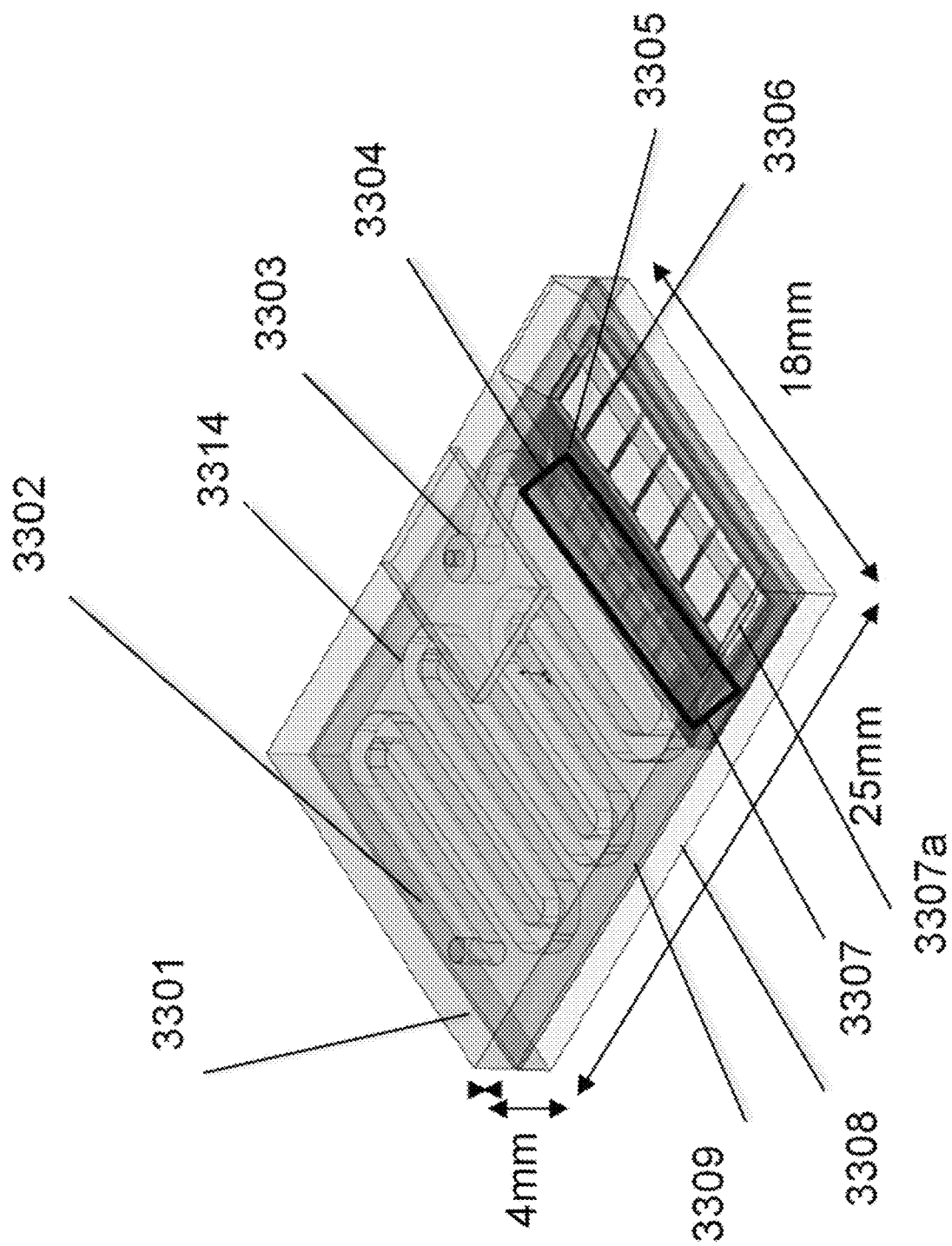
FIG. 33 shows an exemplary close-up of the electrochemistry cartridge.

FIG. 33 discloses an electrochemistry consumable 391. 3301 depicts an upper chip housing with integrated fluidics cell. 3302 depicts the end of fluidic channel vent. 3303 depicts an elastomeric perforated septum for pipette tip entry seal. This allows active positive and negative pressure flow from the instrument. 3304 depicts an active electrode sensor area. 3305 depicts the combination electrode chip. 3306 depicts an enlarged contact for analyzer interface. 3307 depicts ion-selective membranes between channel 3314 and electrodes 3307a. A first portion of the electrode is exposed to air, a second portion of electrode is under the membrane 3307 and channel 3314. 3308 depicts the lower chip housing. 3309 depicts PSA or an equivalent bonding layer. The electrochemistry consumable 391 is about 10-20 mm wide, about 20-30 mm long and about 2-6 mm tall.

In some embodiments, the electrochemistry consumable 391 is independent of the disc, support pack, and monolayer. In some embodiments, the electrochemistry consumable 391 is incorporated into any one of the disc, support pack, or monolayer. In some embodiments, the electrochemistry consumable 391 is incorporated into the disc, support pack, monolayer or combinations thereof. The electrochemistry consumable 391 can accept either isolated plasma, whole blood, or both. In some embodiments, the plasma/whole blood is diluted. In some embodiments, the plasma/whole blood is un-diluted. The electrochemistry consumable 391 comprises a liquid input port 3303 for delivery of sample by the pipettor (module 400).

The electrochemistry consumable 391 contains a vented channel 3314 through which liquid can flow so that it comes in contact with each ion-selective membrane 3307. Ion-selective membranes are selective for each analyte of interest (sodium, potassium, chloride, bicarbonate). The electrochemistry consumable 391 may or may not contain on-board calibration electrodes for each assay. The electrochemistry consumable 391 may or may not comprise a tag for calibration for each assay. The electrochemistry consumable 391 tag may be read by the bar code scanner and/or the camera.

Figure 34A:
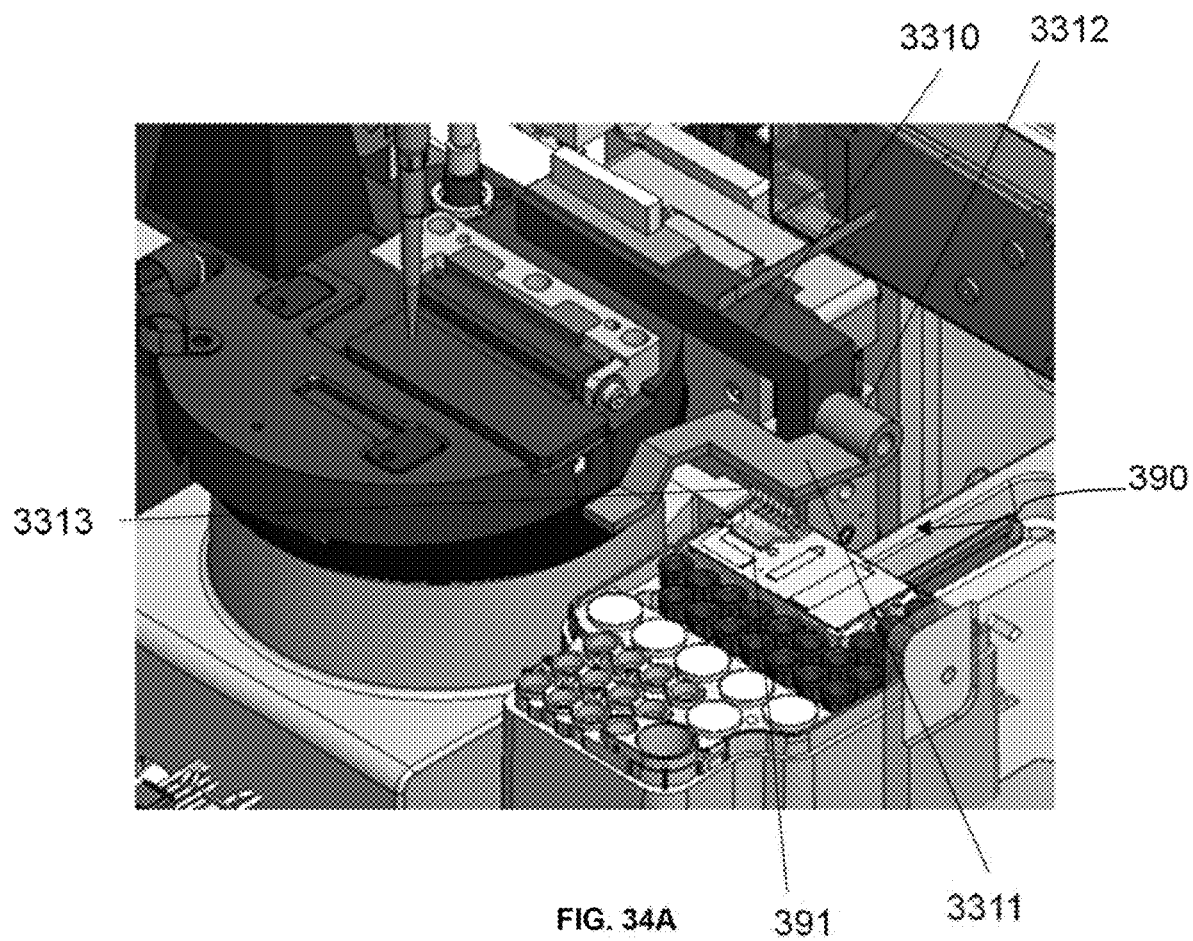
FIG. 34A shows an exemplary close-up of the interface between the support pack comprising an electrochemistry cartridge and the detection instrument.
Figure 34B:
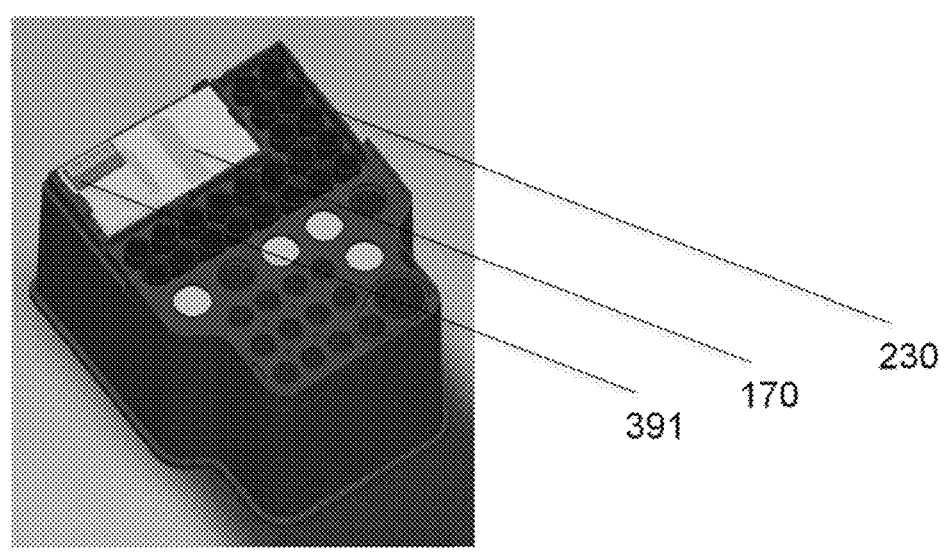
FIG. 34B shows an exemplary close-up of a support pack, in accordance with an exemplary embodiment.

FIG. 34A depicts an instrument/electrochemistry module interface for electrochemistry module 390. 3310 depicts a stationary mount for a paddle pivot 3311. Electronics and a stationary cable routed to ISE power/data daughter board run through the stationary mount 3310. 3312 is a pivot point. 391 depicts an electrochemistry consumable. 3311 depicts a contact paddle that is spring-loaded upward, to be actuated mechanically by pipettor (module 400) in Z without a pipette tip attached to create electrical contact with the electrochemistry consumable 391 via spring-loaded pins and to have the electrodes make contact with the ISE chip (not shown). 170 depicts a monolayer with electrochemistry consumable 391 on a support pack 230. In this way the electrochemistry module comprises the shared resource of the pipettor module 400 but, in some instances, uses the resource with a different/unexpected function, i.e., rather than having the function of a pipettor (to extract, transport and dispense liquid samples) it is functioning to make an electrical connection. The electrical sensor 3313 comprises electrical contacts to connect to the electrochemistry consumable 391 to measure analyte detection. FIG. 34B depicts a support pack 230 comprising an electrochemistry consumable 391 and monolayer 170. In some embodiments, rather than electrical connections 3313 actuating from the top down, they are positioned to come from the bottom up. In some embodiments, a passively activated arm moves up and down as the support pack tray 220 slides in and out. In some embodiments, the passively activated arm moves up and down via a ramp. As a roller moves along the ramp the passively activated arm moves up to make an electrical connection with the electrochemistry consumable 391 from the underside of the support pack.

The electrochemistry module can be further understood by the following numbered paragraphs:

Paragraph 1. A diagnostic instrument comprising:
A pipettor module;
An electrochemistry cartridge wherein the pipettor module is positioned to hold the electrochemistry cartridge in electrical communication with the diagnostic instrument.

Paragraph 2. A method for processing a patient sample in a diagnostic instrument, the method comprising:
  loading by the detection instrument a sample via a pipet tip in fluid communication with a pipettor module into an electrochemistry cartridge;
  holding by the detection instrument the electrochemistry cartridge in electrical communication with the diagnostic instrument wherein when the electrochemistry cartridge is in electrical communication with the diagnostic instrument the pipettor module does not have a pipet tip in fluid communication with the pipettor module.

What is claimed is:

1. An optical method for detecting the presence of a target analyte in a sample, the method comprising: a) moving automatically a first portion of a whole blood sample from a support pack to a first well in a disk in a detection instrument and moving automatically a second portion of the whole blood sample from the support pack to a reaction well in the support pack, the disk comprising dried chemistries for processing the sample, plasma separation features configured to separate whole blood into plasma, and a hematocrit channel configured to execute the hematocrit assay, the support pack comprising the whole blood sample, pipette tips, buffers, a reagent for processing the sample, reagent preparation wells, and a monolayer assay device configured to operate as a hematology slide; b) separating by the detection instrument plasma from the first portion of the whole blood sample in the disk while simultaneously moving reagent in the support pack for processing the plasma generated in the disk and diluting the second portion of the whole blood sample in the support pack; c) moving automatically by the detection instrument the plasma generated from the first portion of the whole blood sample from the disk to the support pack; d) diluting by the detection instrument the plasma generated from the first portion of the whole blood sample in the support pack; e) moving automatically by the detection instrument the plasma generated from the first portion of the whole blood sample from the support pack to the disk; and f) optically detecting by the detection instrument the presence or absence of said first target analyte, the detection instrument comprising a laser and at least one of a spectrophotometer, or a camera.

2. The optical method of claim 1, further comprising moving a third portion of the whole blood sample from the support pack to a second well in the disk; separating by the detection instrument, plasma from the third portion of the whole blood sample in the disk and taking an image by a second camera associated with the disk prior to detecting the presence or absence of the first target analyte in the disk.

3. An optical method for detecting the presence of a target analyte in a sample, the method comprising: a) moving automatically a first portion of a whole blood sample from a support pack to a first well in a disk in a detection instrument, the disk comprising dried chemistries for processing the sample, plasma separation features configured to separate whole blood into plasma, and a hematocrit channel configured to execute the hematocrit assay, the support pack comprising the whole blood sample, pipette tips, buffers, a reagent for processing the sample, reagent preparation wells, and a monolayer assay device configured to operate as a hematology slide: b) separating by the detection instrument plasma from the first portion of the whole blood sample in the disk while simultaneously moving reagent in the support pack for processing the plasma generated in the disk: c) moving automatically by the detection instrument the plasma generated from the first portion of the whole blood sample from the disk to the support pack: d) diluting by the detection instrument the plasma generated from the first portion of the whole blood sample in the support pack: e) moving automatically by the detection instrument the plasma generated from the first portion of the whole blood sample from the support pack to the disk: f) optically detecting by the detection instrument the presence or absence of said first target analyte, the detection instrument comprising a laser and at least one of a spectrophotometer, or a camera: further comprising moving by the detection instrument a third portion of the whole blood sample from the support pack to a second well in the disk; hybridizing by the detection instrument a probe to a second target analyte in the second well to form a bead-antigen-fluorescent complex; moving by the detection instrument the bead-antigen-fluorescent complex to the support pack; washing automatically by the detection instrument the bead-antigen-fluorescent complex in the support pack; moving the washed bead-antigen-fluorescent complex back to the disk to a third well wherein the second well and the third well are different; and detecting by the detection instrument the presence or absence of said second target analyte in the disk after detecting by the detection instrument the presence or absence of said first target analyte in the disk.

4. The optical method of claim 2, further comprising counting the number of cells in the sample comprising moving a fourth portion of the whole blood sample from the support pack to a third well in the disk, separating by the detection instrument the fourth portion of the whole blood sample into plasma in the disk, moving the plasma generated from the fourth portion of the whole blood sample from the disk to the monolayer assay device in the support pack and detecting the number of cells in the plasma generated from the fourth portion of the whole blood sample in the support pack after optically detecting by the detection instrument the presence or absence of said first target analyte in the first portion of the whole blood sample in the disk.

5. The optical method of claim 1, further comprising: automatically calibrating the detection instrument based on a barcode on the support pack, the barcode comprising information for the assay; collecting by the disk and support pack all waste generated during analysis of the sample; determining the location of the disk by a first camera, the first camera operatively coupled to a first processor and associated with the disk; determining the location of the support pack by a barcode scanner, the barcode scanner operatively coupled to a second processor and associated with the support pack prior to moving the first portion of the whole blood sample from the support pack to the first well in the disk; aligning the support pack and the at least one of the spectrophotometer or the camera by the detection instrument using a first rail associated with a support pack tray the support pack tray holding the support pack and a second rail associated with the spectrophotometer, or the camera prior to moving the first portion of the whole blood sample, wherein the detection instrument is not connected to the internet.

6. An optical method for detecting the presence of target analyte in a sample, the method comprising: a) receiving by a detection instrument a first cartridge comprising dried chemistries, plasma separation features, and a hematocrit channel; b) receiving by the detection instrument a second cartridge comprising the whole blood sample, pipette tips, buffers, reagent preparation wells, and a monolayer assay device; c) moving automatically by the detection instrument a first portion of a whole blood sample from the second cartridge to a first well in the first cartridge and moving automatically by the detection instrument a second portion of a whole blood sample from the second cartridge to a reaction well in the second cartridge; d) moving automatically by the detection instrument a reagent from the second cartridge to the first well in the first cartridge; e) and diluting the second portion of the whole blood sample in the second cartridge; and f) optically detecting by the detection instrument the presence or absence of a first target analyte in the first portion, the instrument comprising a laser and at least one of a spectrophotometer, and a camera.

7. An optical method for detecting the presence of target analyte in a sample, the method comprising:
  a) moving automatically a first portion of a whole blood sample from a second cartridge to a first well in a first cartridge in a detection instrument, the first cartridge comprising dried chemistries, plasma separation features, and a hematocrit channel, the second cartridge comprising the whole blood sample, pipette tips, buffers, reagent preparation wells, and a monolayer assay device;
  b) moving reagent from the second cartridge to the first well in the first cartridge;
  c) optically detecting by the detection instrument the presence or absence of a first target analyte in the first well, the detection instrument comprising a laser and at least one of a spectrophotometer or a camera;
  (d) moving automatically a second portion of the whole blood sample from the second cartridge to a first tube in the second cartridge in a detection instrument;
  (e) moving automatically a buffer from the second cartridge to the first tube in the second cartridge;
  (f) optically detecting by the detection instrument the presence or absence of a second target analyte in the first tube.

8. The method of claim 3, further comprising mixing by the detection instrument the bead-antigen-fluorescent complex in the disk by rotating the disk clockwise and counterclockwise and moving by the detection instrument the reagent for processing the plasma generated in the disk by aspirating with a pipette.

9. The method of claim 1, further comprising receiving sequentially by the detection instrument the support pack supported by a support pack tray and associated with a first rail and the disk supported by a disk tray and associated with a second rail.

10. An optical method for detecting the presence of a target analyte in a sample, the method comprising: a) moving automatically a first portion of a whole blood sample from a support pack to a first well in a disk in a detection instrument, the disk comprising dried chemistries for processing the sample, plasma separation features configured to separate whole blood into plasma, and a hematocrit channel configured to execute the hematocrit assay, the support pack comprising the whole blood sample, pipette tips, buffers, a reagent for processing the sample, reagent preparation wells, and a monolayer assay device configured to operate as a hematology slide: b) separating by the detection instrument plasma from the first portion of the whole blood sample in the disk while simultaneously moving reagent in the support pack for processing the plasma generated in the disk: c) moving automatically by the detection instrument the plasma generated from the first portion of the whole blood sample from the disk to the support pack: d) diluting by the detection instrument the plasma generated from the first portion of the whole blood sample in the support pack: e) moving automatically by the detection instrument the plasma generated from the first portion of the whole blood sample from the support pack to the disk: f) optically detecting by the detection instrument the presence or absence of said first target analyte, the detection instrument comprising a laser and at least one of a spectrophotometer, or a camera; and further comprising optically detecting by the detection instrument the presence or absence of said first target analyte in the first portion of the whole blood sample in the disk while simultaneously optically detecting by the detection instrument the presence or absence of an additional target analyte in an additional portion of the whole blood sample in the support pack.

11. The optical method of claim 1, wherein optically detecting by the detection instrument is by the camera aligned with the disk the presence, absence, or value of the first target analyte wherein the first target analyte is selected from the group comprising Glucose, BUN, Creatinine, Calcium, Protein, Total, Albumin, Bilirubin, Total, Alkaline Phosphatase, AST (SGOT), ALT (SGPT), Cholesterol Total, Triglycerides, HDL Cholesterol, Hemoglobin, or Hemoglobin A1c.

12. The optical method of claim 11, further comprising optically detecting by the detection instrument by a second optical detector aligned with the disk the presence or absence of a third target analyte wherein the third target analyte is TSH (Thyroid Stimulating Hormone).

13. The optical method of claim 1, further comprising
  detecting by a third detector aligned with the support pack the value of a third target analyte in the second portion of the whole blood sample wherein the third target analyte is WBC, RBC, Platelets, Neutrophils (%), Lymphocytes (%), Neutrophils (Absolute), or Lymphocytes (Absolute).

14. The optical method of claim 13, wherein detecting by the detection instrument by a third detector aligned with the support pack occurs at the same time as detecting by a first detector aligned with the disk.

15. The optical method of claim 13, wherein detecting by the detection instrument by a third detector aligned with the support pack occurs at the same time as detecting the first target analyte by the camera aligned with the disk.

16. The optical method of claim 3, further comprising, moving automatically a second portion of the whole blood sample from the support pack to a second well in the disk; separating by the detection instrument plasma from the second portion of the whole blood sample in the disk; moving automatically by the detection instrument the plasma generated from the second portion of the whole blood sample from the disk back to the support pack; incubating by the detection instrument the plasma generated from the second portion of the whole blood sample in the support pack; detecting a third target analyte in the plasma generated from the second portion of the whole blood sample by a third detector aligned with the support pack wherein detecting by a third detector aligned with the support pack cannot occur at the same time as washing automatically the bead-antigen-fluorescent complex in the support pack.

17. The optical method of claim 1, wherein the reagent is an immunoassay wash buffer.

18. The method of claim 3, wherein the spectrophotometer detects the second target analyte.

19. The method of claim 3, further comprising moving a second portion of the whole blood sample from the support pack to a reaction well in the support pack and simultaneous to optically detecting by the detection instrument the presence or absence of said first target analyte in the first portion of the whole blood sample in the disk, processing the second portion of the whole blood sample in the support pack.

\* \* \* \* \*